US007935724B2

(12) United States Patent
Miller et al.

(10) Patent No.: US 7,935,724 B2
(45) Date of Patent: May 3, 2011

(54) THIOPHENE AND BENZOTHIOPHENE HYDROXAMIC ACID DERIVATIVES

(75) Inventors: Thomas A. Miller, Brookline, MA (US); David J. Witter, Norfolk, MA (US); Sandro Belvedere, Verona (IT)

(73) Assignee: Merck HDAC Research, LLC, Boston, MA (US)

( * ) Notice: Subject to any disclaimer, the term of this patent is extended or adjusted under 35 U.S.C. 154(b) by 1071 days.

(21) Appl. No.: 10/574,992

(22) PCT Filed: Oct. 8, 2004

(86) PCT No.: PCT/US2004/033386
§ 371 (c)(1),
(2), (4) Date: Jan. 12, 2007

(87) PCT Pub. No.: WO2005/034880
PCT Pub. Date: Apr. 21, 2005

(65) Prior Publication Data
US 2007/0213392 A1  Sep. 13, 2007

Related U.S. Application Data

(60) Provisional application No. 60/510,282, filed on Oct. 9, 2003, provisional application No. 60/566,634, filed on Apr. 28, 2004.

(51) Int. Cl.
A61K 31/381 (2006.01)
C07D 333/70 (2006.01)
(52) U.S. Cl. .......................................... 514/443; 549/57
(58) Field of Classification Search .................. 549/57, 549/55; 514/443
See application file for complete search history.

(56) References Cited

U.S. PATENT DOCUMENTS

| 4,522,811 | A | 6/1985 | Eppstein et al. ................... 514/2 |
| 5,369,108 | A | 11/1994 | Breslow et al. ................ 514/266 |
| 5,608,108 | A | 3/1997 | Marks et al. .................... 562/621 |
| 5,700,811 | A | 12/1997 | Breslow et al. ................ 514/314 |
| 5,932,616 | A | 8/1999 | Breslow et al. ................ 514/532 |
| 6,087,367 | A | 7/2000 | Breslow et al. ................ 514/266 |
| 6,511,990 | B1 | 1/2003 | Breslow et al. ................ 514/314 |
| 6,541,661 | B1 | 4/2003 | Delorme et al. ............... 560/318 |
| 7,772,238 | B2 | 8/2010 | Hubbs et al. |
| 2003/0013757 | A1 | 1/2003 | Leser-Reiff et al. .......... 514/448 |
| 2003/0235588 | A1 | 12/2003 | Richon et al. ................. 514/575 |
| 2004/0087657 | A1 | 5/2004 | Richon et al. ................. 514/575 |
| 2004/0106599 | A1 | 6/2004 | Delorme et al. |
| 2004/0142953 | A1 | 7/2004 | Delorme et al. |
| 2004/0157841 | A1 | 8/2004 | Fertig et al. |
| 2009/0069391 | A1 | 3/2009 | Hubbs et al. |
| 2009/0082308 | A1 | 3/2009 | Hubbs et al. |

FOREIGN PATENT DOCUMENTS

| EP | 0 158 380 A | 5/2009 |
| WO | WO 97/11366 | 3/1977 |
| WO | WO 98/48825 | 11/1998 |
| WO | WO 00/08048 | 2/2000 |
| WO | WO03/013484 | * 2/2003 |
| WO | WO03/024448 | * 3/2003 |
| WO | WO2004/069823 | * 8/2004 |
| WO | WO 2005/348800 | 4/2005 |
| WO | WO2005/066151 A | 7/2005 |
| WO | WO2006/115833 | * 11/2006 |

OTHER PUBLICATIONS

Abe, E., et al., Proc. Natl. Acad. Sci. (USA) 78: 4990-4994 (1981).
Andrews et al., International J. Parasitology 30,761-768 (2000).
Archer, S. et al., PNAS 95:6791-96 (1998).
Brosch et al., Plant Cell 7, 1941-1950 (1995).
Butler, L.M. et al., Cancer Res. 60:5165-5170 (2000).
Cohen, L.A. et al, Anticancer Research 19:4999-5006 (1999).
Cousens et al., J. Biol. Chem. 254,1716-1723 (1979).
Darkin-Rattray et al., Proc. Natl. Acad. Sci. USA 93,13143-13147 (1996).
Dressel, U. et al., Anticancer Research 20(2A):1017-22 (2000).
Ebert, P. S., et al. Cancer Res. 36: 1809-1813 (1976).
Finnin, M.S., et al., Nature 401:188-193 (1999).
Frey et al, Bioorganic & Med. Chem. Lett., 12, 3443-3447 (2002).
Friend, C., et al., Proc. Natl. Acad. Sci., U. S., 68:378-382 (1971).
Grunstein, M., Nature, 389: 349-52 (1997).
Guan et al., Cancer Research, 60,749-755 (2000).
Hayashi, M., et al., Gann 70: 235-238 (1979).
Huberman, E. et al., Proc. Natl. Acad. Sci. (USA) 76: 1293-1297 (1979).
Kijima et al., J Biol. Chem. 268,22429-22435 (1993).
Kim et al., Oncogene, 18: 2461-2470 (1999).
Koghe et al., Biochem. Pharmacol. 56: 1359-1364 (1998).
Kwon et al., PNAS 95: 3356-3361 (1998).
Lea et al., Anticancer Research, 15, 879-873 (1995).

(Continued)

Primary Examiner — Bernard Dentz
(74) Attorney, Agent, or Firm — Li Su; David A. Muthard

(57) ABSTRACT

The present invention relates to a novel class of hydroxamic acid derivatives having a benzothiophene or thiophene backbone. The hydroxamic acid compounds can be used to treat cancer. The hydroxamic acid compounds can also inhibit historic deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention are also useful in the prevention and treatment of TRX-mediated diseases, such as autoimmune, allergic and inflammatory diseases, and in the prevention and/or treatment of diseases of the central nervous system (CNS), such as neurodegenerative diseases, The present invention further provides pharmaceutical compositions comprising the hydroxamic acid derivatives and safe dosing regimens of these pharmaceutical compositions, which are easy to follow, and which result in a therapeutically effective amount of the hydroxamic acid derivatives in vivo.

17 Claims, No Drawings

OTHER PUBLICATIONS

Lin, R.J. et al., *Nature 391*:811-14 (1998).
Lotem, J., et al., Int. J. Cancer 15: 731-740 (1975).
Lotem, J. et al., Proc. Natl. Acad. Sci. (USA) 76: 5158-516) (1979).
Marks et al., Cancer Res. 47:659 (1987).
Marks, P.A. et al., J. Natl. Cancer Inst., 92:1210-1215 (2000).
McBain et al., Biochem. Pharm. 53: 1357-1368 (1997).
Metcalf, D., et al., Science, 229: 16-22 (1985).
Morin, M. J., et al., Cancer Res. 44: 2807-2812 (1984).
Nakajima et al., Ex. Cell Res. 241,126-133 (1998).
Qiu et al., Mol. Biol. Cell 11, 2069-2083 (2000).
Reuben, R. C., et al., Proc. Natl. Acad. Sci. (USA) 73: 862-866 (1976).
Richon et al., Proc. Natl. Acad. Sci. USA, 93:5705-5708 (1996).
Richon, V. M. et al., Proc. Natl. Acad. Sci., USA, 95:3003-3007 (1998).
Sachs, L., Nature (Lond.) 274: 535 (1978).
Saito et al., Proc. Natl. Acad. Sci. USA 96, 4592-4597 (1999).
Scher, W. et al., Exp. Hematol. 11: 490-498 (1983).
Scher, W., et al., Biochem. & Biophys. Res. Comm. 109: 348-354) (1982).
Schwartz, E. L. et al., Cancer Res. 42: 2651-2655 (1982).
Schwartz, E. L., et al., Cancer Res. 43: 2725-2730 (1983).
Schwartz, E. L., et al., Proc. Am. Assoc. Cancer Res. 24: 18 (1983).
Su et al., Cancer Research, 60: 3137-3142 (2000).
Sugano, H., et al., Bibl. Hematol. 39: 943-954 (1973).
Takenaga, K., et al., Cancer Res. 40: 914-919 (1980).
Tanaka, M., et al., Proc. Natl. Acad. Sci. (USA) 72: 1003-1006 (1975).
Terada, M., et al., Proc. Natl. Acad. Sci. (USA) 75: 2795-2799 (1978).
Van Lint, C. et al., *Gene Expression 5*:245-53 (1996).
Wang et al., Cancer Research, 59, 2766-2799 (1999).
Yoshida, M. et al., J. Biol. Chem., 265:17174-17179, (1990).
International Search Report for PCT/US04/33386 mailed Jun. 8, 2005.
Database WPI Week 199840, Thomson Scientific, London, GB; AN 1998-462838, XP002521157 & JP 10 195065A, 1998.*
Official Action mailed Nov. 27, 2009 in U.S. Appl. No. 11/918,912.
Notice of Allowance mailed Jul. 6, 2010 in U.S. Appl. No. 11/918,913.
Notice of Allowance mailed Sep. 2, 2010 in U.S. Appl. No. 11/918,911.

* cited by examiner

US 7,935,724 B2

THIOPHENE AND BENZOTHIOPHENE HYDROXAMIC ACID DERIVATIVES

FIELD OF THE INVENTION

The present invention relates to a novel class of hydroxamic acid derivatives having a benzothiophene or thiophene backbone. The hydroxamic acid compounds can be used to treat cancer. The hydroxamic acid compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention are also useful in the prevention and treatment of TRX-mediated diseases, such as autoimmune, allergic and inflammatory diseases, and in the prevention and/or treatment of diseases of the central nervous system (CNS), such as neurodegenerative diseases.

BACKGROUND OF THE INVENTION

Compounds having a hydroxamic acid moiety have been shown to possess useful biological activities. For example, many peptidyl compounds possessing a hydroxamic acid moiety are known to inhibit matrix metalloproteinases (MMPs), which are a family of zinc endopeptidases. The MMPs play a key role in both physiological and pathological tissue degradation. Therefore, peptidyl compounds that have the ability to inhibit the action of MMPs show utility for the treatment or prophylaxis of conditions involving tissue breakdown and inflammation. Further, compounds having a hydroxamic acid moiety have been shown to inhibit histone deacetylases (HDACs), based at least in part on the zinc binding property of the hydroxamic acid group.

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., *Nature*, 389: 349-52 (1997)). These effects are thought to occur through changes in the structure of chromatin by altering the affinity of histone proteins for coiled DNA in the nucleosome. There are five types of histones that have been identified. Histones H2A, H2B, H3 and H4 are found in the nucleosome, and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., *Nature* 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, the contents of which are hereby incorporated by reference, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003, the entire content of which is hereby incorporated by reference). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002, the entire content of which is hereby incorporated by reference).

The inhibition of HDAC by the hydroxamic acid containing compound suberoylanilide hydroxamic acid (SAHA) disclosed in the above referenced U.S. Patents, is thought to occur through direct interaction with the catalytic site of the enzyme as demonstrated by X-ray crystallography studies (Finnin, M. S. et al., *Nature* 401:188-193 (1999)). The result of HDAC inhibition is not believed to have a generalized effect on the genome, but rather, only affects a small subset of the genome (Van Lint, C. et at., *Gene Expression* 5:245-53 (1996)). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (Archer, S. Shufen, M. Shei, A., Hodin, R. *PNAS* 95:6791-96 (1998)). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (Dressel, U. et al., *Anticancer Research* 20(2A):1017-22 (2000)).

Further, hydroxamic acid derivatives such as SAHA have the ability to induce tumor cell growth arrest, differentiation and/or apoptosis (Richon et al., *Proc. Natl. Acad. Sci. USA*, 93:5705-5708 (1996)). These compounds are targeted towards mechanisms inherent to the ability of a neoplastic cell to become malignant, as they do not appear to have toxicity in doses effective for inhibition of tumor growth in animals (Cohen, L. A. et al., *Anticancer Research* 19:4999-5006 (1999)).

In view of the wide variety of applications for compounds containing hydroxamic acid moieties, the development of new hydroxamic acid derivatives having improved properties, for example, increased potency or increased bioavailability is highly desirable.

SUMMARY OF THE INVENTION

The present invention relates to a novel class of hydroxamic acid derivatives having a benzothiophene or thiophene backbone. The hydroxamic acid compounds can be used to treat cancer. The hydroxamic acid compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention are also useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the hydroxamic acid derivatives, and safe, dosing regimens of these pharmaceutical compositions, which are easy to follow, and which result in a therapeutically effective amount of the hydroxamic acid derivatives in vivo.

It has been unexpectedly discovered that certain hydroxamic acid derivatives having a thiophene or benzothiophene backbone, show improved activity as histone deacetylase (HDAC) inhibitors.

The present invention thus relates to compounds represented by Formula I and pharmaceutically acceptable salts, solvates and hydrates thereof, as detailed herein.

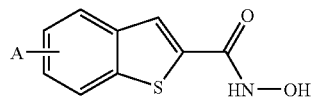

The foregoing and other objects, features and advantages of the invention will be apparent from the following more particular description of preferred embodiments of the invention.

DETAILED DESCRIPTION OF THE INVENTION

The present invention relates to a novel class of hydroxamic acid derivatives having a benzothiophene or thiophene backbone. In one embodiment, the hydroxamic acid derivatives can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating cancer in a subject. The compounds of the invention are also useful in the prevention and treatment of TRX-mediated diseases, such as autoimmune, allergic and inflammatory diseases, and in the prevention and/or treatment of diseases of tie central nervous system (CNS), such as neurodegenerative diseases.

It has been unexpectedly and surprisingly discovered that certain hydroxamic acid derivatives having a thiophene or benzothiophene backbone, show improved activity as histone deacetylase (HDAC) inhibitors.

Compounds

The present invention relates to compounds represented by Formula I, i.e., benzothiophene hydroxamic acid derivatives, and/or stereoisomers (including enantiomers), racemates, pharmaceutically acceptable salts, solvates, hydrates or polymorphs thereof.

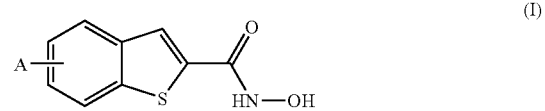

wherein A is alkyl, aryl or a group selected from:

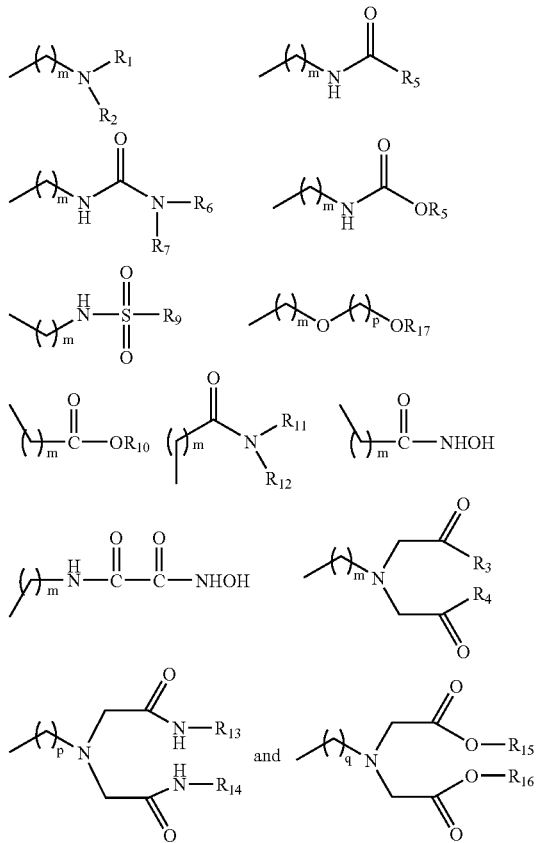

wherein $R_1$-$R_{16}$ are independently of each other a hydrogen or an unsubstituted or substituted alkyl, alkenyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring;

m, p and q are independently of each other 0, 1 or 2;

or a stereoisomer, enantiomer, racemate, pharmaceutically acceptable salt, solvate, hydrate or polymorph thereof.

The present invention further relates to compounds represented by Formula I, i.e., benzothiophene hydroxamic acid derivatives, and/or stereoisomers (including enantiomers), racemates, pharmaceutically acceptable salts, solvates, hydrates or polymorphs thereof.

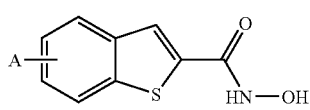

(I)

wherein A is alkyl aryl or a group selected from:

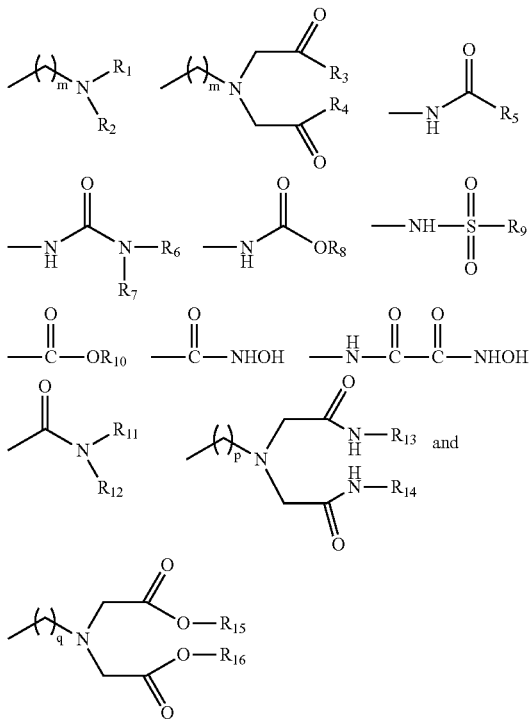

wherein $R_1$-$R_{16}$ are independently of each other a hydrogen or an unsubstituted or substituted alkyl, alkenyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring;

m, p and q are independently of each other 0, 1 or 2;

or a stereoisomer, enantiomer, racemate, pharmaceutically acceptable salt, solvate, hydrate or polymorph thereof.

The present invention further relates to compounds represented by Formula I where A is selected from:

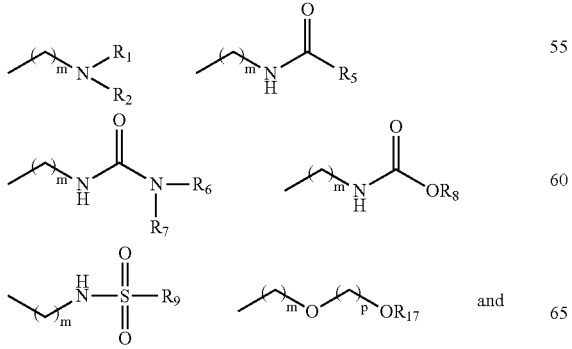

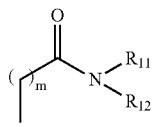

In one particular embodiment, the compound of Formula I is represented by the structure:

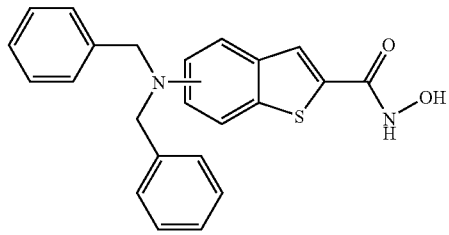

The present invention also relates to compounds represented by Formula II, i.e., thiophene hydroxamic acid derivatives, and/or stereoisomers (including enantiomers), racemates, pharmaceutically acceptable salts, solvates, hydrates or polymorphs thereof.

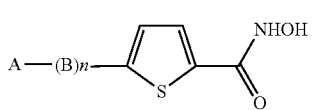

(II)

wherein

A is alkyl, aryl or a group selected from:

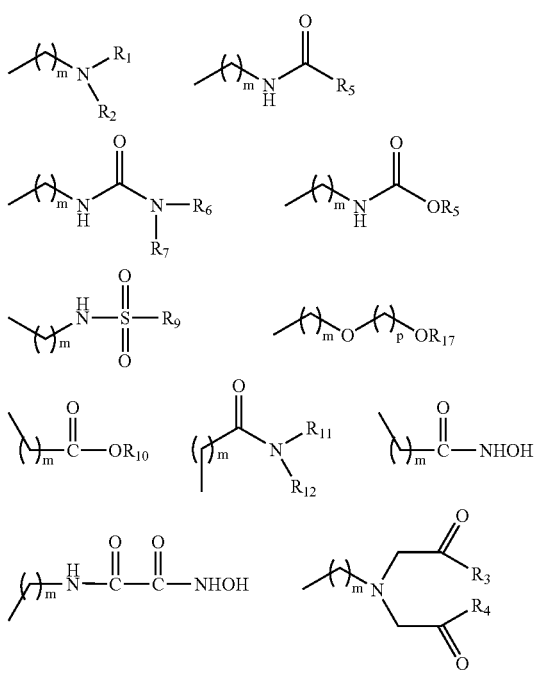

-continued

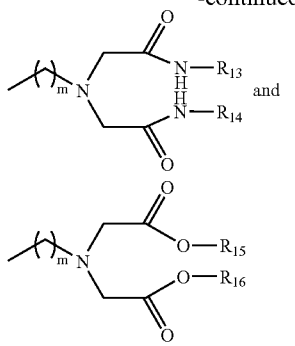
and

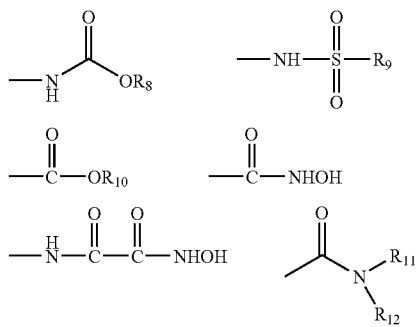

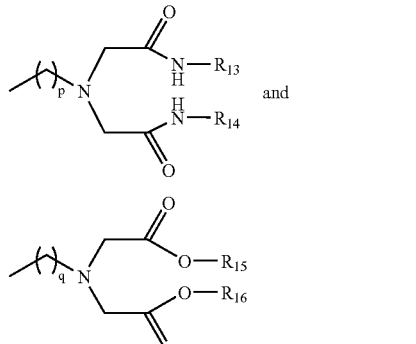
and wherein $R_1$-$R_{17}$ are independently of each other a hydrogen or an unsubstituted or substituted alkyl, alkenyl, aryl, heteroalkyl, cycloalkyl, heterocyclyl, alkylaryl, cycloalkylaryl, alkylcycloalkyl, acyl, sulfonyl, or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring;

B is

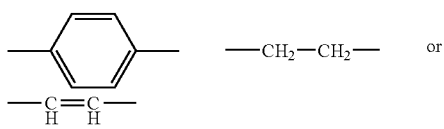

n is 0 or 1;

m, and p are independently of each other 0, 1 or 2;

or a stereoisomer, enantiomer, racemate, pharmaceutically acceptable salt, solvate, hydrate or polymorph thereof.

The present invention also relates to compounds represented by Formula II, i.e., thiophene hydroxamic acid derivatives, and/or stereoisomers (including enantiomers), racemates, pharmaceutically acceptable salts, solvates, hydrates or polymorphs thereof.

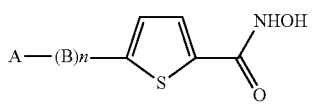 (II)

wherein

A is alkyl, aryl or a group selected from:

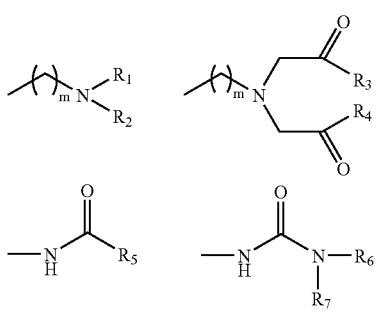

wherein $R_1$-$R_{16}$ are independently of each other a hydrogen or an unsubstituted or substituted alkyl, alkenyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring;

B is

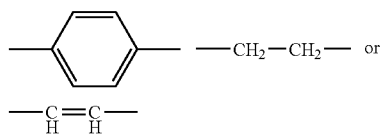

n is 0 or 1;

m, p and q are independently of each other 0, 1 or 2;

or a stereoisomer, enantiomer, racemate, pharmaceutically acceptable salt, solvate, hydrate or polymorph thereof In one embodiment of Formula I or Formula II, A is

wherein $R_1$ and $R_2$ are as described above. In a particular embodiment, at least one of $R_1$ and $R_2$ is phenyl, naphthyl, biphenyl, benzyl, —$CH_2CH_2PH$, —CH=CHPh, cyclohexyl, quinolinyl, isoquinolinyl, —$CH_2$-cyclohexyl, —$CH_2$-quinolinyl, —$CH_2$-isoquinolinyl, pyridyl, —$CH(Ph)_2$, methyl, ethyl, propyl, isopropyl, butyl, isobutyl sec-butyl or tert-butyl.

In another embodiment of Formula I or Formula II, A is

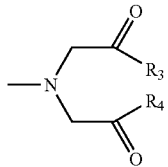

wherein $R_3$ and $R_4$ are as described above. In a particular embodiment, at least one of $R_3$ and $R_4$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

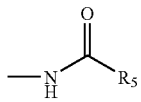

wherein $R_5$ is as described above. In a particular embodiment, $R_5$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

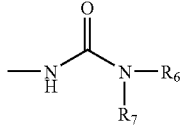

wherein $R_6$ and $R_7$ are as described above. In a particular embodiment, at least one of $R_6$ and $R_7$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

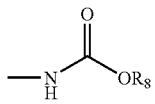

wherein $R_8$ is as described above. In a particular embodiment, $R_8$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

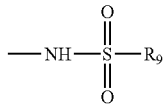

wherein $R_9$ is as described above. In a particular embodiment, $R_9$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

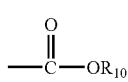

wherein $R_{10}$ is as described above. In a particular embodiment, $R_{10}$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I of Formula II, A is

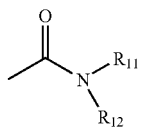

wherein $R_{11}$ and $R_{12}$ are as described above. In a particular embodiment, at least one of $R_{11}$ and $R_{12}$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

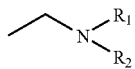

wherein $R_1$ and $R_2$ are as described above. In a particular embodiment, at least one of $R_1$ and $R_2$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

In another embodiment of Formula I or Formula II, A is

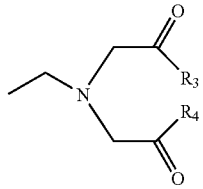

wherein $R_3$ and $R_4$ are as described above. In a particular embodiment, at least one of $R_3$ and $R_4$ is phenyl, naphthyl, biphenyl, benzyl, —$CH_2CH_2Ph$, —CH=CHPh, cyclohexyl, quinolinyl, isoquinolinyl, —$CH_2$-cyclohexyl, —$CH_2$-quinolinyl, —$CH_2$-isoquinolinyl, pyridyl, —$CH(Ph)_2$, methyl, ethyl, propyl, isopropyl, butyl, isobutyl sec-butyl or tert-butyl.

In another embodiment of Formula I or Formula II, A is

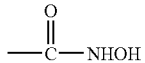

In another embodiment of Formula I or Formula II, A is

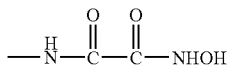

In another embodiment of Formula I or Formula II, A is

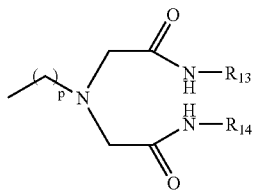

wherein p, $R_{13}$ and $R_{14}$ are as described above. In a particular embodiment, at least one of $R_{13}$ and $R_{14}$ is phenyl, naphthyl, biphenyl, benzyl, —$CH_2CH_2Ph$, —CH=CHPh, cyclohexyl, quinolinyl, isoquinolinyl, —$CH_2$-cyclohexyl, —$CH_2$-quinolinyl, —$CH_2$-isoquinolinyl, pyridyl, —CH$(Ph)_2$, methyl, ethyl, propyl, isopropyl, butyl, isobutyl sec-butyl or tert-butyl. In a particular embodiment, p is 0. In another particular embodiment, p is 1. In another particular embodiment, p is 2.

In another embodiment of Formula I or Formula II, A is

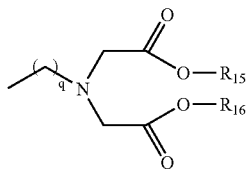

wherein q, $R_{15}$ and $R_{16}$ are as described above. In a particular embodiment, at least one of $R_{15}$ and $R_{16}$ is phenyl, naphthyl, biphenyl, benzyl, —$CH_2CH_2Ph$, —CH=CHPh, cyclohexyl, quinolinyl, isoquinolinyl, —$CH_2$-cyclohexyl, —$CH_2$-quinolinyl, —$CH_2$-isoquinolinyl, pyridyl, —CH$(Ph)_2$, methyl, ethyl, propyl, isopropyl, butyl, isobutyl sec-butyl or tert-butyl. In a particular embodiment, q is 0. In another particular embodiment, q is 1. In another particular embodiment, q is 2.

In one embodiment of Formula I or Formula II, $R_1$ and $R_2$, $R_6$ and $R_7$, and $R_{11}$ and $R_{12}$, together with the nitrogen atom to which they are attached, form a nitrogen-containing heterocyclic ring. The heterocyclic ring can be monocyclic, or can be a fused bicyclic or tricyclic ring. Furthermore, the heterocyclic ring can comprise, in addition to the nitrogen, one or more heteroatoms, e.g., O, S N and P.

Furthermore, in one particular embodiment of Formula II, B is:

In another particular embodiment of Formula II, B is:

—$CH_2$—$CH_2$—

In another particular embodiment of Formula II, B is:

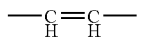

Specific embodiments depicting non-limiting Examples of the benzothiophene hydroxamic acid derivatives of Formula I are provided in Table 1 in the Experimental Section hereinbelow. Specific embodiments depicting non-limiting Examples of the thiophene hydroxamic acid derivatives of Formula II are provided in Table 2 in the Experimental Section hereinbelow.

Chemical Definitions

As used herein, "alkyl" is intended to include both branched and straight-chain saturated aliphatic hydrocarbon groups having te specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on. In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

When used in the phrases "alkylaryl", "alkylcycloalkyl" and "alkylheterocyclyl" the term "alkyl" refers to the alkyl portion of the moiety and does not describe the number of atoms in the aryl and heteroaryl portion of the moiety. In an embodiment, if the number of carbon atoms is not specified, "alkyl" of "alkylaryl", "alkylcycloalkyl" and "alkylheterocyclyl" refers to $C_1$-$C_{12}$ alkyl and in a further embodiment, "aralkyl" refers to $C_1$-$C_6$ alkyl.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylenearyl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

In one embodiment, as used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In another embodiment, "aryl" is an aromatic ring of 5 to 14 carbons atoms, and includes a carbocyclic aromatic group fused with a 5-or 6-membered cycloalkyl group such as indan. Examples of carbocyclic aromatic groups include, but are not limited to, phenyl, naphthyl, e.g., 1-naphthyl and 2-naphthyl; anthracenyl, e.g., 1-anthracenyl, 2-anthracenyl; phenanthrenyl; fluorenonyl, e.g., 9-fluorenonyl, indanyl and the like. A carbocyclic aromatic group is optionally substituted with a designated number of substituents, described below.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

In another embodiment, "heteroaryl" is a monocyclic, bicyclic or tricyclic aromatic ring of 5- to 14-ring atoms of carbon and from one to four heteroatoms selected from O, N, or S. Examples of heteroaryl include, but are not limited to pyridyl, e.g., 2-pyridyl (also referred to as α-pyridyl), 3-pyridyl (also referred to as β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g., 2-quinolinyl, 3-quinolinyl, 4-quinolinyl, 5-quinolinyl, 6-quinolinyl, 7-quinolinyl and 8-quinolinyl, 1-isoqulinolinyl, 3-quinolinyl, 4-isoquinolinyl, 5-isoquinolinyl, 6-isoquinolinyl, 7-isoquinolinyl and 8-isoquinolinyl; benzofuranyl, e.g., 2-benzofuranyl and 3-benzofuranyl; dibenzofuranyl, e.g., 2,3-dihydrobenzofuranyl; dibenzothiophenyl; benzothienyl, e.g., 2-benzothienyl and 3-benzothienyl; indolyl, e.g., 2-indolyl and 3-indolyl; benzothiazolyl, e.g., 2-benzothiazolyl; benzooxazolyl, e.g., 2-benzooxazolyl; benzimidazolyl, e.g., 2-benzoimidazolyl; isoindolyl, e.g., 1-isoindolyl and 3-isoindolyl; benzotriazolyl; purinyl; thianaphthenyl, pyrazinyl and the like. Fused polycyclic aromatic ring systems may optionally be substituted with a designated number of substituents, as described herein.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" (also referred to herein as "heterocyclyl"), is a monocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydrodropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl and the like.

An "alkylaryl group" (arylalkyl) is an alkyl group substituted with an aromatic group, preferably a phenyl group. A preferred alkylaryl group is a benzyl group. Suitable aromatic groups are described herein and suitable alkyl groups are described herein. Suitable substituents for an alkylaryl group are described herein.

An "alkylheterocyclyl" group" is an alkyl group substituted with a heterocyclyl group. Suitable heterocyclyl groups are described herein and suitable alkyl groups are described herein. Suitable substituents for an alkyheterocyclyl group are described herein.

An "alkycycloalkyl group" is an alkyl group substituted with a cycloalkyl group. Suitable cycloalkyl groups are described herein and suitable alkyl groups are described herein. Suitable substituents for an alkycycloalkyl group are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

As used herein, an "arylalkylamino group" is an arylalkyl group that is attached to a compound via a nitrogen on the alkyl portion of the arylalkyl.

As used herein, many moieties or groups are referred to as being either "substituted or unsubstituted". When a moiety is referred to as substituted, it denotes that any portion of the moiety that is known to one skilled in the art as being available for substitution can be substituted. The phrase "optionally substituted with one or more substituents" means, in one embodiment, "zero to five substituents", and in other embodiments, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. For example, the enantiomeric excess can be about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least 99% enantiomeric excess.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof;

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the hydroxamic acid derivatives disclosed herein. A prodrug of any of the compounds can be made using well-known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The hydroxamic acid derivatives described herein can, as noted above, be prepared in the form of their pharmaceutically acceptable salts. Pharmaceutically acceptable salts are salts that retain the desired biological activity of tie parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic: acid, oxalic acid, citric acid, tartaric acid, carbonic acid, phosphoric acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also salts formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the hydroxamic acid derivatives described herein. As demonstrated herein, the hydroxamic acid derivatives of the present invention are useful for the treatment of cancer. In addition, there is a wide range of other diseases for which hydroxamic acid derivatives have been found useful. Non-limiting examples are thioredoxin (TRX)-mediated diseases as described herein, and diseases of the central nervous system (CNS) as described herein.

1. Treatment of Cancer

As demonstrated herein, the hydroxamic acid derivatives of the present invention are useful for the treatment of cancer. Accordingly, in one embodiment, the invention relates to a method of treating cancer in a subject in need of treatment comprising administering to said subject a therapeutically effective amount of the hydroxamic acid derivatives described herein.

The term "cancer" refers to any cancer caused by the proliferation of neoplastic cells, such as solid tumors, neoplasms, carcinomas, sarcomas, leukemias, lymphomas and the like. For example, cancers include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

2. Treatment of Thioredoxin (TRX)-mediated Diseases

In another embodiment, the hydroxamic acid derivatives are used in a method of treating a thioredoxin (TRX)-mediated disease or disorder in a subject in need thereof, comprising administering to the subject a therapeutically effective amount of one or more of the hydroxamic acid compounds described herein.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the hydroxamic acid derivatives are used in a method of treating a disease of the central nervous system in a subject in need thereof comprising administering to the subject a therapeutically effective amount of any one or more of the hydroxamic acid compounds described herein.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly is children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

Definitions

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the hydroxamic acid derivatives of the present invention show improved activity as histone deacetylase (HDAC) inhibitors. In one embodiment, the concentration of compound required for 50% inhibition (IC50) of histone deacetylase is below 1000 nm. In another embodiment, the concentration of compound required for 50% inhibition (IC50) of histone deacetylase is between 500 and 1000 nm. In another embodiment, the concentration of compound required for 50% inhibition (IC50) of histone deacetylase is between 100 and 500 nm. In another embodiment, the concentration of compound required for 50% inhibition (IC50) of histone deacetylase is below 100 nm. In another embodiment, the concentration of compound required for 50% inhibition (IC50) of histone deacetylase is between 10 and 100 nm. In another embodiment, the concentration of compound required for 50% inhibition (IC50) of histone deacetylase is below 50 nm. In another embodiment, the concentration of compound required for 50% inhibition (IC50) of histone deacetylase is between 10 and 50 nm. In another embodiment, the concentration of compound required for 50% inhibition (IC50) of histone deacetylase is below 10 nm. In another embodiment, the concentration of compound required for 50% inhibition (IC50) of histone deacetylase is between 1 and 10 nm. In another embodiment, the concentration of compound required for 50% inhibition (IC50) of histone deacetylase is below 1 nm. In another embodiment, the concentration of compound required for 50% inhibition (IC50) of histone deacetylase is between 0.1 and 1 nm.

As demonstrated herein, the hydroxamic acid derivatives of the present invention show improved activity as histone deacetylase (HDAC) inhibitors. Accordingly, in one embodiment, the invention relates to a method of inhibiting the activity of histone deacetylase comprising contacting the histone deacetylase with an effective amount of one or more of the hydroxamic acid compounds described herein.

In one embodiment, the hydroxamic acid derivatives are potent inhibitors of Class I histone deacetylases (Class I HDACs). Class I HDACs include histone deacetylase 1 (HDAC-1), histone deacetylase 2 (HDAC-2), histone deacetylase 3 (HDAC-3) and histone deacetylase 8 (HDAC-8). In a particular embodiment, the hydroxamic acid derivatives are potent inhibitors of histone deacetylase I (HDAC-1). In another embodiment, the hydroxamic acid derivatives are potent inhibitors of Class II histone deacetylases (Class II HDACs). Class II HDACs include histone deacetylase 4 (HDAC-4), histone deacetylase 5 (HDAC-8), histone deacetylase 6 (HDAC-6), histone deacetylase 7 (HDAC-7) and histone deacetylase 9 (HDAC-9).

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histories in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 μL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIOMOL Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 μg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the p21$^{WAF1}$ gene. The p21$^{WAF1}$ protein is induced within 2 hours of culture with HDAC inhibitors in a variety of transformed cells using standard methods. The induction of the p21$^{WAF1}$ gene is associated with accumulation of acetylated histones in the chromatin region of this gene. Induction of p21$^{WAF1}$ can therefore be recognized as involved in the G1 cell cycle arrest caused by HDAC inhibitors in transformed cells.

Typically, HDAC inhibitors fall into five general classes: 1) hydroxamic acid derivatives; 2) Short-Chain Fatty Acids (SCFAs); 3) cyclic tetrapeptides; 4) benzamides; and 5) electrophilic ketones. Examples of such HDAC inhibitors are set forth below.

A. Hydroxamic Acid Derivatives such as suberoylanilide hydroxamic acid (SAHA) (Richon et al., Proc. Natl. Acad. Sci. USA 95, 3003-3007 (1998)); m-carboxycinnamic acid bishydroxamide (CBHA) (Richon et al., supra); pyroxamide; trichostatin analogues such as trichostatin A (TSA) and trichostatin C (Koghe et al. 1998. Biochem. Pharmacol. 56: 1359-1364); salicylhydroxamic acid (Andrews et al., International J. Parasitology 30, 761-768 (2000)); suberoyl bishydroxamic acid (SBHA) (U.S. Pat. No. 5,608,108); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); 6-(3-chlorophenylureido)carpoic hydroxamic acid (3Cl-UCHA); oxamflatin[(2E)-5-[3-[(phenylsulfonyl) aminol phenyl]-pent-2-en-4-ynohydroxamic acid] (Kim et al. Oncogene, 18: 2461 2470 (1999)); A-161906, Scriptaid (Su et al. 2000 Cancer Research, 60: 3137-3142); PXD-101 (Prolifix); LAQ-824; CHAP; MW2796 (Andrews et al., supra); MW2996 (Andrews et al., supra); or any of the hydroxamic acids disclosed in U.S. Pat. Nos. 5,369,108, 5,932,616, 5,700,811, 6,087,367 and 6,511,990.

B. Cyclic Tetrapeptides such as trapoxin A (TPX)-cyclic tetrapeptide(cyclo-(L-phenylalanyl-L -phenylalanyl-D-pipecolinyl-L-2-amino-8-oxo-9,10-epoxy decanoyl)) (Kijima et al., J Biol. Chem. 268,22429-22435 (1993)); FR901228 (FK 228, depsipeptide) (Nakajima et al., Ex. Cell Res. 241,126-133 (1998)); FR225497 cyclic tetrapeptide (H. Mon. et al., PCT Application WO 00/08048 (17 February 2000)); apicidin cyclic tetrapeptide[cyclo(N—O-methyl-L-tryptophanyl-L-isoleucinyl-D -pipecolinyl-L-2-amino-8-oxodecanoyl)] (Darkin-Raftray et al., Proc. Natl. Acad. Sci. USA 93,1314313147 (1996)); apicidin Ia, apicidin Ib, apicidin Ic, apicidin IIa, and apicidin IIb (P. Dulski et al., PCT Application WO 97/11366); CHAP, HC-toxin cyclic tetrapeptide (Bosch et al., Plant Cell 7, 1941-1950 (1995)); WF27082 cyclic tetrapeptide (PCT Application WO 98/48825); and chlamydocin (Bosch et al., supra).

C. Short chain fatty acid (SCFA) derivatives such as: sodium butyrate (Cousens et al., J. Biol. Chem. 254,1716-1723 (1979)); isovalerate (McBain et al., Biochem. Pharm. 53: 1357-1368 (1997)); valerate (McBain et al., supra); 4-phenylbutyrate (4-PBA) (Lea and Tulsyan, Anticancer Research, 15,879-873 (1995)); phenylbutyrate (PB) (Wang et al., Cancer Research, 59, 2766-2799 (1999)); propionate (McBain et al., supra); butyramide (Lea and Tulsyan, supra); isobutyramide (Lea and Tulsyan, supra); phenylacetate (Lea and Tulsyan, supra); 3-bromopropionate (Lea and Tulsyan, supra); tributyrin (Guan et al., Cancer Research, 60,749-755 (2000)); valproic acid, valproate and Pivanex™.

D. Benzamide derivatives such as CI-994; MS-275 [N-(2-aminophenyl)-4-[N-(pyridin-3-yl methoxycarbonyl)aminomethyl]benzamide] (Saito et al., Proc. Natl. Acad. Sci. USA 96, 4592-4597 (1999)); and 3'-amino derivative of MS-275 (Saito et al., supra).

E. Electrophilic ketone derivatives such as trifluoromethyl ketones (Frey et al, Bioorganic & Med. Chem. Lett. (2002), 12, 3443-3447; U.S. Pat. No. 6,511,990) and α-keto amides such as N-methyl-α-ketoamides F. Other HDAC Inhibitors such as natural products, psammaplins and Depudecin (Kwon et al. 1998. PNAS 95: 3356-3361).

Combination Therapy

The hydroxamic acid compounds of the present invention can be administered alone or in combination with other therapies suitable for the disease or disorder being treated. Where separate dosage formulations are used, the hydroxamic acid compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the hydroxamic acid compound and the other therapeutic agent are realized by the patient at substantially the same time. Such beneficial effect is preferably achieved when the target blood level concentrations of each active drug are maintained at substantially the same time.

The hydroxamic acid derivatives can be administered in combination with any one or more of an HDAC inhibitor, an alkylating agent, an antibiotic agent, an antimetabolic agent, a hormonal agent, a plant-derived agent, an anti-angiogenic agent, a differentiation inducing agent, a cell growth arrest inducing agent, an apoptosis inducing agent, a cytotoxic agent, a biologic agent, a gene therapy agent, or any combination thereof.

Alkylating Agents

Alkylating agents react with nucleophilic residues, such as the chemical entities on the nucleotide precursors for DNA production. They affect the process of cell division by alkylating these nucleotides and preventing their assembly into DNA.

Examples of alkylating agents include, but are not limited to, bischloroethylamines (nitrogen mustards, e.g., chlorambucil, cyclophosphamide, ifosfamide, mechlorethamine, melphalan, uracil mustard), aziridines (e.g., thiotepa), alkyl alkone sulfonates (e.g., busulfan), nitrosoureas (e.g., carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups.

Under physiological conditions, these drugs ionize and produce positively charged ion that attach to susceptible nucleic acids and proteins, leading to cell cycle arrest and/or cell death. The alkylating agents are cell cycle phase nonspecific agents because they exert their activity independently of the specific phase of the cell cycle. The nitrogen mustards and alkyl alkone sulfonates are most effective against cells in the G1 or M phase. Nitrosoureas, nitrogen mustards, and aziridines impair progression from the G1 and S phases to the M phases. Chabner and Collins eds. (1990) "Cancer Chemotherapy: Principles and Practice", Philadelphia: J B Lippincott.

The alkylating agents are active against wide variety of neoplastic diseases, with significant activity in the treatment of leukemias and lymphomas as well as solid tumors. Clinically this group of drugs is routinely used in the treatment of acute and chronic leukemias; Hodgkin's disease; non-Hodgkin's lymphoma; multiple myeloma; primary brain tumors; carcinomas of the breast, ovaries, testes, lungs, bladder, cervix, head and neck, and malignant melanoma.

Antibiotics

Antibiotics (e.g., cytotoxic antibiotics) act by directly inhibiting DNA or RNA synthesis and are effective throughout the cell cycle. Examples of antibiotic agents include anthracyclines (e.g., doxorubicin, daunorubicin, epirubicin, idarubicin and anthracenedione), mitomycin C, bleomycin, dactinomycin, and plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions.

Bleomycin is generally believed to chelate iron and forms an activated complex, which then binds to bases of DNA, causing strand scissions and cell death.

The antibiotic agents have been used as therapeutics across a range of neoplastic diseases, including carcinomas of the breast, lung, stomach and thyroids, lymphomas, myelogenous leukemias, myelomas, and sarcomas.

Antimetabolic Agents

Antimetabolic agents (i.e., antimetabolites) are a group of drugs that interfere with metabolic processes vital to the physiology and proliferation of cancer cells. Actively proliferating cancer cells require continuous synthesis of large quantities of nucleic acids, proteins, lipids, and other vital cellular constituents.

Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Antimetabolic agents have widely used to treat several common forms of cancer including carcinomas of colon, rectum, breast, liver, stomach and pancreas, malignant melanoma, acute and chronic leukemia and hair cell leukemia.

Hormonal Agents

The hormonal agents are a group of drug that regulate the growth and development of their target organs. Most of the hormonal agents are sex steroids and their derivatives and analogs thereof, such as estrogens, progestogens, anti-estrogens, androgens, anti-androgens and progestins. These hormonal agents may serve as antagonists of receptors for the sex steroids to down regulate receptor expression and transcription of vital genes. Examples of such hormonal agents are synthetic estrogens (e.g., diethylstibestrol), antiestrogens (e.g., tamoxifen, toremifene, fluoxymesterol and raloxifene), antiandrogens (bicalutamide, nilutamide, flutamide), aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

Hormonal agents are used to treat breast cancer, prostate cancer, melanoma and meningioma. Because the major action of hormones is mediated through steroid receptors, 60% receptor-positive breast cancer responded to first-line hormonal therapy; and less than 10% of receptor-negative tumors responded. Specifically, progestogens are used to treat endometrial cancers, since these cancers occur in women that are exposed to high levels of oestrogen unopposed by progestogen. Antiandrogens are used primarily for the treatment of prostate cancer, which is hormone dependent. They are used to decrease levels of testosterone, and thereby inhibit growth of the tumor.

Hormonal treatment of breast cancer involves reducing the level of oestrogen-dependent activation of oestrogen receptors in neoplastic breast cells. Anti-oestrogens act by binding to oestrogen receptors and prevent the recruitment of coactivators, thus inhibiting the oestrogen signal.

LHRH analogues are used in the treatment of prostate cancer to decrease levels of testosterone and so decrease the growth of the tumor.

Aromatase inhibitors act by inhibiting the enzyme required for hormone synthesis. In post-menopausal women, the main source of oestrogen is through the conversion of androstenedione by aromatase.

Plant-derived Agents

Plant-derived agents are a group of drugs that are derived from plants or modified based on the molecular structure of the agents. They inhibit cell replication by preventing the assembly of the cell's components that are essential to cell division.

Examples of plant-derived agents include vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission.

Plant-derived agents are used to treat many forms of cancer. For example, vincristine is used in the treatment of the leukemias, Hodgkin's and non-Hodgkin's lymphoma, and the childhood tumors neuroblastoma, rhabdomyosarcoma, and Wilm's tumor. Vinblastine is used against the lymphomas, testicular cancer, renal cell carcinoma, mycosis fungoides, and Kaposi's sarcoma. Docetaxel has shown promising activity against advanced breast cancer, non-small cell lung cancer (NSCLC), and ovarian cancer.

Etoposide is active against a wide range of neoplasms, of which small cell lung cancer, testicular cancer, and NSCLC are most responsive.

Biologic Agents

Biologic agents are a group of biomolecules that elicit cancer/tumor regression when used alone or in combination with chemotherapy and/or radiotherapy. Examples of biologic agents include immuno-modulating proteins such as cytokines, monoclonal antibodies against tumor antigens, tumor suppressor genes, and cancer vaccines.

Cytokines possess profound immunomodulatory activity. Some cytokines such as interleukin-2 (IL-2, aldesleukin) and interferon-a (IFN-a) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself.

Interferon-α includes more than 23 related subtypes with overlapping activities. IFN-a has demonstrated activity against many solid and hematologic malignancies, the later appearing to be particularly sensitive.

Examples of interferons include, interferon-α, interferon-β (fibroblast interferon) and interferon-γ (fibroblast interferon). Examples of other cytokines include erythropoietin (epoietin-α), granulocyte-CSF (filgrastin), and granulocyte, macrophage-CSF (sargramostim). Other immuno-modulating agents other than cytokines include bacillus Calmette-Guerin, levamisole, and octreotide, a long-acting octapeptide that mimics the effects of the naturally occurring hormone somatostatin.

Furthermore, the anti-cancer treatment can comprise treatment by immunotherapy with antibodies and reagents used in tumor vaccination approaches. The primary drugs in this therapy class are antibodies, alone or carrying compounds such as toxins or chemotherapeutics/cytotoxics to cancer cells. Monoclonal antibodies against tumor antigens are antibodies elicited against antigens expressed by tumors, preferably tumor-specific antigens. For example, monoclonal antibody HERCEPTIN® (trastuzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein.

Another example of monoclonal antibodies against tumor antigens is RITUXAN® (rituximab) that is raised against CD20 on lymphoma cells and selectively deplete normal and malignant CD20+ pre-B and mature B cells.

RITUXAN is used as single agent for the treatment of patients with relapsed or refractory low-grade or follicular, CD20+, B cell non-Hodgkin's lymphoma. MYELOTARG® (gemtuzumab ozogamicin) and CAMPATH® (alemtuzumab) are further examples of monoclonal antibodies against tumor antigens that may be used.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle checkpoints and resulting in a higher rate of controlled cell growth-cancer. Examples of the tumor suppressor genes include Duc-4, NF-1, NF-2, RB, p53, WT1, BRCA1 and BRCA2.

DPC4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved, in Wilm's tumor of the kidneys. BRCA1 is involved in breast and ovarian cancer, and BRCA2 is involved in breast cancer. The tumor suppressor gene can be transferred into the tumor cells where it exerts its tumor suppressing functions.

Cancer vaccines are a group of agents that induce the body's specific immune response to tumors. Most of cancer vaccines under research and development and clinical trials are tumor-associated antigens (TAAs). TAAs are structures (i.e., proteins, enzymes or carbohydrates) that are present on tumor cells and relatively absent or diminished on normal cells. By virtue of being fairly unique to the tumor cell, TAAs provide targets for the immune system to recognize and cause their destruction. Examples of TAAs include gangliosides (GM2), prostate specific antigen (PSA), α-fetoprotein (AFP), carcinoembryonic antigen (CEA) (produced by colon cancers and other adenocarcinomas, e.g., breast, lung, gastric, and pancreatic cancers), melanoma-associated antigens (MART-1, gap100, MAGE 1,3 tyrosinase), papillomavirus E6 and E7 fragments, whole cells or portions/lysates of autologous tumor cells and allogeneic tumor cells.

Other Therapies

Recent developments have introduced, in addition to the traditional cytotoxic and hormonal therapies used to treat cancer, additional therapies for the treatment of cancer.

For example, many forms of gene therapy are undergoing preclinical or clinical trials.

In addition, approaches are currently under development that are based on the inhibition of tumor vascularization (angiogenesis). The aim of this concept is to cut off the tumor from nutrition and oxygen supply provided by a newly built tumor vascular system.

In addition, cancer therapy is also being attempted by the induction of terminal differentiation of the neoplastic cells. Suitable differentiation agents include the compounds disclosed in any one or more of the following references, the contents of which are incorporated by reference herein.

a) Polar compounds (Marks et al (1987); , Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res.* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

The use of all of these approaches in combination with the hydroxamic acid compounds described herein are within the scope of the present invention.

Dosages and Dosing Schedules

The dosage regimen utilizing the hydroxamic acid derivatives of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 5-4000 mg/m$^2$ administered orally once-daily, twice-daily or three times-daily, continuous (every day) or intermittently (e.g., 3-5 days a week). For example, when used to treat the desired disease, the dose of the hydroxamic acid can range between about 2 mg to about 2000 mg per day, such as from about 20 mg to about 2000 mg per day, such as from about 400 mg to about 1200 mg per day. For example, oral dosages can be about 2, about 20, about 200, about 400, about 800, about 1200, about 1600 or about 2000 mg per day.

For example, a patient can receive between about 2 mg/day to about 2000 mg/day, for example, from about 20-2000 mg/day, such as from about 200 to about 2000 mg/day, for example from about 400 mg/day to about 1200 mg/day. A suitably prepared medicament for once a day administration can thus contain between about 2 mg and about 2000 mg, such as from about 20 mg to about 2000 mg, such as from about 200 mg to about 1200 mg, such as from about 400 mg/day to about 1200 mg/day. For administration twice a day, a suitably prepared medicament would therefore contain half of the needed daily dose.

The hydroxamic acid derivative is administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

Suitable daily dosages include a total daily dosage of up to 800 mg, e.g., 150 mg, 200 mg, 300 mg, 400 mg, 600 mg or 800 mg, which can be administered in one daily dose or can be divided into multiple daily doses as described above. Preferably, the administration is oral. The compounds can be administered alone or in a pharmaceutical composition comprising the compound, and a pharmaceutically acceptable carrier or excipient.

In one embodiment, the composition is administered once daily at a dose of about 200-600 mg. In another embodiment, the composition is administered twice daily at a dose of about 200-400 mg. In another embodiment, the composition is administered twice daily at a dose of about 200-400 mg intermittently, for example three, four or five days per week. In another embodiment, the composition is administered three times daily at a dose of about 100-250 mg.

In one embodiment, the daily dose is 200 mg, which can be administered once-daily, twice-daily, or three-times daily. In one embodiment, the daily dose is 300 mg, which can be administered once-daily, twice-daily, or three-times daily. In one embodiment, the daily dose is 400 mg, which can be administered once-daily or twice-daily. In one embodiment, the daily dose is 150 mg, which can be, administered twice-daily or three-times daily.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

In one embodiment, the treatment protocol comprises continuous administration (i.e., every day), once, twice or three times daily at a total daily dose in the range of about 200 mg to about 600 mg.

In another embodiment, the treatment protocol comprises intermittent administration of between three to five days a week, once, twice or three times daily at a total daily dose in the range of about 200 mg to about 600 mg.

In one particular embodiment, the administration is continuously once daily at a dose of 400 mg or twice daily at a dose of 200 mg.

In another particular embodiment, the administration is intermittently three days a week, once daily at a dose of 400 mg or twice daily at a dose of 200 mg.

In another particular embodiment, the administration is intermittently four days a week, once daily at a dose of 400 mg or twice daily at a dose of 200 mg.

In another particular embodiment, the administration is intermittently five days a week, once daily at a dose of 400 mg or twice daily at a dose of 200 mg.

In another particular embodiment, the administration is continuously once daily at a dose of 600 mg, twice daily at a dose of 300 mg, or three times daily at a dose of 200 mg.

In another particular embodiment, the administration is intermittently three days a week, once daily at a dose of 600 mg, twice daily at a dose of 300 mg, or three times daily at a dose of 200 mg.

In another particular embodiment, the administration is intermittently four days a week, once daily at a dose of 600 mg, twice daily at a dose of 300 mg, or three times daily at a dose of 200 mg.

In another particular embodiment, the administration is intermittently five days a week, once daily at a dose of 600 mg, twice daily at a dose of 300 mg, or three times daily at a dose of 200 mg.

In addition, the administration can be according to any of the schedules described above, consecutively for a few weeks, followed by a rest period. For example, the compound or composition can be administered according to any one of the schedules described above from two to eight weeks, followed by a rest period of one week, or twice daily at a dose of 300 mg for three to five days a week. In another particular embodiment, the compound or composition can be administered three times daily for two consecutive weeks, followed by one week of rest.

For Intravenous or subcutaneous administration, the patient would receive the HDAC inhibitor in quantities sufficient to deliver between about 5-4000 mg/m$^2$ per day, for example, about 5, 30, 60, 90, 180, 300, 600, 900, 1200 or 1500 mg/m$^2$ per day. Such quantities may be administered in a number of suitable ways, e.g., large volumes of low concentrations of the active compound during one extended period of time or several times a day. The quantities can be administered for one or more consecutive days, intermittent days or a combination thereof per week (7 day period). Alternatively, low volumes of high concentrations of the active compound during a short period of time, e.g., once a day for one or more days either consecutively, intermittently or a combination thereof per week (7 day period). For example, a dose of 300 mg/m$^2$ per day can be administered for 5 consecutive days for a total of 1500 mg/m$^2$ per treatment. In another dosing regimen, the number of consecutive days can also be 5, with treatment lasting for 2 or 3 consecutive weeks for a total of 3000 mg/m$^2$ and 4500 mg/m$^2$ total treatment.

Typically, an intravenous formulation may be prepared which contains a concentration of the hydroxamic acid derivative of between about 1.0 mg/mL to about 10 mg/mL, e.g., 2.0 mg/mL, 3.0 mg/mL, 4.0 mg/mL, 5.0 mg/mL, 6.0 mg/mL, 7.0 mg/mL, 8.0 mg/mL, 9.0 mg/mL and 10 mg/mL and administered in amounts to achieve the doses described above. In one example, a sufficient volume of intravenous formulation can be administered to a patient in a day such that the total dose for the day is between about 300 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations and combinations of the dosages and dosing schedules are included within the scope of the present invention.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. Preferably, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the Hydroxamic acid derivative active compound and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 nM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. The optimal amount of the compound that should be administered to the patient in the practice of the present invention will depend on the particular compound used and the type of cancer being treated.

In Vitro Methods:

The present invention also provides methods of using the hydroxamic acid derivatives of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the hydroxamic acid derivatives described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the hydroxamic acid compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the hydroxamic acid compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the hydroxamic acid compounds described herein.

In another embodiment, the invention relates to an in vitro method of inducing terminal differentiation of tumor cells in a tumor comprising contacting the cells with an effective amount of any one or more of the hydroxamic acid compounds described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the hydroxamic acid derivatives described herein.

In a particular embodiment, the present invention relates to a method of selectively inducing terminal differentiation of neoplastic cells and thereby inhibiting proliferation of such cells in a subject. The method comprises administering to the subject an effective amount of one or more of the hydroxamic acid derivatives described herein.

In another embodiment, the invention relates to a method of selectively inducing cell growth arrest of neoplastic cells and thereby inhibiting proliferation of such cells in a subject. The method comprises administering to the subject an effective amount of one or more of the hydroxamic acid derivatives described herein.

In another embodiment, the invention relates to a method of selectively inducing apoptosis of neoplastic cells and thereby inhibiting proliferation of such cells in a subject. The method comprises administering to the subject an effective amount of one or more of the hydroxamic acid derivatives described herein.

In another embodiment, the invention relates to a method of treating a patient having a tumor characterized by proliferation of neoplastic cells. The method comprises administering to the patient one or more of the hydroxamic acid derivatives described herein. The amount of compound is effective to selectively induce terminal differentiation, induce cell growth arrest and/or induce apoptosis of such neoplastic cells and thereby inhibit their proliferation.

The invention is illustrated in the examples in the Experimental Details Section that follows. This section is set forth to aid in an understanding of the invention but is not intended to, and should not be construed to limit in any way the invention as set forth in the claims which follow thereafter.

EXPERIMENTAL DETAILS SECTION

Example 1

Synthesis

The compounds of the present invention were prepared by the general methods outlined in the synthetic schemes below, as exemplified below.

A. Benzothiophenes

A1. Aminobenzothiophenes. Scheme 1 illustrates the synthesis of amide, sulphonamide, urea, and alkylated amine benzothiophene derivatives from 5- and 6-amino-benzothiophenes.

Scheme 1

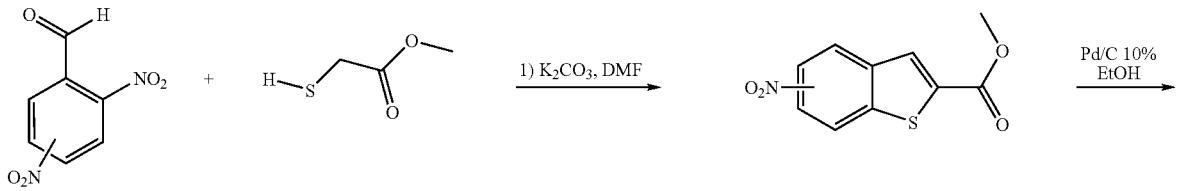

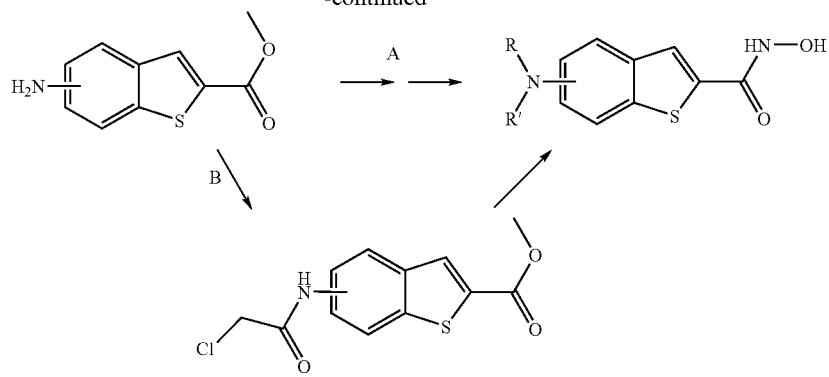
A2. Carboxbenzothiophenes. Scheme 2 illustrates the synthesis of amide and ester benzothiophene derivatives from 5 and 6-carboxybenzothiophenes.
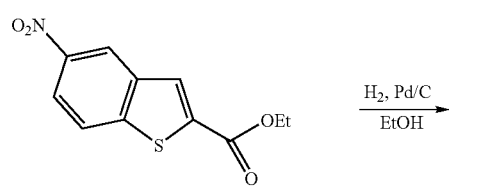
-continued
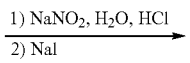
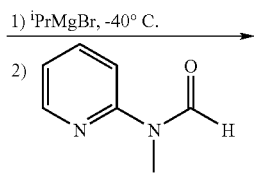
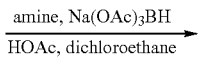
A3. Compounds from 5-formylbenzothiophenes.
Scheme 6 illustrates the use of 5-formylbenzothiophenes to generate 1 and 2 amines, ethers, acylated aminomethyl compounds.
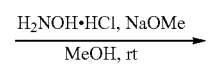
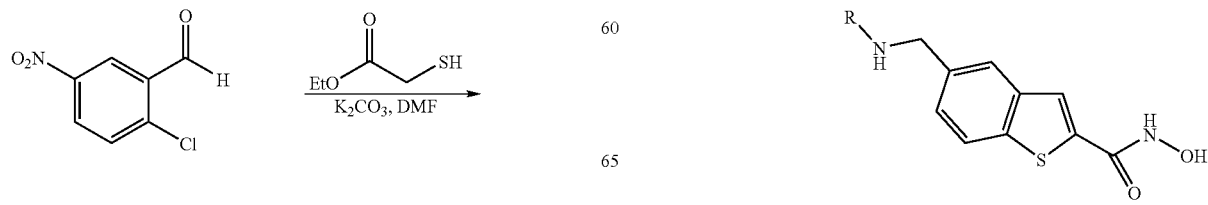

A4. Compounds from 6-formylbenzothiophenes.
Scheme 7 illustrates the use of 6-formylbenzothiophenes to generate 1 and 2 amines, ethers, acylated aminomethyl compounds.
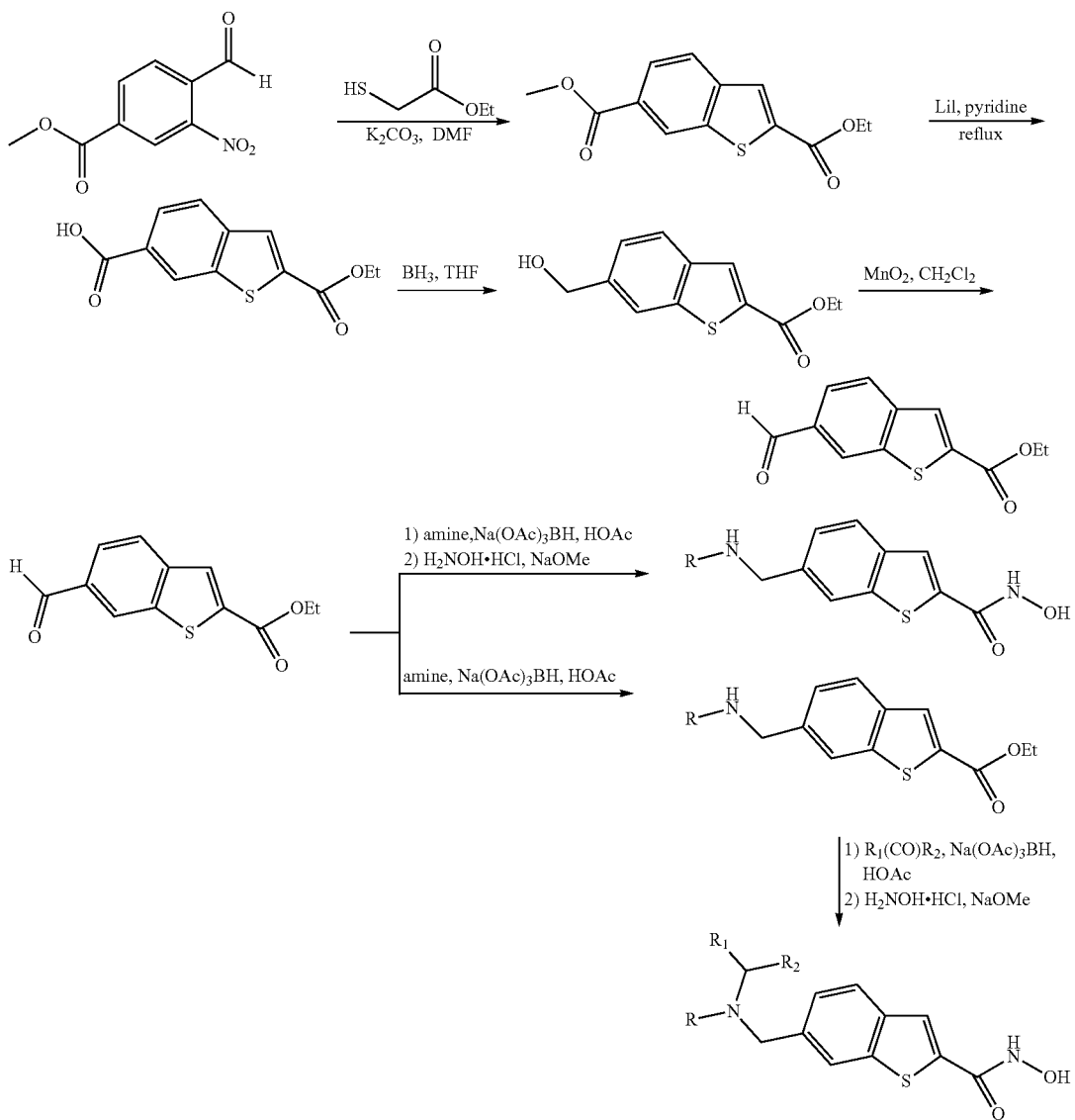
B. Thiophenes
B1. Phenylthiophenes. Scheme 3 illustrates the synthesis of amide and ester 5-phenyl-thiophene derivatives from substituted 5-arylthiophenes.
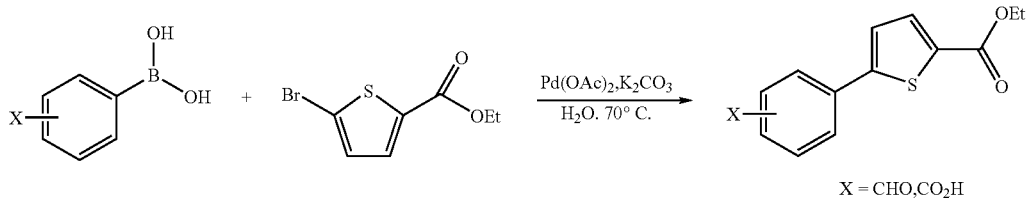

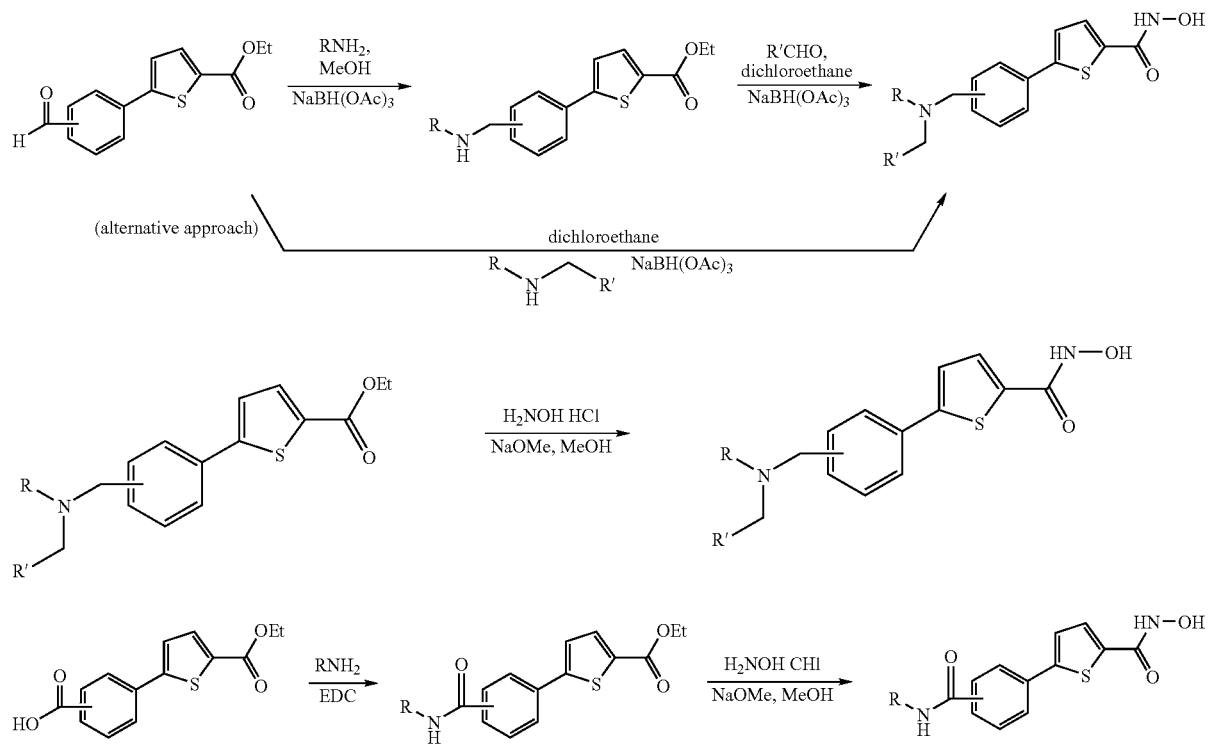
B2. Alkylthiophenes and Alkenylthiophenes. Scheme 4 illustrates the synthesis of amide and ester 5-alkylthiophene and 5-alkenylthiophene derivatives from substituted 5-alkylthiophene and 5-alkenylthiophenes.
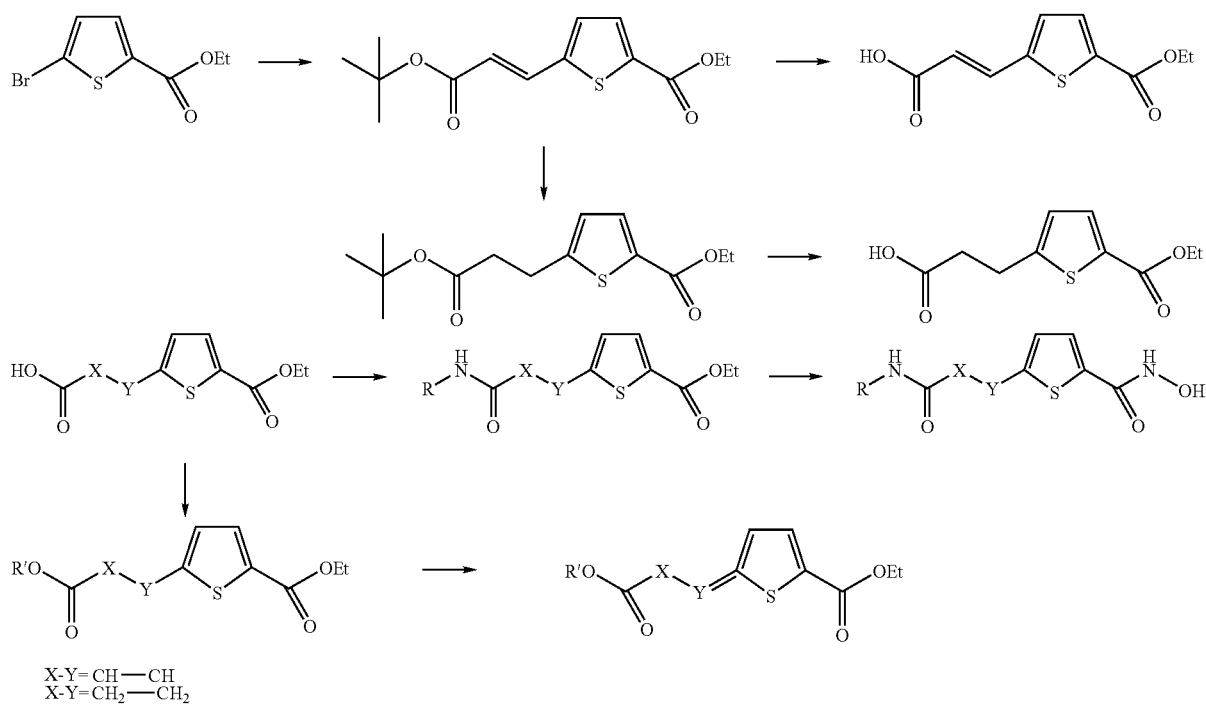

B3. Aminothiophenes. Scheme 5 illustrates the synthesis of amide and ester thiophene derivatives from 5-aminothiophenes.

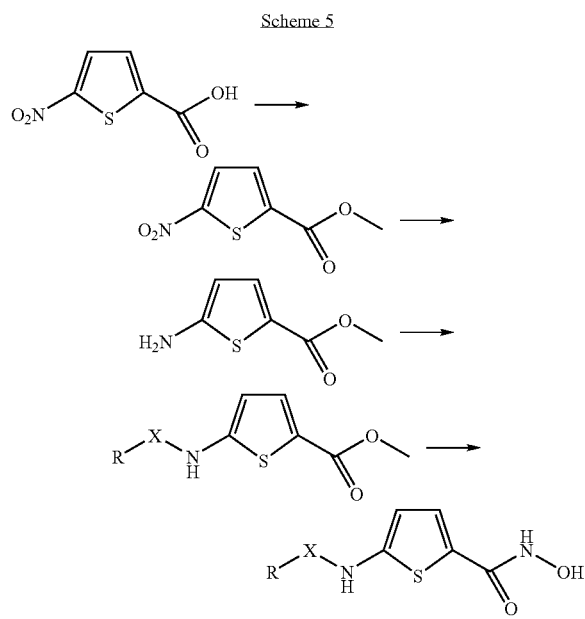

EXPERIMENTAL

Benzothiophenes
Procedure to 6-aminobenzothiophene.

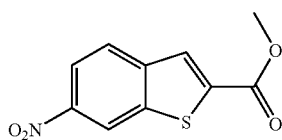

6-Nitro-benzo[b]thiophene-2-carboxylic acid methyl ester. To a mixture of 2,4-dinitrobenzaldehyde (6.45 g, 32.9 mmol) and K$_2$CO$_3$ (5.45 g, 39.4 mmol) in DMF (60 mL) was slowly added methyl thioglycolate (3.0 mL, 32.9 mmol). The mixture was stirred at RT for 1 h, then at 50° C. for 2 hr. The resultant mixture was poured into H$_2$O/ice and stirred until a precipitate formed. The solid was filtered and triturated with hot MeOH. The pale brown solid was filtered. $^1$H NMR (DMSO-d$_6$) δ 9.13 (s, 1H), 8.33 (s, 1H), 8.30-8.17 (m, 2H), 3.89 (s, 3H). MS (EI): cal'd (MH$^+$) 238.01, exp (MH$^+$) 238.10.

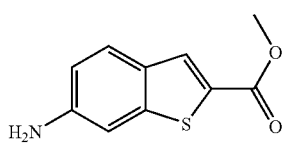

6-Amino-benzo[b]thiophene-2-carboxylic acid methyl ester. To a stirring solution of 6-nitro-benzo[b]thiophene-2-carboxylic acid methyl ester (3.9 g, 15.8 mmol) in DMF (120 mL) was added 10% Pd/C (700 mg, 10 %). The reaction was charged with H$_2$, degassed and refilled with hydrogen three times. The slurry was stirred at RT for 4 days at balloon pressure, then filtered through a plug of Celite, and solvent was removed under reduced pressure. The solid was washed with EtOAc, and filtered to yield the desired amine. $^1$H NMR (CDCl$_3$) δ 7.92 (s, 1H), 7.65 (d, J=8.4 Hz, 1H), 7.08 (s, 1H), 6.78 (d, J=8.4 Hz, 1H), 3.92 (s, 3H). MS (EI): cal'd (MH$^+$) 208.04, exp (MH$^+$) 208.1.

Amides

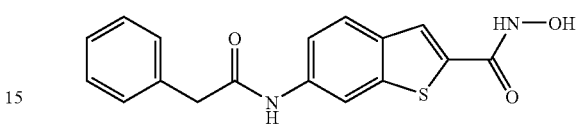

General Experimental for Acylated 6-Amino-benzothiophenes.

6-Phenylacetylamino-benzo[b]thiophene-2-carboxylic acid hydroxyamide. To a solution of 6-amino-benzo[b]thiophene-2-carboxylic acid methyl ester (75 mg, 0.36 mmol) and NMM (51.7 μL, 0.47 mmol) in THF/CH$_2$Cl$_2$ (2/1 mL) was added acid chloride (0.434 mmol). After 24 h, the solvent was removed. To the resultant mixture was added DMA (2 mL) and NH$_2$OH (50% aq., 1 mL). The solution was stirred until the disappearance of starting material as indicated by LC/MS. After removal of solvent, MeOH/H$_2$O was added until a precipitate forms. The solid was filtered yielding the desired amide. $^1$H NMR (DMSO-d$_6$) δ 11.38 (br s, 1H), 10.42 (br s, 1H), 9.21 (br s, 1H), 8.38 (s, 1H), 7.90-7.75 (m, 2H), 7.50-7.15 (m, 6H), 3.65 (s, 2H). MS (EI): cal'd (MH$^+$) 327.07, exp (MH$^+$) 327.28.

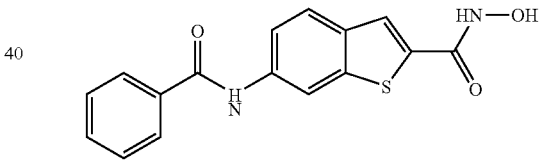

6-Benzoylamino-benzo[b]thiophene-2-carboxylic acid hydroxyamide. $^1$H NMR (DMSO-d$_6$) δ 11.37 (br s, 1H), 10.46 (br s, 1H), 9.21 (br s, 1H), 8.53 (s, 1H), 7.99-7.77 (m, 4H), 7.77-7.64 (m, 1H), 7.64-7.45 (m, 3H). MS (EI): cal'd (MH$^+$) 313.1, exp (MH$^+$) 313.3.

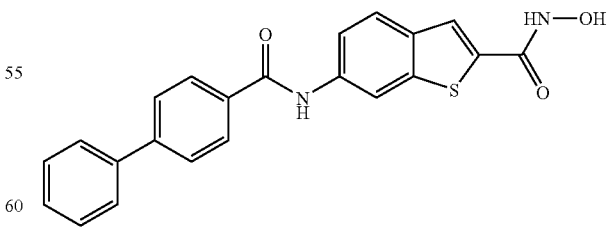

6-[(Biphenyl-4-carbonyl)-amino]-benzo[b]thiophene-2-carboxylic acid hydroxyamide. $^1$H NMR (DMSO-d$_6$) δ 11.39 (br s, 1H), 10.50 (br s, 1H), 9.23 (br s, 1H), 8.56 (s, 2H), 8.05 (d, J=7.8 Hz, 2H), 8.00-7.60 (m, 7H), 7.60-7.34 (m, 3H). MS (EI): cal'd (MH$^+$) 389.1, exp (MH$^+$) 389.3.

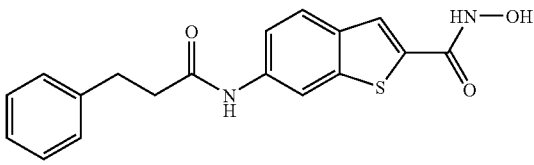

6-(3-Phenyl-propionylamino)-benzo[b]thiophene-2-carboxylic acid hydroxyamide. $^1$H NMR (DMSO-$d_6$) δ 11.37 (br s, 1H), 10.13 (br s, 1-H), 9.19 (br s, 1H), 8.37 (s, 1H), 7.85-7.72 (m, 2H), 7.44-7.33 (m, 1H), 7.33-7.08 (m, 6H), 2.95-2.81 (m, 2H), 2,70-2.59 (m, 2H). MS (EI): cal'd (MH$^+$) 341.1, exp (MH$^+$) 341.3.

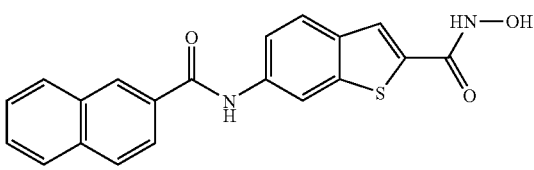

6-[(Naphthalene-2-carbonyl)-amino]-benzo[b]thiophene-2-carboxylic acid hydroxyamide. $^1$H NMR (DMSO-$d_6$) δ 11.39 (br s, 1H), 10.63 (br s, 1H), 9.22 (br s, 1H), 8.57 (s, 2H), 8.15-7.92 (m, 4H), 7.92-7.80 (m, 2H), 7.80-7.70 (m, 1H), 7.70-7.54 (m, 2H). MS (EI): cal'd (MH$^+$) 363.1, exp (MH$^+$) 363.3.

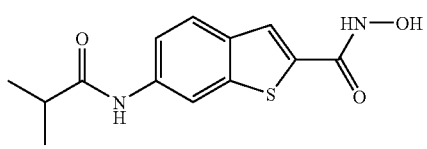

6-Isobutyrylamino-benzo[b]thiophene-2-carboxylic acid hydroxyamide. $^1$H NMR (DMSO-$d_6$) δ 11.35 (br s, 1H), 10.05 (br s, 1H), 9.20 (br s, 1H), 8.39 (s, 1H), 7.85-7.70 (m, 2H), 7.44 (dd, J=8.4, 1.4 Hz, 1H), 2.68-2.48 (m, 1H), 1.08 (d, J=7.0 Hz, 6H). MS (EI): cal'd (MH$^+$) 279.0, exp (MH$^+$) 279.2.

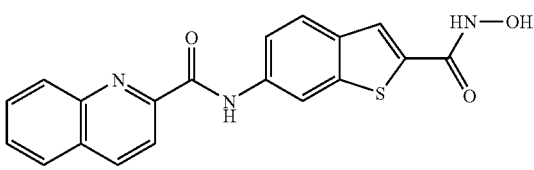

Quinoline-2-carboxylic acid (2-hydroxycarbamoyl-benzo[b]thiophen-6-yl)-amide. $^1$H NMR (DMSO-$d_6$) δ 10.94 (br s, 1H), 10.27 (br s, 1H), 9.22 (br s, 1H), 8.72-8.57 (m, 2H), 8.30-8.18 (m, 2H), 8.10 (d, J=8.4 Hz, 1H), 8.04-7.82 (m, 4H), 7.31 (dd, J=7.4, 7.4 Hz, 1H). MS (EI): cal'd (MH$^+$) 364.1, exp (MH$^+$) 364.3.

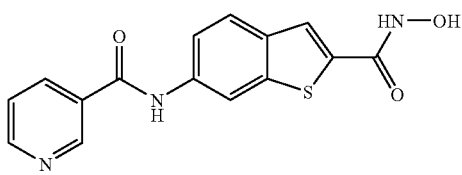

N-(2-Hydroxycarbamoyl-benzo[b]thiophen-6-yl)-nicotinamide. $^1$H NMR (DMSO-$d_6$) δ 11.40 (m, 1H), 10.66 (br s, 1H), 9.25 (br s, 1H), 9.11 (s, 1H), 8.82-8.70 (m, 1H), 8.54 (s, 1H), 8.30 (d, J=7.5 Hz, 1H), 8.00-7.78 (m, 2H), 7.70 (d, J=7.0 Hz, 1-H), 7.65-7.50 (m, 1H). MS (EI): cal'd (MH$^+$) 314.1, exp (MH$^+$) 314.3.

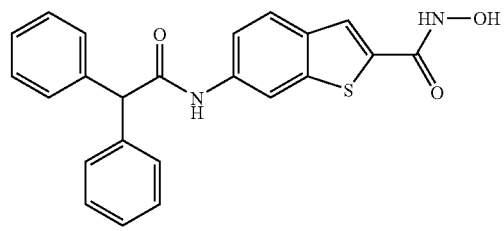

6-Diphenylacetylamino-benzo[b]thiophene-2-carboxylic acid hydroxyamide. $^1$H NMR (DMSO-$d_6$) δ 11.35 (m, 1H), 10.62 (br s, 1H), 9.19 (br s, 1H), 8.43 (s, 1H), 7.90-7.72 (m, 2H), 7.50-7.15 (m, 11H), 5.17 (s, 1H). MS (EI): cal'd (MH$^+$) 403.1, exp (MH$^+$) 403.3.

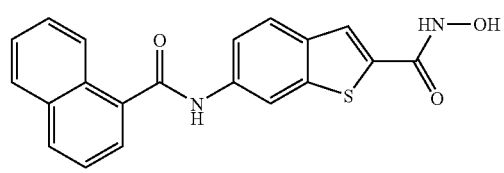

6-[(Naphthalene-1-carbonyl)amino]-benzo[b]thiophene-2-carboxylic acid hydroxyamide. (EI): cal'd (MH$^+$) 363.1, exp (MH$^+$) 363.3.

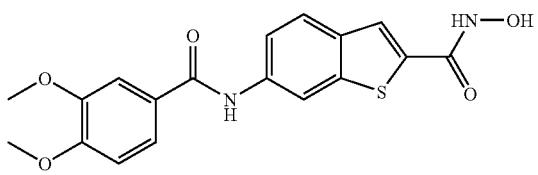

6-(3,4-Dimethoxy-benzoylamino)-benzo[b]thiophene-2-carboxylic acid hydroxyamide. $^1$H NMR (DMSO-$d_6$) δ 11.39 (br s, 1H), 10.27 (br s, 1H), 9.22 (br s, 1H), 8.48 (s, 1H), 7.90-7.75 (m, 2H), 7.75-7.55 (m, 2H), 7.52 (s, 1H), 7.08 (d, J=8.0 Hz, 1H), 3.82 (s, 3H), 3.81 (s, 3H). MS (EI): cal'd (MH$^+$) 373.1, exp (MH$^+$) 373.2.

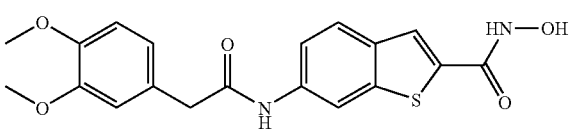

6-[2-(3,4-Dimethoxy-phenyl)-acetylamino]-benzo[b]thiophene-2-carboxylic acid hydroxyamide. $^1$H NMR (DMSO-$d_6$) δ 10.31 (br s, 1H), 8.35 (s, 1H), 7.85-7.72 (m, 2H), 7.42 (dd, J=8.8, 1.8 Hz, 1H), 6.95-6.75 (m, 3H), 3.69 (s, 3H), 3.67 (s, 3H), 3.54 (s, 2H). MS (EI): cal'd (MH$^+$) 387.1, exp (MH$^+$) 387.2.

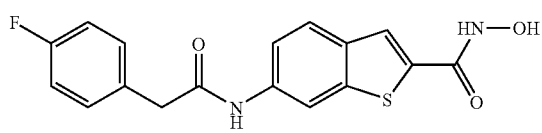

6-[2-(4-Fluoro-phenyl)-acetylamino]-benzo[b]thiophene-2-carboxylic acid hydroxyamide. $^1$H NMR (DMSO-d$_6$) δ 10.39 (br s, 1H), 9.27 (br s, 1H), 8.37 (s, 1H), 7.88-7.72 (m, 2H), 7.50-7.28 (m, 3H), 7.20-7.05 (m, 2H), 3.65 (s, 2H). MS (EI): cal'd (MH$^+$) 345.1, exp (MH$^+$) 345.2.

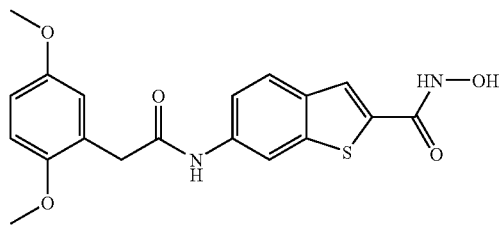

6-[2-(2,5-Dimethoxy-phenyl)-acetylamino]-benzo[b]thiophene-2-carboxylic acid hydroxyamide. $^1$H NMR (DMSO-d$_6$) δ 10.25 (br s, 1H), 9.27 (br s, 1H), 8.35 (s, 1H), 7.85-7.69 (m, 2H), 7.45 (dd, J=8.8, 1.8 Hz, 1H), 6.92-6.68 (m, 3H), 3.66 (s, 3H), 3.65 (s, 3H), 3.60 (s, 2H). MS (EI): cal'd (MH$^+$) 387.1, exp (MH$^+$) 387.2.

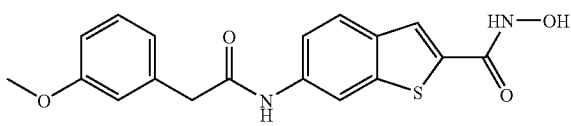

6-[2-(3-Methoxy-phenyl)-acetylamino]-benzo[b]thiophene-2-carboxylic acid hydroxyamide. $^1$H NMR (DMSO-d$_6$) δ 10.38 (br s, 1H), 9.27 (br s, 1H), 8.37 (s, 1H), 7.87-7.73 (m, 2H), 7.45 (dd, J=8.8, 1.8 Hz, 1H), 7.21 (t, J=8.0, 8.0 Hz, 1H), 6.92-6.83 (m, 2H), 6.78 (dd, J=7.0, 1.2 Hz, 1H), 3.71 (s, 3H), 3.61 (s, 2H). MS (EI): cal'd (MH$^+$) 357.1, exp (MH$^+$) 357.3.

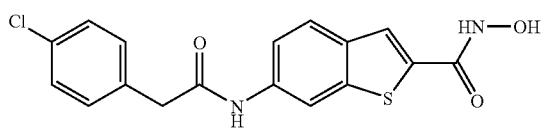

6-[2-(4-Chloro-phenyl)-acetylamino]-benzo[b]thiophene-2-carboxylic acid hydroxyamide. $^1$H NMR (CDCl$_3$) δ 10.42 (s, 1H), 9.20 (br s, 1H), 8.36 (s, 1H), 7.87-7.71 (m, 2H), 7.49-7.25 (m, 5H), 3.66 (s, 2H). MS (EI): cal'd 361.1 (MH+), exp 361.5 (MH+).

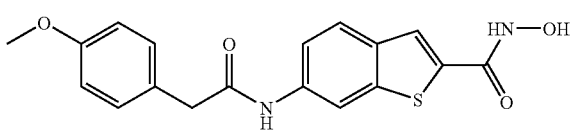

6-[2-(4-Methoxy-phenyl)-acetylamino]-benzo[b]thiophene-2-carboxylic acid hydroxyamide. $^1$H NMR (CDCl$_3$) δ 10.35 (s, 1H), 9.21 (br s, 1H), 8.37 (s, 1H), 7.85-7.70 (m, 2H), 7.51-7.32 (m, 1H), 7.22 (d, 2H, J=8.0 Hz), 6.85 (d, 2H, J=8.0 Hz), 3.69 (s, 3H), 3.57 (s, 2H). MS (EI): cal'd 357.1 (MH+), exp 357.3 (MH+).

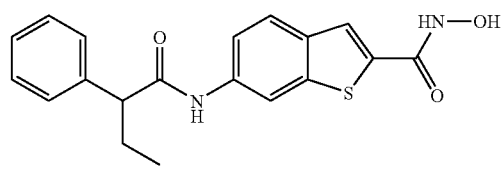

6-(2-Phenyl-butyrylamino)-benzo[b]thiophene-2-carboxylic acid hydroxyamide. $^1$H NMR CDCl$_3$), δ 11.33 (br s, 1H), 10.31 (s, 1H), 9.19 (br s, 1H), 8.39 (s, 1H), 7.83-7.71 (m, 2H), 7.45-7.15 (m, 6H), 3.56 (t, 1H, 7.2 Hz), 2.15-1.90 (m, 1H), 1.78-1.55 (m, 1H), 0.83 (t, 3H, 7.2 Hz). MS (EI): cal'd 355.1 (MH+), exp 355.3 (MH+).

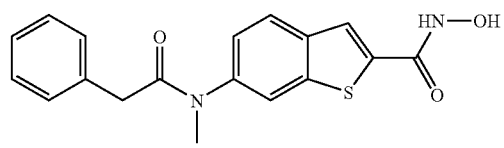

6-(Methyl-phenylacetyl-amino)-benzo[b]thiophene-2-carboxylic acid hydroxyamide. $^1$H NMR (CDCl$_3$) δ 11.48 (br s, 1H), 9.27 (br s, 1H), 8.01-7.85 (m, 3H), 7.33 (d, 1H, J=8.2 Hz), 7.35-7.10 (m, 3H), 7.10-6.02 (m, 2H), 3.29 (s, 3H), 3.21 (s, 2H). MS (EI): cal'd 341.1 (MH+), exp 341.2 (MH+).

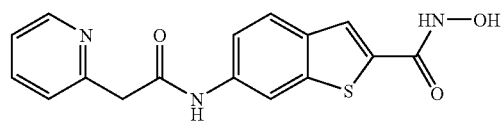

6-(2-Pyridin-2-yl-acetylamino)-benzo[b]thiophene-2-carboxylic acid hydroxyamide. MS (EI): cal'd 328.1 (MH+), exp 328.2 (MH+).

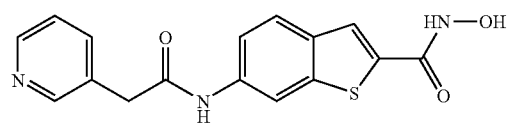

6-(2-Pyridin-3-yl-acetylamino)-benzo[b]thiophene-2-carboxylic acid hydroxyamide. $^1$H NMR (CDCl$_3$) δ 10.45 (s, 1H), 9.22 (br s, 1H), 8.51-8.30 (m, 2H), 7.89-7.65 (m, 3H), 7.58 (d, 1H, J=8.0 Hz), 7.50-7.22 (m, 2H), 3.71 (s, 2H). MS (EI): cal'd 328.1 (MH+), exp 328.2 (MH+).

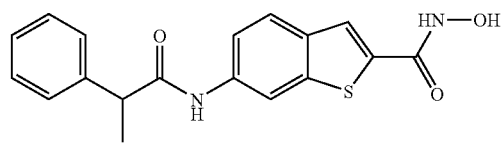

6-(2-Phenyl-propionylamino)-benzo[b]thiophene-2-carboxylic acid hydroxyamide. $^1$H NMR (CDCl$_3$) δ 10.27 (s, 1H), 9.19 (br s, 1H), 8.38 (s, 1H), 7.83-7.71 (m, 2H), 7.49-

7.15 (m, 6H), 3.85 (q, 1H, 7.0 Hz), 1.39 (t, 3H, 7.0 Hz). MS (EI): cal'd 341.1 (MH+), exp 341.2 (MH+).

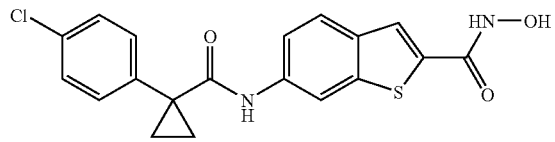

6-{[1-(4-Chloro-phenyl)-cyclopropanecarbonyl]-amino}-benzo[b]thiophene-2-carboxylic acid hydroxyamide. MS (EI): cal'd 387.1 (MH+), exp 387.3 (MH+).

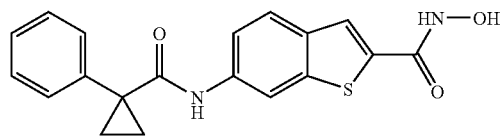

6-[(1-Phenyl-cyclopropanecarbonyl)-amino]-benzo[b]thiophene-2-carboxylic acid hydroxyamide. MS (EI): cal'd 353.1 (MH+), exp 353.2 (MH+).

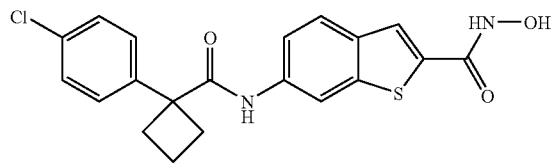

6-{[1-(4-Chloro-phenyl)-cyclobutanecarbonyl]-amino}-benzo[b]thiophene-2-carboxylic acid hydroxyamide. MS (EI): cal'd 401.1 (MH+), exp 401.2 (MH+).

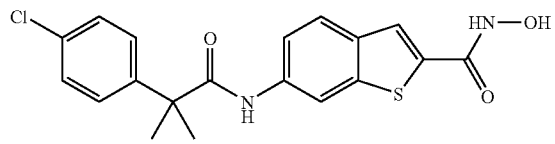

6-[2-(4-Chloro-phenyl)-2-methyl-propionylamino]-benzo[b]thiophene-2-carboxylic acid hydroxyamide. MS (EI): cal'd 389.1 (MH+), exp 389.2 (MH+).

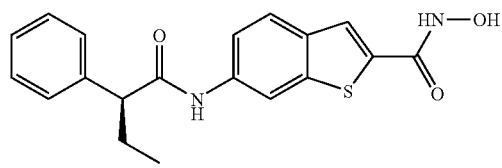

6(2S-Phenyl-butyrylamino)-benzo[b]thiophene-2-carboxylic acid hydroxyamide. MS (EI): cal'd 355.1 (MH+), exp 355.2 (MH+).

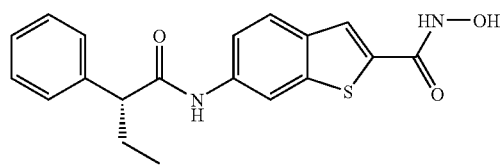

6-(2R-Phenyl-butyrylamino)-benzo[b]thiophene-2-carboxylic acid hydroxyamide. MS (EI): cal'd 355.1 (MH+), exp 355.2 (MH+).

Acylated Compounds from Aminomethyl-benzothiophenes

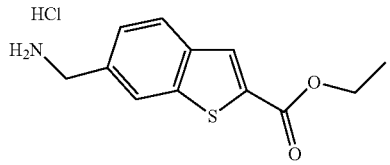

6-Aminomethyl-benzo[b]thiophene-2-carboxylic acid ethyl ester, hydrochloride salt. To a solution of 6-hydroxymethyl-benzo[b]thiophene-2-carboxylic acid ethyl ester (2.52 g, 10.7 mmol) and triethylamine (3.00 mL, 21.5 mmol) in anhydrous THF (80 mL) at 0° C. was added metahnesulfonyl chloride (1.24 mL, 16.0 mmol). The resulting mixture was allowed to stir at 0° C. for 30 min, diluted with EtOAc (400 mL), washed with saturated NaHCO$_3$, water and brine. The organic layer was dried over Na$_2$SO$_4$. After filtration, the filtrate was concentrated and the residue was dissolved in anhydrous DMF (60 mL). After sodium azide (1.41 g, 21.6 mmol) was added, the mixture was heated at 50° C. for 30 min. After cooling to rt, the mixture was diluted with EtOAc (300 mL) and water (60 mL). The organic layer was further washed with water and brine, and then dried over Na$_2$SO$_4$. After filtration, the filtrate was concentrated and the residue was dissolved in THF (60 mL) and water (6 mL). Triphenylphosphine (3.64 g, 13.9 mmol) was added and the mixture was allowed to stir at rt overnight and then concentrated. The residue was dissolved in ether (400 mL) and 4M HCl in dioxane (6 mL) was added dropwise. The solid formed was washed with ether (5×30 mL) and dried to give 6-aminomethyl-benzo[b]thiophene-2-carboxylic acid ethyl ester, hydrochloride salt as a pale solid. $^1$H NMR (DMSO-d$_6$, 200 MHz) δ 8.66 (brs, 2H), 8.24-8.10 (m, 2H), 8.06 (d, J=8.6 Hz, 1H), 7.62 (dd, J=8.4, 1.6 Hz, 1H), 4.34 (q, J=7.4 Hz, 2H), 4.13 (s, 2H), 1.32 (t, J=7.0 Hz, 3H). MS (EI): cal'd 236.1 (MH$^+$), exp 236.1 (MH$^+$).

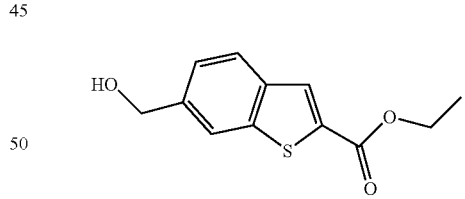

6-Hydroxymethyl-benzo[b]thiophene-2-carboxylic acid methyl ester. A solution of 6-hydroxymethyl-benzo[b]thiophene-2-carboxylic acid ethyl ester (9.45 g, 40.0 mmol) and DBU (6.00 mL, 40.1 mmol) in anhydrous MeOH (200 mL) was allowed to stir for 2 d. After concentration, the residue was dissolved in EtOAc (800 mL) and washed with 1N HCl, water, saturated NaHCO$_3$ and brine. The organic layer was dried, filtered and the filtrate was concentrated and dried to give 6-hydroxymethyl-benzo[b]thiophene-2-carboxylic acid methyl ester as off white solid. $^1$H NMR (CDCl$_3$, 200 MHz) δ 8.03 (d, J=0.6 Hz, 1H), 7.90-7.80 (m, 2H), 7.39 (dd, J=8.0, 1.4 Hz, 1H), 4.83 (s, 2H), 3.94 (s, 3H), 1.98 (brs, 1H). MS (EI): cal'd 223.0 (MH$^+$), exp 223.1 (MH$^+$).

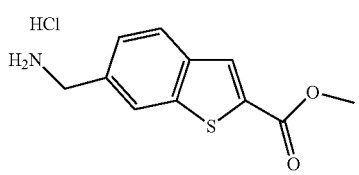

6-Aminomethyl-benzo[b]thiophene-2-carboxylic acid methyl ester, hydrochloride salt. The title compound was prepared from 6-hydroxymethyl-benzo[b]thiophene-2-carboxylic acid methyl ester in procedures similar to those described for the preparation of 6-aminomethyl-benzo[b]thiophene-2-carboxylic acid ethyl ester, hydrochloride salt. $^1$H NMR (DMSO-$d_6$, 200 MHz) δ 8.70 (brs, 2H), 8.24-8.12 (m, 2H), 8.05 (d, J=8.4 Hz, 1H), 7.63 (dd, J=8.0, 1.0 Hz, 1H), 4.20-4.14 (m, 2H), 3.88 (s, 3H). MS (EI): cal'd 222.0 (MH$^+$), exp 222.1 (MH$^+$).

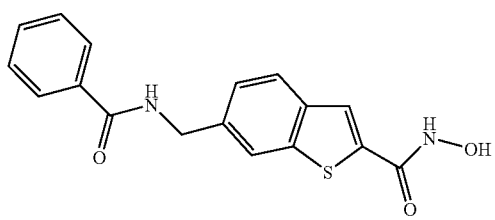

6-(Benzoylamino-methyl)-benzo[b]thiophene-2-carboxylic acid hydroxyamide. To a mixture of 6-aminomethyl-benzo[b]thiophene-2-carboxylic acid ethyl ester, hydrochloride salt (109 mg, 0.40 mmol), NMM (132 μL, 1.20 mmol) an DMAP (10 mg, 0.08 mmol) in anhydrous THF (5 mL) were added benzoyl chloride (55.7 μL, 0.48 mmol) and DMF (2.0 mL). After the reaction was complete, the reaction mixture was concentrated. To the residue were added MeOH (1 mL) and water (10 mL). The solid formed was filtered, washed with water and dried. This solid residue was dissolved in anhydrous MeOH (5 mL) and hydroxylamine hydrochloride (106 mg, 1.52 mmol) was added, followed by the addition of NaOMe solution (4.37 M in MeOH, 0.70 mL, 3.1 mmol). The mixture was allowed to stir at rt till the reaction was complete. The reaction mixture was concentrated and the residue was dissolved in a minimal amount of water. The obtained solution was acidified with 2N HCl to pH≈8. The solid formed was filtered, washed with water, collected and purified by flash column chromatography to give 6-(benzoylamino-methyl)-benzo[b]thiophene-2-carboxylic acid hydroxyamide as a white solid. $^1$H NMR (DMSO-$d_6$, 200 MHz) δ 11.44 (brs, 1H), 9.27 (brs, 1H), 9.13 (t, J=6.2 Hz, 1H), 8.00-7.78 (m, 5H), 7.58-7.28 (m, 4H), 4.60 (d, J=5.8 Hz, 2H). MS (EI): cal'd 327.1 (MH$^+$), exp 327.1 (MH$^+$).

The following compounds were prepared in procedures similar to those described for the preparation of 6-(benzoylamino-methyl)-benzo[b]thiophene-2-carboxylic acid hydroxyamide.

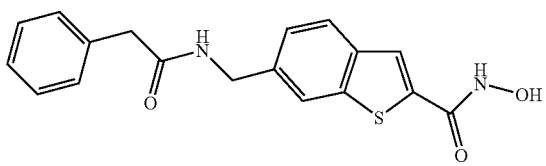

6-(Phenylacetylamino-methyl)-benzo[b]thiophene-2-carboxylic acid hydroxyamide. $^1$H NMR (DMSO-$d_6$, 200 MHz) δ 8.64 (t, J=6.2 Hz, 1H), 7.94-7.70 (m, 3H), 7.34-7.14 (m, 6H), 4.38 (d, J=5.8 Hz, 2H), 3.49 (s, 2H). MS (EI): cal'd 341.1 (MH$^+$), exp 341.1 (MH$^+$).

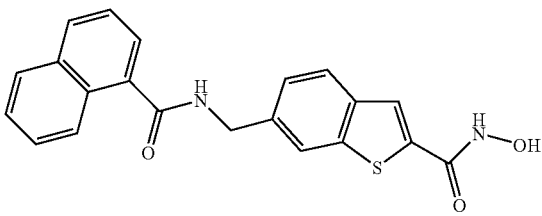

6-{[(Naphthalene-1-carbonyl)-amino]-methyl}-benzo[b]thiophene-2-carboxylic acid hydroxyamide. $^1$H NMR (DMSO-$d_6$, 200 MHz) δ 9.18 (t, J=5.8 Hz, 1H), 8.24-8.14 (m, 1H), 8.06-7.84 (m, 5H), 7.69 (dd, J=7.0, 1.0 Hz, 1H), 7.62-7.42 (m, 4H), 4.67 (d, J=6.0 Hz, 2H). MS (EI): cal'd 377.1 (MH$^+$), exp 377.1 (MH$^+$).

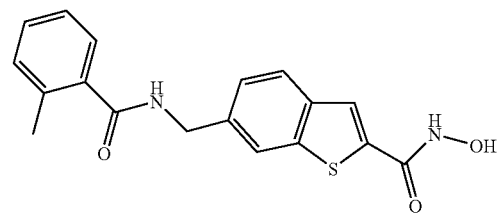

6-[(2-Methyl-benzoylamino)-methyl]-benzo[b]thiophene-2-carboxylic acid hydroxyamide. $^1$H NMR (DMSO-$d_6$, 200 MHz) δ 11.46 (brs, 1H), 9.26 (brs, 1H), 8.87 (t, J=6.2 Hz, 1H), 7.98-7.82 (m, 3H), 7.46-7.16 (m, 5H), 4.55 (d, J=5.8 Hz, 2H), 2.32 (s, 31H). MS (EI): cal'd 341.1 (MH$^+$), exp 341.2 (MH$^+$).

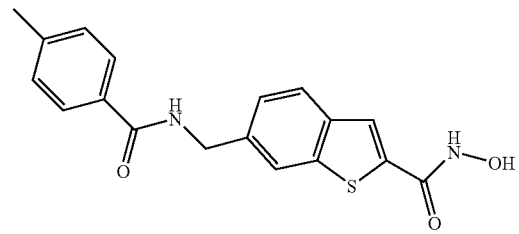

6-[(4-Methyl-benzoylamino)-methyl]-benzo[b]thiophene-2-carboxylic acid hydroxyamide. $^1$H NMR (DMSO-$d_6$, 200 MHz) δ 11.44 (brs, 1H), 9.25 (brs, 1H), 9.03 (t, J=4.6Hz, 1H), 7.96-7.72 (m, 5H), 7.38 (d, J=8.0 Hz, 2H), 7.27 (d, J=8.2 Hz, 2H), 4.58 (d, J=6.0 Hz, 2H), 2.34 (s, 3H). MS (EI): cal'd 341.1 (MH$^+$), exp 341.2 (MH$^+$).

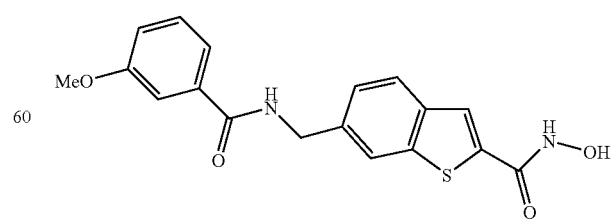

6-[(3-Methoxy-benzoylamino)-methyl]-benzo[b]thiophene-2-carboxylic acid hydroxyamide. $^1$H NMR (DMSO-d$_6$, 200 MHz) δ 11.45 (brs, 1H), 9.25 (brs, 1H), 9.11 (t, J=6.0 Hz, 1H), 7.96-7.80 (m, 3H), 7.54-7.30 (m, 3H), 7.14-7.04 (m, 1H), 4.59 (d, J=5.6 Hz, 2H), 3.79 (s, 3H). MS (EI): cal'd 357.1 (MH$^+$), exp 357.2 (MH$^+$).

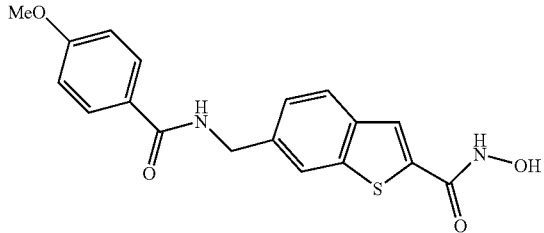

6-[(4-Methoxy-benzoylamino)-methyl]-benzo[b]thiophene-2-carboxylic acid hydroxyamide. $^1$H NMR (DMSO-d$_6$, 200 MHz) δ 11.44 (brs, 1H), 9.27 (brs, 1H), 8.89 (t, J=5.4 Hz, 1H), 8.00-7.78 (m, 5H), 7.39 (d, J=8.0 Hz, 2H), 7.00 (d, J=9.0 Hz, 2H), 1H), 4.58 (d, J=5.8 Hz, 2H), 3.80 (s, 3H). MS (EI): cal'd 357.1 (MH$^+$), exp 357.2 (MH$^+$).

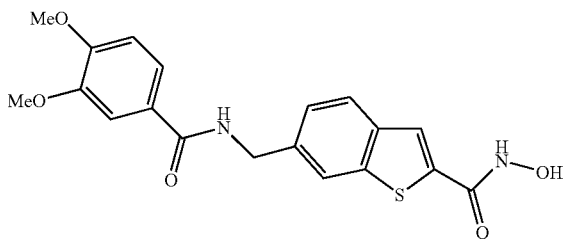

6-[1(3,4-Dimethoxy-benzoylamino)-methyl]-benzo[b]thiophene-2-carboxylic acid hydroxyamide. $^1$H NMR (DMSO-d$_6$, 200 MHz) δ 11.45 (brs, 1H), 9.27 (brs, 1H), 8.99 (t, J=6.0 Hz, 1H), 7.94-7.80 (m, 3H), 7.60-7.46 (m, 2H), 7.38 (dd, J=8.4, 1.6 Hz, 1H), 7.02 (d, J=8.4 Hz, 1H), 1H), 4.59 (d, J=5.4 Hz, 2H), 3.80 (s, 3H), 3.79 (s, 3H). MS (EI): cal'd 387.1 (MH$^+$), exp 387.2 (MH$^+$).

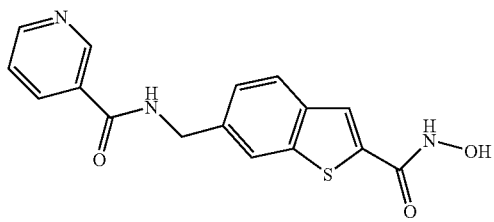

N-(2-Hydroxycarbamoyl-benzo[b]thiophen-6-ylmethyl)-nicotinamide. $^1$H NMR (DMSO-d$_6$, 200 MHz) δ 9.32 (t, J=5.6 Hz, 1H), 9.06 (d, J=1.4 Hz, 1H), 8.71 (dd, J=4.8, 2.0 Hz, 1H), 8.24 (ddd, J=7.8, 2.0, 2.0 Hz, 1H), 7.96 (s, 1H), 7.92-7.80 (m, 2H), 7.60-7.46 (m, 1H), 7.40 (dd, J=8.4, 1.4 Hz, 1H), 4.62 (d, J=6.0 Hz, 2H). MS (EI): cal'd 328.1 (MH$^+$), exp 328.2 (MH$^+$).

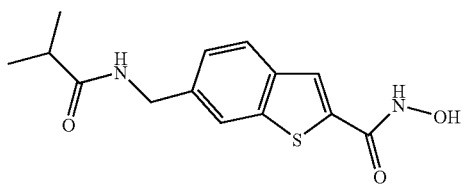

6-(Isobutyrylamino-methyl)-benzo[b]thiophene-2-carboxylic acid hydroxyamide. $^1$H NMR (DMSO-d$_6$, 200 MHz) δ 9.26 (brs, 1H), 8.34 (t, J=5.6 Hz, 1H), 7.94-7.74 (m, 3H), 7.29 (d, J=8.0 Hz, 1H), 4.36 (d, J=6.0 Hz, 2H), 2.46-2.30 (m, 1H), 1.03 (d, J=6.6 Hz, 6H). MS (EI): cal'd 293.1 (MH$^+$), exp 293.1 (MH$^+$).

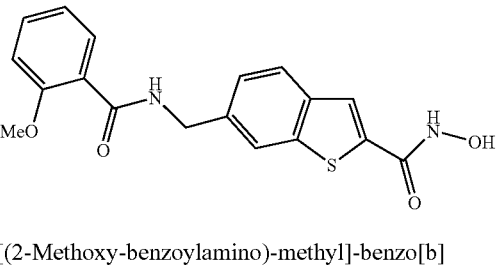

6-[(2-Methoxy-benzoylamino)-methyl]-benzo[b]thiophene-2-carboxylic acid hydroxyamide. $^1$H NMR (DMSO-d$_6$, 200 MHz) δ 9.27 (brs, 1H), 8.80 (t, J=6.2 Hz, 1H), 7.98-7.82 (m, 3H), 7.73 (dd, J=8.0, 1.8 Hz, 1H), 7.54-7.36 (m, 2H), 7.14 (d, J=8.6 Hz, 1H), 7.03 (t, J=7.4 Hz, 1H), 4.61 (d, J=5.8 Hz, 2H), 3.89 (s, 3H). MS (EI): cal'd 357.1 (MH$^+$), exp 357.1 (MH$^+$).

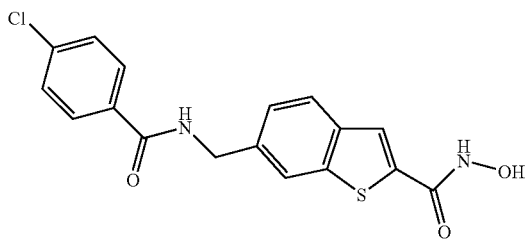

6-[(4-Chloro-benzoylamino)-methyl]-benzo[b]thiophene-2-carboxylic acid hydroxyamide. $^1$H NMR (DMSO-d$_6$, 200 MHz) δ 9.20 (t, J=5.8 Hz, 1H), 7.98-7.80 (m, 5H), 7.55 (d, J=8.4 Hz, 2H), 7.38 (dd, J=8.4, 1.6 Hz, 1H), 4.59 (d, J=5.8 Hz, 2H). MS (EI): cal'd 361.0 (MH$^+$), exp 361.1 (MH$^+$).

Sulphonamides

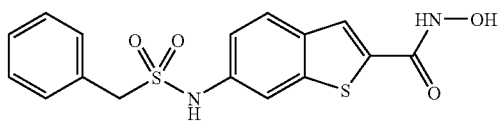

6-Phenylmethanesulfonylamino-benzo[b]thiophene-2-carboxylic acid hydroxyamide. The same procedure as for the preparation of 6-phenylacetylamino-benzo[b]thiophene-2-carboxylic acid hydroxyamide was employed. $^1$H NMR (DMSO-d$_6$) δ 11.18 (br s, 1H), 9.99 (br s, 1H), 9.19 (br s, 1H), 7.91-7.60 (m, 3H), 7.42-7.15 (m, 5H), 4.51 (s, 2H). MS (EI): cal'd (MH$^+$) 363.04, exp (MH$^+$) 363.28.

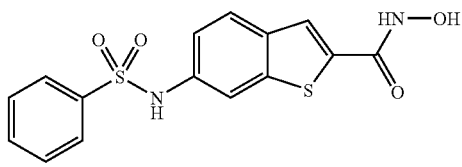

6-Benzenesulfonylamino-benzo[b]thiophene-2-carboxylic acid hdroxyamide. $^1$H NMR (DMSO -d$_6$) δ 11.38 (br s, 1H), 10.47 (br s, 1H), 9.22 (br s, 1H), 7.90-7.40 (m, 8H), 7.20-7.03 (m, 1H). MS (EI): cal'd (MH$^+$) 349.0, exp (MH$^+$) 349.2.

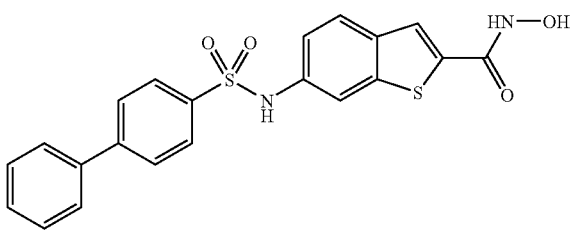

6-(Biphenyl-4-sulfonylamino)-benzo[b]thiophene-2-carboxylic acid hydroxyamide. $^1$H NMR (DMSO-$d_6$) δ 11.37 (br s, 1H), 10.46 (br s, 1H), 9.21 (br s, 1H), 7.96-7.59 (m, 9H), 7.59-7.30 (m, 3H), 7.30-7.03 (m, 1H). MS (EI): cal'd (MH$^+$) 425.1, exp (MH$^+$) 425.3.

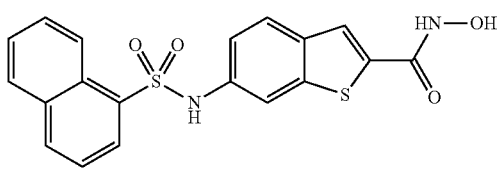

6-(Naphthalene-1-sulfonylamino)-benzo[b]thiophene-2-carboxylic acid hydroxyamide. MS (EI): cal'd (MH$^+$) 399.1, exp (MH$^+$) 399.3.

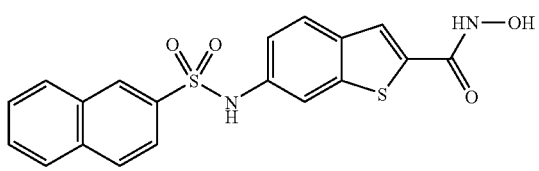

6-(Naphthalene-2-sulfonylamino)-benzo[b]thiophene-2-carboxylic acid hydroxyamide. $^1$H NMR (DMSO-$d_6$) δ 11.32 (br s, 1H), 10.63 (br s, 1H), 9.17 (br s, 1H), 8.45 (s, 1H), 8.25-7.96 (m, 2H), 7.93 (d, J=7.4 Hz, 1H), 7.61-7.58 (m, 6H), 7.13 (dd, J=8.6, 1.6 Hz, 1H). MS (EI): cal'd (MH$^+$) 399.1, exp (MH$^+$) 399.3.

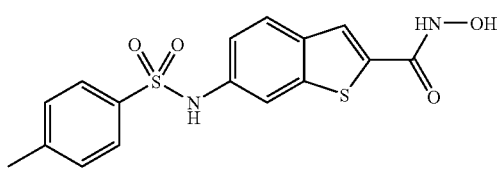

6-(Toluene4-sulfonylamino)-benzo[b]thiophene-2-carboxylic acid hydroxyamide. $^1$H NMR (DMSO-$_6$) δ 11.35 (br s, 1H), 10.46 (br s, 1H), 9.20 (br s, 1H), 7.80-7.57 (m, 5H), 7.28 (d, J=8.0 Hz, 2H), 7.14 (d, J=8.4 Hz, 1H), 5.72 (s, 1H), 2.27 (s, 3H). MS (EI): cal'd (MH$^+$) 363.0, exp (MH$^+$) 363.2.

General Procedure:

A fine suspension of 2-methoxycarbonyl-benzo[b]thiophen-6-ylmethyl-ammonium chloride (100 mg, 0.388 mmol) and diisopropylethylamine (160 µL, 0.919 mmol) in 2.5 mL of anhydrous DMF was added to a vial containing 0.40 mmol of a sulfonyl chloride. The mixture was stirred and became clear after a few seconds. The resulting solution was stirred for 1 hour. A 50% aqueous solution of hydroxylamine (1 mL, 16.7 mmol) was added slowly to the solution of the intermediate. In the cases when a precipitate formed, enough DMF was added to obtain a clear solution. The reaction was stirred for 2 days at room temperature. The product was precipitated by addition of water (4 mL) and brine (2 mL). The solid was collected by filtration, triturated with sat. NaHCO$_3$ (1 mL) and EtOAc (0.5 mL) and washed with water. After filtration, the product was left under high vacuum and isolated as a powder.

Data

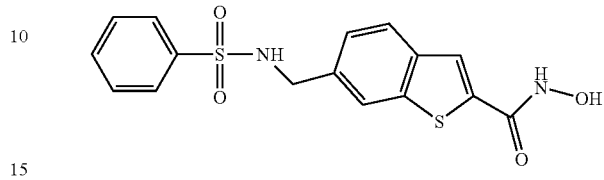

6-(Benzenesulfonylamino-methyl)-benzo[b]thiophene-2-carboxylic acid hydroxyamide. $^1$H NMR (DMSO-$d_6$, 200 MHz) δ 8.26 (t, J=6.2 Hz, 1H), 7.94-7.72 (m, 5H), 7.64-7.46 (m, 3H), 7.28 (d, J=8.6 Hz, 1H), 4.11 (d, J=5.8 Hz, 2H). MS (EI): cal'd 363.0 (MH$^+$), exp 363.0 (MH$^+$).

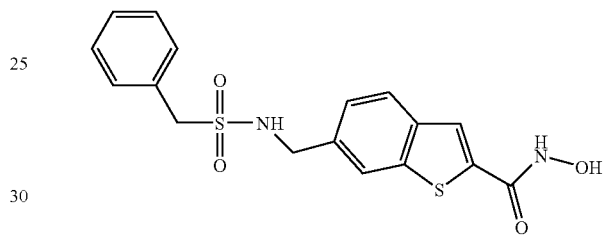

6-(Phenylmethanesulfonylamino-methyl)-benzo[b]thiophene-2-carboxylic acid hydroxyamide. $^1$H NMR (DMSO-$d_6$, 200 MHz) δ 7.96-7.84 (m, 3H), 7.42-7.28 (m, 6H), 4.35 (s, 2H), 4.21 (d, J=5.8 Hz, 2H). MS (EI): cal'd 377.1 (MH$^+$), exp 377.0 (MH$^+$).

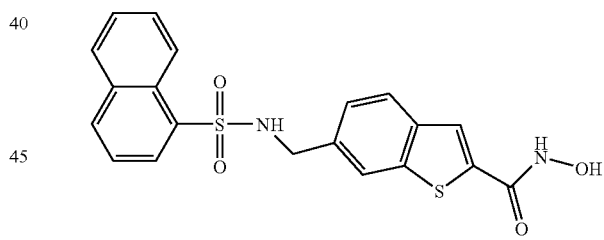

6-[(Naphthalene-1-sulfonylamino)-methyl]-benzo[b]thiophene-2-carboxylic acid hydroxyamide. $^1$H NMR (DMSO-$d_6$, 200 MHz) δ 8.76-8.54 (m, 2H), 8.18-7.96 (m, 3H), 7.84-7.48 (m, 6H), 7.16 (dd, J=8.0, 1.0 Hz, 1H), 4.16 (d, J=5.8 Hz, 2H). MS (EI): cal'd 413.1 (MH$^+$), exp 413.0 (MH$^+$).

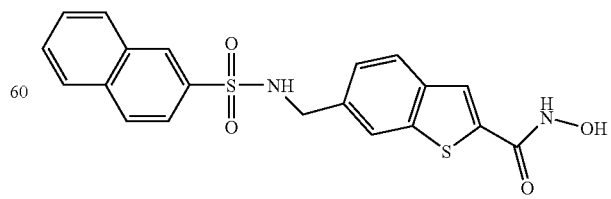

6-[(Naphthalene-2-sulfonylamino)-methyl]-benzo[b]thiophene-2-carboxylic acid hydroxyamide. $^1$H NMR (DMSO-$d_6$, 200 MHz) δ 8.41 (d, J=1.6 Hz, 1H), 8.16-7.95 (m, 3H), 7.88-7.56 (m, 6H), 7.28 (d, J=8.2 Hz, 1H), 4.14 (s, 2H). MS (EI): cal'd 413.1 (MH$^+$), exp 413.1 (MH$^+$).

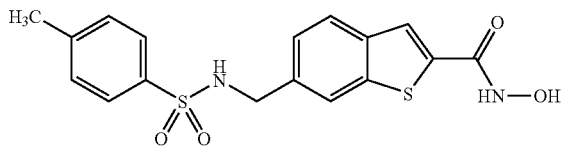

6-[(Toluene-4-sulfonylamino)-methyl]-benzo[b]thiophene-2-carboxylic acid hydroxyamide. $^1$H NMR (DMSO-$d_6$, 200 MHz) 8.16 (br t, 1H), 7.86 (s, 1H), 7.81 (d, J=8.4 Hz, 1H), 7.76 (s, 1H), 7.66 (d, J=8.2 Hz, 2H), 7.33 (d, J=8.0 Hz, 2H), 7.28 (d, J=8.0 Hz, 1H), 4.08 (d, J=4.4 Hz, 2H), 2.33 (s, 3H). MS(ES−): Cal'd. 375.05 (M−H$^+$), exp. 375.12 (M−H$^+$).

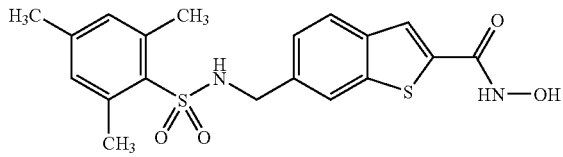

6-[(2,4,6-Trimethyl-benzenesulfonylamino)-methyl]-benzo[b]thiophene-2-carboxylic acid hydroxyamide. $^1$H NMR (DMSO-$d_6$, 200 MHz) 8.09 (br t, 1H), 7.83 (s, 1H), 7.76 (d, J=8.4 Hz, 1H), 7.64 (s, 1H), 7.24 (d, J=8.0 Hz, 2H), 6.90 (s, 2H), 4.10 (d, J=5.2 Hz, 2H), 2.51 (s, 6H), 2.16 (s, 3H). MS(ES+): Cal'd. 405.10 (MH$^+$), exp. 405.18 (MH$^+$).

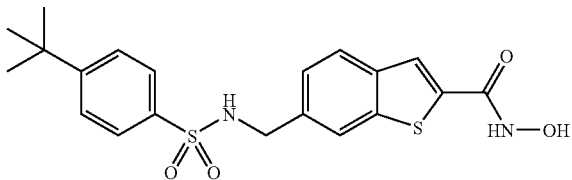

6-[(4-tert-Butyl-benzenesulfonylamino)-methyl]-benzo[b]thiophene-2-carboxylic acid hydroxyamide. $^1$H NMR (DMSO-$d_6$, 200 MHz) 7.78-7.62 (m, 5H), 7.50 (d, J=8.4 Hz, 2H), 7.20 (d, J=8.0 Hz, 2H), 4.09 (br s, 2H), 1.25 (s, 9H). MS(ES−): Cal'd. 417.09 (M−H$^+$) exp. 417.19 (M−H$^+$).

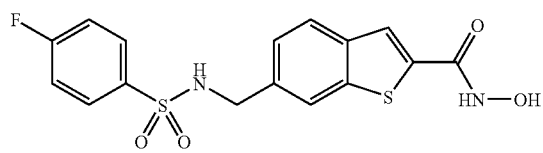

6-[(4-Fluoro-benzenesulfonylamino)-methyl]-benzo[b]thiophene-2-carboxylic acid hydroxyamide. $^1$H NMR (DMSO-$d_6$, 200 MHz) 8.25 (br s, 1H), 7.85-7.77 (m, 5H), 7.40-7.24 (m, 3H), 4.12 (d, J=1.0 Hz, 2H). MS(ES−): Cal'd. 379.02 (M−H$^+$), exp. 379.12 (M−H$^+$).

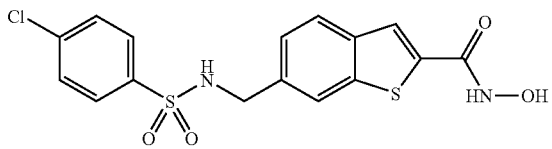

6-[(4-Chloro-benzenesulfonylamino)-methyl]-benzo[b]thiophene-2-carboxylic acid hydroxyamide. $^1$H NMR (DMSO-$d_6$, 200 MHz) 7.86 (s, 1H), 7.80 (d, J=8.4 Hz, 1H), 7.76 (d, J=7.8 Hz, 2H), 7.58 (d, J=8.4 Hz, 2H), 7.27 (d, J=8.4 Hz, 1H), 4.13 (s, 2H). MS(ES+): Cal'd. 397.01 (MH$^+$), exp. 397.09 (MH$^+$).

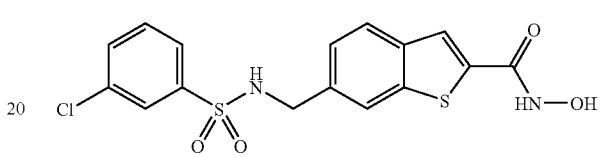

6-[(3-Chloro-benzenesulfonylamino)-methyl]-benzo[b]thiophene-2-carboxylic acid hydroxyamide. $^1$H NMR (DMSO-$d_6$, 200 MHz) 7.84-7.66 (m, 5H), 7.66-7.50 (m, 2H), 7.25 (d, J=8.4 Hz, 1H), 4.16 (s, 2H). MS(ES−): Cal'd. 394.99 (M−H$^+$) exp. 395.09 (M−H$^+$).

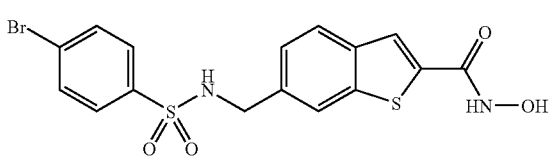

6-[(4-Bromo-benzenesulfonylamino)-methyl]-benzo[b]thiophene-2-carboxylic acid hydroxyamide. $_1$H NMR (DMSO-$d_6$, 200 MHz) 7.85-7.65 (m, 7H), 7.23 (d, J=8.4 Hz, 1H), 4.11 (s, 2H). MS(ES−): Cal'd. 438.94 (M−H$^+$), exp. 439.03 (M−H$^+$).

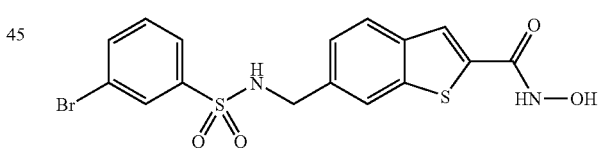

6-[(3-Bromo-benzenesulfonylamino)-methyl]-benzo[b]thiophene-2-carboxylic acid hydroxyamide. $^1$H NMR (DMSO-$d_6$, 200 MHz) 7.85-7.60 (m, 6H), 7.65 (t, J=8.2 Hz, 1H), 7.26 (d, J=9.2 Hz, 1H), 4.16 (s, 2H). MS(ES+): Cal'd. 440.96 (MH$^+$), exp. 441.03 (MH$^+$).

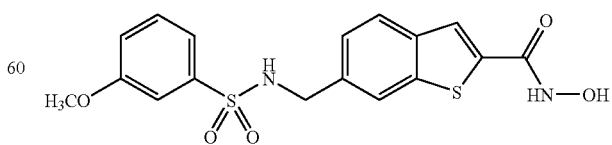

6-[(3-Methoxy-benzenesulfonylamino)-methyl]-benzo[b]thiophene-2-carboxylic acid hydroxyamide. $^1$H NMR (DMSO-$d_6$, 200 MHz) 8.27 (br s, 1H), 7.85-7.70 (m, 3H), 7.50-7.25 (m, 3H), 7.24 (s, 1H), 7.13 (d, J=8.4 Hz, 1H), 4.11 (s, 2H), 3.76 (s, 3H). MS(ES+): Cal'd. 393.06 (MH⁺), exp. 393.14 (MH⁺).

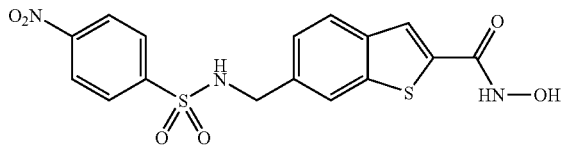

6-[(4-Nitro-benzenesulfonylamino)-methyl]-benzo[b]thiophene-2-carboxylic acid hydroxyamide. $^1$H NMR (DMSO-d$_6$, 200 MHz) 8.28 (d, J=8.8 Hz, 1H), 7.96 (d, J=8.8 Hz, 1H), 7.80-7.70 (m, 3H), 7.25 (d, J=8.4 Hz, 1H), 4.19 (s, 2H). MS(ES−): Cal'd. 406.01 (M−H⁺), exp. 406.10 (M−H⁺).

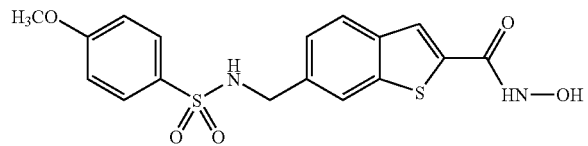

6-[(4-Methoxy-benzenesulfonylamino)-methyl]-benzo[b]thiophene-2-carboxylic acid hydroxyamide. $^1$H NMR (DMSO-d$_6$, 200 MHz) 7.80-7.65 (m, 5H), 7.23 (d, J=8.6 Hz, 1H), 7.05 (d, J=8.8 Hz, 2H), 4.04 (s, 2H), 3.79 (s, 3H). MS(ES−): Cal'd. 391.04 (M−H⁺), exp. 391.17 (M−H⁺).

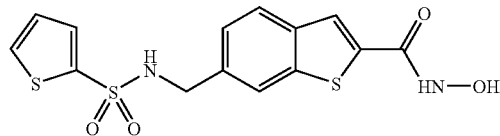

6-[(Thiophene-2-sulfonylamino)-methyl]-benzo[b]thiophene-2-carboxylic acid hydroxyamide. $^1$H NMR (DMSO-d$_6$, 200 MHz) 7.90 (d, J=4.6 Hz, 1H), 7.90-7.70 (m, 3H), 7.59 (d, J=3.8 Hz, 1H), 7.28 (d, J=8.2 Hz, 1H), 7.14 (t, J=3.8 Hz, 1H), 4.18 (s, 2H). MS(ES+): Cal'd. 369.01 (MH⁺), exp. 369.07 (MH⁺).

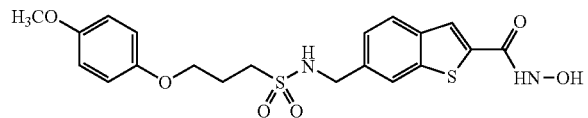

6-{[3-(4-Methoxy-phenoxy)-propane-1-sulfonylamino]-methyl}-benzo[b]thiophene-2-carboxylic acid hydroxyamide. $^1$H NMR (DMSO-d$_6$, 200 MHz) 7.95-7.70 (m, 4H), 7.36 (d, J=8.4 Hz, 1H), 6.90-6.75 (m, 4H), 4.26 (s, 2H), 3.91 (t, J=6.2 Hz, 2H), 3.67 (s, 3H), 3.08 (t, J=7.4 Hz, 2H), 2.01 (m, 2H). MS(ES−): Cal'd. 449.08 (M−H⁺), exp 449.15 (M−H⁺).
Ureas/Carbamates

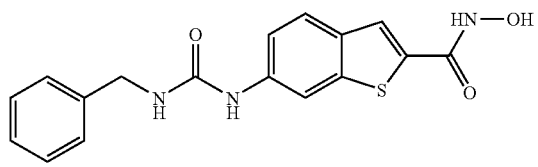

6-(3-Benzyl-ureido)-benzo[b]thiophene-2-carboxylic acid hydroxyamide. The same procedure as for the preparation of 6-phenylacetylamino-benzo[b]thiophene-2-carboxylic acid hydroxyamide was employed. $^1$H (DMSO-d$_6$) δ 11.28 (br s, 1H), 9.19 (br s, 1H), 8.82 (s, 1H), 8.16 (s, 1H), 7.80-7.62 (m, 2H), 7.38-7.17 (m, 5H), 6.68 (t, J=5.8 Hz, 1H), 4.28 (d, J=5.8 Hz, 2H). MS (EI): cal'd (MH⁺) 342.08, exp (MH⁺) 342.31.

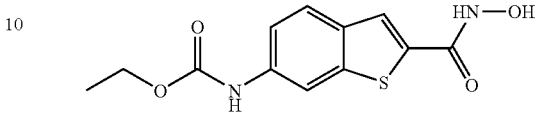

(2-Hydroxycarbamoyl-benzo[b]thiophen-6-yl)-carbamic acid ethyl ester. $^1$H NMR (DMSO-d$_6$) δ 9.86 (br s, 1H), 9.18 (br s, 1H), 8.11 (s, 1H), 7.82-7.70 (m, 2H), 7.38 (dd, J=8.4, 1.2 Hz, 1H), 4.11 (q, J=6.8 Hz, 2H), 1.22 (t, J=6.8 Hz, 2H). MS (EI): cal'd (MH⁺) 281.1, exp (MH⁺) 281.2.

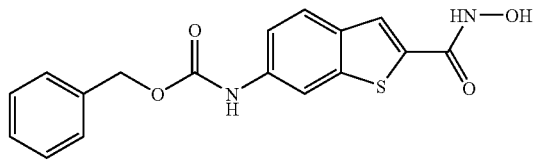

(2-Hydroxycarbamoyl-benzo[b]thiophen-6-yl)-carbamic acid benzyl ester. $^1$H NMR (DMSO-d$_6$) δ 11.34 (br s, 1H), 10.02 (br s, 1H), 9.18 (br s, 1H), 8.13 (s, 1H), 7.90-7.70 (m, 2H), 7.49-7.25 (m, 6H), 5.14 (s, 2H). MS (EI): cal'd (MH⁺) 343.1, exp (MH⁺) 343.2.

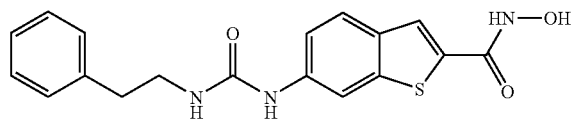

6-(3-Phenethyl-ureido)-benzo[b]thiophene-2-carboxylic acid hydroxyamide. $^1$H NMR (DMSO-d$_6$) δ 8.74 (br s, 1H), 8.16 (s, 1H), 7.90-7.70 (m, 2H), 7.40-7.10 (m, 5H), 6.21 (m, 1H), 3.40-3.22 (m, 2H), 2.72 (t, J=7.0 Hz, 2H). MS (EI): cal'd (MH⁺) 390.1, exp (MH⁺) 390.3.

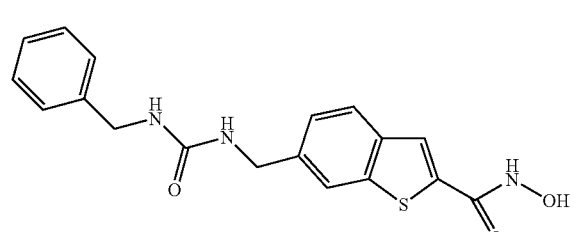

6-(3-Benzyl-ureidomethyl)-benzo[b]thiophene-2-carboxylic acid hydroxyamide. $^1$H NMR (DMSO-d$_6$, 200 MHz) δ 7.94-7.78 (m, 3H), 7.40-7.16 (m, 6H), 6.68-6.46 (m, 2H), 4.34 (d, J=6.0 Hz, 2H), 4.23 (d, J=6.0 Hz, 2H). MS (EI): cal'd 356.1 (MH⁺), exp 356.1 (MH⁺).

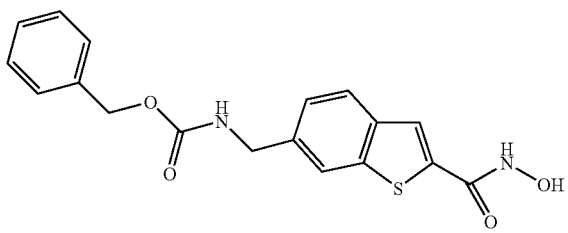

(2-Hydroxycarbamoyl-benzo[b]thiophen-6-ylmethyl)-carbamic acid benzyl ester. $^1$H NMR (DMSO-d$_6$, 200 MHz) δ 7.98-7.80 (m, 4H), 7.40-7.26 (m, 6H), 5.05 (s, 2H), 4.32 (d, J=6.0 Hz, 2H). MS (EI): cal'd 357.1 (MH$^+$), exp 357.1 (MH$^+$).

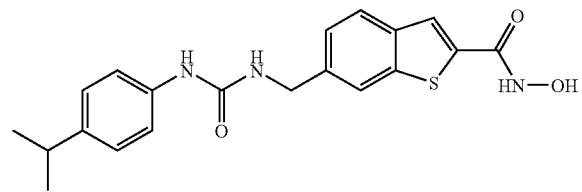

6-[3-(4-Isopropyl-phenyl)-ureidomethyl]-benzo[b]thiophene-2-carboxylic acid hydroxyamide. $^1$H NMR (DMSO-d$_6$, 200 MHz) 8.42 (br s, 1H), 7.66 (s, 1H), 7.68-7.50 (m, 2H), 7.16 (d, J=8.0 Hz, 2H), 7.20-7.10 (m, 1H), 6.93 (d, J=8.0 Hz, 2H), 6.59 (br s, 1H), 4.23 (br s, 2H), 2.64 (m, 1H), 1.01 (d, J=4.8 Hz, 6H). MS(ES+): Cal'd. 384.14 (MH$^+$), exp. 384.19 (MH$^+$).

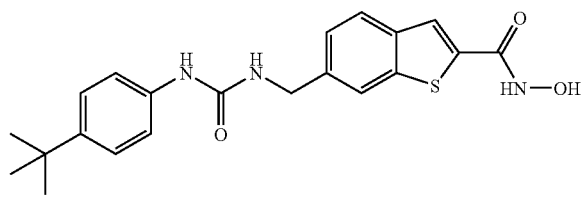

6-[3-(4-tert-Butyl-phenyl)-ureidomethyl]-benzo[b]thiophene-2-carboxylic acid hydroxyamide. $^1$H NMR (DMSO-d$_6$, 200 MHz) 8.38 (br s, 1H), 7.76-7.64 (m, 3H), 726-7.02 (m, 5H), 6.53 (t, J=4.8 Hz, H), 4.26 (d, J=4.8 Hz, H), 1.08 (s, 9H). MS(ES+): Cal'd. 398.15 (MH$^+$), exp. 398.22 (MH$^+$).

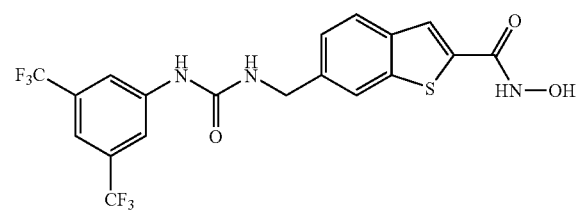

6-[3-(3,5-Bis-trifluoromethyl-phenyl)-ureidomethyl]-benzo[b]thiophene-2-carboxylic acid hydroxyamide. $^1$H NMR (DMSO-d$_6$, 200 MHz) 9.32 (br s, 1H), 7.96 (s, 2H), 7.75-7.68 (m, 3H), 7.41 (s, 1H), 7.23 (d, J=8.0 Hz, 1H), 7.02 (br t, 1H), 4.30 (d, J=6.0 Hz, 2H). MS(ES+): Cal'd. 478.07 (MH$^+$), exp. 478.15 (MH$^+$).

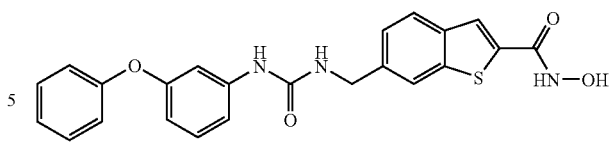

6-[3-(3-Phenoxy-phenyl)-ureidomethyl]-benzo[b]thiophene-2-carboxylic acid hydroxyamide. $^1$H NMR (DMSO-d$_6$, 200 MHz) 8.70 (br s, 1H), 7.69 (d, J=5.4 Hz, 2H), 7.30-7.80 (m, 9H), 6.67 (br s, 1H), 6.38 (d, J=8.2 Hz, 1H), 4.22 (br s, 2H). MS(ES+): Cal'd. 434.12 (MH$^+$), exp. 434.21 (MH$^+$).

Acylated compounds from 5-aminobenzothiophenes

Amides

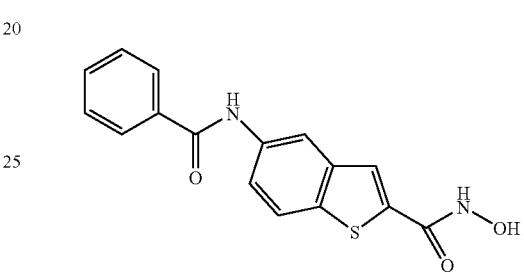

5-Benzoylamino-benzo[b]thiophene-2-carboxylic acid hydroxyamide. To 5-benzoylamino-benzo[b]thiophene-2-carboxylic acid ethyl ester (102.9 mg, 0.32 mmol) were added NH$_2$OH.HCl (76.2 mg, 0.97 mmol) and 5 mL of anhydrous MeOH. A solution of NaOMe (4.37 M in MeOH, 0.50 mL, 2.18 mmol) was added. The resulting mixture was allowed to stir at rt for 2 days. The reaction mixture was concentrated and the residue was dissolved in a minimal amount of water. After extracted with 5 mL of hexanes/EtOAc (4:1), the aqueous layer was acidified with 2N aqueous HCl to pH≈7. The precipitate was filtered, collected and dried to give 5-benzoylamino-benzo[b]thiophene-2-carboxylic acid hydroxyamide as a pale solid. $^1$H NMR (DMSO-d$_6$, 200 MHz) δ 10.41 (s, 1H), 8.44 (s, 1H), 8.10-7.82 (m, 4H), 7.76 (dd, J=8.7, 2.1 Hz, 1H), 7.68-7.35 (m, 4H). MS (EI): cal'd 313.1 (MH$^+$), exp 313.2 (MH$^+$).

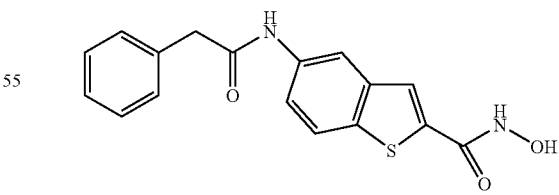

5-Phenylacetylamino-benzo[b]thiophene-2-carboxylic acid hydroxyamide. $^1$H NMR (DMSO-d$_6$, 200 MHz) 10.36 (s, 1H), 8.28 (s, 1H), 7.91 (d, J=8.4 Hz, 1H), 7.82 (s, 1H), 7.52 (d, J=8.4 Hz, 1H), 7.45-7.00 (m, 5H), 3.67 (s, 2H). MS (EI): cal'd 327.1 (MH$^+$), exp. 327.3 (MH$^+$).

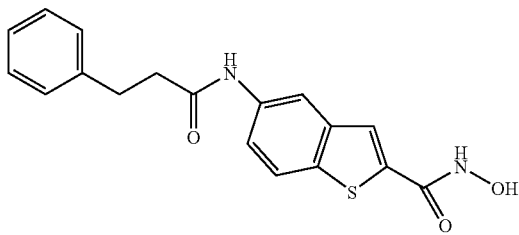

5-(3-Phenyl-propionylamino)-benzo[b]thiophene-2-carboxylic acid hydroxyamide. $^1$H NMR (DMSO-$d_6$, 200 MHz) δ 10.08 (s, 1H), 8.28 (s, 1H), 7.90 (d, J=8.8 Hz, 1H), 7.84 (s, 1H), 7.48 (dd, J=8.8, 1.8 Hz, 1H), 7.39-6.90 (m, 5H), 2.93 (t, J=7.2 Hz, 2H), 2.65 (t, J=7.2 Hz, 2H). MS (EI): cal'd 341.1 (MH$^+$), exp 341.2 (MH$^+$).

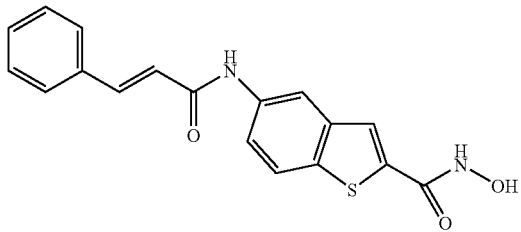

5-(3-Phenyl-acryloylamino)-benzo[b]thiophene-2-carboxylic acid hydroxyamide. $^1$H NMR (DMSO-$d_6$, 200 MHz) δ 10.45 (s, 1H), 8.42 (s, 1H), 8.10-7.20 (m, 9H), 6.88 (d, J=15.6 Hz, 1H). MS (EI): cal'd 339.1 (MH$^+$), exp 339.3 (MH$^+$).

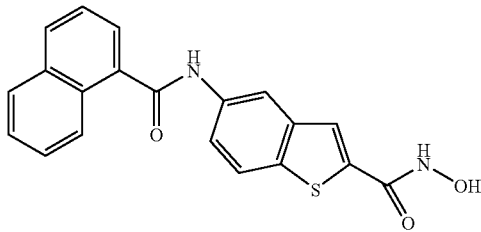

5-[(Naphthalene-1-carbonyl)-amino]-benzo[b]thiophene-2-carboxylic acid hydroxyamide. $^1$H NMR (DMSO-$d_6$, 200 MHz) δ 10.74 (s, 1H), 8.54 (s, 1H), 8.28-7.86 (m, 5H), 7.84-7.48 (m, 5H). MS (EI): cal'd 363.1 (MH$^+$), exp 363.3 (MH$^+$).

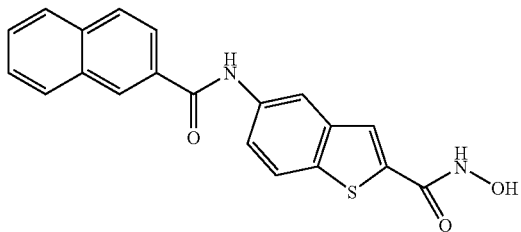

5-[(Napthalene-2-carbonyl)-amino]-benzo[b]thiophene-2-carboxylic acid hydroxyamide. $^1$H NMR (DMSO-$d_6$, 200 MHz) δ 10.59 (s, 1H, 8.61 (s, 1H), 8.49 (d, J=1.4 Hz, 1H), 8.18-7.74 (m, 7H), 7.72-7.50 (m, 2H). MS (EI): cal'd 363.1 (MH$^+$), exp 363.3 (MH$^+$).

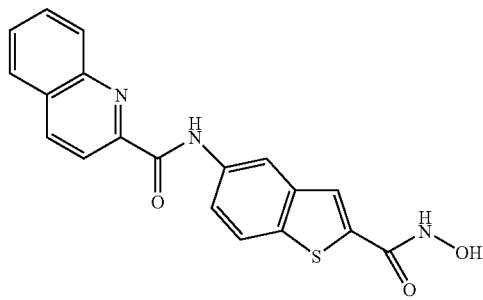

Quinoline-2-carboxylic acid (2-hydroxycarbamoyl-benzo[b]thiophen-5-yl)-amide. $^1$NMR (DMSO-$d_6$, 200 MHz) δ 11.50 (brs, 1H), 10.92 (s, 1H), 9.30 (brs, 1H), 8.84-8.50 (m, 2H), 8.40-8.20 (m, 2H), 8.20-7.86 (m, 5H), 7.76 (dd, J=7.2, 7.2 Hz, 1H). MS (EI): cal'd 364.1 (MH$^+$), exp 364.3 (MH$^+$).

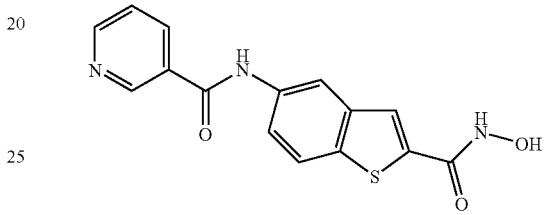

N-(2-Hydroxycarbamoyl-benzo[b] thiophen-5-yl)-nicotinamide. $^1$H NMR (DMSO-$d_6$, 200 MHz) δ 11.47 (brs, 1H), 10.60 (s, 1H), 9.30 (brs, 1H), 9.13 (d, J=1.4 Hz, 1H), 8.77 (dd, J=4.6, 1.4 Hz, 1H), 8.44 (d, J=1.4 Hz, 1H), 8.32 (ddd, J=7.8, 1.8, 1.8 Hz, 1H), 8.00 (d, J=8.8 Hz, 1H), 7.91 (s, 1H), 7.74 (dd, J=8.8, 1.8 Hz, 1H), 7.58 (dd, J=7.8, 4.6 Hz, 1H). MS (EI): cal'd 314.0 (MH$^+$), exp 314.2 (MH$^+$).

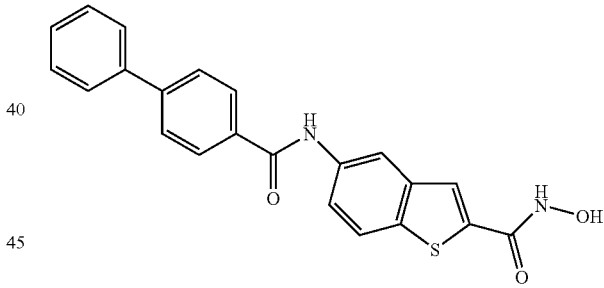

5-[(Biphenyl-4-carbonyl)-amino]-benzo[b]thiophene-2-carboxylic acid hydroxyamide. $^1$H NMR (DMSO-$d_6$, 200 MHz) δ 8.14-7.94 (m, 3H), 7.86-7.60 (m, 6H), 7.58-7.32 (m, 4H). MS (EI): cal'd 389.1 (MH$^+$), exp 389.3 (MH$^+$).

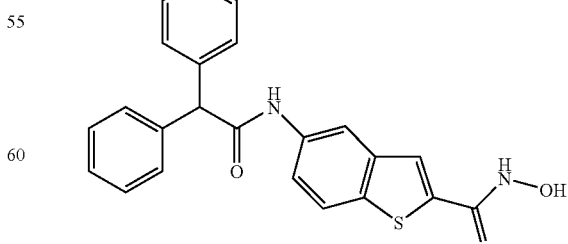

5-Diphenylacetylamino-benzo[b]thiophen-2-carboxylic acid hydroxyamide. $^1$H NMR (DMSO -$d_6$, 200 MHz) δ 10.60

(s, 1H), 8.36 (s, 1H), 8.20-6.40 (m, 13H), 5.20 (s, 1H). MS (EI): cal'd 403.1 (MH$^+$), exp 403.4 (MH$^+$).

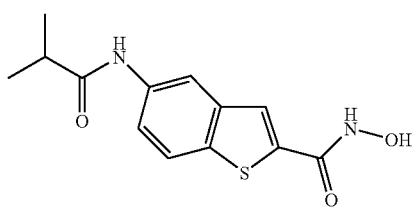

5-Isobutyrylamino-benzo[b]thiophen-2-carboxylic acid hydroxyamide. $^1$H NMR (DMSO-d$_6$, 200 MHz) δ 11.41 (brs, 1H), 9.98 (s, 1H), 9.27 (brs, 1H), 8.32 (d, J=1.8 Hz, 1H), 8.11 (d, J=8.8 Hz, 1H), 7.84 (s, 1H), 7.52 (dd, J=8.8, 2.0 Hz, 1H), 2.61 (?, J=6.8 Hz, 1H), 1.10 (d, J=6.8 Hz, 6H). MS (EI): cal'd 279.1 (MH$^+$), exp 279.3 (MH$^+$).

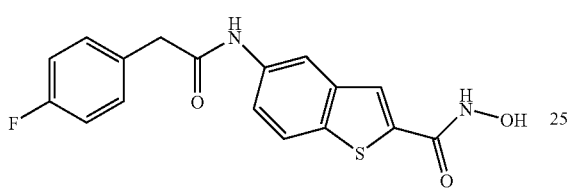

5-[2-(4-Fluoro-phenyl)-acetylamino]-benzo[b]thiophene-2-carboxylic acid hydroxyamide. $^1$H NMR (DMSO-d$_6$, 200 MHz) δ 11.43 (brs, 1H), 10.34 (s, 1H), 9.28 (brs, 1H), 8.29 (d, J=2.0 Hz, 1H), 7.92 (d, J=8.8 Hz, 1H), 7.84 (s, 1H), 7.51 (dd, J=8.8, 1.6 Hz, 1H), 7.44-7.28 (m, 2H), 7.24-7.04 (m, 2H), 3.67 (s, 2H). MS (EI): cal'd 345.1 (MH$^+$), exp 345.2 (MH$^+$).

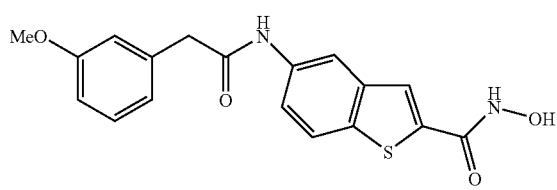

5-[2-(3-Methoxy-phenyl)-acetylamino]-benzo[b]thiophene-2-carboxylic acid hydroxyamide. $^1$H NMR (DMSO-d$_6$, 200 MHz) δ 10.36 (brs, 1H), 8.24 (s, 1H), 7.86 (d, J=8.4 Hz, 1H), 7.73 (s, 1H), 7.49 (d, J=9.8 Hz, 1H), 7.23 (dd, J=8.1, 8.1 Hz, 1H), 7.00-6.60 (m, 3H), 3.73 (s, 3H), 3.63 (s, 2H). MS (EI): cal'd 357.1 (MH$^+$), exp 357.3 (MH$^+$).

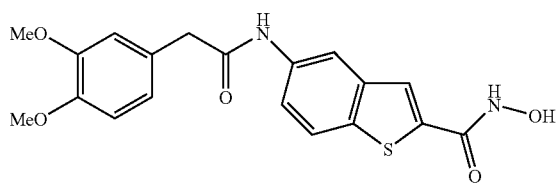

5-[2-(3,4-Dimethoxy-phenyl)-acetylamino]-benzo[b]thiophene-2-carboxylic acid hydroxyamide. $^1$H NMR (DMSO-d$_6$, 200 MHz) δ 10.27 (brs, 1H), 8.26 (s, 1H), 7.89 (d, J=8.8 Hz, 1H), 7.78 (s, 1H), 7.50 (d, J=8.6 Hz, 1H), 7.10-6.70 (m, 3H), 3.74 (s, 3H), 3.71 (s, 3H), 3.57 (s, 2H). MS (EI): cal'd 387.1 (MH$^+$), exp 387.3 (MH$^+$).

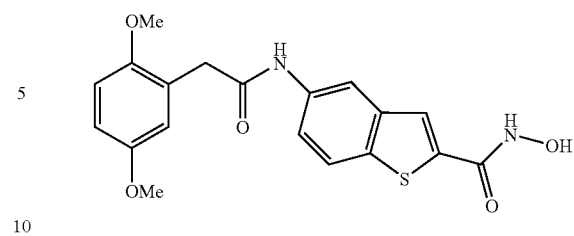

5-[2-(2,5-Dimethoxy-phenyl)-acetylamino]-benzo[b]thiophene-2-carboxylic acid hydroxyamide. $^1$H NMR (DMSO-d$_6$, 200 MHz) δ 10.22 (brs, 1H), 8.29 (d, J=1.6 Hz, 1H), 7.90 (d, J=8.8 Hz, 1H), 7.81 (s, 1H), 7.51 (dd, J=8.8, 1.8 Hz, 1H), 7.05-6.60 (m, 3H), 3.70 (s, 3H), 3.69 (s, 3H), 3.63 (s, 2H). MS (EI): cal'd 387.1 (MH$^+$), exp 387.3 (MH$^+$).

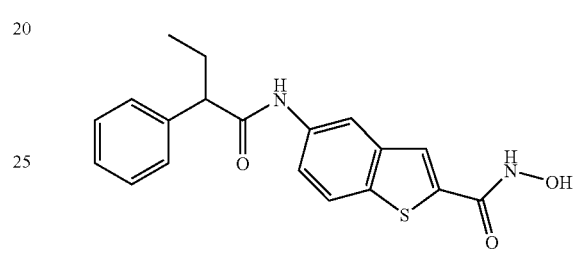

5-(2-Phenyl-butyrylamino)-benzo[b]thiophene-2-carboxylic acid hydroxyamide. $^1$H NMR (DMSO-d$_6$, 200 MHz) δ 10.26 (brs, 1H), 8.28 (s, 1H), 7.87 (d, J=8.8 Hz, 1H), 7.77 (s, 1H), 7.60-7.10 (m, 6H), 3.58 (t, J=7.5 Hz, 1H), 2.18-1.92 (m, 1H), 1.82-1.58 (m, 1H), 0.86 (t, J=7.1 Hz, 3H). MS (EI): cal'd 355.1 (MH$^+$), exp 355.3 (MH$^+$).

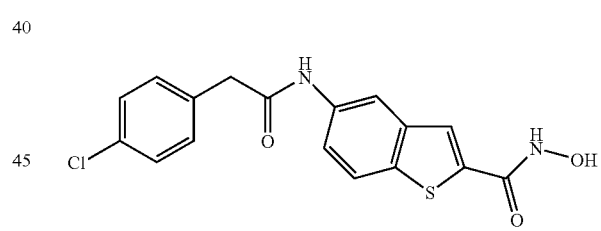

5-[2-(4-Chloro-phenyl)-acetylamino]-benzo[b]thiophene-2-carboxylic acid hydroxyamide. MS (EI): cal'd 361.0 (MH$^+$), exp 361.2 (MH$^+$).

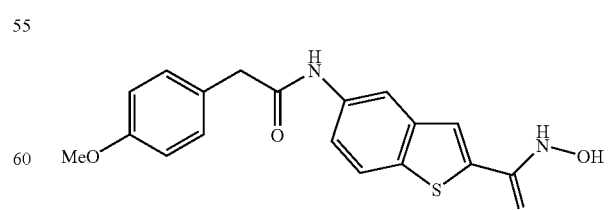

5-[2-(4-Methoxy-phenyl)-acetylamino]-benzo[b]thiophene-2-carboxylic acid hydroxyamide. MS (EI): cal'd 357.1 (MH$^+$), exp 357.2 (MH$^+$).

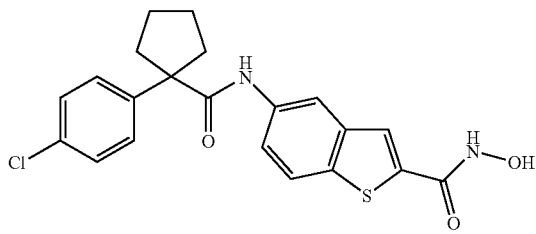

5-{[1-(4-Chloro-phenyl)-cyclopentanecarbonyl]-amino}-benzo[b]thiophene-2-carboxylic acid hydroxyamide. MS (EI): cal'd 415.1 (MH$^+$), exp 415.2 (MH$^+$).

Sulphonamides

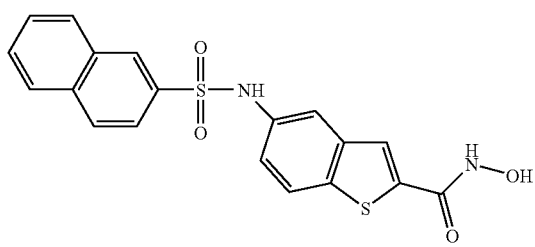

5-(Naphthalene-2-sulfonylamino)-benzo[b]thiophene-2-carboxylic acid hydroxyamide. Using a procedure similar to that of 5-benzoylamino-benzo[b]thiophene-2-carboxylic acid hydroxyamide, 5-(naphthalene-2-sulfonylamino)-benzo[b]thiophene-2-carboxylic acid ethyl ester (163.6 mg, 0.40 mmol) was converted into 5-(naphthalene-2-sulfonylamino)-benzo[b]thiophene-2-carboxylic acid hydroxyamide as a pale solid. $^1$H NMR (DMSO-d$_6$, 200 MHz) δ 8.41 (s, 1H), 8.20-7.86 (m, 3H), 7.86-7.40 (m, 6H), 7.15 (d, J=8.4 Hz, 1H). MS (EI): cal'd 399.04 (MH$^+$), exp 399.31 (MH$^+$).

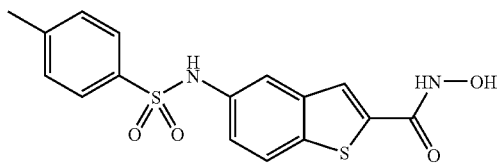

5-(Toluene-4-sulfonylamino)-benzo[b]thiophene-2-carboxylic acid hydroxyamide. $^1$H NMR (DMSO-d$_6$) δ 10.30 (br s, 1H), 9.25 (br s, 1H), 7.90-7.70 (m, 2H), 7.68-7.50 (m, 3H), 7.27 (d, J=8.4 Hz, 2H), 7.12 (dd, J=8.4, 1.6 Hz, 1H), 2.27 (s, 3H). MS (EI): cal'd (MH$^+$) 363.0, exp (MH$^+$), 363.2.

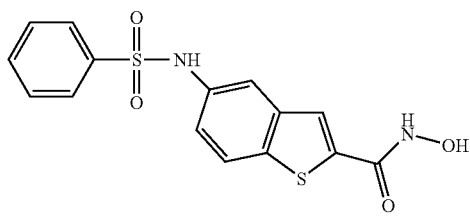

5-Benzenesulfonylamino-benzo[b]thiophene-2-carboxylic acid hydroxyamide. $^1$H NMR (DMSO-d$_6$, 200 MHz) δ 7.85 (d, J=8.8 Hz, 1H), 7.80-7.68 (m, 3H), 7.62-7.42 (m, 4H), 7.16 (dd, J=8.6, 2.0 Hz, 1H). MS (EI): cal'd 349.0 (MH$^+$), exp 349.3 (MH$^+$).

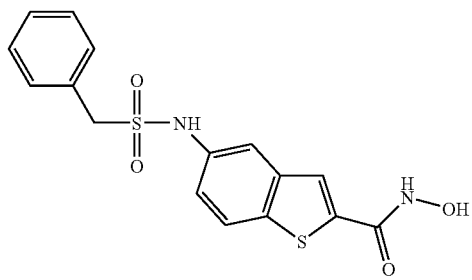

5-Phenylmethanesulfonylamino-benzo[b]thiophene-2-carboxylic acid hydroxyamide. $^1$H NMR (DMSO-d$_6$, 200 MHz) δ 7.95 (d, J=8.8 Hz, 1H), 7.84 (s, 1H), 7.68 (s, 1H), 7.44-7.10 (m, 6H), 4.48 (s, 2H). MS (EI): cal'd 363.0 (MH$^+$), exp 363.3 (MH$^+$).

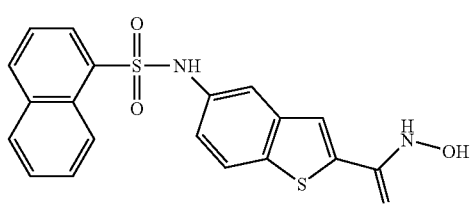

5-(Naphthalene-1-sulfonylamino)-benzo[b]thiophene-2-carboxylic acid hydroxyamide. $^1$H NMR (DMSO-d$_6$, 200 MHz) δ 8.75 (d, J=8.4 Hz, 1H), 8.30-7.94 (m, 3H), 7.88-7.38 (m, 6H), 7.08 (dd, J=8.6, 2.2 Hz, 1H). MS (EI): cal'd 399.0 (MH$^+$), exp 399.2 (MH$^+$).

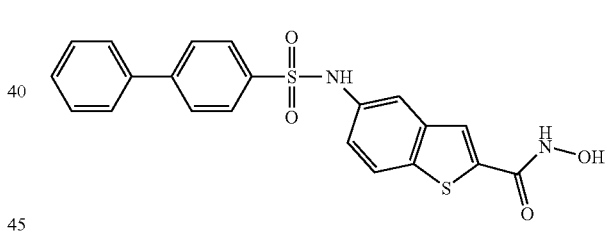

5-(Biphenyl-4-sulfonylamino)-benzo[b]thiophene-2-carboxylic acid hydroxyamide. $^1$H NMR (DMSO-d$_6$, 200 MHz) δ 7.92-7.73 (m, 6H), 7.72-7.58 (m, 3H), 7.53-7.35 (m, 3H), 7.21 (dd, J=8.8, 1.8 Hz, 1H). MS (EI): cal'd 425.1 (MH$^{30}$), exp 425.3 (MH$^+$).

Ureas/Carbamates

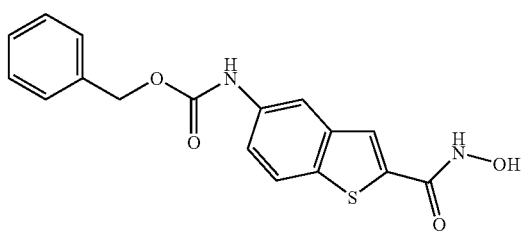

(2-Hydroxycarbamoyl-benzo[b]thiophen-5-yl)-carbamic acid benzyl ester. $^1$H NMR (DMSO-d$_6$, 200 MHz) δ 9.94 (s, 1H), 8.08 (s, 1H), 7.89 (d, J=8.8 Hz, 1H), 7.82 (s, 1H), 7.60-7.10 (m, 6H), 5.17 (s, 2H). MS (EI): cal'd 343.1 (MH+), exp 343.3 (MH+).

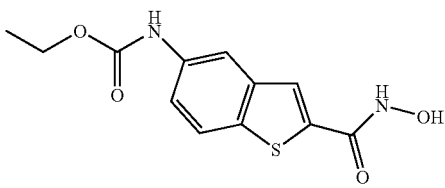

(2-Hydroxycarbamoyl-benzo[b]thiophen-5-yl)-carbamic acid ethyl ester. $^1$H NMR (DMSO d$_6$, 200 MHz) δ 11.43 (brs, 1H), 9.78 (s, 1H), 9.28 (brs, 1H), 8.07 (d, J=1.8 Hz, 1H), 7.88 (d, J=9.2 Hz, 1H), 7.82 (s, 1H), 7.45 (dd, J=8.8, 2.2 Hz, 1H), 4.14 (q, J=7.0 Hz, 2H), 1.25 (t, J=7.0 Hz, 3H). MS (EI): cal'd 281.0 (MH+), exp 281.2 (MH+).

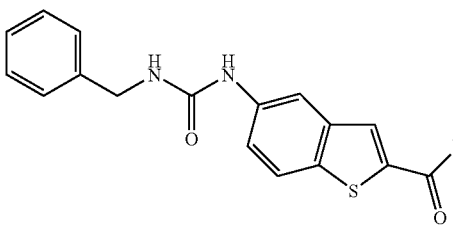

5-(3-Benzyl-ureido)-benzo[b]thiophene-2-carboxylic acid hydroxyamide. $^1$H NMR (DMSO-d$_6$, 200 MHz) δ 11.40 (brs, 1H), 9.25 (brs, 1H), 8.74 (s, 1H), 8.10 (s, 1H), 8.00-7.60 (m, 2H), 7.55-7.10 (m, 5H), 6.70 (brs, 1H), 4.31 (d, J=4.4 Hz, 2H). MS (EI): cal'd 342.1 (MH+), exp 342.3 (MH+).

Alkylated Compounds from 5- and 6-aminobenzothiophenes

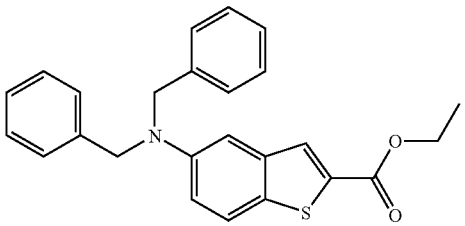

5-Dibenzylamino-benzo[b]thiophene-2-carboxylic acid ethyl ester. Ethyl 5-aminobenzothiophene-2-carboxylate (74 mg, 0.344 mmol) was dissolved in 1 mL of anhydrous DMF and reacted with benzyl bromide (100 μL, 0.84 mmol) in the presence of potassium carbonate (97 mg, 0.70 mmol) at 80° C. under a nitrogen atmosphere for 16 h. The reaction mixture was diluted with water and sat. sodium bicarbonate and extracted with ethyl acetate. The organic phase was dried over sodium sulfate. The solvent was removed under reduced pressure and the crude left under high vacuum overnight. It was used in the next step without further purification. MS (EI): cal'd 402 (MH+), exp 402 (MH+).

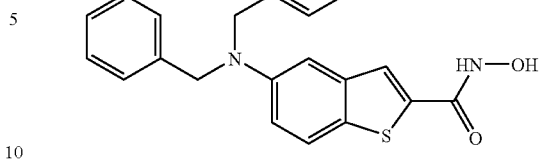

5-Dibenzylamino-benzo[b]thiophene-2-carboxylic acid hydroxyamide. The crude ethyl ester was solubilized in a mixture of anhydrous methanol (1 mL) and DMF (2 mL). Hydroxylamine hydrochloride (175 mg, 2.52 mmol) was added to the solution, followed by a 4.37 M NaOMe solution (1 mL, 4.37 mmol). The reaction was stirred under a nitrogen atmosphere for 16 h. Water (5 mL) was added to the reaction and the pH was brought to 6 by addition of 1M HCl. The precipitate was collected and purified by column chromatography (Silica gel, Hexanes: EtOAc 80:20-20:80) and isolated as an oil. $^1$H-NMR (d$_6$-DMSO): δ=11.27 (s, 1H), 9.17 (s, 1H), 7.68 (d, J=9.2 Hz, 1H), 7.60 (s, 1H), 7.4-7.2 (m, 10H), 7.1-6.9 (m, 2H), 4.75 (s, 4H). MS (EI): cal'd 389 (MH+), exp 389 (MH+).

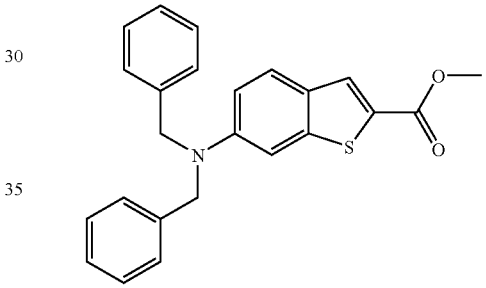

6-Dibenzylamino-benzo[b]thiophene-2-carboxylic acid methyl ester. Methyl 6-aminobenzothiophene-2-carboxylate (29 mg, 0.140 mmol) was dissolved in 1 mL of anhydrous DMF and reacted with benzyl bromide (40 μL, 0.38 mmol) in the presence of potassium carbonate (41 mg, 0.30 mmol) at 80° C. under a nitrogen atmosphere for 16 h. The reaction mixture was used in the next step without further purification. MS (EI): cal'd 388 (MH+), exp 388 (MH+).

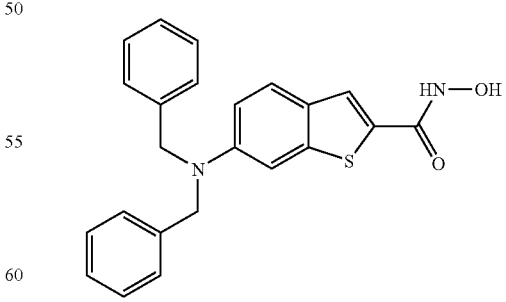

6-Dibenzylamino-benzo[b]thiophene-2-carboxylic acid hydroxyamide. The crude methyl ester DMF solution was treated with 0.7 mL of a 50% aqueous hydroxylamine solution. Some DMA (0.5 mL) was added to avoid precipitation. The reaction was stirred at room temperature for 40 h, then additional hydroxylamine (0.7 mL) was added. The total reaction time was 5 days. The solvent was removed under high vacuum and the oily residue was triturated with methanol. The insoluble product was collected by filtration as a solid. ¹H-NMR (d₆-DMSO): δ=10.31 (s, 1H), 9.08 (s, 1H), 8.64 (s, 1H), 7.66 (s, 1H), 7.60 (d, J=8.8 Hz, 1H), 7.4-7.2 (m, 10H), 6.88 (dd, J1=8.8 Hz, J2=1.4 Hz, 1H), 4.78 (s, 4H). MS (EI): cal'd 389 (MH⁺), exp 389 (MH⁺).

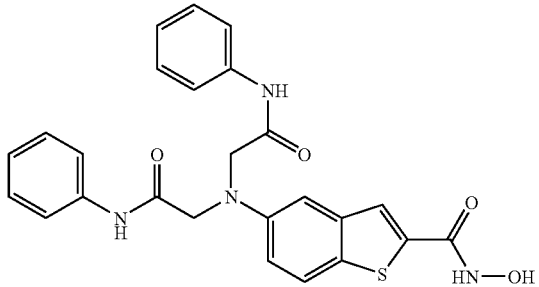

5-(Bis-phenylcarbamoylmethyl-amino)-benzo[b]thiophene-2-carboxylic acid hydroxyamide. ¹H NMR (DMSO-d₆) δ 10.74 (s, 1H), 10.34 (s, 1H), 10.21 (br s, 1H), 7.66-7.26 (m, 11H), 7.07 (t, J=6.6 Hz, 2H), 6.49 (d, J=15.8 Hz, 1H), 4.33 (s, 2H), 4.20 (s, 1H). MS (EI): cal'd (MH⁺) 475.1, exp (MH⁺), 475.2.

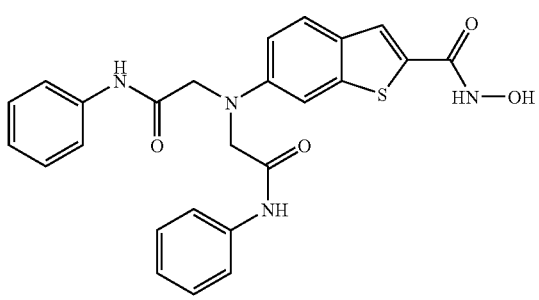

6-(Bis-phenylcarbamoylmethyl-amino)-benzo[b]thiophene-2-carboxylic acid hydroxyamide. ₁H NMR (DMSO-d₆) δ 10.88 (s, 2H), 9.10 (br s, 1H), 7.76-7.63 (m, 6H), 7.34 (t, J=7.0 Hz, 4H), 7.07 (t, J=7.2 Hz, 3H), 6.74 (d, J=9.08 Hz, 1H), 4.44 (s, 4H). MS (EI): cal'd (MH⁺) 475.1, exp (MH⁺), 475.2.

Procedure for chloride Displacement and Resultant Compounds from 6-aminobenzothiophenes

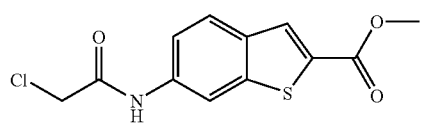

6-(2-Chloro-acetylamino)-benzo[b]thiophene-2-carboxylic acid methyl ester. To a mixture of 6-amino-benzo[b]thiophene-2-carboxylic acid methyl ester (1.0 g, 4.83 mmol) and Na₂CO₃ (2.05 g, 19.3 mmol) in DMF (10 mL) was added chloroacetylchloride (460 μL, 5.79 mmol). After stirring for 18 h, the mixture was diluted with EtOAc, filtered and concentrated. The residue was purified by column chromatography (2:8; EtOAc:hexanes) to give a pale-white solid. MS (EI): cal'd (MH⁺) 284.01, exp (MH⁺) 284.15. Also retained ~50.5% of impure fractions.

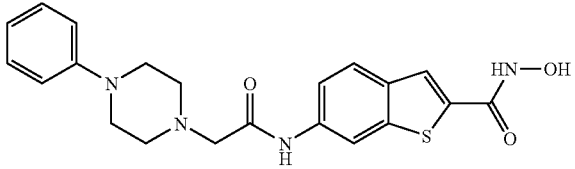

General Experimental for Acylated 6-Amino-benzothiophenes (From Chloride).

6-[2-(4-Phenyl-piperazin-1-yl)-acetylamino]-benzo[b]thiophene-2-carboxylic acid hydroxyamide. To a solution of 6-(2-chloro-acetylamino)-benzo[b]thiophene-2-carboxylic acid methyl ester (75 mg, 0.26 mmol) in DMF (2 mL) was added amine (85.8 mg, 0.52 mmol). The reaction mixture was heated to 50° C. After 24 h, NH₂OH (50% aq., 1 mL) was added to the solution. The solution was stirred until the disappearance of starting material. After removal of solvent, MeOH/H₂O was added until a precipitate forms. The solid was filtered yielding the desired amide. ¹H NMR (DMSO-d₆) δ 11.32 (br s, 1H), 9.97 (s, 1H), 9.28 (br s, 1H), 8.39 (s, 1H), 7.85-7.72 (m, 2H), 7.55 (d, J=7.0 Hz, 1H), 7.24-7.10 (m, 2H), 6.94-6.84 (m, 2H), 6.72 (t, J=7.0 Hz, 1H), 3.24-3.05 (m, 5H), 2.70-2.58 (m, 4H). MS (EI): cal'd (MH⁺) 411.14, exp (MH⁺) 411.33.

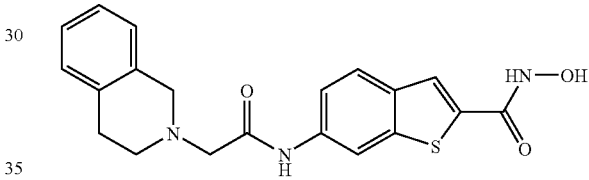

6-(2-3,4-Dihydro-1H-isoquinolin-2-yl-acetylamino)-benzo[b]thiophene-2-carboxylic acid hydroxyamide. ¹H NMR (DMSO-d₆) δ 11.37 (br s, 1H), 10.00 (s, 1H), 9.20 (br s, 1H), 8.41 (s, 1H), 7.85-7.75 (m, 2H), 7.56 (d, J=8.6 Hz, 1H), 7.15-6.99 (m, 4H), 3.71 (s, 2H), 3.35-3.15 (m, 2H), 2.92-2.72 (m, 4H). MS (EI): cal'd (MH⁺) 382.1, exp (MH⁺), 382.3.

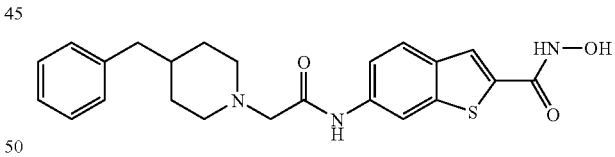

6-[2-(4-Benzyl-piperidin-1-yl)-acetylamino]-benzo[b]thiophene-2-carboxylic acid hydroxyamide. ¹H NMR (CDCl₃) δ 11.32 (br s, 1H), 9.876 (s, 1H), 9.21 (br s, 1H), 8.37 (s, 1H), 7.87-7.74 (m, 2H), 7.52 (dd, 1H, J=8.2, 1.8 Hz), 7.30-7.05 (m, 5H), 3.07 (s, 2H), 2.88-2.74 (m, 2H), 2.54-2.44 (m, 2H), 2.14-1.94 (m, 2H), 1.60-1.20 (m, 5H). MS (EI): cal'd 424.1 (MH+), exp 424.4 (MH+).

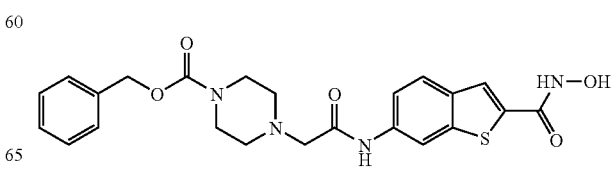

4-[(2-Hydroxycarbamoyl-benzo[b]thiophen-6-ylcarbamoyl)-methyl]-piperazine-1-carboxylic acid benzyl ester. ¹H NMR (CDCl₃) δ 11.28 (br s, 1H), 9.96 (s, 1H), 9.20 (br s, 1H), 8.37 (s, 1H), 7.87-7.72 (m, 2H), 7.52 (dd, 1H, J=8.2, 1.8 Hz), 7.40-7.14 (m, 5H), 5.04 (s, 2H), 3.43 (m, 4H), 3.28 (m, 4H), 3.16 (s, 2H). MS (EI): cal'd 469.1 (MH+), exp 469.3 (MH+).

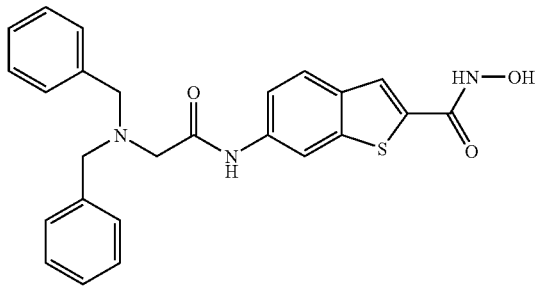

6-(2-Dibenzylamino-acetylamino)-benzo[b]thiophene-2-carboxylic acid hydroxyamide. ¹NMR (CDCl₃) δ 9.83 (s, 1H), 9.21 (br s, 1H), 8.35 (s, 1H), 7.83-7.71 (m, 2H), 7.45-7.15 (m, 11H), 3.74 (s, 4H), 3.15 (s, 2H). MS (EI): cal'd 446.1 (MH+), exp 446.3 (MH+).

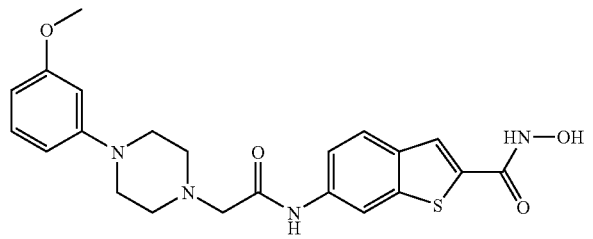

6-{2-[4-(3-Methoxy-phenyl)-piperazin-1-yl-acetylamino}-benzo[b]thiophene-2-carboxylic acid hydroxyamide. ¹H NMR (CDCl₃) δ 11.38 (br s, 1H), 9.97 (s, 1H), 9.21 (br s, 1H), 8.39 (s, 1H), 7.87-7.75 (m, 2H), 7.56 (dd, 1H, J=8.0, 1.8 Hz), 7.07 (dd, 1H, J=8.0, 7.9 Hz), 6.49 (d, 1H, J=8.0 Hz), 6.42 (s, 1H), 6.32 (d, 1H, J=8.0 Hz), 3.67 (s, 3H), 3.20 (s, 2H), 3.15 (m, 4H), 2.63 (m, 4H). MS (EI): cal'd 441.1 (MH+), exp 441.3 (MH+).

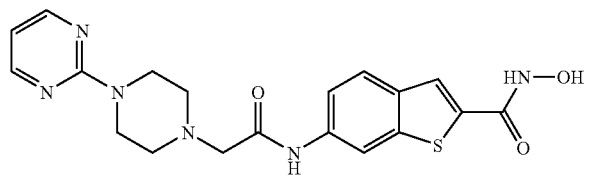

6-[2-(4-Pyrimidin-2-yl-piperazin-1-yl)-acetylamino]-benzo[b]thiophene-2-carboxylic acid hydroxyamide. ¹H NMR (CDCl₃) δ 11.38 (br s, 1H), 10.00 (s, 1H), 9.20 (br s, 1H), 8.39 (s, 1H), 8.32 (d, 2H, J=4.8 Hz), 7.85-7.75 (m, 2H), 7.56 (dd, 1H, J=8.0, 1.8 Hz), 6.58 (t, 1H, J=4.8 Hz), 3.77 (m, 4H), 3.19 (s, 2H), 2.54 (m, 4H). MS (EI): cal'd 413.1 (MH+), exp 413.3 (MH+).

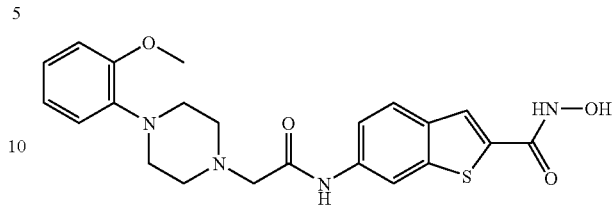

6-{2-[4-(2-Methoxy-phenyl)-piperazin-1-yl]-acetylamino}-benzo[b]thiophene-2-carboxylic acid hydroxyamide. ¹H NMR (CDCl₃) δ 11.38 (br s, 1H), 9.98 (s, 1H), 9.21 (br s, 1H), 8.40 (s, 1H), 7.88-7.74 (m, 2H), 7.56 (d, 1H, J=8.2 Hz), 6.94-6.79 (m, 4H), 3.73 (s, 3H), 3.19 (s, 2H), 3.00 (m, 4H), 2.65 (m, 4H). MS (EI): cal'd 441.1 (MH+), exp. 441.2 (MH+).

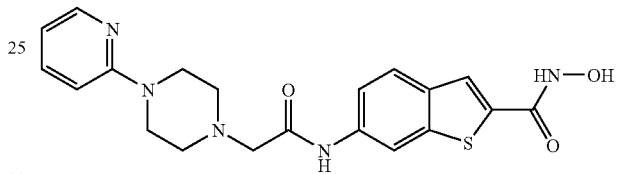

6-[2-(4-Pyridin-2-yl-piperazin-1-yl)-acetylamino]-benzo[b]thiophene-2-carboxylic acid hydroxyamide. ¹H NMR (CDCl₃) δ 11.39 (br s, 1H), 10.00 (s, 1H), 9.22 (br s, 1H), 8.40 (s, 1H), 8.07 (br d, 1H, J=2.0 Hz), 7.88-7.74 (m, 2H), 7.60-7.40 (m, 2H), 6.79 (d, 1H, J=8.3 Hz), 6.61 (dd, 1H, J=7.0, 5.2 Hz), 3.53 (m, 4H), 3.20 (s, 2H), 2.59 (m, 4H). MS (EI): cal'd 412.1 (MH+), exp 412.3 (MH+).

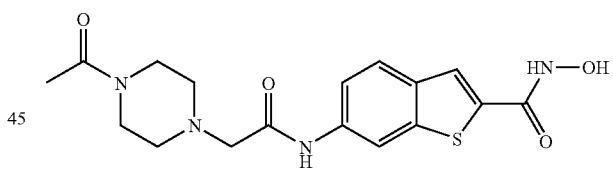

6-[2-(4-Acetyl-piperazin-1-yl)-acetylamino]-benzo[b]thiophene-2-carboxylic acid hydroxyamide. ¹H NMR (CDCl₃) δ 9.96 (s, 1H), 8.38 (s, 1H), 7.87-7.72 (m, 2H), 7.54 (d, 1H, J=8.0 Hz), 3.45 (m, 4H), 3.17 (s, 2H), 2.46 (m, 4H), 1.95 (s, 3H). MS (EI): cal'd 377.1 (MH+), exp 377.3 (MH+).

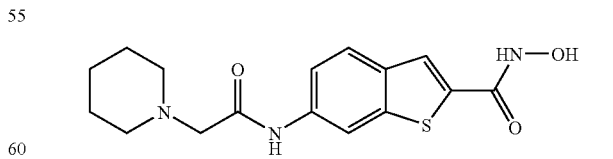

6-(2-Piperidin-1-yl-acetylamino)-benzo[b]thiophene-2-carboxylic acid hydroxyamide. ¹H NMR (CDCl₃) δ 9.86 (s, 1H), 8.38 (s, 1H), 7.87-7.72 (m, 2H), 7.55 (d, 1H, J=8.0 Hz), 3.07 (s, 2H), 2.45 (m, 4H), 1.55 (m, 4H), 1.39 (m, 2H). MS (EI): cal'd 334.1 (MH+), exp 334.3 (MH+).

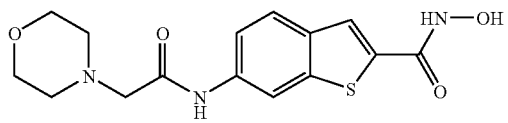

6-(2-Morpholin-4-yl-acetylamino)-benzo[b]thiophene-2-carboxylic acid hydroxyamide. $^1$H NMR (CDCl$_3$) δ 9.94 (s, 1H), 9.21 (br s, 1H), 8.38 (s, 1H), 7.87-7.72 (m, 2H), 7.54 (dd, 1H, J=8.0, 1.8 Hz), 3.61 (m, 4H), 3.13 (s, 2H), 2.48 (m, 4H). MS (EI): cal'd 336.1 (MH+), exp 336.2 (MH+).

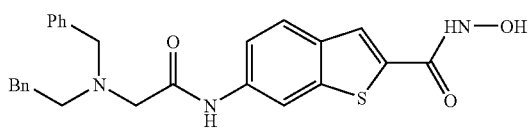

6-[2-(Benzyl-phenethyl-amino)-acetylamino]-benzo[b]thiophene-2-carboxylic acid hydroxyamide. $^1$H NMR (CDCl$_3$) δ 11.32 (br s, 1H), 9.58 (s, 1H), 9.20 (br s, 1H), 8.18 (s, 1H), 7.83-7.71 (m, 2H), 7.45-7.05 (m, 11H), 3.78 (s, 2H), 3.15 (s, 2H), 2.85-2.60 (m, 4H). MS (EI): cal'd 460.1 (MH+), exp 460.3 (MH+).

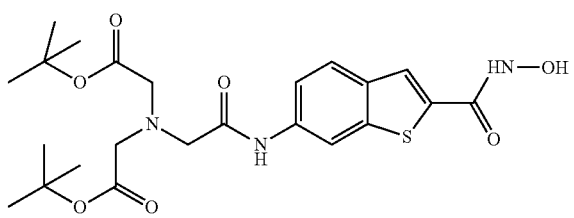

{tert-Butoxycarbonylmethyl-[(2-hydroxycarbamoyl-benzo[b]thiophen-6-ylcarbamoyl)-methyl]-amino}-acetic acid tert-butyl ester. $^1$H NMR (CDCl$_3$) δ 10.38 (s, 1H), 9.19 (br s, 1H), 8.41 (s, 1H), 7.83-7.72 (m, 2H), 7.45 (d, 2H, J=8.0 Hz), 3.49-3.45 (m, 4H), 3.15-3.11 (m, 2H), 1.38 (s, 18H). MS (EI): cal'd 494.1 (MH+), exp 494.3 (MH+).

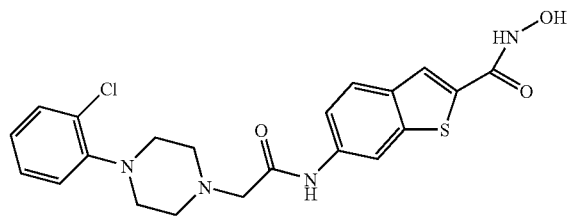

6-{2-[4-(2-Chloro-phenyl)-piperazin-1-yl]-acetylamino}-benzo[b]thiophene-2-carboxylic acid hydroxyamide. $^1$H NMR (CDCl$_3$) δ 11.31 (br s, 1H), 9.98 (s, 1H), 9.20 (br s, 1H), 8.40 (s, 1H), 7.88-7.76 (m, 2H), 7.56 (dd, 1H, J=8.2, 1.8 Hz), 7.36 (d, 1H, J=7.2 Hz), 7.27 (dd, 1H, J=7.2, 7.1 Hz), 7.14 (d, 1H, J=7.2 Hz), 7.00 (dd, 1H, J=7.2, 7.1 Hz), 3.22 (s, 2H), 3.02 (m, 4H), 2.69 (m, 4H). MS (EI): cal'd 445.1 (MH+), exp 445.2 (MH+).

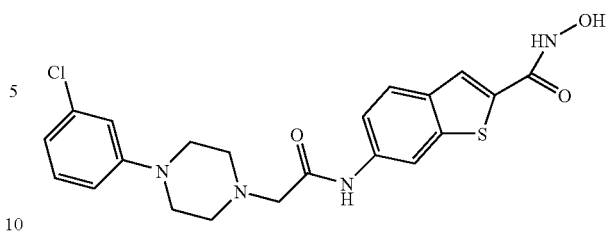

6-{2-[4-(3-Chloro-phenyl)-piperazin-1-yl]-acetylamino}-benzo[b]thiophene-2-carboxylic acid hydroxyamide. $^1$H NMR (CDCl$_3$) δ 9.98 (s, 1H), 9.20 (br s, 1H), 8.39 (s, 1H), 7.88-7.76 (m, 2H), 7.56 (d, 1H, J=8.2 Hz), 7.17 (dd, 1H, J=7.2, 7.1 Hz), 6.95-6.82 (m, 2H), 6.74 (d, 1H, J=7.2 Hz), (s, 1H), 3.26 (m, 4H), 3.20 (s, 2H), 2.63 (m, 4H). MS (EI): cal'd 445.1 (MH+), exp 445.2 (MH+).

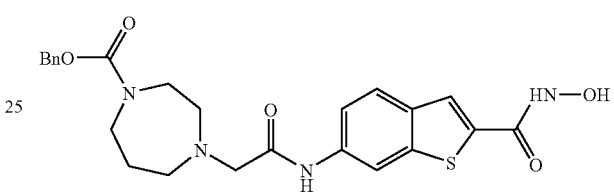

4-[(2-Hydroxycarbamoyl-benzo[b]thiophen-6-ylcarbamoyl)-methyl]-[1,4]diazepane-1-carboxylic acid benzyl ester. $^1$H NMR (CDCl$_3$) δ 10.25 (br s, 1H), 9.88 (s, 1H), 8.38 (s, 1H), 7.87-7.72 (m, 2H), 7.52 (d, 1H, J=8.0 Hz), 7.32 (m, 5H), 5.04 (s, 2H), 3.55-3.33 (m, 4H), 3.29 (s, 2H), 2.76 (m, 2H), 2.69 (m, 2H), 1.77 (m, 2H). MS (EI): cal'd 483.1 (MH+), exp 483.3 (MH+).

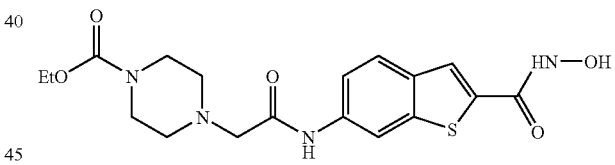

4-[(2-Hydroxycarbamoyl-benzo[b]thiophen-6-ylcarbamoyl)-methyl]-piperazine-1-carboxylic acid ethyl ester. $^1$H NMR (CDCl$_3$) δ 10.37 (br s, 1H), 9.94 (s, 1H), 8.37 (s, 1H), 7.87-7.72 (m, 2H), 7.54 (dd, 1H, J=8.0, 1.8 Hz), 4.02 (q, 2H, J=7.2 Hz), 3.95 (m, 4H), 3.16 (s, 2H), 1.14 (t, 3H, J=7.2 Hz). MS (EI): cal'd 407.1 (MH+), exp 407.3 (MH+).

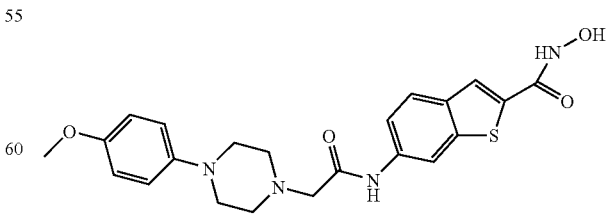

6-{2-[4-(4-Methoxy-phenyl)-piperazin-1-yl]acetylamino}-benzo[b]thiophene-2-carboxylic acid hydroxyamide. MS (EI): cal'd 441.1 (MH+), exp 441.2 (MH+).

Compounds from 6-carboxybenzothiophenes

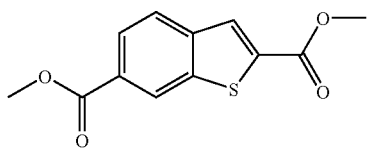

Benzo[b]thiophene-2,6-dicarboxylic acid dimethyl ester. To a mixture of methyl 4-formyl-3-nitrobenzoate (6.68 g, 31.9 mmol) and $K_2CO_3$ (5.55 g, 38.3 mmol) in DMF (70 mL) was slowly added methyl thioglycolate (2.91 mL, 31.9 mmol). The mixture was stirred at RT for 1 h, then at 50° C. for 24 h. The resultant mixture was poured into $H_2O$/ice and stirred until a precipitate formed. The green solid was filtered. $^1$H NMR (DMSO-$d_6$) δ 8.72 (s, 1H), 8.25 (s, 1H), 8.12 (d, J=8.0 Hz), 7.95 (d, J=8.0 Hz), 3.87 (s, 6H). MS (EI): cal'd (MH$^+$) 251.03, exp (MH$^+$) 251.18.

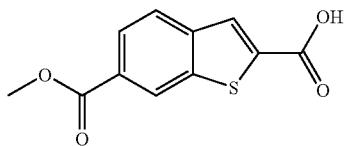

Benzo[b]thiophene-2,6-dicarboxylic acid 6-methyl ester. To a solution of benzo[b]thiophene-2,6-dicarboxylic acid dimethyl ester (139 mg, 0.56 mmol) in THF/MeOH (2/2 mL) was added 1 N NaOH (555 µL). After 5 h, the solution was diluted with $CH_2Cl_2$ and acidified with 5% citric acid. The combined organic fractions were dried, filtered, and concentrated to yield the desired acid, which was used without further purification. MS (EI): cal'd (MH$^+$) 237.01, exp (MH$^+$), 237.13.

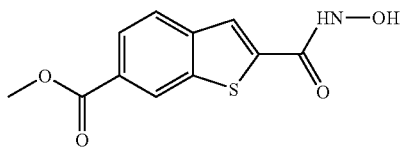

2-Hydroxycarbamoyl-benzo[b]thiophene-6-carboxylic acid methyl ester. To a solution of benzo[b]thiophene-2,6-dicarboxylic acid dimethyl ester (115 mg, 0.46 mmol) in DMA/MeOH (3/1 mL) $NH_2OH$ (50% aq., 1.5 mL). The solution was stilted until the disappearance of starting material as indicated by LC/MS. After removal of solvent, MeOH/$H_2O$ was added until a precipitate forms. The solid was filtered yielding the desired material. $^1$H NMR (DMSO-$d_6$) δ 11.57 (br s, 1H), 9.36 (br s, 1H), 8.67 (s, 1H), 8.05-7.87 (m, 3H), 3.87 (s, 3H). MS (EI): cal'd (MH$^+$) 252.07, exp (MH$^+$), 252.20.

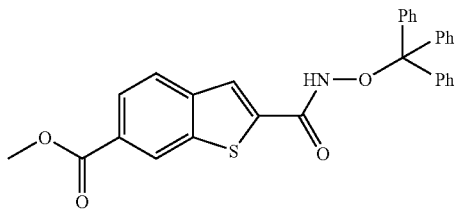

2-Trityloxycarbamoyl-benzo[b]thiophene-6-carboxylic acid methyl ester. To a solution of benzo[b]thiophene-2,6-dicarboxylic acid 6-methyl ester (3.4 g, 14.4 mmol), HOBT (2.92 g, 21.6 mmol), trityl-protected hydroxylamine (4.76 g, 17.3 mmol) in DMF (100 mL) was added EDCl (4.14 g, 21.6 mmol). After 18 h, the solvent was removed. The residue was diluted with EtOAc (200 mL), and washed with $H_2O$ (100 mL), and sat. $NaHCO_3$ (100 mL). The organic fraction was dried, filtered, and concentrated. A solid formed upon addition of MeOH to the residue. The pale yellow solid was filtered and washed with additional MeOH to yield the desired protected hydroxamic acid, which was used without further purification. $^1$H NMR (DMSO $d_6$), δ 11.37 (br s, 1H), 8.56 (br s, 1H), 8.01-7.85 (m, 3H), 7.79 (s, 1H), 7.45-7.18 (m, 15H), 3.85 (s, 3H). MS (EI): cal'd (MH$^+$) 494.1, exp (MH$^+$) did not see parent peak.

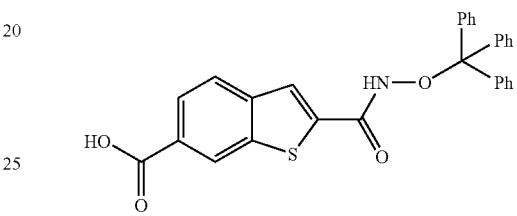

2-Trityloxycarbamoyl-benzo[b]thiophene-6-carboxylic acid. To a solution of 2-trityloxycarbamoyl-benzo[b]thiophene-6-carboxylic acid methyl ester (4.12 g, 8.35 mmol) in THF/MeOH (50/10 mL) was added 2 N NaOH (16 mL). After 1.5 h, added an additional 5 mL of 3 N NaOH. After another 1 h, added an additional 16 mL of 2 N NaOH, and stirred overnight. The solution was diluted with EtOAc (100 mL) and $H_2O$ (100 mL) and washed with EtOAc. The aqueous fractions were acidified with 5% citric acid, and extracted with EtOAc. The combined organic fractions were dried, filtered, and concentrated to yield the desired acid, which was used without further purification. MS (EI): cal'd (M$^-$), 478.1, exp (M$^-$), 478.6.

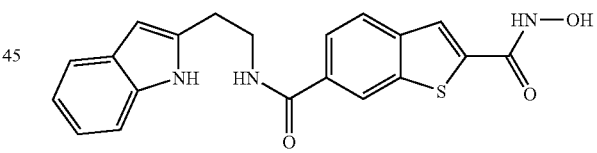

General Experimental for Amide Formation Using 6-carboxybenzothiophene.

Benzo[b]thiophene-2,6-dicarboxylic acid 2-hydroxyamide 6-{[2-(1H-indol-2-yl)-ethyl]-amide}. To a solution of 2-trityloxycarbamoyl-benzo[b]thiophene-6-carboxylic acid (130 mg, 0.271 mmol), HOBT (55.0 g, 0.407 mmol) in $CH_2Cl_2$ (3 mL) was added EDCl (78.0 mg, 0.407 mmol). After 30 min, the resultant solution was added to a solution of amine (56.5 mg, 0.352 mmol) in $CH_2Cl_2$ (1 mL). After 18 h, a solution of TFA/$CH_2Cl_2$ (1/1; 0.5 mL) was added, followed by the drop-wise addition of $Et_3SiH$ until the color faded. The solvent was removed. The residue was washed with EtOAc (2 mL), and sat. $NaHCO_3$ (1.5 mL). The resultant solid was filtered and washed with EtOAc to yield the desired hydroxamic acid. $^1$H NMR (CDCl$_3$) δ 10.75 (br s, 1H), 8.57 (m, 1H), 8.24 (s, 1H), 7.72 (s, 2H), 7.77 (d, 1H, J=7.4 Hz), 7.41 (s, 1H), 7.32-7.12 (m, 4H), 7.12-6.88 (m, 4H), 3.51 (m, 2H), 2.93 (m, 2H). MS (EI): cal'd 380.1 (MH+), exp 380.3 (MH+).

Note: in certain amide formation reactions, solids were filtered prior to trityl deprotection. Also sometimes MeOH was used to triturate the final hydroxamic acids.

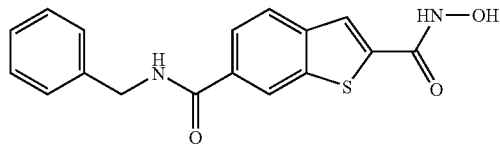

Benzo[b]thiophene-2,6-dicarboxylic acid 6-benzylamide 2-hydroxyamide. ¹H NMR (CDCl₃) δ 9.02 (br t, 1H, J=6.0 Hz), 8.32 (s, 1H), 7.80-7.70 (m, 2H), 7.44 (m, 1H), 7.36-7.15 (m, 5H), 4.46 (d, 2H, J=6.0 Hz). MS (EI): cal'd 327.1 (MH+), exp 327.2 (MH+).

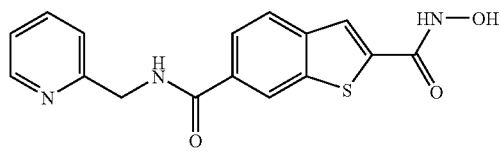

Benzo[b]thiophene-2,6-dicarboxylic acid 2-hydroxyamide 6-[(pyridin-2-ylmethyl)-amide]. ¹H NMR (CDCl₃) δ 9.15 (br t, 1H, J=5.2 Hz), 8.52-8.40 (m, 2H), 7.80-7.80 (m, 2H), 7.78-7.64 (m, 2H), 7.36-7.18 (m, 2H), 4.55 (d, 2H, J=5.2 Hz). MS (EI): cal'd 326.1 (MH+), exp 326.2 (MH+).

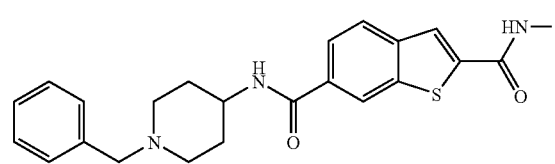

Benzo[b]thiophene-2,6-dicarboxylic acid 6-[(1-benzyl-piperidin-4-yl)-amide]2-hydroxyamide. ¹H NMR (CDCl₃) δ 8.42 (br s, 1H), 8.33 (d, 1H, J=8.1 Hz), 7.96-7.76 (m, 3H), 7.35-7.10 (m, 5H), 3.73 (m, 1H), 3.43 (s, 2H), 2.78 (m, 2H), 1.99 (m, 2H), 1.75 (m, 2H), 1.57 (m, 2H). MS (EI): cal'd 410.1 (MH+), exp 410.3 (MH+).

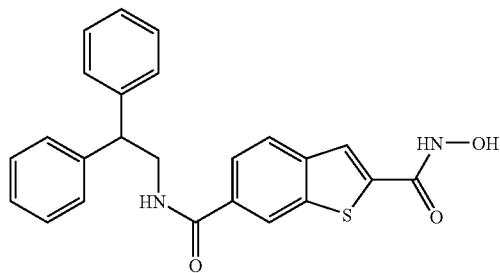

Benzo[b]thiophene-2,6-dicarboxylic acid 6-[(2,2-diphenyl-ethyl)-amide]2-hydroxyamide. ¹H NMR (CDCl₃) δ 8.61 (m, 1H), 8.30 (s, 1H), 7.92-7.82 (m, 2H), 7.70 (d, 1H, J=8.0 Hz), 7.36-7.06 (m, 10H), 4.41 (t, 1H, J=7.0 Hz), 3.90 (m, 2H). MS (EI): cal'd 417.1 (MH+), exp 417.2 (MH+).

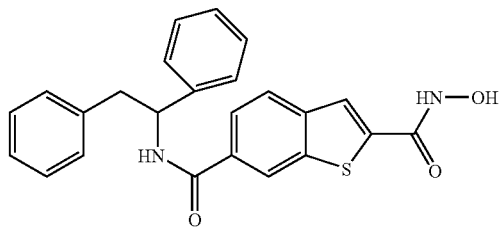

Benzo[b]thiophene-2,6-dicarboxylic acid 6-[(1,2-diphenyl-ethyl)-amide]2-hydroxyamide. ¹H NMR (CDCl₃) δ 11.51 (br s, 1H), 9.28 (br s, 1H), 8.96 (d, 1H, J=8.2 Hz), 8.40 (s, 1H), 7.92-7.82 (m, 2H), 7.77 (d, 1H, J=8.0 Hz), 7.49-7.06 (m, 10H), 5.28 (m, 1H), 3.20-3.00 (m, 2H). MS. (EI): cal'd 417.1 (MH+), exp 417.2 (MH+).

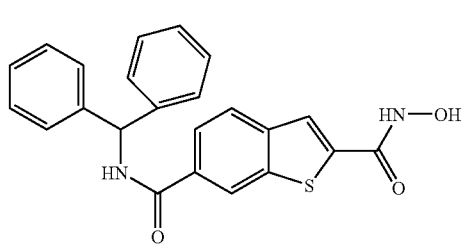

Benzo[b]thiophene-2,6-dicarboxylic acid 6-benzhydrylamide 2-hydroxyamide. ¹H NMR (CDCl₃) δ 11.51 (br s, 1H), 8.35 (d, 1H, J=8.2 Hz), 8.59 (s, 1H), 8.02-7.85 (m, 3H), 7.49-7.06 (m, 10H), 6.40 (d, 1H, 8.2 Hz). MS (EI): cal'd 403.1 (MH+), exp 403.2 (MH+).

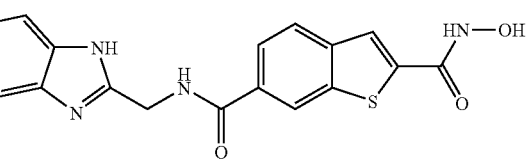

Benzo[b]thiophene-2,6-dicarboxylic acid 6-[(1H-benzoimidazol-2-ylmethyl)-amide]2-hydroxyamide ¹H NMR (CDCl₃) δ 11.57 (br s, 1H), 9.54 (br t, 1H, J=4.8 Hz), 8.59 (s, 1H), 8.12-7.88 (m, 3H), 7.71 (m, 2H), 7.42 (m, 2H), 4.90 (d, 2H, J=4.8 Hz). MS (EI): cal'd 367.1 (MH+), exp 367.2 (MH+).

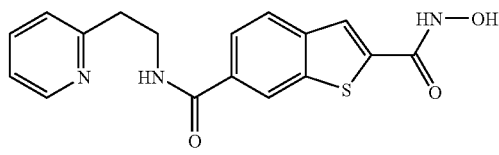

Benzo[b]thiophene-2,6-dicarboxylic acid 2-hydroxyamide 6-[(2-pyridin-2-yl-ethyl)-amide]. ¹H NMR (CDCl₃) δ 11.51 (br s, 1H), 8.80-8.59 (m, 2H), 8.39 (s, 1H), 8.15 (m, 1H), 7.92-7.82 (m, 2H), 7.77 (d, 1H, J=8.0 Hz), 7.70-7.55 (m, 2H), 3.69 (m, 2H), 3.20-3.05 (m, 2H). MS (EI): cal'd 342.1 (MH+), exp 342.2 (MH+).

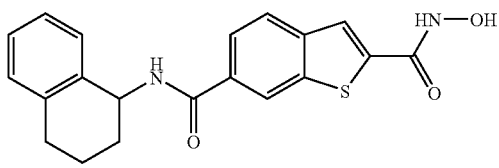

Benzo[b]thiophene-2,6-dicarboxylic acid 2-hydroxyamide 6-[(1,2,3,4-tetrahydro-naphthalen-1-yl)-amide]. $^1$H NMR (CDCl$_3$) δ 11.51 (br s, 1H), 9.30 (br s, 1H), 8.84 (d, 1H, J=8.0 Hz), 8.53 (s, 1H), 7.98-7.84 (m, 3H), 7.30-7.02 (m, 4H), 5.22 (m, 1H), 2.72 (m, 2H), 1.94 (m, 2H), 1.80 (m, 2H). MS (EI): cal'd 367.1 (MH+), exp 367.3 (MH+).

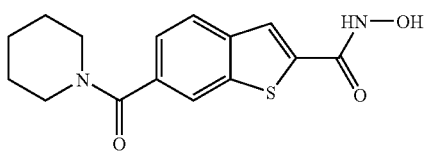

6-(Piperidine-1-carbonyl)-benzo[b]thiophene-2-carboxylic acid hydroxyamide. $^1$H NMR (CDCl$_3$) δ 9.29 (br s, 1H), 8.01 (s, 1H), 7.98-7.82 (m, 2H), 7.35 (dd, 1H, J=8.0, 1.2 Hz), 3.69-3.12 (m, 4H), 1.52 (m, 6H). MS (EI): cal'd 305.1 (MH+), exp 305.2 (MH+).

Benzo[b]thiophene-2,6-dicarboxylic acid 2-hydroxyamide 6-phenylamide. $^1$H NMR (CDCl$_3$) δ 10.32 (br s, 1H), 8.57 (s, 1H), 8.04-7.82 (m, 3H), 7.77 (d, 2H, J=7.2 Hz), 7.33 (dd, 2H, J=7.2, 7.2 Hz), 7.07 (t, 1H, 7.2 Hz). MS (EI): cal'd 313.1 (MH+), exp 313.2 (MH+).

Benzo[b]thiophene-2,6-dicarboxylic acid 2-hydroxyamide 6-indan-1-ylamide. MS (EI): cal'd 353.1 (MH+), exp 353.2 (MH+).

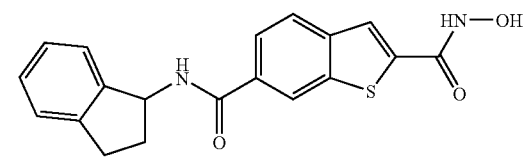

6-(4-Phenyl-piperazine-1-carbonyl)-benzo[b]thiophene-2-carboxylic acid hydroxyamide. $^1$H NMR (CDCl$_3$) δ 11.48 (br s, 1H), 9.28 (br s, 1H), 8.11 (s, 1H), 8.01-7.86 (m, 2H), 7.42 (d, 1H, J=8.1 Hz), 7.30-7.00 (m, 2H), 6.92 (m, 2H), 6.77 (m, 1H). MS (EI): cal'd 382.1 (MH+), exp 382.3 (MH+).

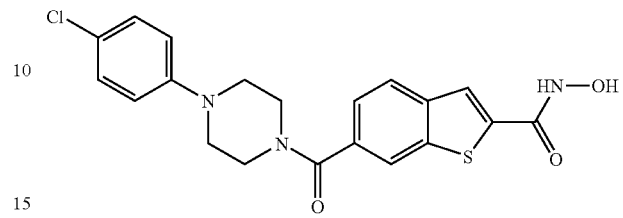

6-[4-(4-Chloro-phenyl)-piperazine-1-carbonyl]-benzo[b]thiophene-2-carboxylic acid hydroxyamide. MS (EI): cal'd 416.1 (MH+), exp 416.2 (MH+).

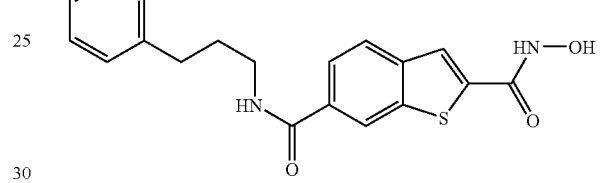

Benzo[b]thiophene-2,6-dicarboxylic acid 2-hydroxyamide 6-[(3-phenyl-propyl)-amide]. $^1$H NMR (CDCl$_3$) δ 11.54 (br s, 1H), 9.29 (br s, 1H), 8.56 (br t, 1H, J=5.6 Hz), 8.43 (s, 1H), 7.98-7.86 (m, 2H), 7.83 (d, 1H, J=8.4 Hz), 7.30-7.00 (m, 5H), 3.45-3.30 (m, 2H), 2.64-2.54 (m, 2H), 1.88-1.72 (m, 2H). MS (EI): cal'd 355.1 (MH+), exp 355.2 (MH+).

Benzo[b]thiophene-2,6-dicarboxylic acid 2-hydroxyamide 6-(phenethyl-amide). $^1$HNMR (CDCl$_3$) δ 8.57 (br s, 1H), 8.28 (br s, 1H), 7.86-7.68 (m, 2H), 7.57 (s, 1H), 7.34-7.10 (m, 5H), 3.56-3.35 (m, 2H), 2.88-2.74 (m, 2H). MS (EI): cal'd 341.1 (MH+), exp 341.3 (MH+).

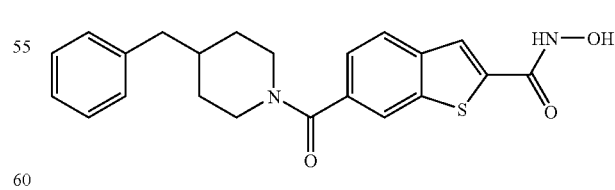

6-(4-Benzyl-piperidine-1-carbonyl)-benzo[b]thiophene-2-carboxylic acid hydroxyamide. $^1$H NMR (CDCl$_3$) δ 11.45 (br s, 1H), 9.26 (br s, 1H), 8.01 (s, 1H), 7.98-7.82 (m, 2H), 7.68 (d, 1H, J=8.0 Hz), 7.30-7.00 (m, 5H), 3.50-3.12 (m, 4H), 2.80 (m, 2H), 1.88 (m, 1H), 1.55 (m, 4H). MS (EI): cal'd 395.1 (MH+), exp 395.1 (MH+).

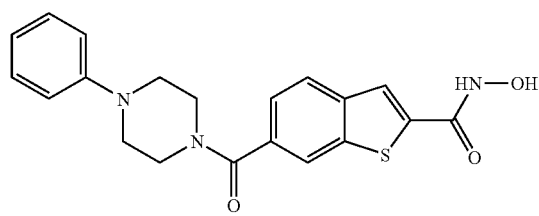

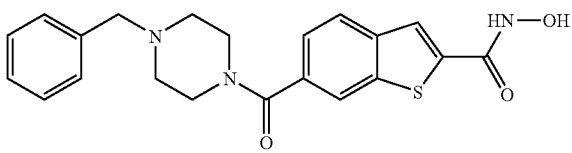

6-(4-Benzyl-piperazine-1-carbonyl)-benzo[b]thiophene-2-carboxylic acid hydroxyamide. $^1$H NMR (CDCl$_3$) δ 11.52 (br s, 1H), 9.30 (br s, 1H), 8.10 (s, 1H), 7.96-7.76 (m, 2H), 7.60-7.25 (m, 5H), 3.43 (s, 2H), 3.30 (m, 4H), 3.00 (m, 4H), 1.75 (m, 2H), 1.57 (m, 2H). MS (EI): cal'd 396.1 (MH+), exp 396.1 (MH+).

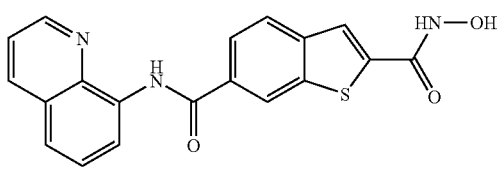

Benzo[b]thiophene-2,6-dicarboxylic acid 2-hydroxyamide 6-quinolin-8-ylamide. MS (EI): cal'd 364.1 (MH+), exp 364.2 (MH+).

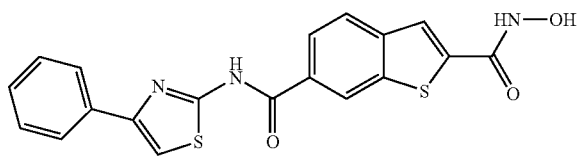

Benzo[b]thiophene-2,6-dicarboxylic acid 2-hydroxyamide 6-[(4-phenyl-thiazol-2-yl)-amide]. MS (EI): cal'd 396.1 (MH+), exp 396.2 (MH+).

Compounds from 6-carboxybenzothiophenes

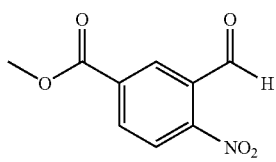

3-Formyl-4-nitro-benzoic acid methyl ester. A solution of 3-methyl4-nitro-benzoic acid methyl ester (24.99 g, 128.1 mmol) and N,N-dimethylformamide dimethyl acetal (40.0 mL, 300 mmol) was heated at 140° C. for 22.5 h. After cooling to rt, the reaction mixture was concentrated and the residue was crystallized from MeOH to give a purple solid. This solid was dissolved in THF (500 mL) and water (500 mL), and sodium periodate (62.62 g, 292.8 mmol) was added followed by additional sodium periodate (15.6 g, 72.9 mmol) two hours later. After stirring at rt for an additional 1 h, the reaction mixture was filtered through Celite washing with EtOAc (2 L). The filtrate was washed with saturated NaHCO$_3$ (600 mL) and the organic layer was dried over Na$_2$SO4. After filtration, the filtrate was concentrated and the residue was passed through a pad of silica gel, washing with CH$_2$Cl$_2$/hexanes (75%-100%). The filtrate was concentrated and dried to give 3-formyl-4-nitro-benzoic acid methyl ester as yellowish solid. MS (EI): cal'd 210.0 (MH$^+$), exp 210.2 (MH$^+$).

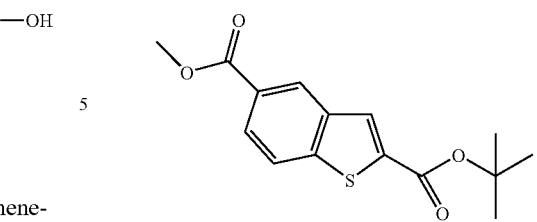

Benzo[b]thiophene-2,5-dicarboxylic acid 2-tert-butyl ester 5-methyl ester. To a suspension of sodium sulfide (7.95 g, 102 mmol) in anhydrous DMF (200 mL) at 0° C. were added acetic acid (5.80 mL, 102 mmol) and additional DMF (100 mL). The mixture was allowed to stir at 0° C. for 30 min and chloro-acetic acid tert-butyl ester (14.6 mL, 102 mmol) was added followed by additional DMF (50 mL). The resulting mixture was allowed to stir at 0° C. for 30 min and at rt for 30 min. To this mixture were added K$_2$CO$_3$ (16.4 g, 119 mmol) and 3-formyl-4-nitro-benzoic acid methyl ester (17.68 g, 84.55 mmol) in DMF (30 mL). The resulting mixture was heated at 55° C. for 22 h, cooled to rt and poured into water (1.2 L). The solid formed was filtered, washed with water (300 mL) and crystallized from MeOH to give benzo[b]thiophene-2,5-dicarboxylic acid 2-tert-butyl ester 5-methyl ester as a pale solid. MS (EI): cal'd 237.0 (M-$^t$butyl+H$^+$) exp 237.1 (M-$^t$butyl+H$^+$).

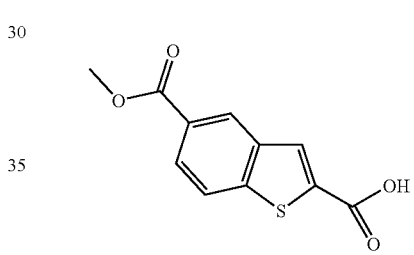

Benzo[b]thiophene-2,5-dicarboxylic acid 5-methyl ester. A solution of benzo[b]thiophene-2,5-dicarboxylic acid 2-tert-butyl ester 5-methyl ester (3.018 g, 10.32 mmol) and TFA (20 mL) in CH$_2$Cl$_2$ (50 mL) was allowed to stir at rt for four days. The reaction mixture was concentrated and dried under high vacuum to give benzo[b]thiophene-2,5-dicarboxylic acid 5-methyl ester as a pale solid. MS (EI): cal'd 237.0 (MH$^+$), exp 237.1 (MH$^+$).

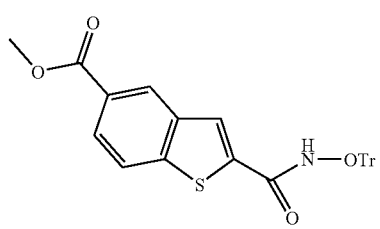

2-Trityloxycarbamoyl-benzo[b]thiophene-5-carboxylic acid methyl ester. A solution of benzo[b]thiophene-2,5-dicarboxylic acid 5-methyl ester (2.592 g, 10.97 mmol), O-trityl-hydroxylamine (3.020 g, 10.97 mmol), EDC (3.150 g, 16.48 mmol), HOBt (1.482 g, 10.97 mmol) and DIEA (4.80 mL, 27.6 mmol) in anhydrous THF (100 mL) was allowed to stir at rt for one week and then concentrated. To the residue was added MeOH (10 mL) and water (100 mL). The syrup obtained was washed with water (10 mL) and triturated with water (90 mL) to give 2-trityloxycarbamoyl-benzo[b]thiophene-5-carboxylic acid methyl ester as a pale solid. MS (EI): cal'd 243.1 (M-benzothiophene moiety+H⁺), exp 243.2 (M-benzothiophene moiety+H⁺).

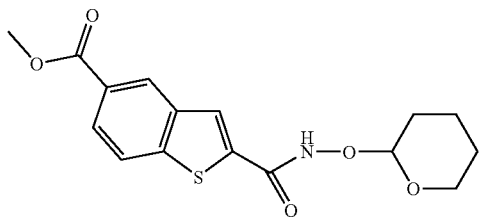

2-(Tetrahydro-pyran-2-yloxycarbamoyl)-benzo[b]thiophene-5-carboxylic acid methyl ester. A solution of benzo[b]thiophene-2,5-dicarboxylic acid 5-methyl ester (191.3 mg, 0.81 mmol), O-(Tetrahydro-pyran-2-yl)-hydroxylamine (93 mg, 0.79 mmol), EDC (231 mg, 1.20 mmol), HOBt (107 mg, 0.79 mmol) and DIEA (0.30 mL, 2.2 mmol) in anhydrous THF (8 mL) was allowed to stir at rt for three days and then concentrated. To the residue was added MeOH (1 mL) and water (10 mL) and Et$_2$O (5 mL). After stirring for 2 h, the solid formed was washed with water (2×3 mL) and Et$_2$O (5 mL), and dried to give 2-(tetrahydro-pyran-2-yloxycarbamoyl)-benzo[b]thiophene-5-carboxylic acid methyl ester as a pale solid). MS (EI): cal'd 252.0 (M−THP+H⁺), exp 252.1 (M−THP+H⁺).

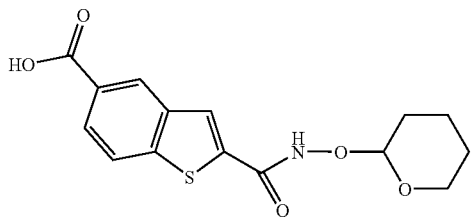

2-(Tetrahydro-pyran-2-yloxycarbamoyl)-benzo[b]thiophene-5-carboxylic acid. A solution of 2-(tetrahydro-pyran-2-yloxycarbamoyl)-benzo[b]thiophene-5-carboxylic acid methyl ester (131.6 mg, 0.39 mmol) in THF (2 mL) and 1M aqueous NaOH (4 mL) was allowed to stir at rt for 18 h. After removal of THF, the aqueous phase was acidified with HOAc to pH≈3. The solid formed was filtered, collected and dried to give 2-(tetrahydro-pyran-2-yloxycarbamoyl)-benzo[b]thiophene-5-carboxylic acid as a white solid. ¹H NMR (DMSO-d$_6$, 200 MHz) δ 12.04 (brs, 1H), 8.54 (s, 1H), 8.22-8.08 (m, 2H), 7.97 (dd, J=8.4, 1.2 Hz, 1H), 5.01 (s, 1H), 4.18-3.94 (m, 1H), 3.68-3.46 (m, 2H), 1.88-1.40 (m, 6H). MS (EI): cal'd 322.1 (MH⁺), exp 322.2 (MH⁺).

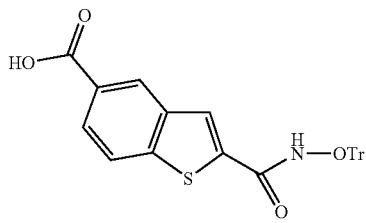

2-Trityloxycarbamoyl-benzo[b]thiophene-5-carboxylic acid. A solution of 2-trityloxycarbamoyl-benzo[b]thiophene-5-carboxylic acid methyl ester (4.439 g, 8.99 mmol) in THF (50 mL) and 2M aqueous NaOH (50 mL) was allowed to stir at rt for six days. After removal of THF, the aqueous phase was acidified with HOAc/H$_2$O (1:1) to pH≈4. The solid formed was filtered, collected and dried to give 2-trityloxycarbamoyl-benzo[b]thiophene-5-carboxylic acid as a white solid. ¹H NMR (DMSO-d$_6$, 200 MHz) δ 11.33 (brs, 1H), 8.47 (s, 1H), 8.10-7.80 (m, 3H), 7.56-7.14 (m, 15H). MS (EI): cal'd 243.1 (M-benzothiophene moiety+H⁺,) exp 243.1 (M-benzothiophene moiety+H⁺).

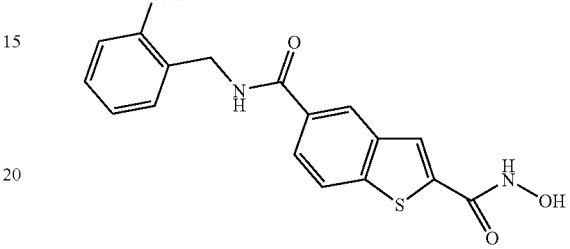

Benzo[b]thiophene-2,5-dicarboxylic acid 2-hydroxyamide 5-(2-methoxy-benzylamide). To a suspension of 2-trityloxycarbamoyl-benzo[b]thiophene-5-carboxylic acid (960 mg, 2.00 mmol) in CH$_2$Cl$_2$ (15 mL) were added EDC (575 mg, 3.00 mmol) and HOBt (320 mg, 2.37 mmol). The mixture was allowed to stir at rt for 40 min and then was equally split into 10 aliquots. An aliquot was then added to 2-methoxy-benzylamine (35 μL, 0.27 mmol) in CH$_2$C$_2$ (0.5 mL). After stirring at rt overnight, the reaction mixture was concentrated. The residue was suspended in MeOH (1 mL) and water (10 mL) was added. The solid formed was filtered, collected and dried under high vacuum. The obtained solid was suspended in CH$_2$Cl$_2$ (4 mL) and TFA (0.20 mL) was added, followed by addition of Et$_3$SiH till the yellow color faded away. The mixture was allowed to stir at rt for 20 min and a solid formed during that period. After addition of CH$_2$Cl$_2$/hexanes (1:1, 4 mL), the solid was filtered, washed with CH$_2$Cl$_2$/hexanes (1:1, 4×1 mL) and dried to give benzo[b]thiophene-2,5-dicarboxylic acid 2-hydroxyamide 5-(2-methoxy-benzylamide) as a pale solid. ¹H NMR (DMSO-d$_6$, 200 MHz) δ 8.96 (t, J=5.4 Hz, 1H), 8.48 (s, 1H), 8.11 (d, J=8.4 Hz, 1H), 8.06-7.84 (m, 2H), 7.21 (d, J=7.2 Hz, 2H), 7.06-6.80 (m, 2H), 4.48 (d, J=5.8 Hz, 2H), 3.83 (s, 3H). MS (EI): cal'd 357.1 (MH⁺), exp 357.2 (MH⁺).

The following compounds were prepared in procedures similar to those described for the preparation of benzo[b]thiophene-2,5-dicarboxylic acid 2-hydroxyamide 5-(2-methoxy-benzylamide).

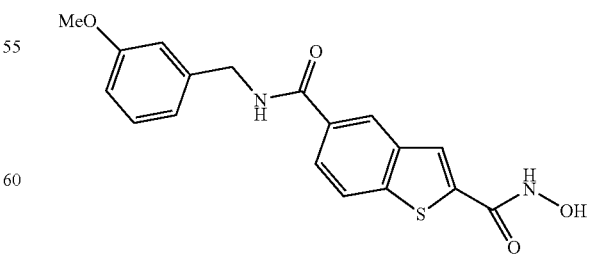

Benzo[b]thiophene-2,5-dicarboxylic acid 2-hydroxyamide 5-(3-methoxy-benzylamide). ¹H NMR (DMSO-d$_6$, 200 MHz) δ 9.13 (t, J=5.8 Hz, 1H), 8.45 (s, 1H), 8.11 (d, J=8.4 Hz, 1H), 8.06-7.84 (m, 2H), 7.24 (d, J=7.6 Hz, 1H), 7.00-6.70 (m, 3H), 4.48 (d, J=6.0 Hz, 2H), 3.72 (s, 3H). MS (EI): cal'd 357.1 (MH+), exp 357.2 (MH+).

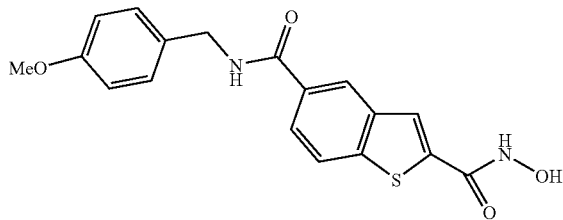

Benzo[b]thiophene-2,5dicarboxylic acid 2-hydroxyamide 5-(4-methoxy-benzylamide). $^1$H NMR (DMSO-d$_6$, 200 MHz) δ 9.06 (t, J=5.8 Hz, 1H), 8.43 (s, 1H), 8.09 (d, J=8.4 Hz, 1H), 8.04-7.84 (m, 2H), 7.26 (d, J=8.8 Hz, 2H), 6.88 (d, J=8.8 Hz, 2H), 4.43 (d, J=5.8 Hz, 2H), 3.72 (s, 3H). MS (EI): cal'd 357.1 (MH+), exp 357.2 (MH+).

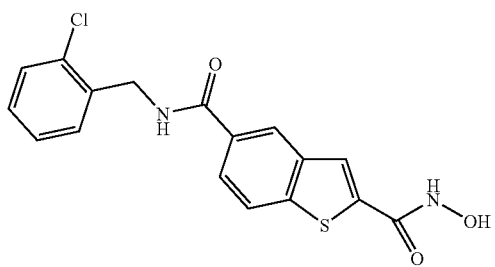

Benzo[b]thiophene-2,5-dicarboxylic acid 5-(2-chloro-benzylamide)2-hydroxyamide. $^1$H NMR (DMSO-d$_6$, 200 MHz) δ 9.16 (t, J=6.0 Hz, 1H), 8.48 (s, 1H), 8.13 (d, J=8.4 Hz, 1H), 8.06-7.84 (m, 2H), 7.54-7.18 (m, 4H), 4.58 (d, J=5.8 Hz, 2H). MS (EI): cal'd 361.0 (MH+), exp 361.1 (MH+).

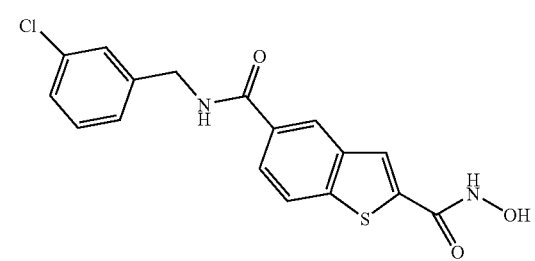

Benzo[b]thiophene-2,5-dicarboxylic acid 5-(3-chloro-benzylamide)2-hydroxyamide. $^1$H NMR DMSO-d$_6$, 200 MHz) δ 9.20 (t, J=6.0 Hz, 1H), 8.46 (s, 1H), 8.12 (d, J=8.4 Hz, 1H), 8.20-7.84 (m, 2H), 7.46-7.24 (m, 4H), 4.51 (d, J=5.4 Hz, 2H). MS (EI): cal'd 361.0 (MH+), exp 361.1 (MH+).

Benzo[b]thiophene-2,5-dicarboxylic acid 5-(4-chloro-benzylamide)2-hydroxyamide. $^1$H NMR (DMSO-d$_6$, 200 MHz) δ 9.19 (t, J=5.0 Hz, 1H), 8.45 (s, 1H), 8.11 (d, J=8.8 Hz, 1H), 8.04-7.84 (m, 2H), 7.37 (s, 4H), 4.49 (d, J=5.8 Hz, 2H). MS (EI): cal'd 361.0 (MH+), exp 361.1 (MH+).

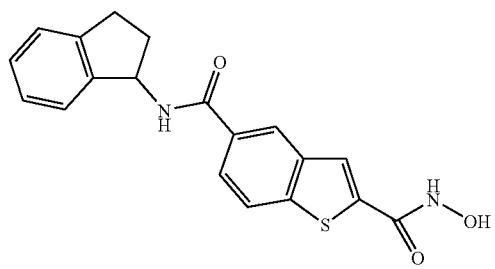

Benzo[b]thiophene-2,5-dicarboxylic acid 2-hydroxyamide 5-indan-1-ylamide. $^1$H NMR (DMSO-d$_6$, 200 MHz) δ 10.24 (s, 1H), 8.52 (s, 1H), 8.15 (d, J=8.6 Hz, 1H), 8.10-7.90 (m, 2H), 7.69 (s, 1H), 7.50 (d, J=8.0 Hz, 1H), 7.18 (d, J=8.2 Hz, 1H), 2.98-2.70 (m, 3H), 2.10-1.90 (m, 2H). MS(EI): cal'd 353.1 (MH+), exp 353.2 (MH+).

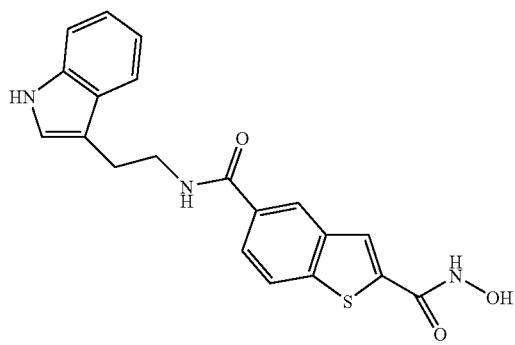

Benzo[b]thiophene-2,5-dicarboxylic acid 2-hydroxyamide 5-{[2-(1H-indol-3-yl)-ethyl]-amide}. $^1$H NMR (DMSO-d$_6$, 200 MHz) δ 10.80 (s, 1H), 8.73 (t, J=5.2 Hz, 1H), 8.40 (s, 1H), 8.10 (d, J=8.4 Hz, 1H), 7.99 (s, 1H), 7.91 (dd, J=8.4, 1.6 Hz, 1H), 7.59 (d, J=7.4 Hz, 1H), 7.33 (d, J=7.6 Hz, 1H), 7.19 (d, J=2.2 Hz, 1H), 7.13-6.88 (m, 2H), 3.55 (t, J=7.0 Hz, partially overlap H$_2$O, 2H), 2.97 (t, J=7.6 Hz, 2H). MS (EI): cal'd 380.1 (MH+), exp 380.2 (MH+).

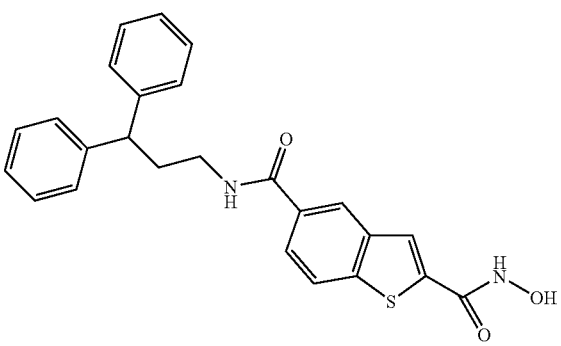

Benzo[b]thiophene-2,5-dicarboxylic acid 5-[(3,3-diphenyl-propyl)-amide]2-hydroxyamide. $^1$H NMR (DMSO-d$_6$, 200 MHz) δ 8.59 (t, J=4.8 Hz, 1H), 8.36 (s, 1H), 8.08 (d, J=8.4 Hz, 1H), 7.98 (s, 1H), 7.87 (dd, J=8.4, 1.4 Hz, 1H), 7.50-7.10 (m, 10H), 4.05 (t, J=7.8 Hz, 1H), 3.40-3.04 (m, 2H), 2.42-2.20 (m, 2H). MS (EI): cal'd 431.1 (MH+), exp 431.2 (MH+).

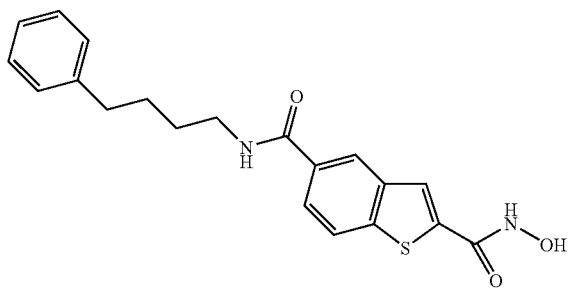

Benzo[b]thiophene-2,5-dicarboxylic acid 2-hydroxyamide 5-[(4-phenyl-butyl)-amide]. ¹H NMR (DMSO-d₆, 200 MHz) δ 8.57 (t, J=5.0 Hz, 1H), 8.38 (s, 1H), 8.08 (d, J=8.6 Hz, 1H), 7.98 (s, 1H), 7.88 (dd, J=8.4, 1.4 Hz, 1H), 7.40-7.02 (m, 5H), 3.48-3.16 (m, 2H), 2.60 (t, J=6.8 Hz, 2H), 1.80-1.38 (m, 4H). MS (EI): cal'd 369.1 (MH⁺), exp 369.2 (MH⁺).

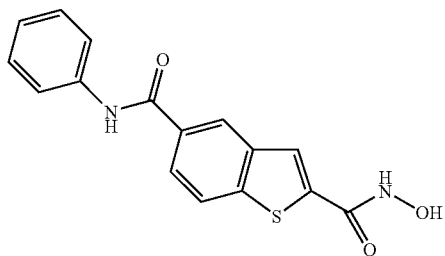

Benzo[b]thiophene-2,5-dicarboxylic acid 2-hydroxyamide 5-phenylamide. ¹H NMR (DMSO-d₆, 200 MHz) δ 11.61 (brs, 1H), 11.37 (brs, 1H), 9.36 (brs, 1H), 8.53 (s, 1H), 8.17 (d, J=8.4 Hz, 1H), 8.10-7.90 (m, 2H), 7.79 (d, J=7.4 Hz, 2H), 7.36 (dd, J=7.8, 7.8 Hz, 2H), 7.10 (dd, J=7.8, 7.8 Hz, 1H). MS (EI): cal'd 313.1 (MH⁺), exp 313.2 (MH⁺).

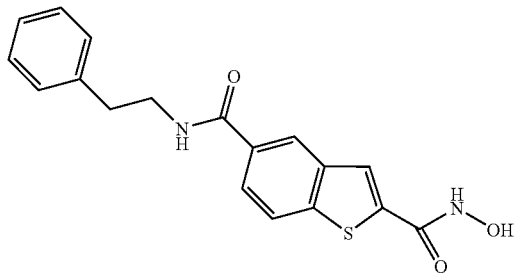

Benzo[b]thiophene-2,5-dicarboxylic acid 2-hydroxyamide 5-(phenethyl-amide). ¹H NMR (DMSO-d₆, 200 MHz) δ 8.90 (t, J=5.2 Hz, 1H), 8.56 (s, 1H), 8.28 (d, J=8.0Hz, 1H), 8.18 (s, 1H), 8.07 (dd, J=8.4, 1.4 Hz, 1H), 7.60-7.20 (m, 5H), 3.80-3.60 (m, 2H), 3.05 (t, J=7.0 Hz, 2H). MS (EI): cal'd 341.1 (MH⁺), exp 341.2 (MH⁺).

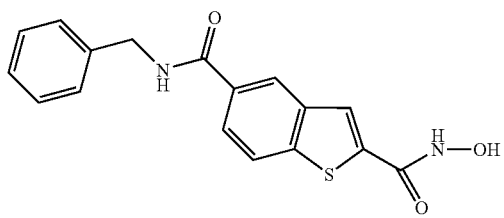

Benzo[b]thiophene-2,5-dicarboxylic acid 5-benzylamide 2-hydroxyamide. A solution of 2-(tetrahydro-pyran-2-yloxycarbamoyl)-benzo[b]thiophene-5-carboxylic acid (53 mg, 0.16 mmol), benzylamine (25 μL, 0.23 mmol), EDC (50 mg, 0.26 mmol), HOBt (25 mg, 0.18 mmol) and DIEA (60 μL, 0.34 mmol) in THF (3 mL) was allowed to stir at rt for five days. The reaction mixture was concentrated and the residue was dissolved in MeOH (0.5 mL) and water was added. The syrup formed was treated with MeOH and water once more time. After drying, the solid obtained was dissolved in CH₂Cl₂ (3 mL) and TFA (75 μL) and water (30 μL) were added. The mixture was allowed to stir at rt overnight and a solid formed during that period. After addition of hexanes (6 mL), the solid was filtered, washed with hexanes (2×3 mL) and dried to give benzo[b]thiophene-2,5-dicarboxylic acid 5-benzylamide 2-hydroxyamide as a pale solid. ¹H NMR (DMSO-d₆, 200 MHz) δ 9.16 (t, J=6.0 Hz, 1H), 8.46 (s, 1H), 8.11 (d, J=8.8 Hz, 1H), 8.07-7.86 (m, 2H), 7.50-7.10 (m, 5H), 4.51 (d, J=5.8 Hz, 2H). MS (EI): cal'd 327.1 (MH⁺), exp 327.1 (MH⁺).

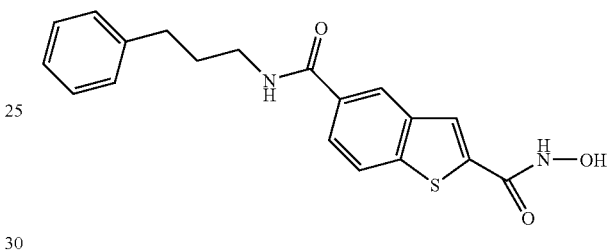

Benzo[b]thiophene-2,5-dicarboxylic acid 2-hydroxyamide 5-[(3-phenyl-propyl)-amide]. This title compound was prepared in procedures similar to those described for the preparation of benzo[b]thiophene-2,5-dicarboxylic acid 5-benzylamide 2-hydroxyamide. MS (EI): cal'd 355.1 (MH⁺), exp 355.2 (MH⁺).

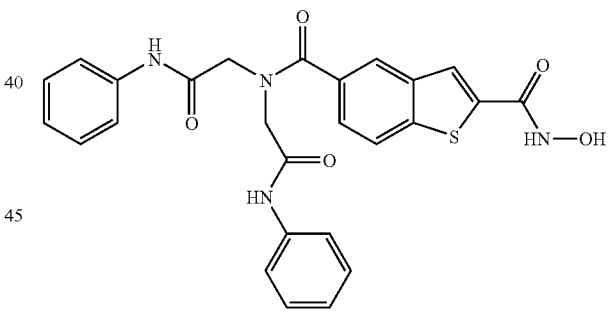

Benzo[b]thiophene-2,5-dicarboxylic acid 5-(bis-phenyl-carbamoylmethyl-amide) 2-hydroxyamide. ¹H NMR (DMSO-d₆) δ 11.50 (s, 1H), 10.34 (s, 1H), 10.23 (s, 1H), 9.28 (s, 1H), 8.10 (d, J=8.2 Hz, 1H), 7.96 (d, J=8.8 Hz, 1H), 7.64 (d, J=8.2 Hz, 2H), 7.56-7.44 (m, 3H), 7.38-7.26 (m, 4H), 7.07 (t, J=7.4 Hz, 2H), 4.35 (s, 2H), 4.23 (s, 2H). MS (EI): cal'd (MH⁺) 503.1, exp (MH⁺) 503.2.

Compounds with 5-formylbenzothiophenes

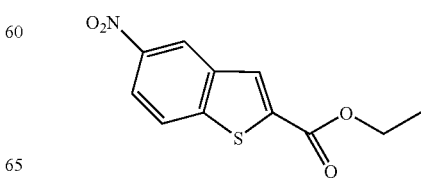

5-Nitro-benzo[b]thiophene-2-carboxylic acid ethyl ester. To a solution of 2-chloro-5-nitro-benzaldehyde (31.01 g, 167.1 mmol) in 330 mL of anhydrous DMF at 0° C. was added $K_2CO_3$ (27.80 g, 201.1 mmol), followed by slow addition of mercapto-acetic acid ethyl ester (18.5 mL, 168.7 mmol). After stirring at 0° C. for 20 min, the resulting mixture was allowed to warm to rt and stir at rt overnight. The reaction mixture was then poured into 1.5 L of water. The solid formed was filtered and washed with 600 mL of water. After drying, 5-nitro-benzo[b]thiophene-2-carboxylic acid ethyl ester was obtained as pale solid. MS (EI): cal'd 252.0 ($MH^+$), exp 252.1 ($MH^+$).

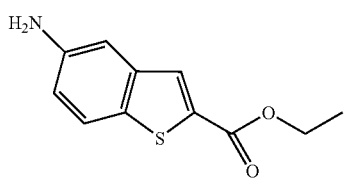

5-Amino-benzo[b]thiophene-2-carboxylic acid ethyl ester. A suspension of 5-nitro-benzo[b]thiophene-2-carboxylic acid ethyl ester (10.52 g, 41.89 mmol) and 10% Pd/C (1.1 g) in 450 mL of EtOH was hydrogenated under 1 atm of $H_2$ for 4 d at rt. The reaction mixture was filtered and the filtrate was concentrated and dried to give 5-amino-benzo[b]thiophene-2-carboxylic acid ethyl ester as a green solid. A parallel reaction was preformed on 10.61 g of 5-nitro-benzo[b]thiophene-2-carboxylic acid ethyl ester in the same manner. A total of 18.37 g of 5-amino-benzo[b]thiophene-2-carboxylic acid ethyl ester was obtained. MS (EI): cal'd 222.0 ($MH^+$), exp 222.2 ($MH^+$).

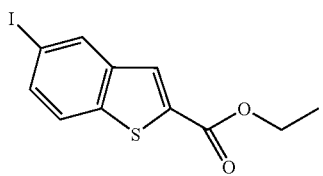

5-Iodo-benzo[b]thiophene-2-carboxylic acid ethyl ester. To 5-amino-benzo[b]thiophene-2-carboxylic acid ethyl ester (18.37 g, 83.02 mmol) was added an aqueous HCl solution (21 mL conc. HCl in 200 mL $H_2O$, 252 mmol)) and the resulting mixture was cooled to 0° C. A solution of $NaNO_2$ (6.02 g in 60 mL $H_2O$, 87.25 mmol) was added and the mixture was allowed to stir at 0° C. for 10 min. A solution of NaI (13.07 g in 60 mL $H_2O$, 87.20 mmol) was added slowly. The reaction mixture became difficult to stir during the addition of NaI. A total of 300 mL of water was added in several portions. After the addition was complete, the reaction was warmed to rt and allowed to stir at rt for 2 h. The mixture was then diluted with $CH_2Cl_2$ (800 mL) and water (100 mL). The organic layer was separated, washed with 200 mL of saturated $NaHCO_3$ and dried over $Na_2SO_4$. After filtration, the filtrate was concentrated and the residue was filtered through a pad of silica gel, washing with EtOAc/hexanes (0% to 10%). The filtrate was then concentrated and the residue was recrystallized from MeOH to give 5-iodo-benzo[b]thiophene-2-carboxylic acid ethyl ester as light orange solid. MS (EI): cal'd 332.9 ($MH^+$), exp 333.1 ($MH^+$).

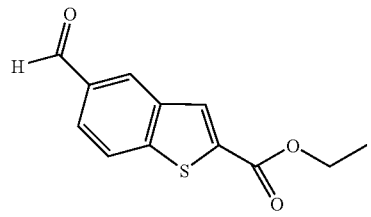

5-Formyl-benzo[b]thiophene-2-carboxylic acid ethyl ester. To a solution of 5-iodo-benzo[b]thiophene-2-carboxylic acid ethyl ester (14.09 g, 42.42 mmol) at −40° C. was slowly added a solution of isopropylmagnesium bromide (0.7 M in THF, 85 mL, 59.5 mmol). The mixture was allowed to stir at −40° C. for 2 h and N-methyl-N-pyridin-2-yl-formamide (7.65 mL, 63.9 mmol) was added slowly. After warming to rt, the mixture was allowed to stir for additional 2.5 h. To the mixture was carefully added 250 mL of 1N HCl. After stirring for 10 min, the reaction mixture was diluted with $CH_2Cl_2$ (800 mL). The organic layer was separated, washed with 200 mL of saturated $NaHCO_3$ and dried over $Na_2SO_4$. After filtration, the filtrate was concentrated and the residue was recrystallized from MeOH to give 5-formyl-benzo[b]thiophene-2-carboxylic acid ethyl ester as a yellow solid. $^1$H NMR ($CDCl_3$, 200 MHz) δ 10.12 (s, 1H), 8.37 (s, 1H), 8.18 (s, 1H), 8.08-7.90 (m, 2H), 4.44 (q, J=7.2 Hz, 2H), 1.44 (t, J=7.4 Hz, 3H). MS (EI): cal'd 235.0 ($MH^+$), exp 235.1 ($MH^+$).

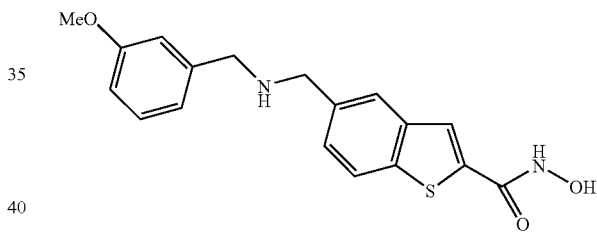

5-[(3-Methoxy-benzylamino)-methyl]-benzo[b]thiophene-2-carboxylic acid hydroxyamide. To a solution of 5-formyl-benzo[b]thiophene-2-carboxylic acid ethyl ester (85 mg, 0.36 mmol) and 3-methoxy-benzylamine (60 μL, 0.46 mmol) in anhydrous dichloroethane (5 mL) were added sodium triacetoxyborohydride (230 mg, 1.08 mmol) and acetic acid (20 μL, 0.35 mmol). After the reaction was complete, 4 mL of saturated $NaHCO_3$ was added. The organic was separated, washed with 4 mL of water and then concentrated. After drying under high vacuum, the residue was dissolved in anhydrous MeOH (5 mL) and hydroxylamine hydrochloride (95 mg, 1.37 mmol) was added, followed by the addition of NaOMe solution (4.37 M in MeOH, 0.60 mL, 2.6 mmol). The mixture was allowed to stir at rt till the reaction was complete. The reaction mixture was concentrated and the residue was dissolved in a minimal amount of water. The obtained solution was acidified with 2N HCl to pH≈8. The solid formed was filtered, washed with water, collected and purified by flash column chromatography to give 5-[(3-methoxy-benzylamino)-methyl]-benzo[b]thiophene-2-carboxylic acid hydroxyamide as a yellowish syrup. $^1$H NMR (DMSO-$d_6$, 200 MHz) δ 7.94 (d, J=8.4 Hz, 1H), 7.88 (s, 1H), 7.85 (s, 1H), 7.44 (dd, J=8.4, 1.4 Hz, 1H), 7.21 (t, J=7.6 Hz, 1H), 7.00-6.72 (m, 3H), 3.78 (s, 2H), 3.73 (s, 3H), 3.66 (s, 2H). MS (EI): cal'd 343.1 ($MH^+$), exp 343.2 ($MH^+$).

The following compounds were prepared in procedures similar to those described for the preparation of 5-[(3-methoxy-benzylamino)-methyl]-benzo[b]thiophene-2-carboxylic acid hydroxyamide.

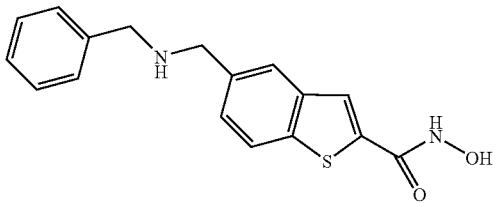

5-(Benzylamino-methyl)-benzo[b]thiophene-2-carboxylic acid hydroxyamide. $^1$H NMR (DMSO -d$_6$, 200 MHz) δ 7.98-7.78 (m, 3H), 7.43 (d, J=8.0 Hz, 1H), 7.38-7.14 (m, 5H), 3.78 (s, 2H), 3.68 (s, 2H). MS (EI): cal'd 313.1 (MH$^+$), exp 313.2 (MH$^+$).

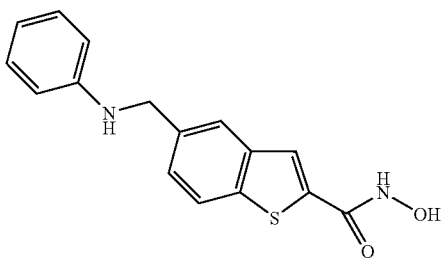

5-Phenylaminomethyl-benzo[b]thiophene-2-carboxylic acid hydroxyamide. $^1$H NMR (DMSO-d$_6$, 200 MHz) δ 7.93 (d, J=8.4 Hz, 1H), 7.83 (s, 2H), 7.42 (d, J=8.8 Hz, 1H), 7.14-6.88 (m, 2H), 6.70-6.40 (m, 3H), 6.29 (t, J=6.2 Hz, 1H), 4.36 (d, J=6.2 Hz, 2H). MS (EI): cal'd 299.1 (MH$^+$), exp 299.2 (MH$^+$).

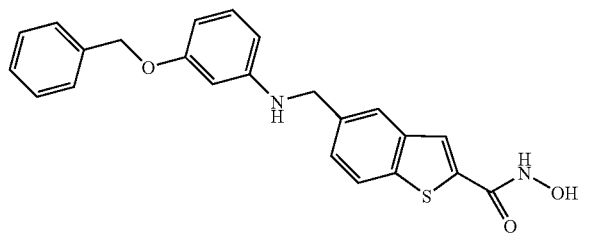

5-[(3-Benzyloxy-phenylamino)-methyl]-benzo[b]thiophene-2-carboxylic acid hydroxyamide. $^1$H NMR (DMSO-d$_6$, 200 MHz) δ 7.94 (d, J=8.2 Hz, 1H), 7.84 (s, 2H), 7.50-7.20 (m, 16H), 6.91 (t, J=8.0 Hz, 1H), 6.40-6.10 (m, 4H), 4.95 (s, 2H), 4.34 (d, J=5.8 Hz, 2H). MS (EI): cal'd 405.1 (MH$^+$), exp 405.2 (MH$^+$).

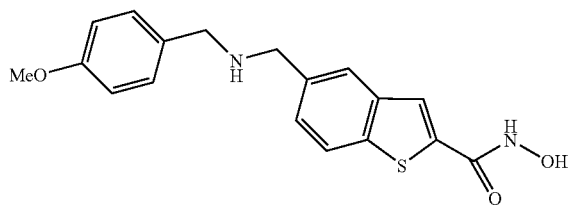

5-[(4-Methoxy-benzylamino)-methyl]-benzo[b]thiophene-2-carboxylic acid hydroxyamide. $^1$H NMR (DMSO-d$_6$, 200 MHz) δ 7.98 (d, J=8.4 Hz, 1H), 7.91 (s, 2H), 7.48 (dd, J=8.0, 1.4 Hz, 1H), 7.31 (t, J=8.8 Hz, 2H), 6.90 (d, J=8.8 Hz, 2H), 3.91 (s, 2H), 3.76 (s, 2H), 3.73 (s, 3H). MS (EI): cal'd 343.1 (MH$^+$), exp 343.2 (MH$^+$).

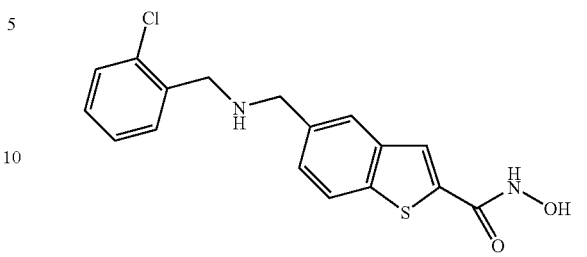

5-[(2-Chloro-benzylamino)-methyl]-benzo[b]thiophene-2-carboxylic acid hydroxyamide. $^1$H NMR (DMSO-d$_6$, 200 MHz) δ 7.94 (d, J=8.4 Hz, 1H), 7.88 (s, 2H), 7.58 (dd, J=7.4, 1.8 Hz, 1H), 7.51-7.20 (m, 4H), 3.85 (s, 2H), 3.77 (s, 2H). MS (EI): cal'd 347.0 (MH$^+$), exp 347.1 (MH$^+$).

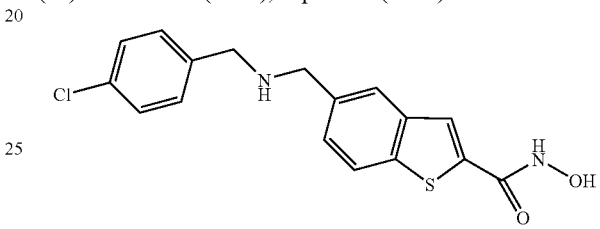

5-[(4-Chloro-benzylamino)-methyl]-benzo[b]thiophene-2-carboxylic acid hydroxyamide. $^1$H NMR (DMSO-d$_6$, 200 MHz) δ 7.94 (d, J=8.4 Hz, 1H), 7.88 (s, 2H), 7.84 (s, 1H), 7.50-7.30 (m, 5H), 3.77 (s, 2H), 3.67 (s, 2H). MS (EI): cal'd 347.0 (MH$^+$), exp 347.2 (MH$^+$).

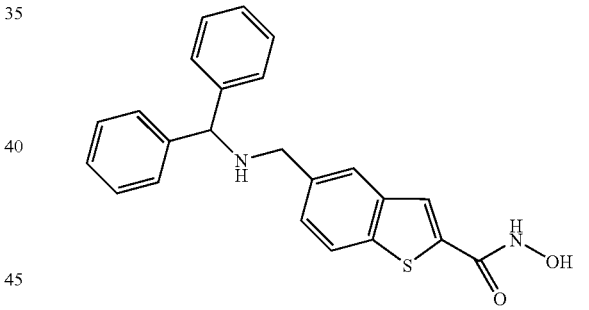

5-[(Benzhydryl-amino)-methyl]-benzo[b]thiophene-2-carboxylic acid hydroxyamide. $^1$H NMR (DMSO-d$_6$, 200 MHz) δ 7.93 (d, J=8.4 Hz, 1H), 7.87 (s, 1H), 7.80 (s, 1H), 7.50-7.12 (m, 11H), 4.77 (s, 1H), 3.71 (s, 2H). MS (EI): cal'd 389.1 (MH$^+$), exp 389.2 (MH$^+$).

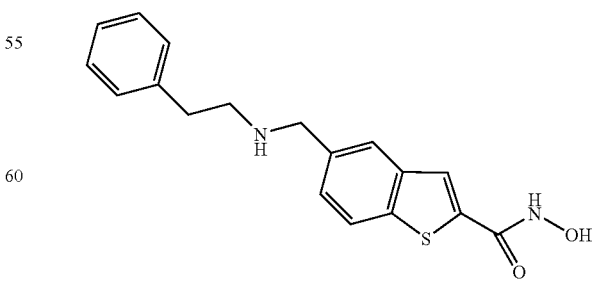

5-(Phenethylamino-methyl)-benzo[b]thiophene-2-carboxylic acid hydroxyamide. $^1$H NMR (DMSO-d$_6$, 200 MHz)

δ 7.94 (d, J=8.4 Hz, 1H), 7.87 (s, 1H), 7.83 (s, 1H), 7.42 (dd, J=8.6, 1.6 Hz, 1H), 7.32-7.10 (m, 5H), 3.88 (s, 2H), 2.76 (s, 4H). MS (EI): cal'd 327.1 (MH⁺), exp 327.2 (MH⁺).

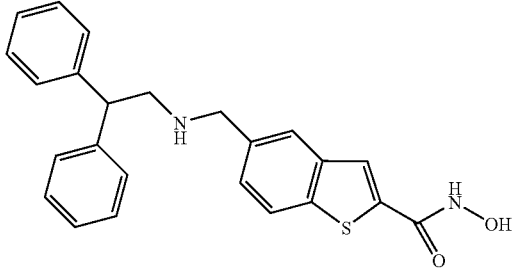

5-[(2,2-Diphenyl-ethylamino)-methyl]-benzo[b]thiophene-2-carboxylic acid hydroxyamide. ¹H NMR (DMSO-d₆, 200 MHz) δ 7.90 (d, J=8.4 Hz, 1H), 7.84 (s, 1H), 7.74 (s, 1H), 7.40-7.10 (m, 11H), 4.15 (t, J=7.4Hz, 1H), 3.82 (s, 2H), 3.11 (d, J=7.6Hz, 2H). MS (EI): cal'd 403.1 (MH⁺), exp 403.3 (MH⁺).

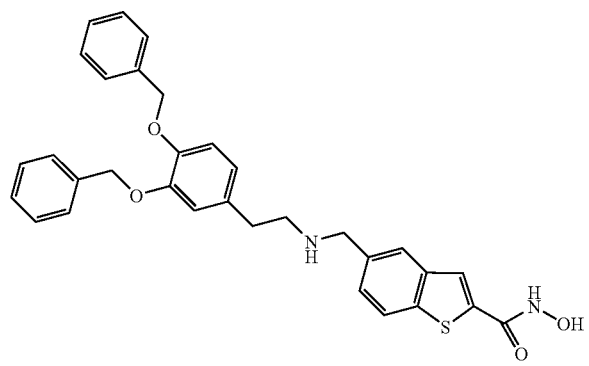

5-{[2-(3,4-Bis-benzyloxy-phenyl)-ethylamino]-methyl}-benzo[b]thiophene-2-carboxylic acid hydroxyamide. ¹H NMR (DMSO-d₆, 200 MHz) δ 7.97 (d, J=8.0 Hz, 1H), 7.89 (s, 2H), 7.52-7.22 (m, 12H), 7.00-6.88 (m, 2H), 6.70 (dd, J=8.4, 2.0 Hz, 1H), 5.07 (s, 4H), 3.95 (s, 2H), 2.90-2.60 (m, 4H). MS (EI): cal'd 539.2 (MH⁺), exp 539.4 (MH⁺).

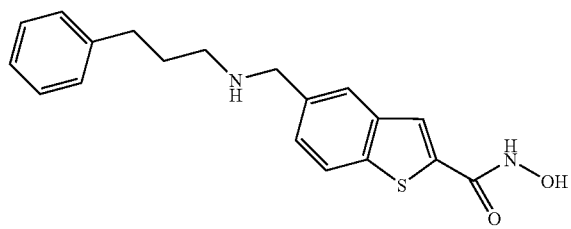

5-[(3-Phenyl-propylamino)-methyl]-benzo[b]thiophene-2-carboxylic acid hydroxyamide. ¹H NMR (DMSO-d₆, 200 MHz) δ 8.06-7.84 (m, 3H), 7.51 (dd, J=8.4, 1.4 Hz, 1H), 7.32-7.06 (m, 5H), 4.02 (s, 2H), 2.80-2.54 (m, 4H), 1.94-1.70 (m, 2H). MS (EI): cal'd 341.1 (MH⁺), exp 341.2 (MH⁺).

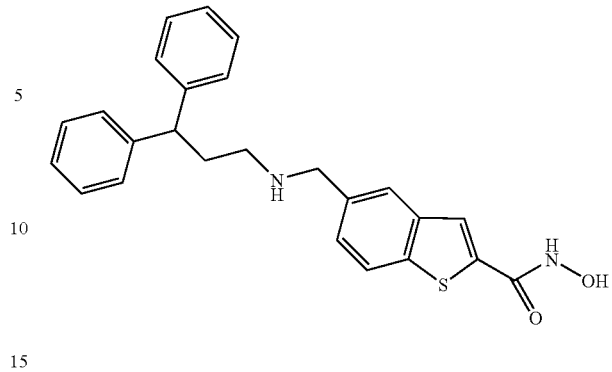

5-[(3,3-Diphenyl-propylamino)-methyl]-benzo[b]thiophene-2-carboxylic acid hydroxyamide. ¹H NMR (DMSO-d₆, 200 MHz) δ 8.02-7.82 (m, 3H), 7.44 (d, J=8.4 Hz, 1H), 7.38-7.06 (m, 10H), 4.07 (t, J=8.0 Hz, 1H), 3.94 (s, 2H), 2.62-2.52 (m, 2H), 2.38-2.18 (m, 2H). MS (EI): cal'd 417.2 (MH⁺), exp 417.3(MH⁺).

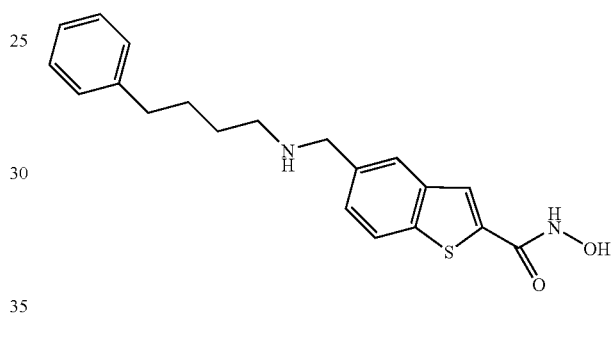

5-[(4-Phenyl-butylamino)-methyl]-benzo[b]thiophene-2-carboxylic acid hydroxyamide ¹H NMR (DMSO-d₆, 200 MHz) δ 7.96 (d, J=8.6 Hz, 1H), 7.89 (s, 2H), 7.46 (dd, J=8.4, 1.4 Hz, 1H), 7.32-7.08 (m, 5H), 3.90 (s, 2H), 2.69-2.43 (m, 4H), 1.68-1.40 (m, 4H). MS (EI): cal'd 355.1 (MH⁺), exp 355.3 (MH⁺).

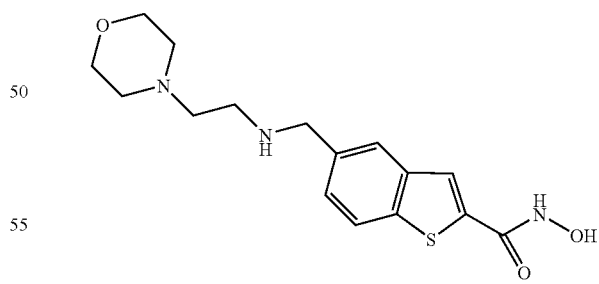

5-[(2-Morpholin-4-yl-ethylamino)-methyl]-benzo[b]thiophene-2-carboxylic acid hydroxyamide ¹H NMR (DMSO-d₆, 200 MHz) δ 7.98 (d, J=8.4 Hz, 1H), 7.93 (s, 2H), 7.49 (dd, J=8.4, 1.4 Hz, 1H), 3.96 (s, 2H), 3.55 (t, J=4.4 Hz, 4H), 2.72 (t, J=6.6 Hz, 2H), 2.46 (t, J=6.6 Hz, 2H). MS (EI): cal'd 336.1 (MH⁺), exp 336.3 (MH⁺).

97

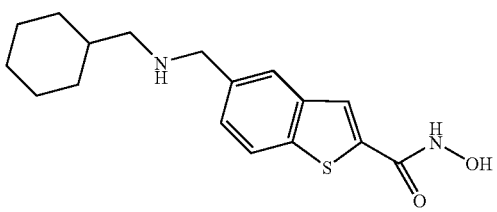

5-[(Cyclohexylmethyl-amino)-methyl]-benzo[b]thiophene-2-carboxylic acid hydroxyamide $^1$H NMR (DMSO-d$_6$, 200 MHz) δ 7.94 (d, J=8.4 Hz, 1H), 7.88 (s, 1H), 7.86 (s, 1H), 7.44 (d, J=8.0 Hz, 1H), 3.84 (s, 2H), 2.38 (d, J=6.6 Hz, 2H), 1.84-0.68 (m, 11H). MS (EI): cal'd 319.1 (MH$^+$), exp 319.3 (MH$^+$).

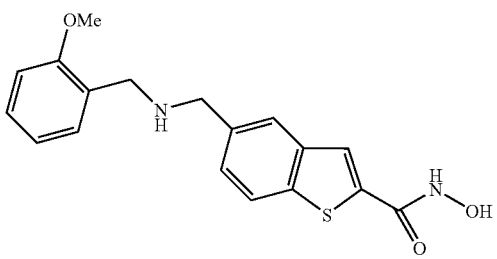

5-[(2-Methoxy-benzylamino)-methyl]-benzo[b]thiophene-2-carboxylic acid hydroxyamide $^1$H NMR (DMSO-d$_6$, 200 MHz) δ 8.06-7.80 (m, 3H), 7.54-7.18 (m, 3H), 7.02-6.84 (m, 2H), 3.92 (s, 2H), 3.75 (s, 5H). MS (EI): cal'd 343.1 (MH$^+$), exp 343.2 (MH$^+$).

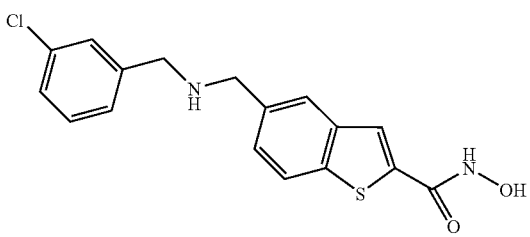

5-[(3-Chloro-benzylamino)-methyl]-benzo[b]thiophene-2-carboxylic acid hydroxyamide $^1$H NMR (DMSO-d$_6$, 200 MHz) δ 8.00-7.78 (m, 3H), 7.50-7.38 (m, 2H), 7.36-7.20 (m, 3H), 3.78 (s, 2H), 3.69 (s, 2H). MS (EI): cal'd 347.0 (MH$^+$), exp 347.2 (MH$^+$).

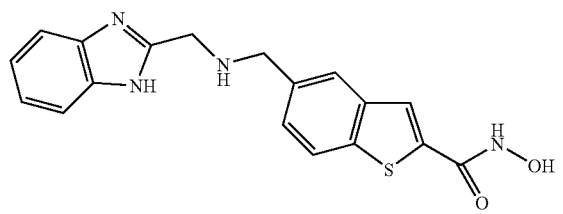

98

5-{[(1H-Benzoimidazol-2-ylmethyl)-amino]-methyl}-benzo[b]thiophene-2-carboxylic acid hydroxyamide $^1$H NMR (DMSO-d$_6$, 200 MHz) δ 7.98 (d, J=8.4 Hz, 1H), 7.94-7.86 (m, 2H), 7.56-7.44 (m, 3H), 7.20-7.08 (m, 2H), 3.98 (s, 2H), 3.96 (s, 2H). MS (EI): cal'd 353.1 (MH$^+$), exp 353.2 (MH$^+$).

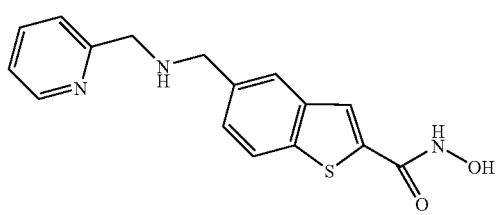

5-{[(Pyridin-2-ylmethyl)-amino]-methyl}-benzo[b]thiophene-2-carboxylic acid hydroxyamide $^1$H NMR (DMSO-d$_6$, 200 MHz) δ 8.47 (d, J=3.4 Hz, 1H), 7.93 (d, J=8.0 Hz, 1H), 7.92-7.82 (m, 2H), 7.80-7.68 (m, 1H), 7.52-7.38 (m, 2H), 7.28-7.18 (m, 1H), 3.83 (s, 2H), 3.78 (s, 2H). MS (EI): cal'd 314.1 (MH$^+$), exp 314.2 (MH$^+$).

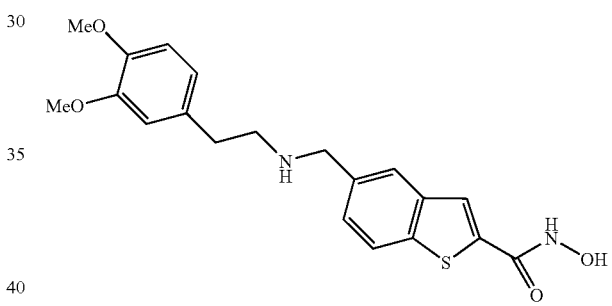

5-{[2-(3,4-Dimethoxy-phenyl)-ethylamino]-methyl}-benzo[b]thiophene-2-carboxylic acid hydroxyamide $^1$H NMR (DMSO-d$_6$, 200 MHz) δ 7.94 (d, J=8.0 Hz, 1H), 7.90-7.80 (m, 2H), 7.50-7.38 (m, 1H), 6.90-6.62 (m, 3H), 3.87 (s, 2H), 3.70 (s, 3H), 3.69 (s, 3H), 2.80-2.66 (m, 4H). MS (EI): cal'd 387.1 (MH$^+$), exp 387.3 (MH$^+$).

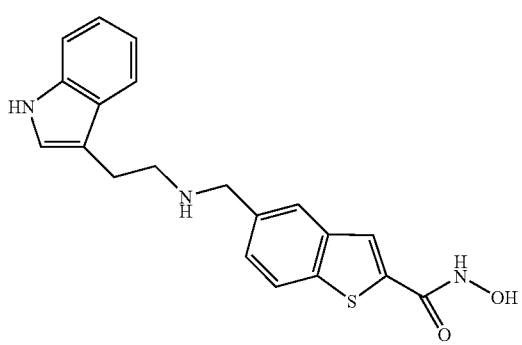

5-{[2-(1H-Indol-3-yl)-ethylamino]-methyl}-benzo[b]thiophene-2-carboxylic acid hydroxyamide $^1$H NMR (DMSO-$d_6$, 200 MHz) δ 7.93 (d, J=8.4 Hz, 1H), 7.86 (s, 2H), 7.54-7.40 (m, 2H), 7.31 (d, J=8.0 Hz, 1H), 7.18-6.86 (m, 3H), 3.90 (s, 2H), 2.86 (s, 4H). MS (EI): cal'd 366.1 (MH$^+$), exp 366.3 (MH$^+$).

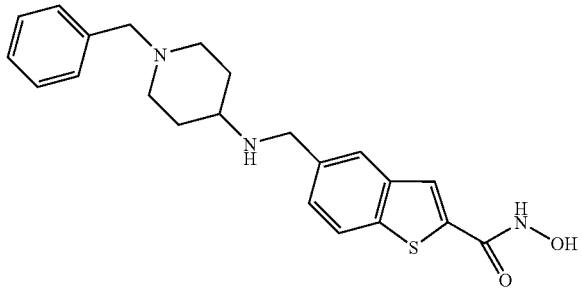

5-[(1-Benzyl-piperidin-4-ylamino)-methyl]-benzo[b]thiophene-2-carboxylic acid hydroxyamide $^1$H NMR (DMSO-$d_6$, 200 MHz, partial) δ 7.89 (d, J=8.2 Hz, 1H), 7.82 (s, 2H), 7.46-7.16 (m, 6H), 3.81 (s, 2H), 2.40 (s, 2H). MS (EI): cal'd 396.2 (MH$^+$), exp 396.3 (MH$^+$).

Compounds with 6-formylbenzothiophenes

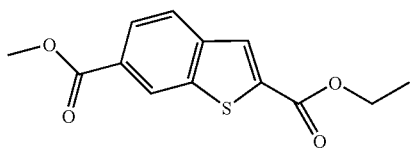

Benzo[b]thiophene-2,6-dicarboxylic acid 2-ethyl ester 6-methyl ester

A mixture of 4-formyl-3-nitro-benzoic acid methyl ester (15.22 g, 72.78 mmol), mercapto-acetic acid ethyl ester (8.70 mL, 79.3 mmol) and K$_2$CO$_3$ (12.87 g, 93.12 mmol) in 140 mL of anhydrous DMF was heated at 50° C. overnight. After cooling to rt, the mixture was poured into 1 L of ice-water and the resulting mixture was stirred for 40 min. The solid formed was filtered and washed with 4×70 mL of water. After drying, benzo[b]thiophene-2,6-dicarboxylic acid 2-ethyl ester 6-methyl ester was obtained as a pale solid. $^1$H NMR (CDCl$_3$, 200 MHz) δ 8.56 (s, 1H), 8.09-7.97 (m, 2H), 7.88 (d, J=8.0 Hz, 1H), 4.40 (q, J=7.2 Hz, 2H), 3.95 (s, 3H), 1.40 (t, J=6.8 Hz, 3H). MS (EI): cal'd 265.0 (MH$^+$), exp 265.0 (MH$^+$).

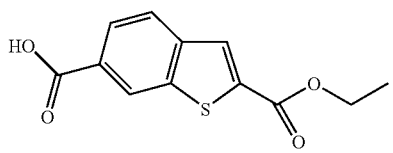

Benzo[b]thiophene-2,6-dicarboxylic acid 2-ethyl ester

A mixture of benzo[b]thiophene-2,6-dicarboxylic acid 2-ethyl ester 6-methyl ester (14.90 g, 56.38-mmol) and LiI (37.96 g, 283.6 mmol) in 120 mL of anhydrous pyridine was refluxed for 3 h. After cooling to rt, the mixture was poured into ice-cold 2N HCl (800 mL). The solid formed was filtered and washed with 3×100 mL of water. After drying, the solid was crystallized from MeOH to give benzo[b]thiophene-2,6-dicarboxylic acid 2-ethyl ester as a pale solid. $^1$H NMR (DMSO-$d_6$, 200 MHz) δ 8.66 (s, 1H), 8.21 (s, 1H), 8.08 (d, J=8.4 Hz, 1H), 7.96 (dd, J=8.4, 1.0 Hz, 1H), 4.34 (q, J=7.2 Hz, 2H), 1.40 (t, J=6.8 Hz, 3H). MS (EI): cal'd 251.0 (MH$^+$), exp 251.1 (MH$^+$).

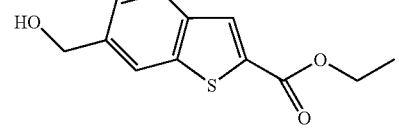

6-Hydroxymethyl-benzo[b]thiophene-2-carboxylic acid ethyl ester

To a solution of benzo[b]thiophene-2,6-dicarboxylic acid 2-ethyl ester (6.40 g, 25.57 mmol) in 250 mL of anhydrous THF at 0° C. was slowly added BH$_3$ (1.5M in THF, 80.0 mL, 120 mmol). The resulting mixture was allowed to stir at 0° C. for 30 min and at rt overnight. After cooling to 0° C., the reaction mixture was quenched with 1N HCl (30 mL). Additional 120 mL of water was added and THF was removed in vacuo. The solid formed was filtered and washed with 2×20 mL of water. After drying, 6-hydroxymethyl-benzo[b]thiophene-2-carboxylic acid ethyl ester was obtained as pale solid. $^1$H NMR (CDCl$_3$, 200 MHz) δ 8.00 (s, 1H), 7.88-7.76 (m, 2H), 7.36 (d, J=9.4 Hz, 1H), 4.80 (s, 2H), 4.38 (q, J=7.0 Hz, 2H), 2.00 (brs, 1H), 1.39 (t, J=7.0 Hz, 3H). MS (EI): cal'd 237.0. (MH$^+$), exp 237.1 (MH$^+$).

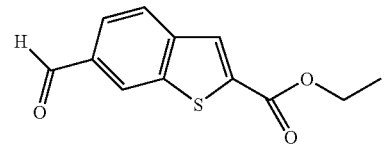

6-Formyl-benzo[b]thiophene-2-carboxylic acid ethyl ester

To a solution of 6-hydroxymethyl-benzo[b]thiophene-2-carboxylic acid ethyl ester (2.651 g, 11.22 mmol) in 110 mL of CH$_2$Cl$_2$ was added MnO$_2$ (13.50 g). The mixture was allowed to stir at rt for 30 min and then filtered through a pad of Celite. The filtrate was concentrated and dried to give 6-formyl-benzo[b]thiophene-2-carboxylic acid ethyl ester as a pale solid. $^1$H NMR (CDCl$_3$, 200 MHz) δ 10.09 (s, 1H), 8.34 (s, 1H), 8.07 (s, 1H), 7.97 (d, J=8.0 Hz, 2H), 7.88 (dd, J=8.4, 1.4 Hz, 1H), 4.40 (q, J=7.0 Hz, 2H), 1.41 (t, J=7.0 Hz, 3H). MS (EI): cal'd 235.0 (MH$^+$), exp 235.1 (MH$^+$).

2° Amines

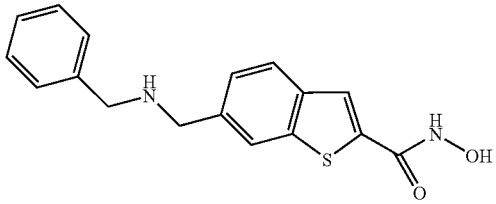

General Procedure:

6-(Benzylamino-methyl)-benzo[b]thiophene-2-carboxylic acid hydroxyamide

To a solution of 6-formyl-benzo[b]thiophene-2-carboxylic acid ethyl ester (85 mg, 0.36 mmol) and benzylamine (51 µL, 0.47 mmol) in anhydrous dichloroethane (5 mL) were added sodium triacetoxyborohydride (230 mg, 1.08 mmol) and acetic acid (20 µL, 0.35 mmol). After the reaction was complete, 5 mL of saturated NaHCO$_3$ was added. The organic layer was separated, washed with 5 mL of water and then concentrated. After drying under high vacuum, the residue was dissolved in anhydrous MeOH (5 mL) and hydroxylamine hydrochloride (95 mg, 1.37 mmol) was added, followed by the addition of NaOMe solution (4.37 M in MeOH, 0.60 mL, 2.6 mmol). The mixture was allowed to stir at rt till the reaction was complete. The reaction mixture was concentrated and the residue was dissolved in a minimal amount of water. The obtained solution was acidified with 2N HCl to pH≈8. The solid formed was filtered, washed with water, collected and purified by flash column chromatography to give 6-(benzylamino-methyl)-benzo[b]thiophene-2-carboxylic acid hydroxyamide as a pale solid. $^1$H NMR (DMSO-d$_6$, 200 MHz) δ 7.94 (d, J=8.4 Hz, 1H), 7.88 (s, 1H), 7.85 (s, 1H), 7.44 (dd, J=8.4, 1.4 Hz, 1H), 7.21 (t, J=7.6 Hz, 1H), 7.00-6.72 (m, 3H), 3.78 (s, 2H), 3.73 (s, 3H), 3.66 (s, 2H). MS (EI): cal'd 343.1 (MH$^+$), exp 343.2 (MH$^+$). $^1$H NMR (DMSO-d$_6$, 200 MHz) δ 7.94 (s, 1H), 7.90-7.78 (m, 2H), 7.46-7.14 (m, 6H), 3.80 (s, 2H), 3.69 (s, 2H). MS (EI): cal'd 313.1 (MH$^+$), exp 313.1 (MH$^+$).

The following compounds were prepared in procedures similar to those described for the preparation of 6-(benzylamino-methyl)-benzo[b]thiophene-2-carboxylic acid hydroxyamide.

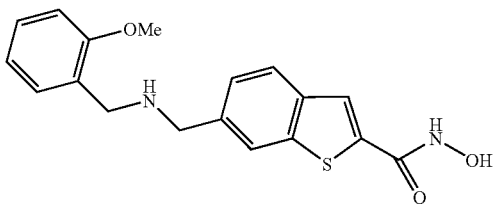

6-[(2-Methoxy-benzylamino)-methyl]-benzo[b]thiophene-2-carboxylic acid hydroxyamide $^1$H NMR (DMSO-d$_6$, 200 MHz) δ 7.95 (s, 1H), 7.90-7.78 (m, 2H), 7.46-7.30 (m, 2H), 7.28-7.14 9 m, 1H), 7.00-6.82 (m, 2H), 3.82 (s, 2H), 3.75 (s, 3H), 3.65 (s, 2H). MS (EI): cal'd 343.1 (MH$^+$), exp 343.1 (MH$^+$).

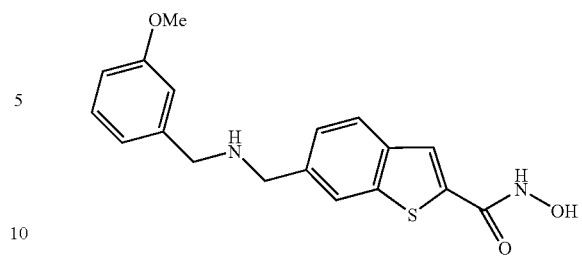

6-[(3-Methoxy-benzylamino)-methyl]-benzo[b]thiophene-2-carboxylic acid hydroxyamide $^1$H NMR (DMSO-d$_6$, 200 MHz) δ 7.94 (s, 1H), 7.91-7.78 (m, 2H), 7.40 (dd, J=8.4, 1.4 Hz, 1H), 7.21 (t, J=7.6 Hz, 1H), 6.97-6.84 (m, 2H), 6.82-6.72 (m, 1H), 3.79 (s, 2H), 3.73 (s, 3H), 3.66 (s, 2H). MS (EI): cal'd 343.1 (MH$^+$), exp 343.1 (MH$^+$).

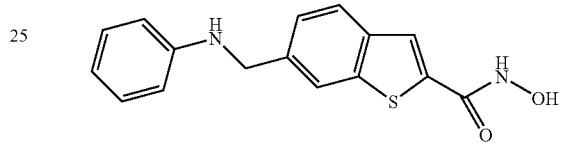

6-Phenylaminomethyl-benzo[b]thiophene-2-carboxylic acid hydroxyamide $^1$H NMR (DMSO-d$_6$, 200 MHz) δ 11.40 (brs, 1H), 9.25 (brs, 1H), 8.06-7.76 (m, 3H), 7.42 (d, J=8.4 Hz, 1H), 7.16-6.92 (m, 2H), 6.66-6.40 (m, 3H), 6.33 (brs, 1H), 4.37 (d, J=4.8 Hz, 2H). MS (EI): cal'd 299.1 (MH$^+$), exp 299.1 (MH$^+$).

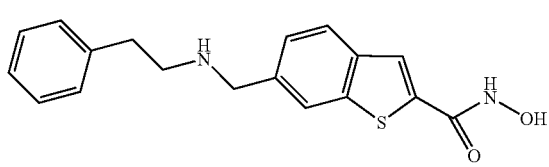

6-(Phenethylamino-methyl)-benzo[b]thiophene-2-carboxylic acid hydroxyamide $^1$H NMR (DMSO-d$_6$, 200 MHz) δ 7.92-7.76 (m, 3H), 7.40-7.08 (m, 6H), 3.83 (s, 2H), 2.72 (s, 4H). MS (EI): cal'd 327.1 (MH$^+$), exp 327.2 (MH$^+$).

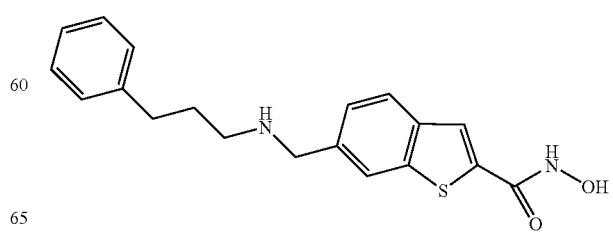

6-[(3-Phenyl-propylamino)-methyl]-benzo[b]thiophene-2-carboxylic acid hydroxyamide $^1$H NMR (partial, DMSO-d$_6$, 200 MHz) δ 7.94-7.78 (m, 3H), 7.39 (d, J=8.4 Hz, 1H), 7.30-7.06 (m, 5H), 3.81 (s, 2H), 2.60 (t, J=7.6 Hz, 2H), 1.72 (dd, J=7.4, 7.4 Hz, 2H). MS (EI): cal'd 341.1 (MH$^+$), exp 341.1 (MH$^+$).

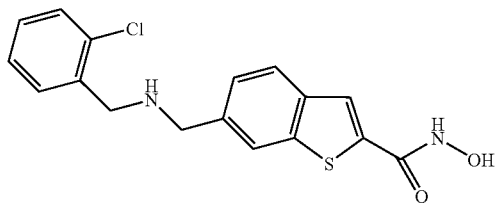

6-[(2-Chloro-benzylamino)-methyl]-benzo[b]thiophene-2-carboxylic acid hydroxyamide $^1$H NMR (DMSO-d$_6$, 200 MHz) δ 7.97 (s, 1H), 7.92-7.80 (m, 2H), 7.59 (dd, J=7.6, 1.8 Hz, 1H), 7.48-7.18 (m, 4H), 3.85 (s, 2H), 3.76 (s, 2H). MS (EI): cal'd 347.0 (MH$^+$), exp 347.1 (MH$^+$).

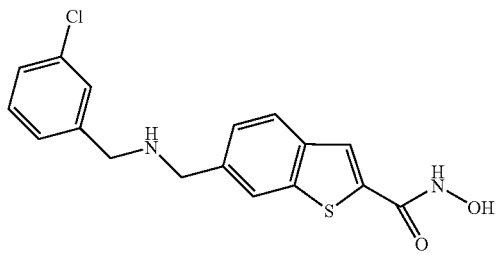

6-[(3-Chloro-benzylamino)-methyl]-benzo[b]thiophene-2-carboxylic acid hydroxyamide $^1$H NMR (DMSO-d$_6$, 200 MHz) δ 7.94. (s, 1H), 7.90-7.80 (m, 2H), 7.46-7.22 (m, 5H), 3.78 (s, 2H), 3.69 (s, 2H). MS (EI): cal'd 347.0 (MH$^+$), exp 347.1 (MH$^+$).

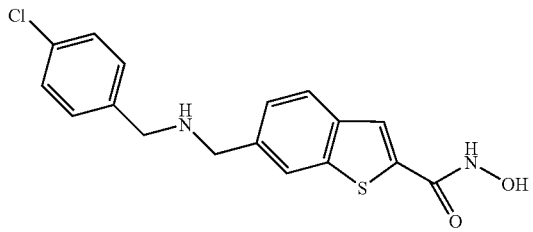

6-[(4-Chloro-benzylamino)-methyl]-benzo[b]thiophene-2-carboxylic acid hydroxyamide $^1$H NMR (DMSO-d$_6$, 200 MHz) δ 7.94 (s, 1H), 7.90-7.80 (m, 2H), 7.44-7.30 (m, 5H), 3.78 (s, 2H), 3.67 (s, 2H). MS (EI): cal'd 347.0 (MH$^+$), exp 347.1 (MH$^+$).

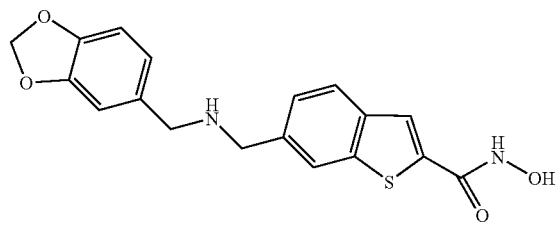

6-{[(Benzo[1,3]dioxol-5-ylmethyl)-amino]-methyl}-benzo[b]thiophene-2-carboxylic acid hydroxyamide $^1$H NMR (DMSO-d$_6$, 200 MHz) δ 7.93 (s, 1H), 7.90-7.80 (m, 2H), 7.40 (dd, J=8.0, 1.6 Hz, 1H), 6.94 (s, 1H), 6.88-6.70 (m, 2H), 5.96 (s, 2H), 3.76 (s, 2H), 3.60 (s, 2H). MS (EI): cal'd 357.1 (MH$^+$), exp 357.1 (MH$^+$).

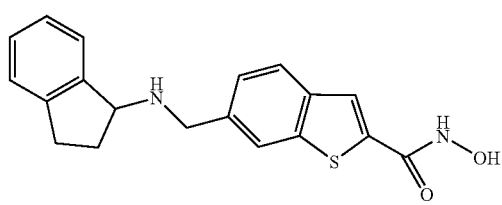

6-(Indan-1-ylaminomethyl)-benzo[b]thiophene-2-carboxylic acid hydroxyamide $^1$H NMR (DMSO-d$_6$, 200 MHz) δ 7.98-7.76 (m, 3H), 7.41 (d, J=8.0, Hz, 1H), 6.86 (d, J=8.2 Hz, 1H), 6.50-6.28 (m, 2H), 4.35 (s, 2H), 2.76-2.58 (m, 3H), 1.98-1.78 (m, 2H). MS (EI): cal'd 339.1 (MH$^+$), exp 339.2 (MH$^+$).

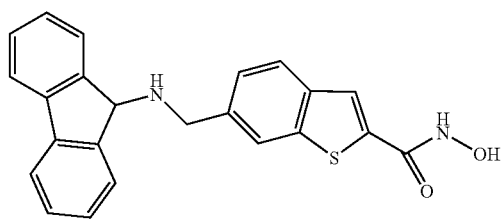

6-[(9H-Fluoren-9-ylamino)-methyl]-benzo[b]thiophene-2-carboxylic acid hydroxyamide $^1$H NMR (DMSO-d$_6$, 200 MHz) δ 7.94-7.66 (m, 7H), 7.44-7.26 (m, 5H), 4.99 (s, 1H), 3.41 (s, 2H). MS (EI): cal'd 387.1 (MH$^+$), exp 387.2 (MH$^+$).

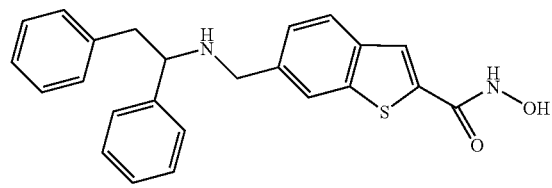

6-[(1,2-Diphenyl-ethylamino)-methyl]-benzo[b]thiophene-2-carboxylic acid hydroxyamide $^1$H NMR (DMSO-d$_6$, 200 MHz) δ 7.85 (s, 1H), 7.76 (d, J=8.4 Hz, 1H), 7.63 (s, 1H), 7.40-7.00 (m, 11H), 4.08 (t, J=7.0 Hz, 1H), 3.82-3.42 (m, 3H), 2.84 (d, J=7.0 Hz, 2H). MS (EI): cal'd 403.1 (MH$^+$), exp 403.2 (MH$^+$).

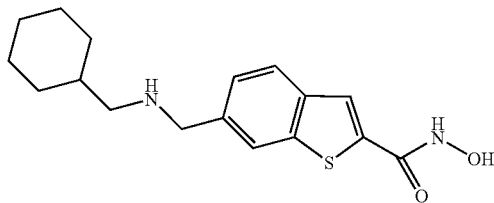

6-[(Cyclohexylmethyl-amino)-methyl]-benzo[b]thiophene-2-carboxylic acid hydroxyamide $^1$H NMR (DMSO-d$_6$, 200 MHz) δ 8.17 (s, 1H), 8.04-7.88 (m, 2H), 7.68-7.50 (m, 1H), 4.20 (s, 2H), 2.70 (brs, 2H), 1.88-1.46 (m, 6H), 1.25-0.72 (m, 5H). MS (EI): cal'd 319.1 (MH$^+$), exp 319.2 (MH$^+$).

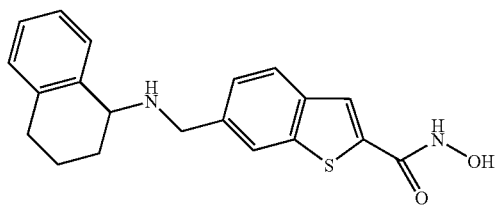

6-[(1,2,3,4-Tetrahydro-naphthalen-1-ylamino)-methyl]-benzo[b]thiophene-2-carboxylic acid hydroxyamide $^1$H NMR (DMSO-d$_6$, 200 MHz) δ 8.00 (s, 1H), 7.92-7.76 (m, 2H), 7.48 (dd, J=8.0, 1.0 Hz, 1H), 7.42-7.32 (m, 1H), 7.18-6.96 (m, 3H), 4.02-3.75 (m, 2H), 3.66 (t, J=5.2 Hz, 1H), 2.84-2.52 (m, 2H), 2.06-1.50 (m, 4H). MS (EI): cal'd 353.1 (MH$^+$), exp 353.2 (MH$^+$).

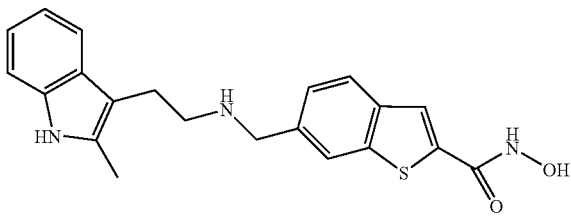

6-{[2-(2-Methyl-1H-indol-3-yl)-ethylamino]-methyl}-benzo[b]thiophene-2-carboxylic acid hydroxyamide $^1$H NMR (DMSO-d$_6$, 200 MHz) δ 10.68 (s, 1H), 7.96-7.78 (m, 3H), 7.44-7.28 (m, 2H), 7.19 (d, J=7.0 Hz, 1H), 7.00-6.78 (m, 2H), 3.86 (s, 2H), 2.88-2.60 (m, 4H), 2.29 (s, 3H). MS (EI): cal'd 380.1 (MH$^+$), exp 380.2 (MH$^+$).

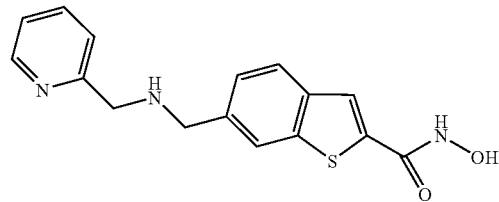

6-{[(Pyridin-2-ylmethyl)-amino]-methyl}-benzo[b]thiophene-2-carboxylic acid hydroxyamide $^1$H NMR (DMSO-d$_6$, 200 MHz) δ 8.48 (d, J=4.0 Hz, 1H), 8.00-7.82 (m, 3H), 7.76 (ddd, J=8.2, 8.2, 1.8 Hz, 1H), 7.53-7.37 (m, 2H), 7.30-7.18 (m, 1H), 3.88 (s, 2H), 3.82 (s, 2H). MS (EI): cal'd 314.1 (MH$^+$), exp 314.1 (MH$^+$).

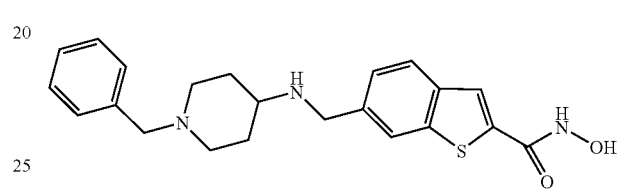

6-[(1-Benzyl-piperidin-4-ylamino)-methyl]-benzo[b]thiophene-2-carboxylic acid hydroxyamide $^1$H NMR (DMSO-d$_6$, 200 MHz) δ 7.96-7.78 (m, 3H), 7.40 (dd, J=8.0, 1.4 Hz, 1H), 7.36-7.18 (m, 5H), 3.84 (s, 2H), 3.40 (s, 2H), 2.82-2.62 (m, 2H), 2.44-2.30 (m, 1H), 2.00-1.70 (m, 4H), 1.48-1.18 (m, 2H). MS (EI): cal'd 396.2 (MH$^+$), exp 396.2 (MH$^+$).

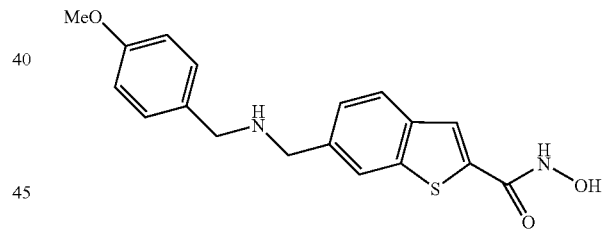

6-[(4-Methoxy-benzylamino)-methyl]-benzo[b]thiophene-2-carboxylic acid hydroxyamide $^1$H NMR (DMSO-d$_6$, 200 MHz) δ 7.93 (s, 1H), 7.90-7.78 (m, 2H), 7.40 (d, J=8.0 Hz, 1H), 7.25 (d, J=8.6 Hz, 2H), 6.86 (d, J=8.8 Hz, 2H), 3.77 (s, 2H), 3.72 (s, 3H), 3.62 (s, 2H). MS (EI): cal'd 343.1 (MH$^+$), exp 343.1 (MH$^+$).

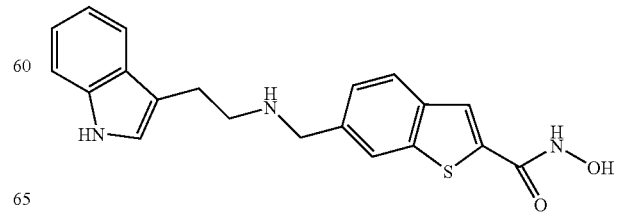

6-{[2-(1H-Indol-3-yl)-ethylamino]-methyl}-benzo[b]thiophene-2-carboxylic acid hydroxyamide $^1$H NMR (DMSO-d$_6$, 200 MHz) δ 7.94 (s, 1H), 7.91-7.78 (m, 2H), 7.52-7.36 (m, 2H), 7.31 (d, J=7.6 Hz, 1H), 7.16-6.84 (m, 3H), 3.92 (s, 2H), 2.86 (s, 4H). MS (EI): cal'd 366.1 (MH$^+$), exp 366.1 (MH$^+$).

3° Amines

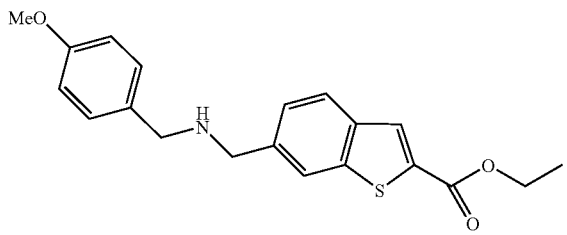

6-[(4-Methoxy-benzylamino)-methyl]-benzo[b]thiophene-2-carboxylic acid ethyl ester To a solution of 6-formyl-benzo[b]thiophene-2-carboxylic acid ethyl ester (1.05 g, 4.48 mmol) and 4-methoxy-benzylamine (0.76 mL, 5.86 mmol) in anhydrous dichloroethane (40 mL) were added sodium triacetoxyborohydride (2.87 g, 13.5 mmol) and acetic acid (0.25 mL, 4.4 mmol). After the reaction was complete, the reaction mixture was diluted with 60 mL of CH$_2$Cl$_2$ and 40 mL of saturated NaHCO$_3$. The organic layer was separated, washed with 50 mL of water, 50 mL of brine and then dried over Na$_2$SO$_4$. After filtration, the filtrate was concentrated and the residue was purified by flash column chromatography to give 6-[(4-methoxy-benzylamino)-methyl]-benzo[b]thiophene-2-carboxylic acid ethyl ester as a white solid. MS (EI): cal'd 356.1 (MH$^+$), exp 356.1 (MH$^+$).

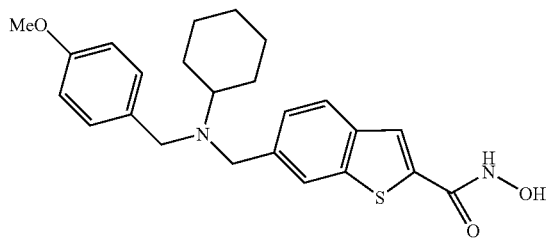

6-{[Cyclohexyl-(4-methoxy-benzyl)-amino]-methyl}-benzo[b]thiophene2-carboxylic acid hydroxyamide To a solution of 6-[(4-methoxy-benzylamino)-methyl]-benzo[b]thiophene-2-carboxylic acid ethyl ester (122 mg, 0.34 mmol) and cyclohexanone (46 μL, 0.44 mmol) in anhydrous dichloroethane (5 mL) were added sodium triacetoxyborohydride (216 mg, 1.02 mmol) and acetic acid (20 μL, 0.35 mmol). After the reaction was complete, 5 mL of saturated NaHCO$_3$ was added. The organic layer was separated, washed with 5 mL of water and then concentrated. After drying under high vacuum, the residue was dissolved in anhydrous MeOH (6 mL) and hydroxylamine hydrochloride (90 mg, 1.30 mmol) was added, followed by the addition of NaOMe solution (4.37 M in MeOH, 0.57 mL, 2.5 mmol). The mixture was allowed to stir at rt till the reaction was complete. The reaction mixture was concentrated and the residue was dissolved in a minimal amount of water. The obtained solution was acidified with 2N HCl to pH≈8. The solid formed was filtered, washed with water, collected and purified by flash column chromatography to give 6-{[cyclohexyl-(4-methoxy-benzyl)-amino]-methyl}-benzo[b]thiophene-2-carboxylic acid hydroxyamide as a brownish solid. $^1$H NMR (DMSO-d$_6$, 200 MHz) δ 11.35 (brs, 1H), 9.23 (brs, 1H), 7.90 (s, 1H), 7.87-7.74 (m, 2H), 7.40 (d, J=8.2 Hz, 1H), 7.23 (d, J=8.8 Hz, 2H), 6.83 (d, J=8.4 Hz, 2H), 3.69 (s, 3H), 3.67 (s, 2H), 3.51 (s, 2H), 2.46-2.24 (m, 1H), 1.92-0.86 (m, 10H). MS (EI): cal'd 425.2 (MH$^+$), exp 425.1 (MH$^+$).

The following compounds were prepared in procedures similar to those described for the preparation of 6-{[cyclohexyl-(4-methoxy-benzyl)-amino]-methyl}-benzo[b]thiophene-2-carboxylic acid hydroxyamide.

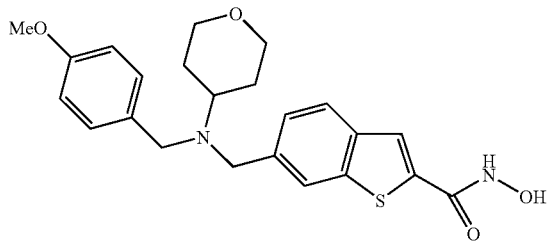

6-{[(4-Methoxy-benzyl)-(tetrahydro-pyran-4-yl)-amino]-methyl}-benzo[b]thiophene-2-carboxylic acid hydroxyamide $^1$H NMR (DMSO-d$_6$, 200 MHz) δ 11.42 (brs, 1H), 9.24 (brs, 1H), 7.92 (s, 1H), 7.90-7.76 (m, 2H), 7.40 (d, J=9.2 Hz, 1H), 7.24 (d, J=8.8 Hz, 2H), 6.84 (d, J=8.4 Hz, 2H), 3.74-3.64 (m, 5H), 3.54 (s, 2H), 3.94-3.78 (m, 2H), 3.14-3.00 (m, 2H), 2.80-2.54 (m, 1H), 1.78-1.46 (m, 4H). MS (EI): cal'd 427.2 (MH$^+$), exp 427.1 (MH$^+$).

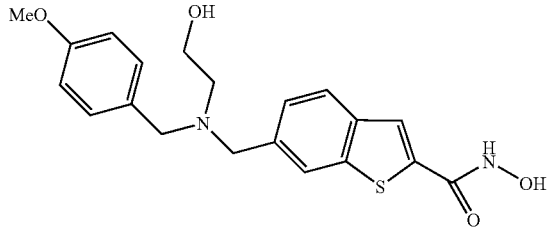

6-{[(2-Hydroxy-ethyl)-(4-methoxy-benzyl)-amino]-methyl}-benzo[b]thiophene-2-carboxylic acid hydroxyamide $^1$H NMR (DMSO-d$_6$, 200 MHz) δ 11.43 (brs, 1H), 9.26 (brs, 1H), 7.96 (s, 1H), 7.90-7.78 (m, 2H), 7.41 (d, J=8.4 Hz, 1H), 7.27 (d, J=8.8 Hz, 2H), 6.87 (d, J=8.4 Hz, 2H), 4.39 (t, J=5.4 Hz, 1H), 3.71 (s, 3H), 3.67 (s, 2H), 3.58-3.38 (m, 6H). MS (EI): cal'd 387.1 (MH$^+$), exp 387.1 (MH$^+$).

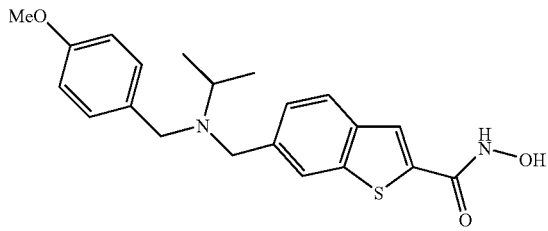

6-{[Isopropyl-(4-methoxy-benzyl)-amino]-methyl}-benzo[b]thiophene-2-carboxylic acid hydroxyamide $^1$H NMR (DMSO-d$_6$, 200 MHz) δ 7.92 (s, 1H), 7.88-7.76 (m, 2H), 7.41 (dd, J=8.4, 1.6 Hz, 1H), 7.24 (d, J=8.8 Hz, 2H), 6.84 (d, J=8.8 Hz, 2H), 3.69 (s, 3H), 3.59 (s, 2H), 3.43 (s, 2H), 2.90-2.68 (m, 1H), 1.02 (d, J=6.6 Hz, 6H). MS (EI): cal'd 385.2 (MH$^+$), exp 385.2 (MH$^+$).

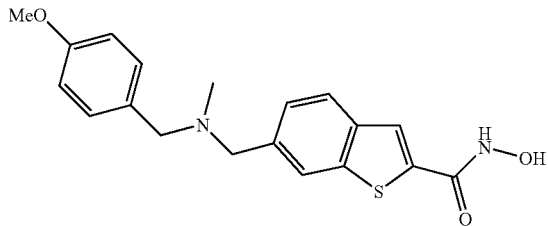

6-{[(4-Methoxy-benzyl)-methyl-amino]-methyl}-benzo[b]thiophene-2-carboxylic acid hydroxyamide $^1$H NMR (DMSO-d$_6$, 200 MHz) δ 7.93 (s, 1H), 7.90-7.80 (m, 2H), 7.40 (dd, J=8.0, 1.0 Hz, 1H), 7.26 (d, J=8.4 Hz, 2H), 6.88 (d, J=8.4 Hz, 2H), 3.72 (s, 3H), 3.57 (s, 2H), 3.44 (s, 2H), 2.05 (s, 3H). MS (EI): cal'd 357.1 (MH$^+$), exp 357.2 (MH$^+$).

Acylated amines

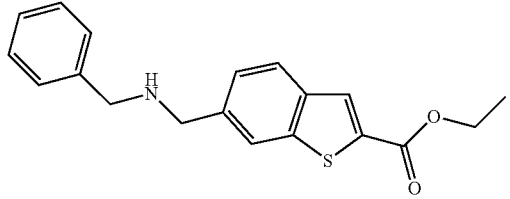

6-(Benzylamino-methyl)-benzo[b]thiophene-2-carboxylic acid ethyl ester

The title compound was prepared in procedures similar to those described for the preparation of 6-[(4-methoxy-benzylamino)-methyl]-benzo[b]thiophene-2-carboxylic acid ethyl ester. $^1$H NMR (DMSO-d$_6$, 200 MHz) δ 8.13 (s, 1H), 7.98-7.86 (m, 2H), 7.44 (dd, J=8.0, 1.0 Hz, 1H), 7.38-7.14 (m, 5H), 4.32 (q, J=7.0 Hz, 2H), 3.79 (s, 2H), 3.68 (s, 2H), 1.31 (t, J=6.8 Hz, 3H).

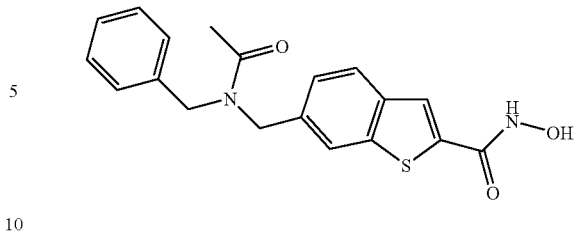

6-[(Acetyl-benzyl-amino)-methyl]-benzo[b]thiophene-2-carboxylic acid hydroxyamide To a solution of 6-(benzylamino)-methyl-benzo[b]thiophene-2-carboxylic acid ethyl ester (112 mg, 0.34 mmol), NMM (0.12 mL, 1.09 mmol) and DMAP (10 mg, 0.08 mmol) in anhydrous dichloromethane (5 mL) at 0° C. was added acetic anhydride (48 μL, 0.51 mmol). The reaction mixture was allowed to warm to rt. After the reaction was complete, 5 mL of saturated NaHCO$_3$ was added. The organic layer was separated, washed with 5 mL of water and then concentrated. After drying under high vacuum, the residue was dissolved in anhydrous MeOH (6 mL) and hydroxylamine hydrochloride (90 mg, 1.30 mmol) was added, followed by the addition of NaOMe solution (4.37 M in MeOH, 0.57 mL, 2.5 mmol). The mixture was allowed to stir at rt till the reaction was complete. The reaction mixture was concentrated and the residue was dissolved in a minimal amount of water. The obtained solution was acidified with 2N HCl to pH≈8. The solid formed was filtered, washed with water, collected and purified by flash column chromatography to give 6-[(acetyl-benzyl-amino)-methyl]-benzo[b]thiophene-2-carboxylic acid hydroxyamide as a pale solid (83.3 mg, 69%). $^1$H NMR (DMSO-d$_6$, 200 MHz) δ 11.47 (brs, 1H), 9.30 (brs, 1H), 7.98-7.74 (m, 3H), 7.44-7.10 (m, 6H), 4.65-4.40 (m, 4H), 2.12 (s, 3H). MS (EI): cal'd 355.1 (MH$^+$), exp 355.2 (MH$^+$).

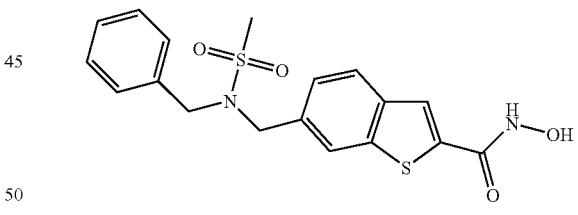

6-[(Benzyl-methanesulfonyl-amino)-methyl]-benzo[b]thiophene-2-carboxylic acid hydroxyamide The title compound was prepared in procedures similar to those described for the preparation of 6-[(acetyl-benzyl-amino)-methyl]-benzo[b]thiophene-2-carboxylic acid hydroxyamide. Methanesulfonyl chloride was used instead of acetic anhydride for the preparation of this title compound. $^1$H NMR (DMSO-d$_6$, 200 MHz) δ 11.46 (brs, 1H), 9.29 (brs, 1H), 7.90-7.76 (m, 3H), 7.36-7.16 (m, 6H), 4.43 (s, 2H), 4.33 (s, 2H), 2.99 (s, 3H). MS (EI): cal'd 389.1 (M−H$^-$), exp 389.2 (M−H$^-$).

Scheme 8

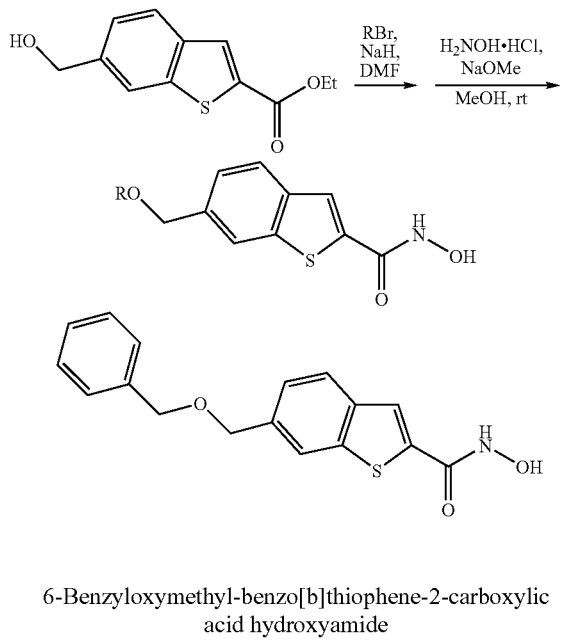

6-Benzyloxymethyl-benzo[b]thiophene-2-carboxylic acid hydroxyamide

To a solution of 6-hydroxymethyl-benzo[b]thiophene-2-carboxylic acid ethyl ester (103 mg, 0.44 mmol) at rt was added NaH (60% dispersion, 54 mg, 1.35 mmol). The resulting mixture was allowed to stir at rt for 15 min and benzyl bromide (60 μL, 0.50 mmol) was added. After stirring at rt for additional 30 min, the mixture was poured into a mixture of 1N HCl (3 mL) and H$_2$O (30 mL) and the solution was extracted with EtOAc (30 mL). The organic layer was washed with 20 ml of brine and dried over Na$_2$SO$_4$. After filtration, the filtrate was concentrated and dried under high vacuum, the residue was dissolved in anhydrous MeOH (7 mL) and hydroxylamine hydrochloride (116 mg, 1.67 mmol) was added, followed by the addition of NaOMe solution (4.37 M in MeOH, 0.74 mL, 3.2 mmol). The mixture was allowed to stir at rt till the reaction was complete. The reaction mixture was concentrated and the residue was dissolved in 4 mL of water. The obtained solution was acidified with 2N HCl to pH≈8. The solid formed was filtered, washed with water and dried to give 6-benzyloxymethyl-benzo[b]thiophene-2-carboxylic acid hydroxyamide as a light orange solid. $^1$H NMR (DMSO-d$_6$, 200 MHz) δ 7.96 (s, 1H), 7.92-7.81 (m, 2H), 7.42-7.20 (m, 6H), 4.64 (s, 2H), 4.55 (s, 2H). MS (EI): cal'd 314.1 (MH$^+$), exp 314.1 (MH$^+$).

Compounds with other Substitution

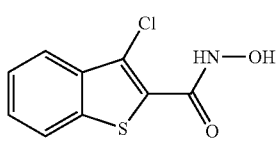

3-Chloro-benzo[b]thiophene-2-carboxylic acid hydroxyamide

The same procedure as for the preparation of 2-hydroxycarbamoyl-benzo[b]thiophene-6-carboxylic acid methyl ester was employed.

$^1$H (DMSO-d$_6$) δ 11.23 (br s, 1H), 9.45 (br s, 1H), 8.15-8.02 (m, 1H), 7.90-7.80 (m, 1H), 7.63-7.50 (m, 2H). MS (EI): cal'd (MH$^+$) 228.03, exp (MH$^+$) 228.17.

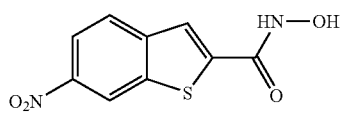

6-Nitro-benzo[b]thiophene-2-carboxylic acid hydroxyamide

The same procedure as for the preparation of 2-hydroxycarbamoyl-benzo[b]thiophene-6-carboxylic acid methyl ester was employed.

MS (EI): cal'd (MH$^+$) 239.03, exp (MH$^+$) 239.16.

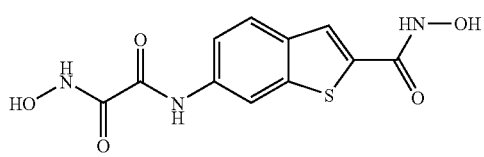

N-Hydroxy-N'-(2-hydroxycarbamoyl-benzo[b]thiophene-6-yl)-oxalamide $^1$H NMR (DMSO-d$_6$) δ 10.80 (br s, 1H), 8.47 (s, 1H), 7.90-7.70 (m, 3H), 6.37 (s, 1H). MS (EI): cal'd (MH$^+$) 296.1, exp (MH$^+$) 296.2.

Thiophenes

Compounds from 5-phenylthiophenes

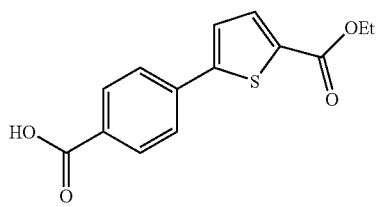

5-(4-Carboxy-phenyl)-thiophene-2-carboxylic acid ethyl ester

Ethyl 5-bromothiophene-2-carboxylate (318 mg, 1.35 mmol) and 4-carboxyphenyl boronic acid (203 mg, 1.23 mmol) were suspended in 1 mL of water under nitrogen atmosphere. Tetrabutylammonium bromide (403 mg, 1.25 mmol), palladium acetate (2 mg, 0.009 mmol) and potassium carbonate (422 mg, 3.05 mmol) were added and the mixture stirred at 70° C. for 1 h. The solution was brought to pH 2 by addition of 1M HCl and the product extracted into 10% MeOH in EtOAc. The organic phase was dried and the solvent was removed. The solid was tritured with ethyl acetate, leaving a solid product. $^1$H-NMR (CDCl$_3$): δ=7.99 (d, J=8.6 Hz, 2H), 7.88 (d, J=8.6 Hz, 2H), 7.83 (d, J=4 Hz, 1H), 7.49 (d, J=4 Hz, 1H), 4.31 (q, J=7.4 Hz, 2H), 1.31 (t, J=7.4 Hz, 3H). MS (EI): cal'd 277 (MH$^+$), exp 277 (MH$^+$).

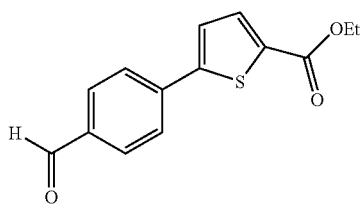

5-(4-Formyl-phenyl)-thiophene-2-carboxylic acid ethyl ester

The title compound was prepared according to the same procedure used for 5-(4-Carboxy-phenyl)-thiophene-2-carboxylic acid ethyl ester. The product was triturated with EtOAc: Hexanes 2:1 and isolated as a solid. $^1$NMR(CDCl$_3$): δ=10.03 (s, 1H), 7.99 (m, 4H), 7.85 (d, J=4 Hz, 1H), 7.80 (d, J=4 Hz, 1H), 4.31 (q, J=7.4 Hz, 2H), 1.31 (t, J=7.4 Hz, 3H). MS (EI): cal'd 261 (MH$^+$), exp 261 (MH$^+$).

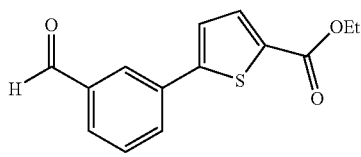

5-(3-Formyl-phenyl)-thiophene-2-carboxylic acid ethyl ester

The title compound was prepared according to die same procedure used for 5-(4-Carboxy-phenyl)-thiophene-2-carboxylic acid ethyl ester. The crude was purified by chromatography (silica gel, hexanes:EtOAc 100:0-100:12), yielding a white solid. $^1$H-NMR (CDCl$_3$): δ=10.07 (s, 1H), 8.14 (m, 1H), 7.92-7.80 (m, 2H), 7.79 (d, J=4 Hz, 1H), 7.60 (t, J=7.8 Hz, 1H), 7.39 (d, 4H, 1H), 4.31 (q, J=7.4 Hz, 2H), 1.31 (t, J=7.4 Hz, 3H). MS (EI): cal'd 261 (MH$^{30}$), exp 261 (MH$^+$).

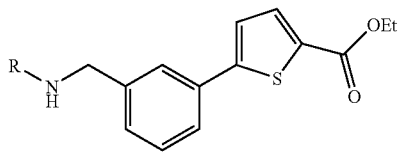

General Experimental for Amine Formation using (Formyl-Phenyl)-Thiophene

N-Alkyl-5-(3-aminomethyl-phenyl)-thiophene-2-carboxylic acid ethyl ester 5-(3-Formyl-phenyl)-thiophene-2-carboxylic acid ethyl ester (0.6 mmol) and a primary amine (1.1 eq.) were refluxed for 4 h in methanol. Sodium triacetoxyborohydride (1.5 eq.) was added and the solution was stirred at room temperature under nitrogen overnight. The solvent was removed under reduced pressure and the residue was dissolved in methylene chloride and washed with sat. sodium bicarbonate. The organic phase was dried and the solvent removed, yielding the product quantitatively as oil that was used in the next step without further purification.

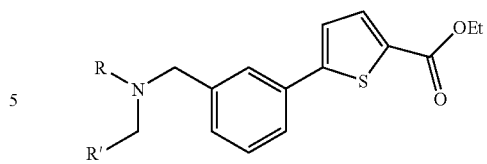

N,N-Dialkyl-5-(3-aminomethyl-phenyl)-thiophene-2-carboxylic acid ethyl ester The secondary amine from the previous step was dissolved in dichloroethane. To this solution were added an aldehyde (1.5 eq.) and sodium triacetoxyborohydride (2.5 eq.). The resulting suspension was stirred overnight at room temperature under nitrogen. The solvent was removed under reduced pressure and the product was purified by column chromatography (silica gel, Hexanes: EtOAc 100: 0-70:30).

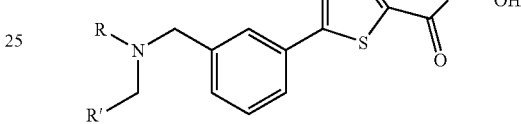

N,N-Dialkyl-5-(3-Aminomethyl-phenyl)-thiophene-2-carboxylic acid hydroxyamide The tertiary amine ethyl ester from the previous step was dissolved in anhydrous methanol. A solution of hydroxylamine hydrochloride (5-10 eq.) in anhydrous methanol was added, followed by a solution of sodium methoxide in methanol (1.8 eq. relative to hydroxylamine hydrochloride). A precipitate (NaCl) formed immediately. The reaction was stirred overnight at room temperature. The solvent was removed under reduced pressure and the residue re-dissolved in water. The solution was neutralized by addition of 1 M HCl. The crude product was isolated by filtration or extracted into EtOAc. It was purified further by column or prep.—TLC chromatography (silica, Hexanes-EtOAc).

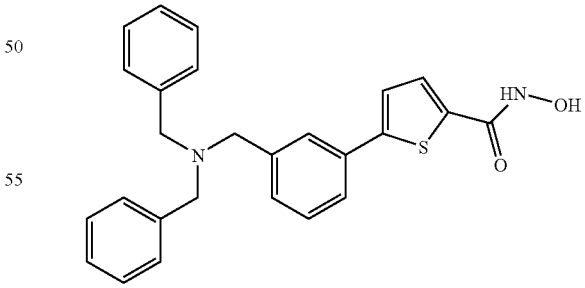

5-{3-[(Dibenzylamino)-methyl]-phenyl}-thiophene-2-carboxylic acid hydroxyamide $^1$H-NMR (CD$_3$OD): δ=7.70 (s, 1H), 7.56 (m, 1H), 7.45-7.20 (m, 13H), 3.56 (s, 2H), 3.55 (s, 4H). MS (EI): cal'd. 429 (MH$^+$), exp 429 (MH$^+$).

115

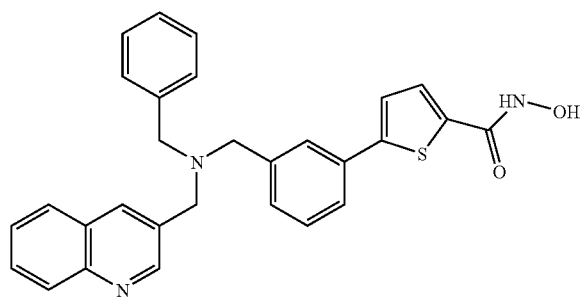

5-{3-[(Benzyl-quinolin-3-ylmethyl-amino)-methyl]-phenyl}-thiophene-2-carboxylic acid hydroxyamide ¹H-NMR (d₆-DMSO): δ=11.28 (s, 1H), 9.18 (m, 1H), 8.90 (d, J=1.8 Hz, 1H), 8.29 (d, J=1.8 Hz, 1H), 8.01-7.96 (m, 2H), 7.77-7.20 (m, 13H), 3.75 (s, 2H), 3.63 (s, 2H), 3.61 (s, 2H). MS (EI): cal'd 480 (MH⁺), exp 480 (MH⁺).

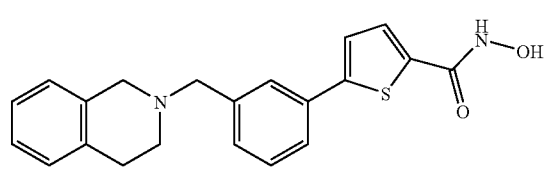

5-[3-(3,4-Dihydro-1H-isoquinolin-2-ylmethyl)-phenyl]-thiophene-2-carboxylic acid hydroxyamide ¹H-NMR (CD₃OD, 200 MHz): δ=7.75 (br s, 1H), 7.64-7.50 (m, 2H), 7.43-7.39 (m, 3H), 7.12-7.06 (m, 3H), 7.04-6.96 (m, 1H), 3.76 (s, 2H), 3.67 (s, 2H), 2.96-2.86 (m, 2H), 2.86-2.76 (m, 2H). MS (EI): cal'd 365 (MH⁺), exp 365 (MH⁺).

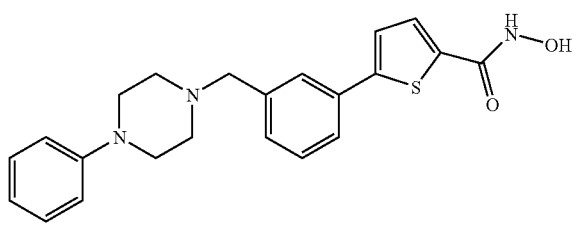

5-[3-(4-Phenyl-piperazin-1-ylmethyl)-phenyl]-thiophene-2-carboxylic acid hydroxyamide ¹H-NMR (CD₃OD, 200 MHz): δ=8.64 (d, J=4.4 Hz, 1H), 8.11 (d, J=8.8 Hz, 1H), 7.95 (d, J=7.0 Hz, 1H), 7.74-7.64 (m, 1H), 7.58-7.40 (m, 5H), 7.28-7.10 (m, 6H), 7.10-7.03 (m, 2H), 4.12 (s, 2H), 3.76 (s, 2H), 2.88 (br s, 4H). MS (EI): cal'd 394 (MH⁺), exp 394 (MH⁺).

116

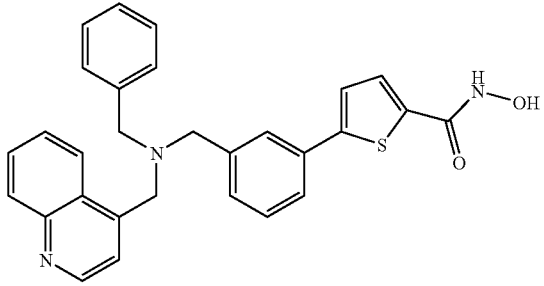

5-{3-[(Benzyl-quinolin-4-ylmethyl-amino)-methyl]-phenyl}-thiophene-2-carboxylic acid hydroxyamide ¹H-NMR (CD₃OD, 200 MHz): δ=8.73 (d, J=4.8 Hz, 1H), 8.16 (dd, J1=8.4 Hz, J2=0.8 Hz, 1H), 7.96 (d, J=9.2 Hz, 1H), 7.78-7.62 (m, 3H), 7.60-7.46 (m, 3H), 7.42-7.18 (m, 8H), 4.05 (s, 2H), 3.64 (s, 2H), 3.62 (s, 2H). MS (EI): cal'd 480 (MH⁺), exp 480 (MH⁺).

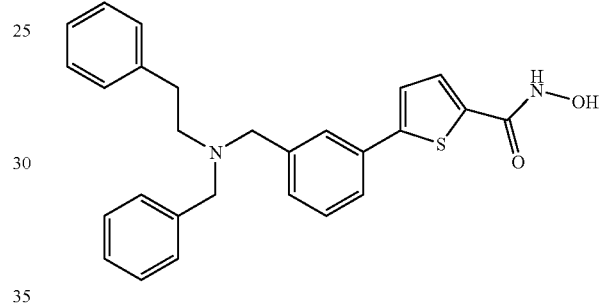

5-{3-[(Benzyl-phenethyl-amino)-methyl]-phenyl}-thiophene-2-carboxylic acid hydroxyamide ¹H-NMR (CD₃OD, 200 MHz): δ=7.60-7.45 (m, 3H), 7.31-7.00 (m, 13H), 3.62 (s, 2H), 3.61 (s, 2H), 2.80-2.72 (m, 2H), 2.72-2.60 (m, 2H). MS (EI): cal'd 443 (MH⁺), exp 443 (MH⁺).

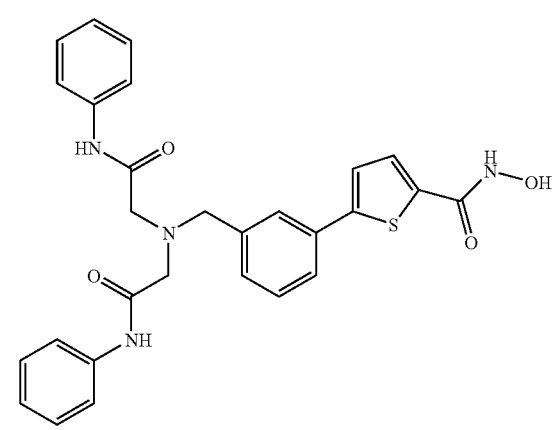

5-{3-[(Bis-phenylcarbamoylmethyl-amino)-methyl]-phenyl}-thiophene-2-carboxylic acid hydroxyamide ¹H-NMR (DMSO-d₆, 200 MHz): δ=11.25 (br s, 1H), 10.68 (s, 1H), 10.26 (s, 2H), 9.92 (s, 1H), 7.77 (br s, 1H), 7.61 (d, J=8.0 Hz, 4H), 7.62-7.59 (m, 1H), 7.46-7.39 (m, 3H), 7.32 (t, J=8.0 Hz, 1H), 7.34-7.30 (m, 1H), 7.05 (t, J=7.0 Hz, 2H), 3.34 (s, 2H), 2.93 (s, 2H), 2.77 (s, 2H).
MS (EI): cal'd 515 (MH+), exp 515 (MH+).

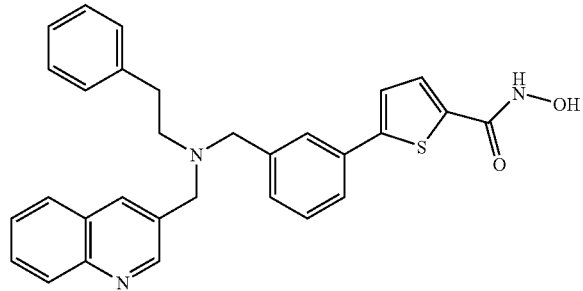

5-{3-[(Phenethyl-quinolin-3-ylmethyl-amino)-methyl]-phenyl}-thiophene-2-carboxylic acid hydroxyamide ¹H-NMR (DMSO-d₆, 200 MHz): δ=11.23 (br s, 1H), 9.18 (br s, 1H), 8.79 (d, J=1.8 Hz, 1H), 8.13 (br s, 1H), 7.97 (d, J=8.0 Hz, 1H), 7.87 (d, J=7.6 Hz, 1H), 7.76-7.50 (m, 5H), 7.44 (d, J=3.6 Hz, 1H), 7.42-6.98 (m, 7H), 3.83 (s, 2H), 3.75 (s, 2H), 2.92-2.80 (m, 2H), 2.76-2.64 (m, 2H).
MS (EI): cal'd 494 (MH+), exp 494 (MH+).

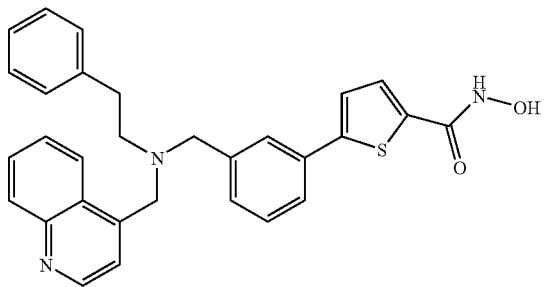

5-{3-[(Phenethyl-quinolin-4-ylmethyl-amino)-methyl]-phenyl}-thiophene-2-carboxylic acid hydroxyamide ¹H-NMR (CD₃OD, 200 MHz): δ=8.64 (d, J=4.4 Hz, 1H), 8.11 (d, J=8.8 Hz, 1H), 7.95 (d, J=7.0 Hz, 1H), 7.69 (t, J=7.0 Hz, 1H), 7.59-7.42 (m, 5H), 7.29-7.02 (m, 8H), 4.11 (s, 2H), 3.76 (s, 2H), 2.87 (br s, 4H). MS (EI): cal'd 494 (MH+), exp 494 (MH+).

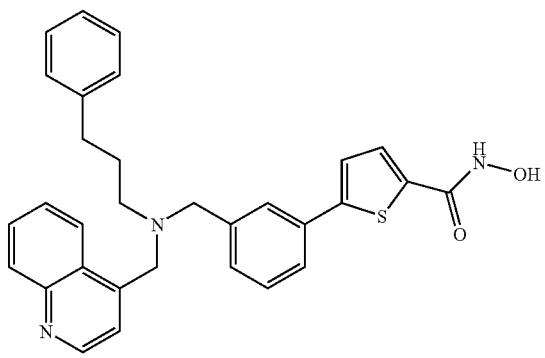

5-(3-{[(3-Phenyl-propyl)-quinolin-4-ylmethyl-amino]-methyl}-phenyl)-thiophene-2-carboxylic acid hydroxyamide ¹H-NMR (DMSO-d₆, 200 MHz): δ=11.22 (br s, 1H), 9.18 (br s, 1H), 8.80 (d, J=4.4 Hz, 1H), 8.25 (d, J=7.4 Hz, 1H), 8.01 (d, J=7.4 Hz, 1H), 7.78-7.54 (m, 5H), 7.43-7.26 (m, 4H), 7.20-6.94 (m, 5H), 4.05 (s, 2H), 3.69 (s, 2H), 3.38-3.28 (m, 4H), 1.88-1.72 (m, 2H). MS (EI): cal'd 508 (MH+), exp 508 (MH+).

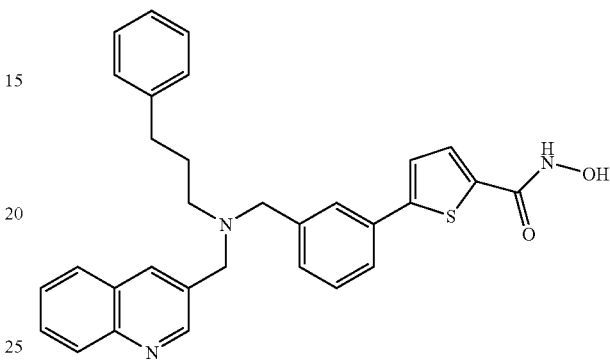

5-(3-{[(3-Phenyl-propyl)-quinolin-3-ylmethyl-amino]-methyl}-phenyl)-thiophene-2-carboxylic acid hydroxyamide ¹H-NMR (DMSO-d₆, 200 MHz): δ=11.22 (br s, 1H), 9.18 (br s, 1H), 8.88 (d, J=2.2 Hz, 1H), 8.22 (br s, 1H), 7.97 (t, J=8.8 Hz, 2H), 7.76-7.30 (m, 8H), 7.16-6.98 (m, 5H), 3.78 (s, 2H), 3.67 (s, 2H), 2.60-2.40 (m, 4H), 1.90-1.74 (m, 2H). MS (EI): cal'd 508 (MH+), exp 508 (MH+).

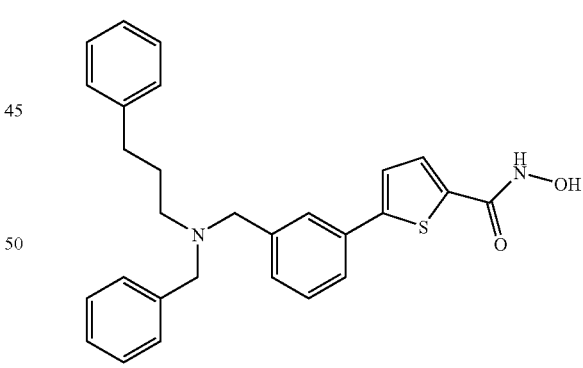

5-(3-{[Benzyl-(3-phenyl-propyl)-amino]-methyl}-phenyl)-thiophene-2-carboxylic acid hydroxyamide ¹H-NMR (DMSO-d₆, 200 MHz): δ=11.23 (br s, 1H), 9.17 (br s, 1H), 7.68-7.56 (m, 3H), 7.48 (d, J=4.0 Hz, 1H), 7.40-7.02 (m, 13H), 3.57 (s, 2H), 3.56 (s, 2H), 2.56-2.37 (m, 4H), 1.86-1.68 (m, 2H). MS (EI): cal'd 457 (MH+), exp 457 (MH+).

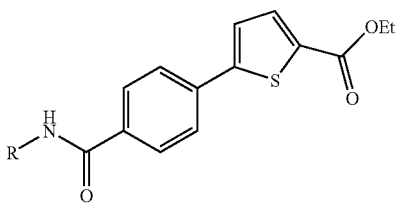

General Experimental for Amide Formation using (Carboxy-Phenyl)-Thiophene 5-(4-Alkylcarbamoyl-phenyl)-thiophene-2-carboxylic acid ethyl ester To a solution of 5-(4-Carboxy-phenyl)-thiophene-2-carboxylic acid ethyl ester (0.26 mmol) in 1:1 anhydrous acetonitrile:DMF was added an aryl- or alkyl-amine (1.6 eq.), followed by EDC (2 eq.). The solution was stirred at room temperature for 6 h and then at 40° C. for 3 h. The solvent was removed under reduced pressure and the residue dissolved in EtOAc (20 mL) and washed with 1 M HCl, sat. sodium bicarbonate and water. The organic phase was dried on sodium sulfate and the solvent was removed leaving the product as a white solid.

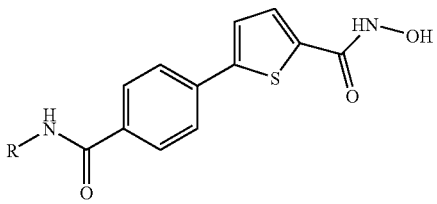

5-(4-Alkylcarbamoyl-phenyl)-thiophene-2-carboxylic acid hydroxyamide

The amide ester coming from the previous reaction was dissolved in anhydrous methanol and treated with hydroxylamine hydrochloride (7 eq.) and NaOMe (1.8 eq. relative to hydroxylamine hydrochloride) at room temperature overnight. The solvent was removed under reduced pressure and the residue dissolved in water. The solution was neutralized by addition of 1 M HCl and the product was collected by filtration. If needed, the product was further purified by trituration with methylene chloride.

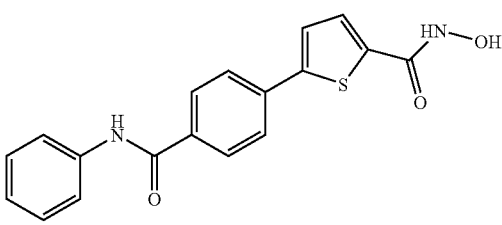

5-(4-Phenylcarbamoyl-phenyl)-thiophene-2-carboxylic acid hydroxyamide $^1$H-NMR (d$_6$-DMSO): δ=10.15 (s, 1H), 8.05-7.60 (m, 8H), 7.36 (t, J=8.4 Hz, 2H), 7.10 (t, J=7.2 Hz, 1H), 3.56 (s, 2H), 3.55 (s, 4H). MS (EI): cal'd 339 (MH$^+$), exp 339 (MH$^+$).

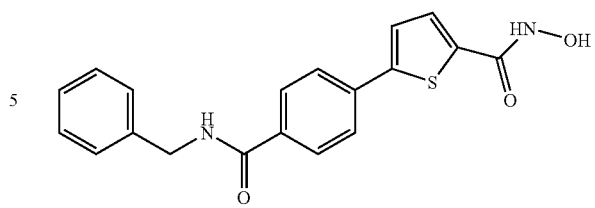

5-(4-Benzylcarbamoyl-phenyl)-thiophene-2-carboxylic acid hydroxyamide $^1$H-NMR (d$_6$-DMSO): δ=9.11 (m, 1H), 8.62 (s, 1H), 7.96 (d, J=8.4 Hz, 2H), 7.80 (d, J=8.4 Hz, 2H), 7.63 (s, 2H), 7.33-7.2 (m, 4H), 4.48 (d, J=6.2 Hz, 2H). MS (EI): cal'd 353 (MH$^+$), exp 353 (MH$^+$).

Compounds from 5-Alkylthiophenes

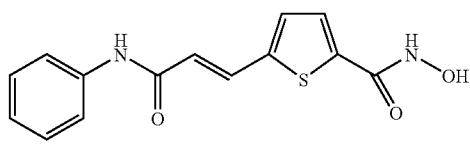

5-(2-Phenylcarbamoyl-vinyl)-thiophene-2-carboxylic acid hydroxyamide

To a solution of 5-(2-carboxy-vinyl)-thiophene-2-carboxylic acid ethyl ester (80 mg, 0.35 mmol), HOBt (50 mg, 0.37 mmol) and EDC (105 mg, 0.55 mmol) in THF (5 mL) was added aniline (40 μL, 0.44 mmol). The resulting mixture was allowed to stir at rt for 2 days. After concentration, 1 mL of MeOH was added to the residue followed by about 10 mL of water. After stirring at rt for 2 h, the solid formed was filtered, collected dried and used directly for next reaction.

To a solution of the solid obtained above in 5 mL of anhydrous MeOH was added NH$_2$OH.HCl (73 mg, 1.05 mmol) followed by a solution of NaOMe (4.37 M in MeOH, 0.44 mL, 1.92 mmol). After stirring at rt for 20.5 h, the reaction mixture was concentrated. The residue was then dissolved in a minimal amount of water and acidified with 2N aqueous HCl to pH≈8. The solid formed was filtered, washed with 2×2 mL of water, collected and dried under high vacuum to give 5-(2-phenylcarbamoyl-vinyl)-thiophene-2-carboxylic acid hydroxyamide as a brownish solid. MS (EI): cal'd 289.06 (MH$^+$), exp 289.18 (MH$^+$).

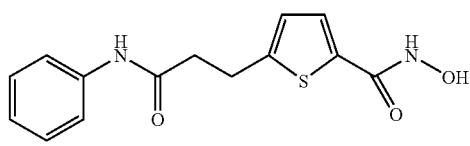

5-(2-Phenylcarbamoyl-ethyl)-thiophene-2-carboxylic acid hydroxyamide

Using a two-step procedure similar to that of 5-(2-phenylcarbamoyl-vinyl)-thiophene-2-carboxylic acid hydroxyamide, 5-(2-carboxy-ethyl)-thiophene-2-carboxylic acid ethyl ester (0.50 M in THF, 0.70 mL, 0.35 mmol) was converted into 5-(2-phenylcarbamoyl-ethyl)-thiophene-2-carboxylic acid hydroxyamide as pale solid. MS (EI): cal'd 291.07 (MH⁺), exp 291.20 (MH⁺).

Using a two-step procedure similar to that of 5-(2-phenyl-carbamoyl-vinyl)-thiophene-2-carboxylic acid hydroxyamide, the following thiophene-2-carboxylic acid hydroxyamides were prepared.

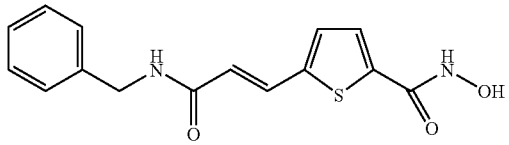

5-(2-Benzylcarbamoyl-vinyl)-thiophene-2-carboxylic acid hydroxyamide $^1$H NMR (DMSO-d$_6$, 200 MHz) δ 11.31 (brs, 1H), 9.23 (brs, 1H), 8.68 (t, J=5.7 Hz, 1H), 7.72-7.08 (m, 8H), 6.52 (d, J=15.4 Hz, 1H), 4.38 (d, J=5.6 Hz, 2H). MS (EI): cal'd 303.1 (MH⁺), exp 303.2 (MH⁺).

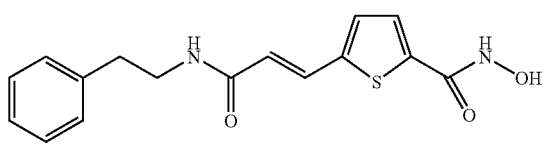

5-(2-Phenethylcarbamoyl-vinyl)-thiophene-2-carboxylic acid hydroxyamide $^1$H NMR (DMSO-d$_6$, 200 MHz) δ 11.32 (brs, 1H), 9.21 (brs, 1H), 8.26 (t, J=5.5 Hz, 1H), 7.62-7.44 (m, 2H), 7.40-7.08 (m, 6H), 6.44 (d, J=15.4 Hz, 1H), 3.41 (t, J=7.3 Hz, 2H), 2.75 (t, J=7.3 Hz, 2H). MS (EI): cal'd 317.1 (MH⁺), exp 317.2 (MH⁺).

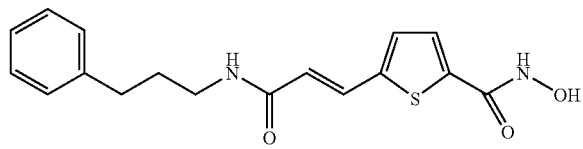

5-[2-(3-Phenyl-propylcarbamoyl)-vinyl]-thiophene-2-carboxylic acid hydroxyamide $^1$H NMR (DMSO-d$_6$, 200 MHz) δ 11.29 (brs, 1H), 9.22 (brs, 1H), 8.22 (t, J=5.2 Hz, 1H), 7.64-7.44 (m, 2H), 7.40-7.06 (m, 6H), 6.46 (d, J=15.4 Hz, 1H), 3.16 (td, J=6.6, 5.8 Hz, 2H), 2.60 (t, J=7.7 Hz, 2H), 1.73 (tt, J=7.3, 7.3 Hz, 2H). MS (EI): cal'd 331.1 (MH⁺), exp 331.3 (MH⁺).

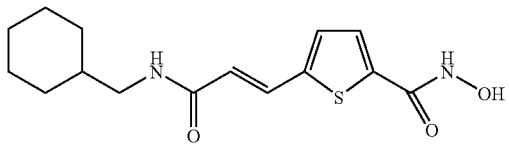

5-[2-(Cyclohexylmethyl-carbamoyl)-vinyl]-thiophene-2-carboxylic acid hydroxyamide $^1$H NMR (DMSO-d$_6$, 200 MHz) δ 11.26 (brs, 1H), 9.20 (brs, 1H), 8.13 (t, J=5.5 Hz, 1H), 7.64-7.40 (m, 2H), 7.33 (d, J=4.0, 1H), 6.48 (d, J=15.8 Hz, 1H), 3.00 (dd, J=6.3, 6.3 Hz, 2H), 1.94-0.68 (m, 11H).

MS (EI): cal'd 309.1 (MH⁺), exp 309.3 (MH⁺).

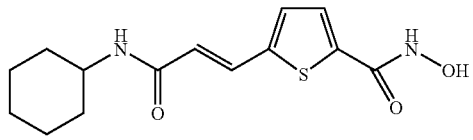

5-(2-Cyclohexylcarbamoyl-vinyl)-thiophene-2-carboxylic acid hydroxyamide $^1$H NMR (DMSO-d$_6$, 200 MHz) δ 8.05 (d, J=7.6 Hz, 1H), 7.64-7.40 (m, 2H), 7.33 (d, J=4.2, 1H), 6.45 (d, J=15.8 Hz, 1H), 3.60 (brs, 1H), 2.05-0.90 (m, 10H). MS (EI): cal'd 295.1 (MH⁺), exp 295.2 (MH⁺).

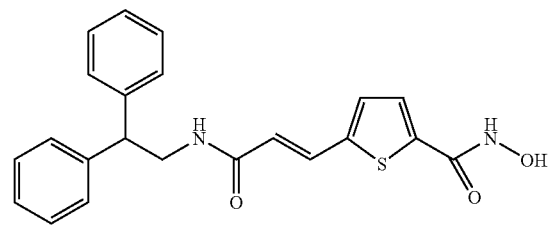

5-[2-(2,2-Diphenyl-ethylcarbamoyl)-vinyl]-thiophene-2-carboxylic acid hydroxyamide MS (EI): cal'd 393.1 (MH⁺), exp 393.3 (MH⁺).

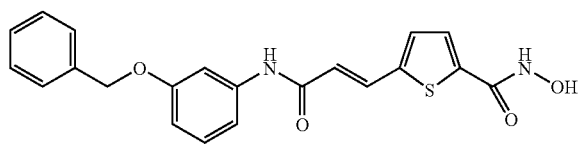

5-[2-(3-Benzyloxy-phenylcarbamoyl)-vinyl]-thiophene-2-carboxylic acid hydroxyamide MS (EI): cal'd 395.1 (MH⁺), exp 395.3 (MH⁺).

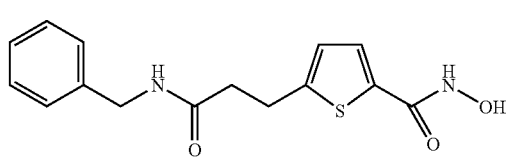

5-(2-Benzylcarbamoyl-ethyl)-thiophene-2-carboxylic acid hydroxyamide

MS (EI): cal'd 305.1 (MH⁺), exp 305.2 (MH⁺).

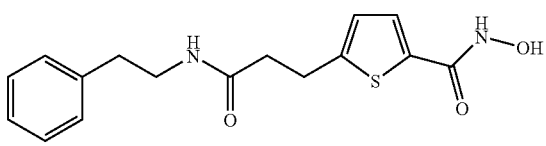

5-(2-Phenethylcarbamoyl-ethyl)-thiophene-2-carboxylic acid hydroxyamide

MS (EI): cal'd 319.1 (MH+), exp 319.3 (MH+).

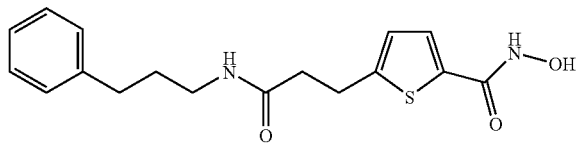

5-[2-(3-Phenyl-propylcarbamoyl)-ethyl]-thiophene-2-carboxylic acid hydroxyamide

MS (EI): cal'd 333.1 (MH+), exp 333.3 (MH+).

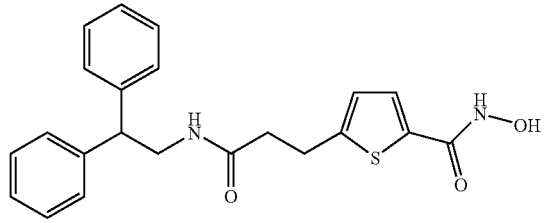

5-[2-(2,2-Diphenyl-ethylcarbamoyl)-ethyl]-thiophene-2-carboxylic acid hydroxyamide $^1$H NMR (DMSO-$d_6$, 200 MHz) δ 7.97 (t, J=4.9 Hz, 1H), 7.50-6.94 (m, 11H), 6.71 (d, J=3.6 Hz, 1H), 4.14 (t, J=7.7 Hz, 1H), 3.68 (dd, J=7.1, 5.7 Hz, 2H), 2.92 (t, J=7.2 Hz, 2H), 2.32 (t, J=7.1 Hz, 2H). MS (EI): cal'd 395.1 (MH+), exp 395.3 (MH+).

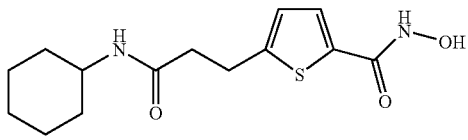

5-(2-Cyclohexylcarbamoyl-ethyl)-thiophene-2-carboxylic acid hydroxyamide

MS (EI): cal'd 297.1 (MH+), exp 297.3 (MH+).

Compounds from 5-aminothiophenes

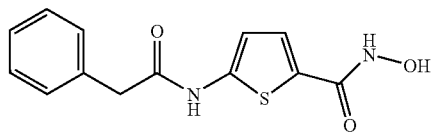

5-Phenylacetylamino-thiophene-2-carboxylic acid hydroxyamide

To 5-phenylacetylamino-thiophene-2-carboxylic acid methyl ester (92.7 mg, 0.34 mmol) were added NH$_2$OH.HCl (110.0 mg, 1.58 mmol) and 5 mL of anhydrous MeOH. A solution of NaOMe (4.37 M in MeOH, 0.75 mL, 3.28 mmol) was added. The resulting mixture was allowed to stir at 50° C. for 6 h, at ii for 14 h, again at 50° C. for 3 days and then at rt for additional 2 days. Five mL of water was added and the mixture was stirred at rt for 3 days. A solution of NaOMe (4.37 M in MeOH, 0.75 mL, 3.28 mmol) was then added and the resulting mixture was allowed to stir at rt for additional 3 days. After the reaction was complete, MeOH was removed and the aqueous layer was acidified with 2N aqueous HCl to pH≈2. After extracted with 2×15 mL of EtOAc, the combined organic layer was concentrated and dried under high vacuum. The residue was subsequently dissolved in 6 mL of anhydrous DMF and the mixture was cooled to 0° C. Diisopropylethylamine (0.20 mL, 1.15 mmol) and HBTU (210.7 mg, 0.56 mmol) were added. After stirring at 0° C. for 1 h and at it for additional 1 h, 1.3 mL of 50% aqueous NH$_2$OH solution was added and the mixture was allowed to stir at rt overnight. After concentration under high vacuum, the resulting residue was purified by flash column chromatography (70% EtOAc/hexanes to EtOAc and then to 10% MeOH/EtOAc) to give 5-phenylacetylamino-thiophene-2-carboxylic acid hydroxyamide as a pale solid. $^1$H NMR (DMSO-$d_6$, 200 MHz) δ 7.55-7.15 (m, 6H), 6.64 (d, J=4.0 Hz, 1H), 3.68 (s, 2H). MS (EI): cal'd 277.31 (MH+), exp 277.25 (MH+).

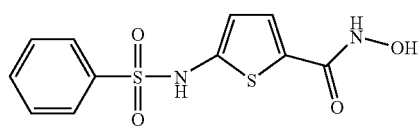

5-Benzenesulfonylamino-thiophene-2-carboxylic acid hydroxyamide

Using a procedure similar to that of 5-phenylacetylamino-thiophene-2-carboxylic acid hydroxyamide, 5-benzenesulfonylamino-thiophene-2-carboxylic acid methyl ester (110.0 mg, 0.37 mmol) was converted into 5-benzenesulfonylamino-thiophene-2-carboxylic acid hydroxyamide as a pale green solid. MS (EI): cal'd 299.01 (MH+), exp 299.13 (MH+).

Using a procedure similar to that of 5-phenylacetylamino-thiophene-2-carboxylic acid hydroxyamide, the following thiophene-2-carboxylic acid hydroxyamides were prepared.

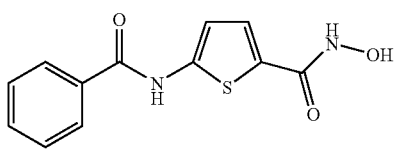

5-Benzoylamino-thiophene-2-carboxylic acid hydroxyamide $^1$H NMR (DMSO-d$_6$, 200 MHz) δ 8.10-7.84 (m, 2H), 7.74-7.26 (m, 4H), 6.90 (d, J=4.0 Hz, 1H). MS (EI): cal'd 263.0 (MH$^+$), exp 263.2 (MH$^+$).

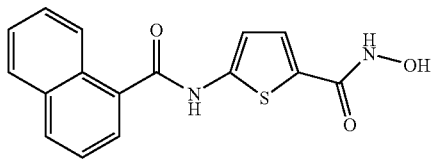

5-[(Naphthalene-1-carbonyl)-amino]-thiophene-2-carboxylic acid hydroxyamide $^1$H NMR (DMSO-d$_6$, 200 MHz) δ 8.54-8.14 (m, 3H), 8.10-7.54 (m, 5H), 7.00 (d, J=4.4 Hz, 1H). MS (EI): cal'd 313.1 (MH$^+$), exp 313.3 (MH$^+$).

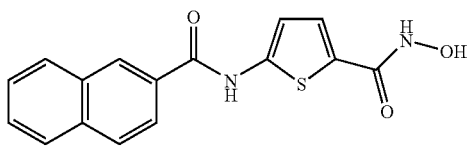

5-[(Naphthalene-2-carbonyl)-amino]-thiophene-2-carboxylic acid hydroxyamide $^1$H NMR (DMSO-d$_6$, 200 MHz) δ 8.64 (s, 1H), 8.24-7.90 (m, 4H), 7.74-7.40 (m, 3H), 6.93 (d, J=4.0 Hz, 1H).

MS (EI): cal'd 313.1 (MH$^+$), exp 313.3 (MH$^+$).

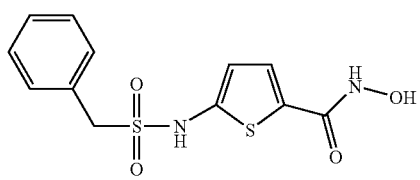

5-Phenylmethanesulfonylamino-thiophene-2-carboxylic acid hydroxyamide

MS (EI): cal'd 313.0 (MH$^+$), exp 313.2 (MH$^+$).

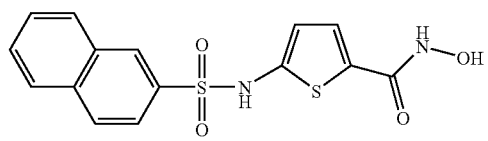

5-(Naphthalene-2-sulfonylamino)-thiophene-2-carboxylic acid hydroxyamide $^1$H NMR (DMSO-d$_6$, 200 MHz) δ 8.41 (s, 1H), 8.22-7.92 (m, 3H), 7.84-7.52 (m, 3H), 7.25 (d, J=3.8 Hz, 1H), 6.47 (d, J=3.6 Hz, 1H). MS (EI): cal'd 349.0 (MH$^+$), exp 349.2 (MH$^+$).

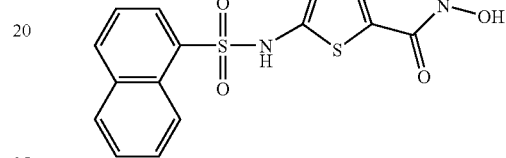

5-(Naphthalene-1-sulfonylamino)-thiophene-2-carboxylic acid hydroxyamide $^1$H NMR (DMSO-d$_6$, 200 MHz) δ 8.65 (d, J=8.4 Hz, 1H), 1H), 8.32-8.02 (m, 3H), 7.84-7.52 (m, 4H), 6.41 (d, J=4.0 Hz, 1H). MS (EI): cal'd 349.0 (MH$^+$), exp 349.2 (MH$^+$).

Example 2

HDAC Inhibition by Novel Compounds

HDAC1-Flag Assay:

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction.

Results:

The IC$_{50}$ values were for the compounds of the present invention were determined according to the method set forth above. All of the compounds were able to inhibit 50% of the deacetylation reaction at a concentration below about 5000 nm. Several of the compounds were able to inhibit 50% of the deacetylation reaction at a concentration below about 1000 nm. Several of the compounds were able to inhibit 50% of the deacetylation reaction at a concentration below about 500 nm. Several of the compounds were able to inhibit 50% of the deacetylation reaction at a concentration below about 100 nm. Several of the compounds were able to inhibit 50% of the deacetylation reaction at a concentration below about 20 nm. Several compounds were able to inhibit 50% of the deacetylation reaction at a concentration range of about 15 and 20 nm. Several compounds were able to inhibit 50% of the deacetylation reaction at a concentration range of about 10 and 15 nm. Several compounds were able to inhibit 50% of the deacetylation reaction at a concentration range of about 5 and 10 nm. Several compounds were able to inhibit 50% of the deacetylation reaction at a concentration of below about 5 nm.

Table 1 below shows the chemical structures and HDAC enzymatic assay results for a selection of novel compounds containing a benzothiophene backbone designed and synthesized in accordance with the present invention.

TABLE 1

| No. | Structure | Mol. Form. | MW | HDAC Inhibition |
|---|---|---|---|---|
| 1 | 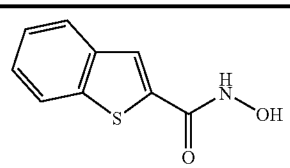 | C9H7NO2S | 193.2198 | 672 ± 98.9 (N = 2) |
| 2 | 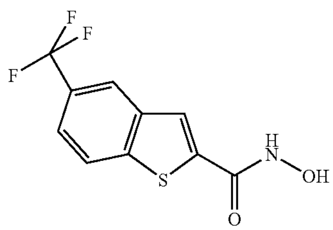 | C10H6F3NO2S | 261.2181 | 608.5 ± 24.7 (N = 2) |
| 3 | 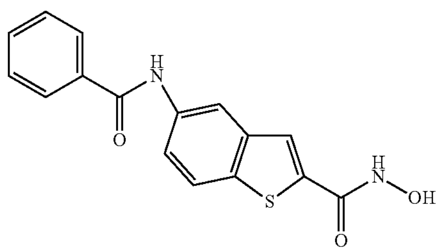 | C16H12N2O3S | 312.3424 | 106.5 ± 13.4 (N = 2) |
| 4 | 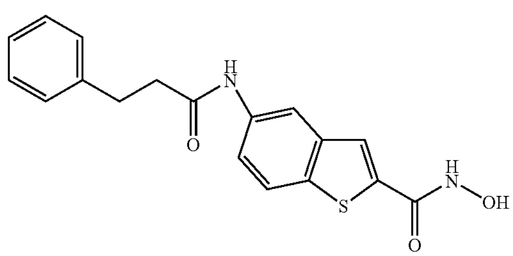 | C18H16N2O3S | 340.396 | 61 ± 9.8 (N = 2) |
| 5 | 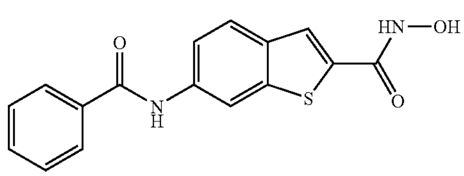 | C16H12N2O3S | 312.3424 | 203.5 ± 48.7 (N = 2) |
| 6 | 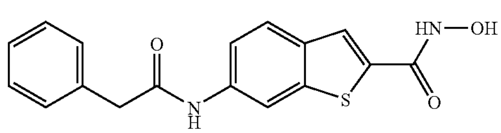 | C17H14N2O3S | 326.3692 | 11.5 ± 2.1 (N = 2) |
| 7 | 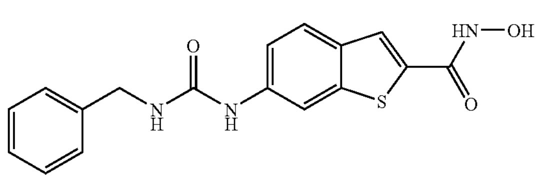 | C17H15N3O3S | 341.3838 | 52 ± 19.7 (N = 2) |

TABLE 1-continued
| No. | Structure | Mol. Form. | MW | HDAC Inhibition |
|---|---|---|---|---|
| 8 | 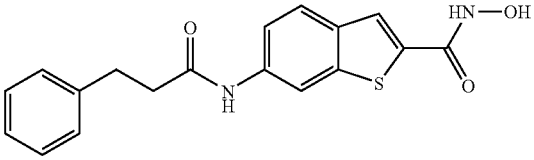 | C18H16N2O3S | 340.396 | 54..5 ± 20.5 (N = 2) |
| 9 | 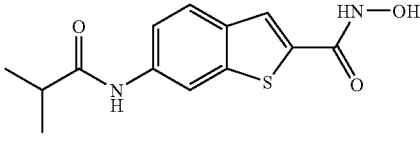 | C13H14N2O3S | 278.3252 | 156.5 ± 33.2 (N = 2) |
| 10 | 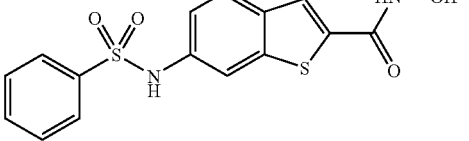 | C15H12N2O4S2 | 348.3908 | 46.5 ± 23.3 (N = 2) |
| 11 | 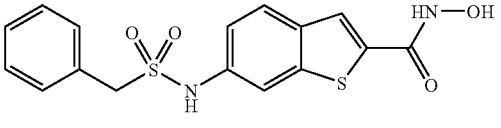 | C16H14N2O4S2 | 362.4176 | 41 ± 11.3 (N = 2) |
| 12 | 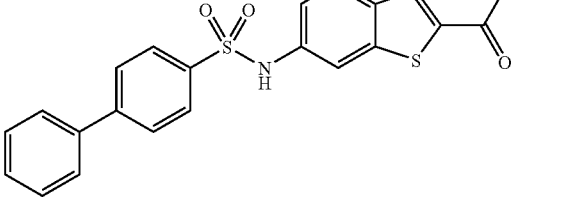 | C21H16N2O4S2 | 424.4884 | 45 ± 32.5 (N = 2) |
| 13 | 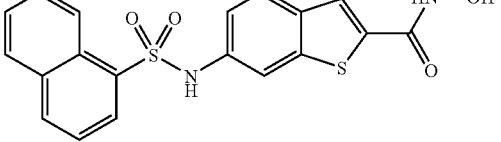 | C19H14N2O4S2 | 398.4506 | 26 ± 1.4 (N = 2) |
| 14 | 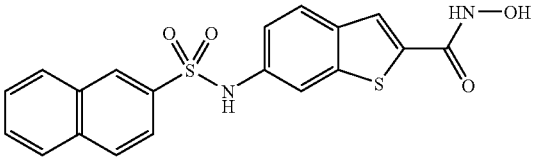 | C19H14N2O4S2 | 398.4506 | 21.5 ± 3.5 (N = 2) |
| 15 | 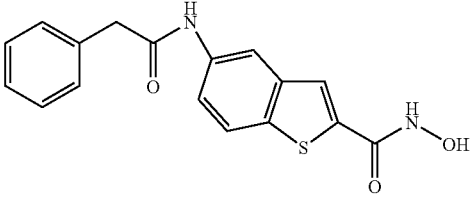 | C17H14N2O3S | 326.3692 | 31 ± 7 (N = 2) |

TABLE 1-continued

| No. | Structure | Mol. Form. | MW | HDAC Inhibition |
|---|---|---|---|---|
| 16 | 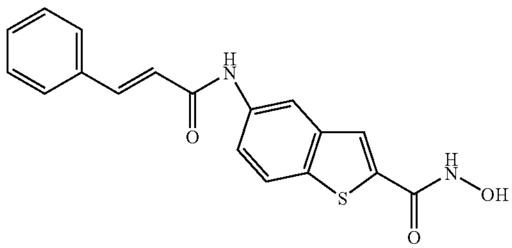 | C18H14N2O3S | 338.3802 | 185 ± 52.3 (N = 2) |
| 17 | 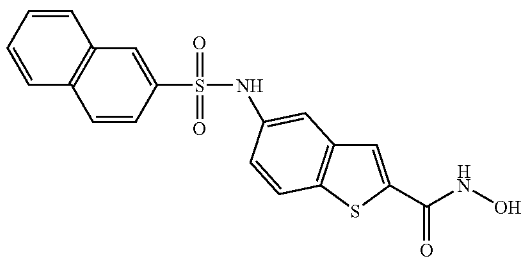 | C19H14N2O4S2 | 398.4506 | 52.5 ± 10.6 (N = 2) |
| 18 | 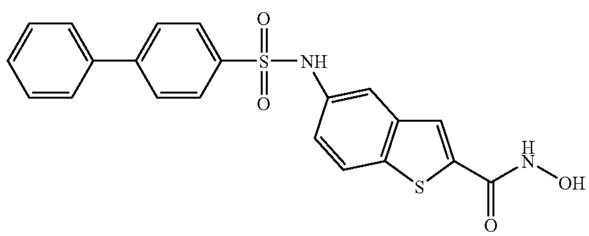 | C21H16N2O4S2 | 424.4884 | 91 ± 49.4 (N = 2) |
| 19 | 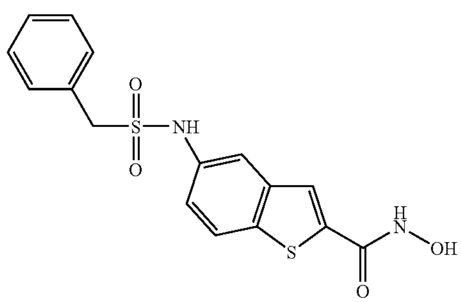 | C16H14N2O4S2 | 362.4176 | 118.5 ± 21.9 (N = 2) |
| 20 | 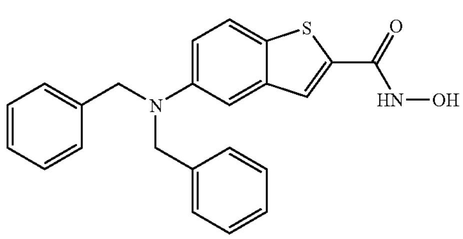 | C23H20N2O2S | 388.4832 | 1645.5 ± 1163 (N = 2) |
| 21 | 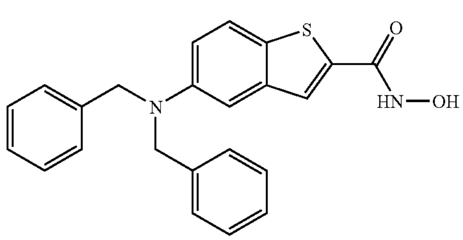 | C23H20N2O2S | 388.4832 | 948.5 ± 833.6 (N = 2) |

TABLE 1-continued

| No. | Structure | Mol. Form. | MW | HDAC Inhibition |
|---|---|---|---|---|
| 22 | 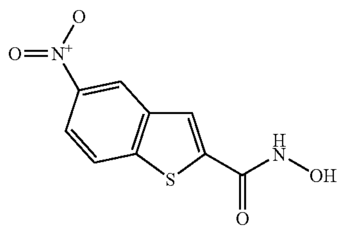 | C9H6N2O4S | 238.2174 | 1739 ± 63.6 (N = 2) |
| 23 | 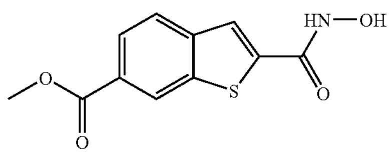 | C11H9NO4S | 251.2564 | 627 ± 5.6 (N = 2) |
| 24 | 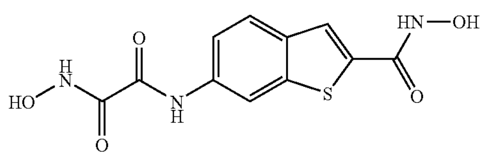 | C11H9N3O5S | 295.2692 | 1170.5 ± 214.2 (N = 2) |
| 25 | 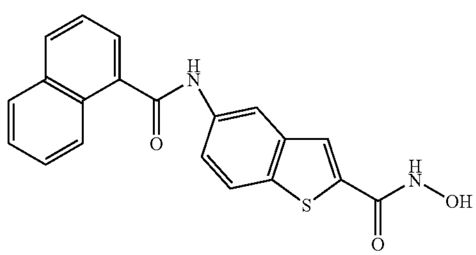 | C20H14N2O3S | 362.4022 | 140 ± 14.1 (N = 2) |
| 26 | 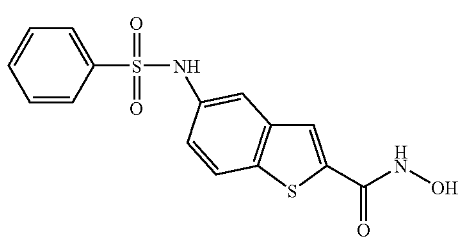 | C15H12N2O4S2 | 348.3908 | 166 ± 22.6 (N = 2) |
| 27 | 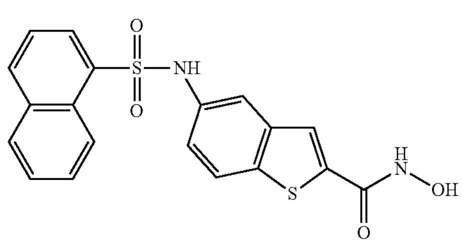 | C19H14N2O4S2 | 398.4506 | 102 ± 24 (N = 2) |
| 28 | 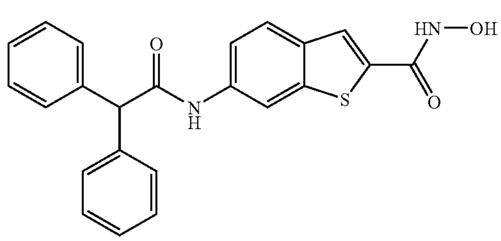 | C23H18N2O3S | 402.4668 | 79.5 ± 0.7 (N = 2) |

TABLE 1-continued

| No. | Structure | Mol. Form. | MW | HDAC Inhibition |
|---|---|---|---|---|
| 29 | 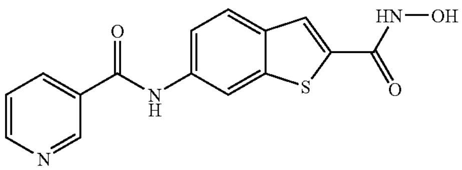 | C15H11N3O3S | 313.3302 | 262 ± 33.9 (N = 2) |
| 30 | 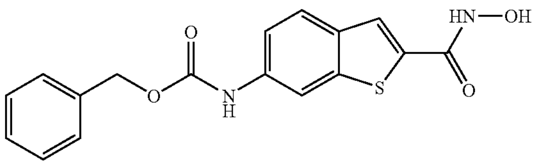 | C17H14N2O4S | 342.3686 | 113.5 ± 33.2 (N = 2) |
| 31 | 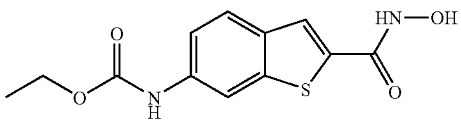 | C12H12N2O4S | 280.2978 | 350.5 ± 13.4 (N = 2) |
| 32 | 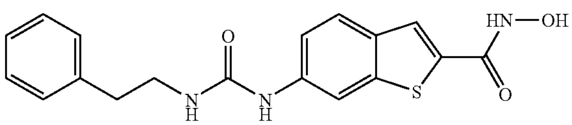 | C18H17N3O3S | 355.4106 | 88.5 ± 33.2 (N = 2) |
| 33 | 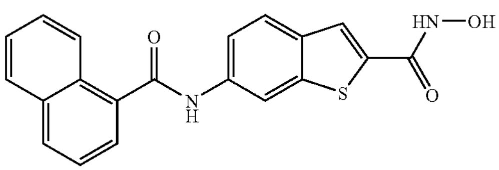 | C20H14N2O3S | 362.4022 | 79 ± 11.3 (N = 2) |
| 34 | 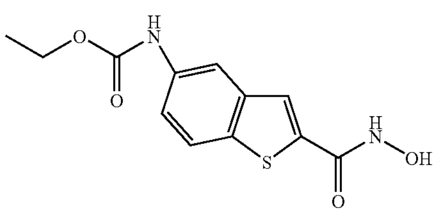 | C12H12N2O4S | 280.2978 | 238 ± 2.8 (N = 2) |
| 35 | 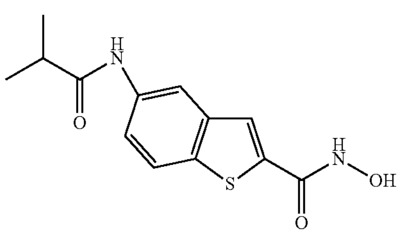 | C13H14N2O3S | 278.3252 | 149.5 ± 23.3 (N = 2) |
| 36 | 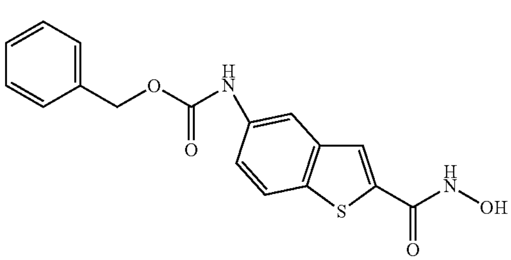 | C17H14N2O4S | 342.3686 | 119 (N = 1) |

TABLE 1-continued

| No. | Structure | Mol. Form. | MW | HDAC Inhibition |
|---|---|---|---|---|
| 37 | 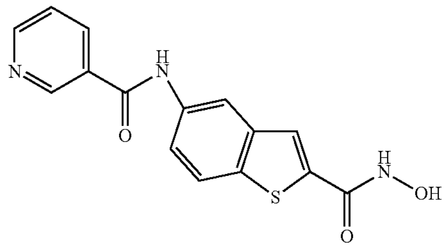 | C15H11N3O3S | 313.3302 | 157 (N = 1) |
| 38 | 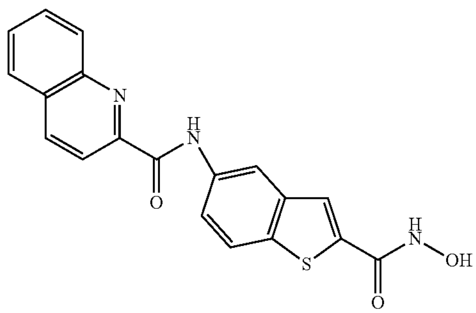 | C19H13N3O3S | 363.39 | 444 (N = 1) |
| 39 | 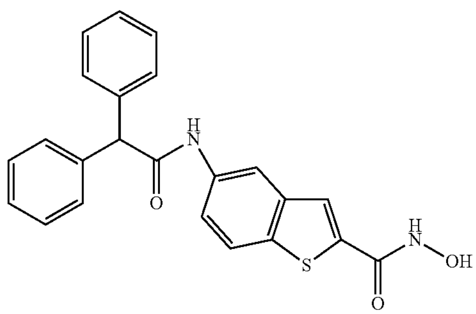 | C23H18N2O3S | 402.4668 | 189.5 ± 4.9 (N = 2) |
| 40 | 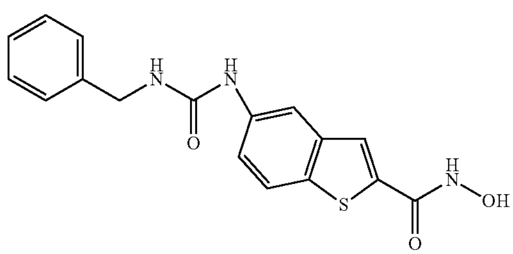 | C17H15N3O3S | 341.3838 | 72 (N = 1) |
| 41 | 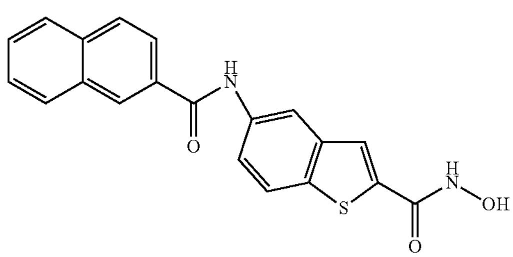 | C20H14N2O3S | 362.4022 | 413 (N = 1) |

TABLE 1-continued

| No. | Structure | Mol. Form. | MW | HDAC Inhibition |
|---|---|---|---|---|
| 42 | 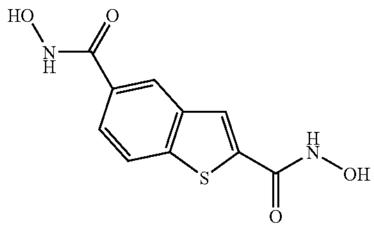 | C10H8N2O4S | 252.2442 | 424 (N = 1) |
| 43 | 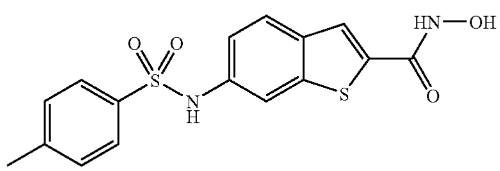 | C16H14N2O4S2 | 362.4176 | 60.5 ± 2.1 (N = 2) |
| 44 | 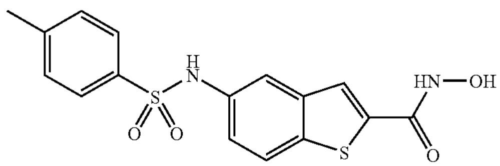 | C16H14N2O4S2 | 362.4176 | 162.5 ± 54.4 (N = 2) |
| 45 | 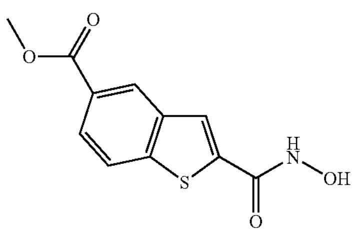 | C11H9NO4S | 251.2564 | 737.5 ± 143.5 (N = 2) |
| 46 | 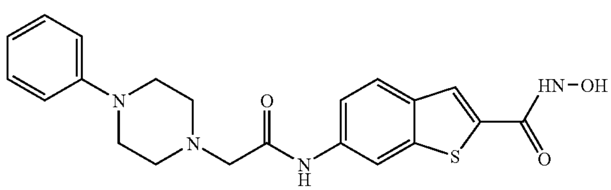 | C21H22N4O3S | 410.4898 | 37 (N = 1) |
| 47 | 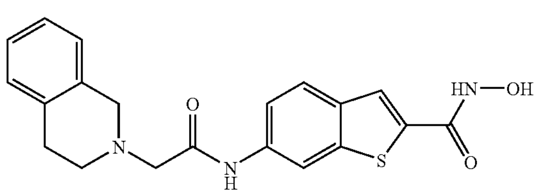 | C20H19N3O3S | 381.4484 | 24 (N = 1) |
| 48 | 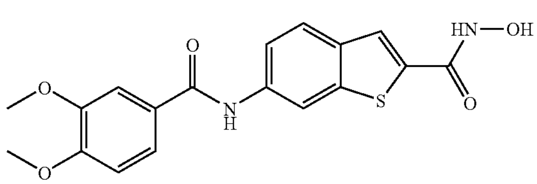 | C18H16N2O5S | 372.3948 | 280 (N = 1) |
| 49 | 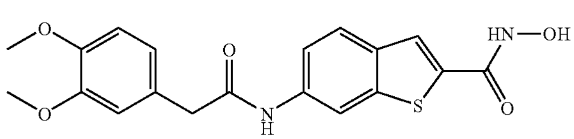 | C19H18N2O5S | 386.4216 | 35 (N = 1) |

TABLE 1-continued
| No. | Structure | Mol. Form. | MW | HDAC Inhibition |
|---|---|---|---|---|
| 50 | 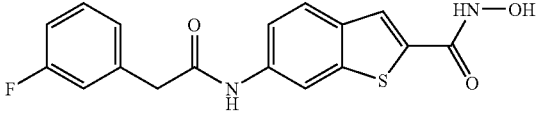 | C17H13FN2O3S | 344.3597 | 14 (N = 1) |
| 51 | 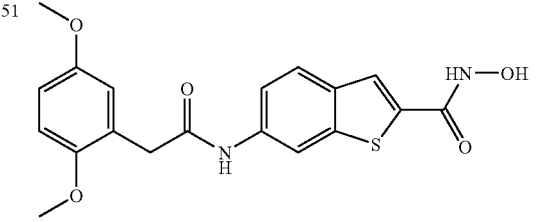 | C19H18N2O5S | 386.4216 | 62 (N = 1) |
| 52 | 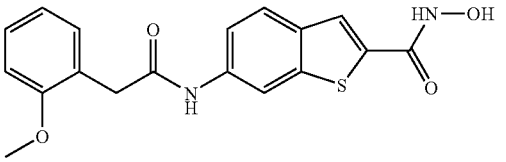 | C18H16N2O4S | 356.3954 | 20 (N = 1) |
| 53 | 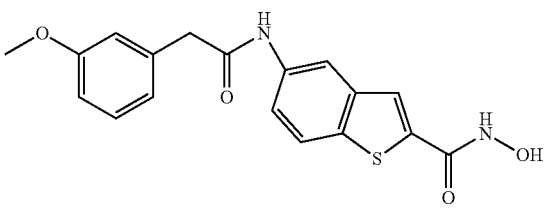 | C18H16N2O4S | 356.3954 | 54 (N = 1) |
| 84 | 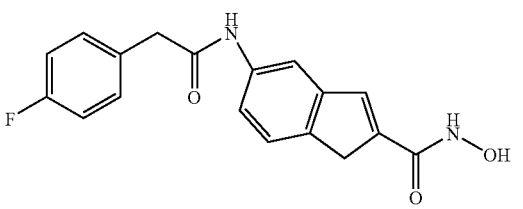 | C17H13FN2O3S | 344.4 | 56.5 ± 16.2 (N = 2) |
| 85 | 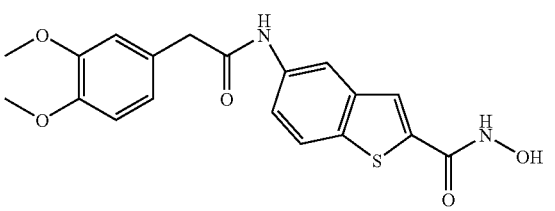 | C19H18N2O5S | 386.4 | 76.0 ± 15.5 (N = 2) |
| 86 | 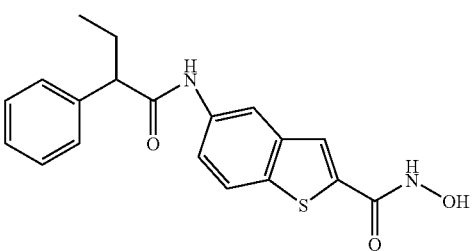 | C19H18N2O3S | 354.4 | 92.5 ± 23.3 (N = 2) |

TABLE 1-continued

| No. | Structure | Mol. Form. | MW | HDAC Inhibition |
|---|---|---|---|---|
| 87 | 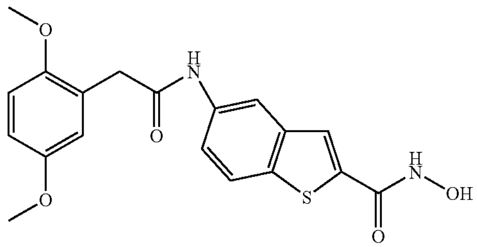 | C19H18N2O5S | 386.4 | 111.5 ± 23.3 (N = 2) |
| 88 | 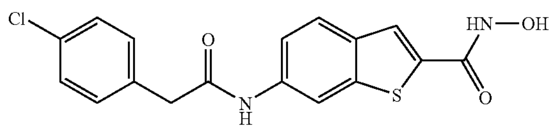 | C17H13ClN2O3S | 360.8 | 19.0 ± 5.6 (N = 2) |
| 89 | 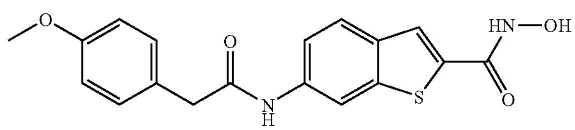 | C18H16N2O4S | 356.4 | 19.5 ± 0.7 (N = 2) |
| 90 | 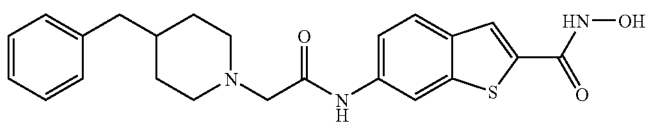 | C23H25N3O3S | 423.5 | 99.5 ± 37.4 (N = 2) |
| 91 | 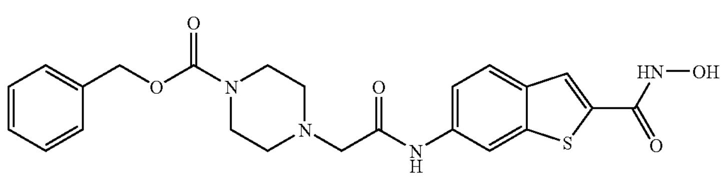 | C23H24N4O5S | 468.5 | 177.5 ± 55.8 (N = 2) |
| 92 | 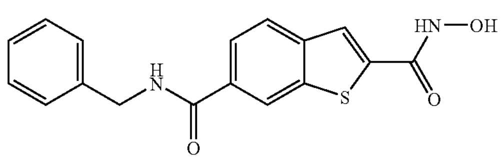 | C17H14N2O3S | 326.4 | 53.0 ± 7.0 (N = 2) |
| 93 | 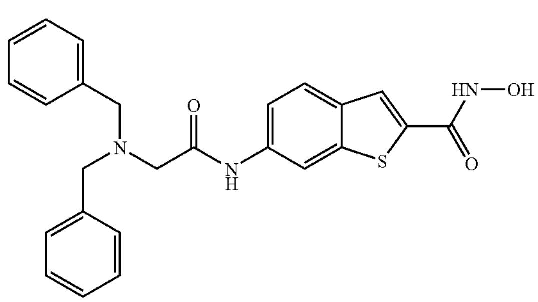 | C25H23N3O3S | 445.5 | 316.0 ± 56.5 (N = 2) |
| 94 | 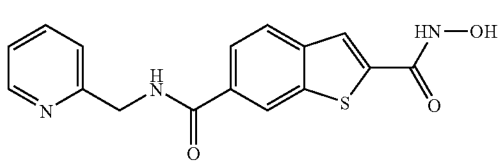 | C16H13N3O3S | 327.4 | 85.7 ± 23.5 (N = 4) |

TABLE 1-continued

| No. | Structure | Mol. Form. | MW | HDAC Inhibition |
|---|---|---|---|---|
| 95 | 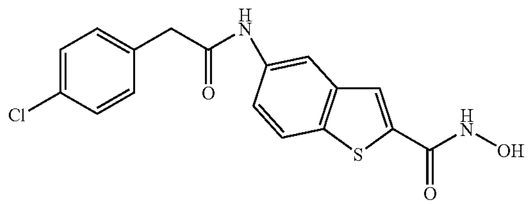 | C17H13ClN2O3S | 360.8 | 79.5 ± 33.2 (N = 2) |
| 96 | 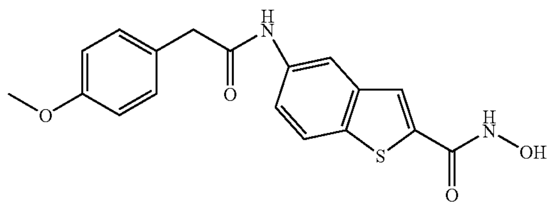 | C18H16N2O4S | 356.4 | 83.0 ± 21.2 (N = 2) |
| 97 | 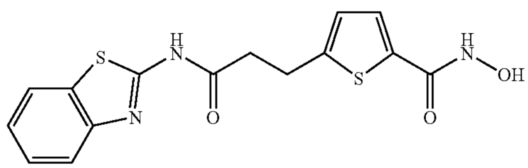 | C21H19ClN2O3S | 347.4 | 133.5 ± 7.7 (N = 2) |
| 98 | 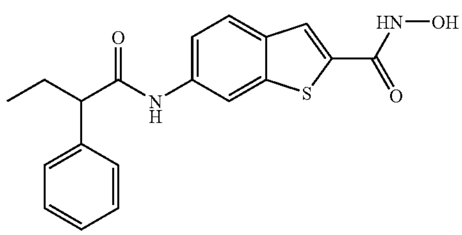 | C19H18N2O3S | 354.4 | 41.5 ± 2.1 (N = 2) |
| 99 | 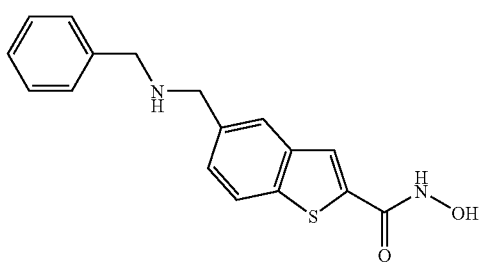 | C17H16N2O2S | 312.4 | 143.5 ± 53.0 (N = 2) |
| 100 | 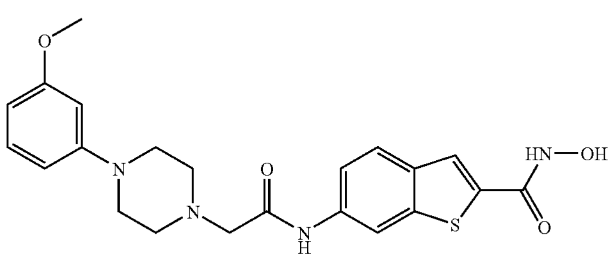 | C22H24N4O4S | 440.5 | 45.0 ± 5.6 (N = 2) |
| 101 | 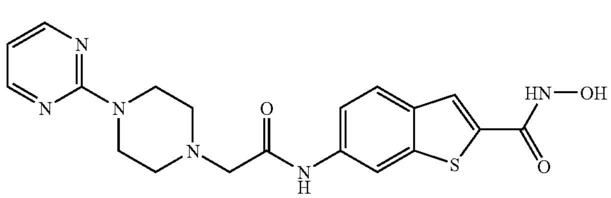 | C19H20N6O3S | 412.5 | 59.0 ± 7.0 (N = 2) |

TABLE 1-continued

| No. | Structure | Mol. Form. | MW | HDAC Inhibition |
|---|---|---|---|---|
| 102 | 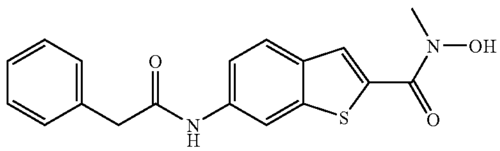 | C18H16N2O3S | 340.4 | 14446.5 (N = 2) |
| 103 | 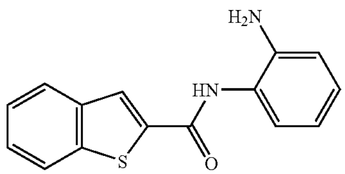 | C15H12N2OS | 268.3 | 1823.0 ± 507.7 (N = 2) |
| 104 | 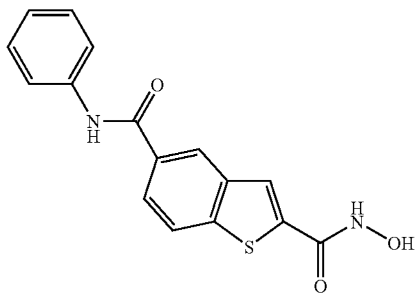 | C16H12N2O3S | 312.3 | 582.0 ± 9.8 (N = 2) |
| 105 | 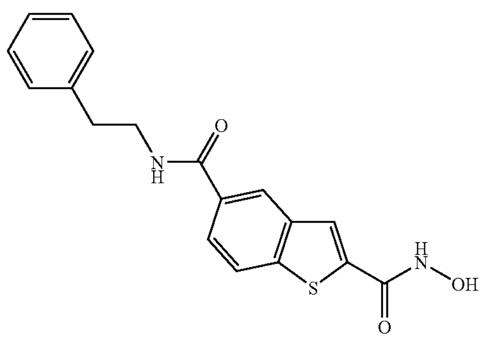 | C18H16N2O3S | 340.4 | 155.5 ± 13.4 (N = 2) |
| 106 | 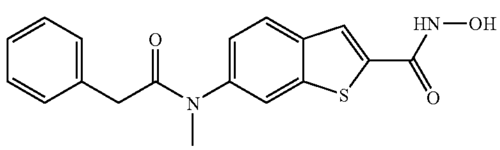 | C18H16N2O3S | 340.4 | 74.5 ± 17.6 (N = 2) |
| 107 | 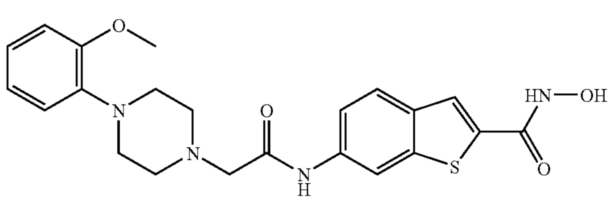 | C22H24N4O4S | 440.5 | 79.0 ± 5.6 (N = 2) |
| 108 | 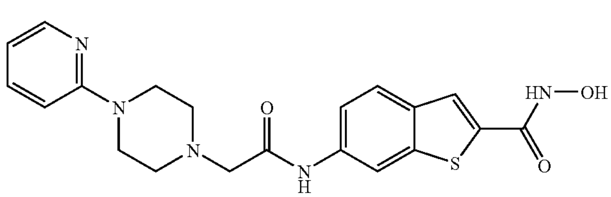 | C20H21N5O3S | 411.5 | 50.0 ± 11.3 (N = 2) |

TABLE 1-continued

| No. | Structure | Mol. Form. | MW | HDAC Inhibition |
|---|---|---|---|---|
| 109 | 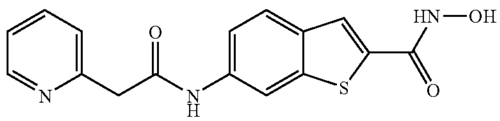 | C16H13N3O3S | 327.4 | 59.0 ± 15.5 (N = 2) |
| 110 | 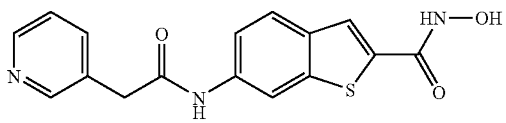 | C16H13N3O3S | 327.4 | 61.0 ± 15.5 (N = 2) |
| 111 | 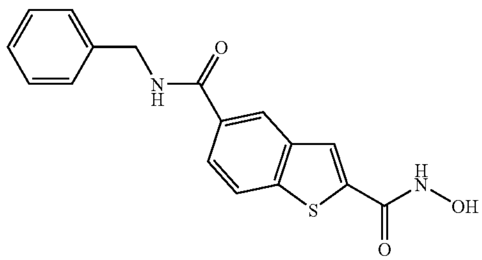 | C17H14N2O3S | 326.4 | 76.0 ± 21.2 (N = 2) |
| 112 | 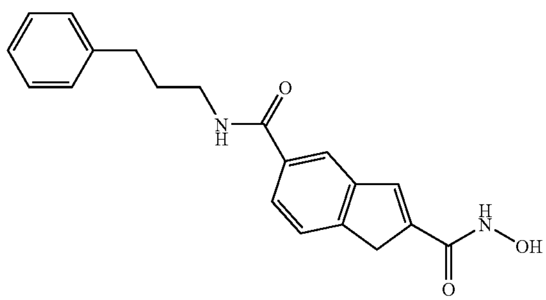 | C19H18N2O3S | 354.4 | 74.5 ± 7.7 (N = 2) |
| 113 | 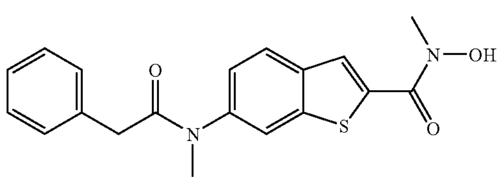 | C19H18N2O3S | 354.4 | 30775.0 ± 7.0 (N = 2) |
| 114 | 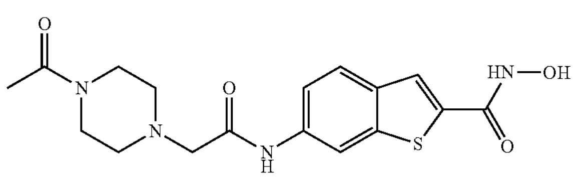 | C17H20N4O4S | 376.4 | 150.0 ± 12.7 (N = 2) |
| 115 | 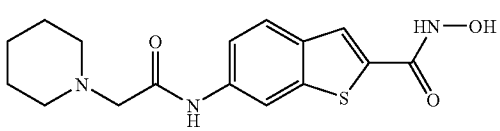 | C16H19N3O3S | 333.4 | 38.0 ± 0.0 (N = 2) |
| 116 | 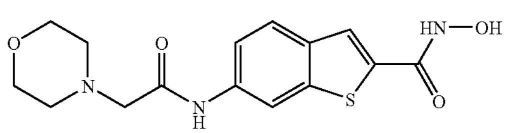 | C15H17N3O4S | 335.4 | 84.0 ± 5.6 (N = 2) |

TABLE 1-continued

| No. | Structure | Mol. Form. | MW | HDAC Inhibition |
|---|---|---|---|---|
| 117 | 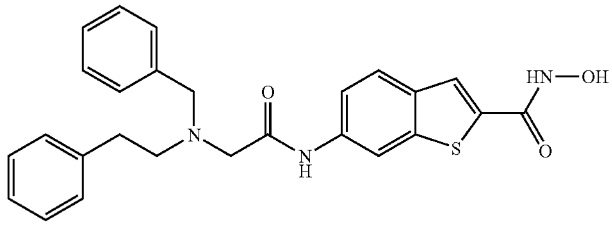 | C26H25N3O3S | 459.6 | 206.0 ± 50.9 (N = 2) |
| 118 | 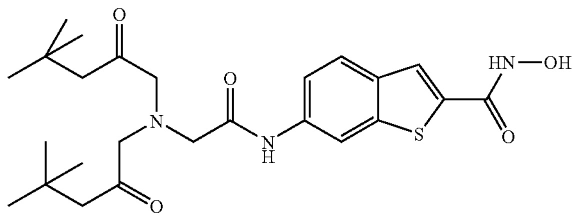 | C23H31N3O7S | 493.6 | 236.5 ± 28.9 (N = 2) |
| 119 | 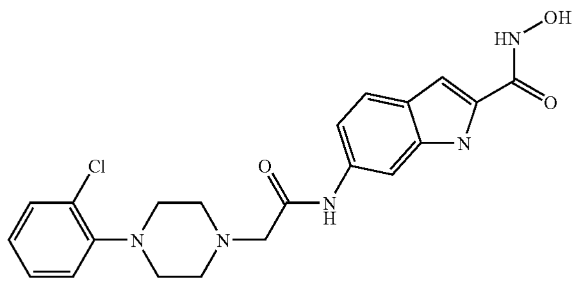 | C21H21ClN4O3S | 444.9 | 36.6 ± 13.2 (N = 3) |
| 120 | 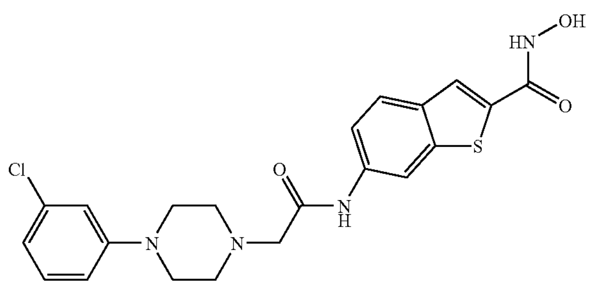 | C21H21ClN4O3S | 444.9 | 97.0 ± 21.0 (N = 4) |
| 121 | 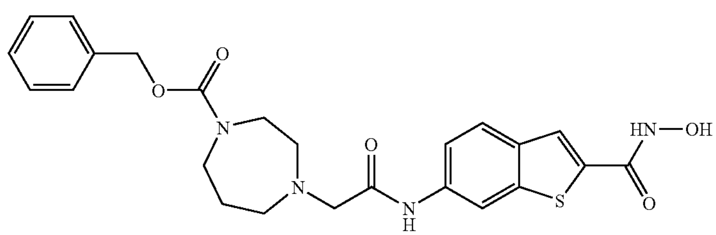 | C24H26N4O5S | 482.6 | 184.0 ± 58.2 (N = 3) |
| 122 | 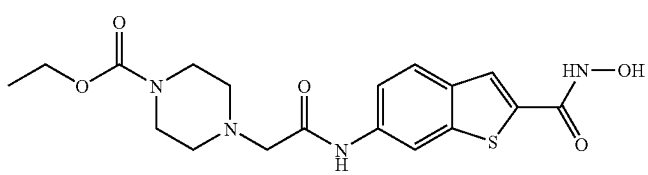 | C18H22N4O5S | 406.5 | 162.6 ± 35.2 (N = 3) |
| 123 | 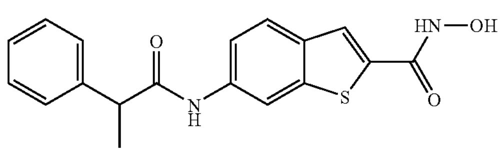 | C18H16N2O3S | 340.4 | 18.0 ± 5.6 (N = 2) |

TABLE 1-continued
| No. | Structure | Mol. Form. | MW | HDAC Inhibition |
|---|---|---|---|---|
| 124 | 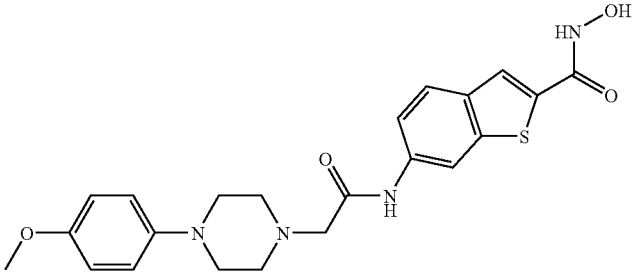 | C22H24N4O4S | 440.5 | 176.6 ± 16.0 (N = 3) |
| 125 | 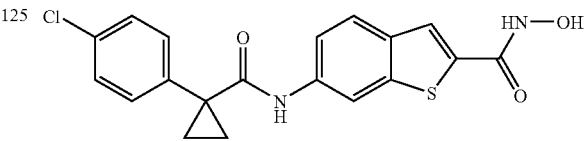 | C19H15ClN2O3S | 386.9 | 164.0 ± 1.4 (N = 2) |
| 126 | 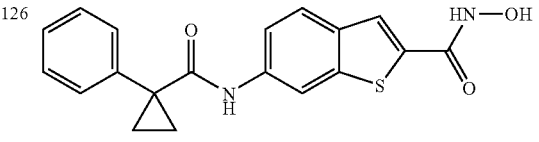 | C19H16N2O3S | 352.4 | 125.0 ± 5.6 (N = 2) |
| 127 | 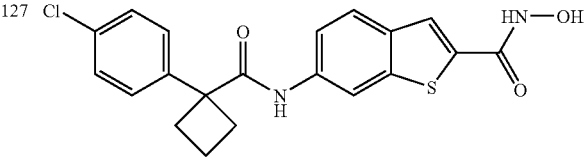 | C20H17ClN2O3S | 400.9 | 115.0 ± 9.8 (N = 2) |
| 128 | 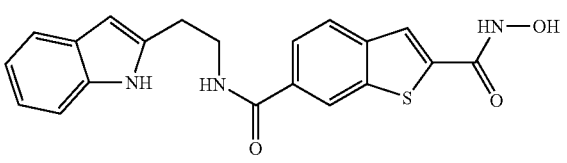 | C20H17N3O3S | 379.4 | 144.3 ± 63.7 (N = 3) |
| 129 | 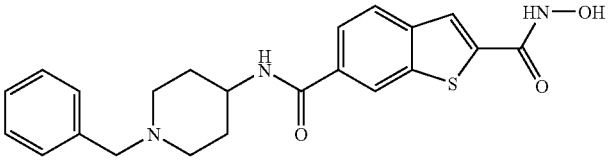 | C22H23N3O3S | 409.5 | 261.3 ± 89.2 (N = 3) |
| 130 | 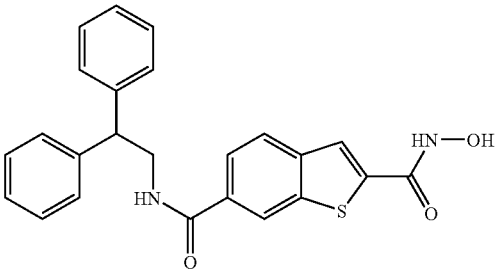 | C24H20N2O3S | 416.5 | 162.5 ± 40.3 (N = 2) |

TABLE 1-continued

| No. | Structure | Mol. Form. | MW | HDAC Inhibition |
|---|---|---|---|---|
| 131 | 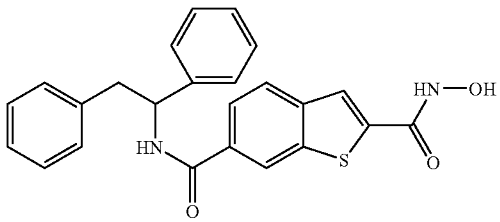 | C24H20N2O3S | 416.5 | 223.0 ± 11.3 (N = 2) |
| 132 | 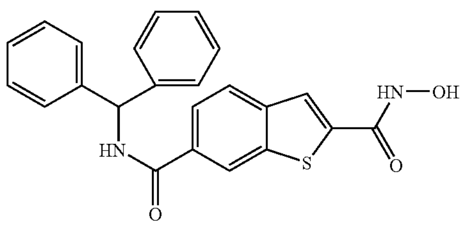 | C23H18N2O3S | 402.5 | 284.0 ± 45.2 (N = 2) |
| 133 | 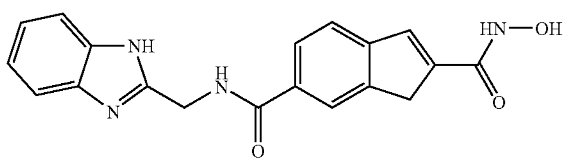 | C18H14N4O3S | 366.4 | 30.3 ± 6.5 (N = 3) |
| 134 | | C17H15N3O3S | 341.4 | 146.0 ± 10.3 (N = 3) |
| 134 | | C20H18N2O3S | 366.4 | 61.0 ± 30.0 (N = 3) |
| 136 | 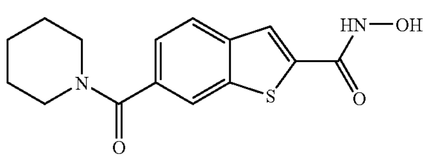 | C15H16N2O3S | 304.4 | 424.3 ± 72.7 (N = 3) |
| 137 | 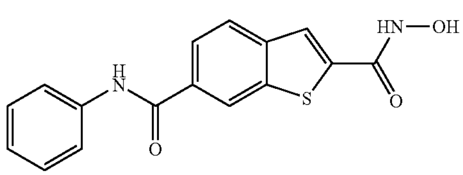 | C16H12N2O3S | 312.3 | 614.6 ± 206.6 (N = 3) |
| 138 | 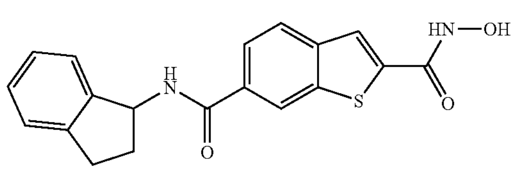 | C19H16N2O3S | 352.4 | 922.3 ± 173.7 (N = 3) |

TABLE 1-continued

| No. | Structure | Mol. Form. | MW | HDAC Inhibition |
|---|---|---|---|---|
| 139 | 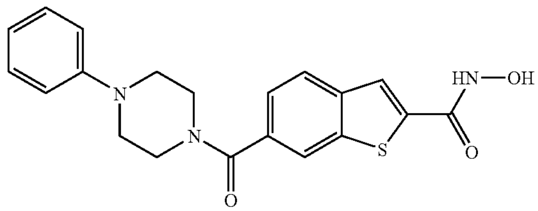 | C20H19N3O3S | 381.4 | 175.5 ± 13.4 (N = 2) |
| 140 | 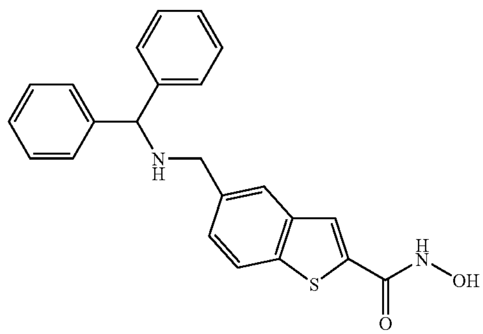 | C23H20N2O2S | 388.5 | 869.3 ± 108.5 (N = 3) |
| 141 | 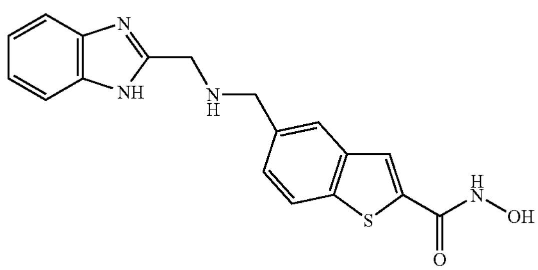 | C18H16N4O2S | 352.4 | 116.5 ± 3.5 (N = 2) |
| 142 | 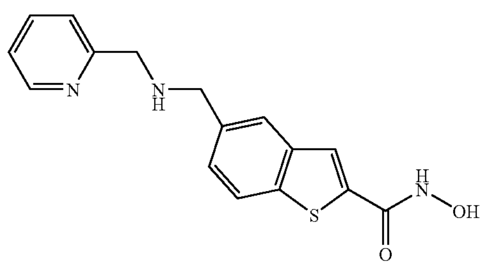 | C16H15N3O2S | 313.4 | 258.3 ± 17.0 (N = 3) |
| 143 | 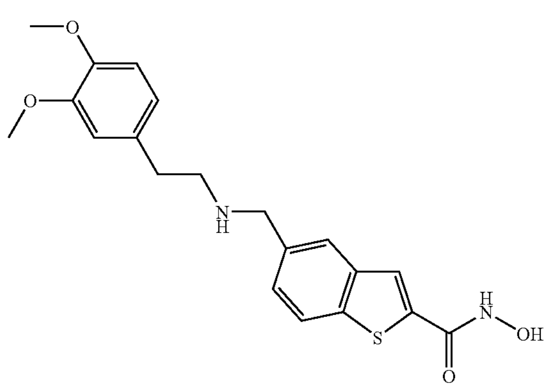 | C20H22N2O4S | 386.5 | 325.0 ± 57.4 (N = 3) |

TABLE 1-continued

| No. | Structure | Mol. Form. | MW | HDAC Inhibition |
|---|---|---|---|---|
| 144 | 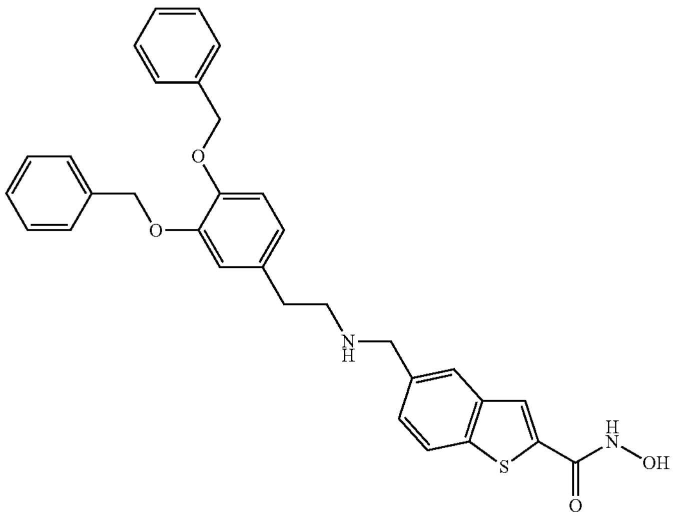 | C32H30N2O4S | 538.7 | 1575.5 ± 334.4 (N = 2) |
| 145 | 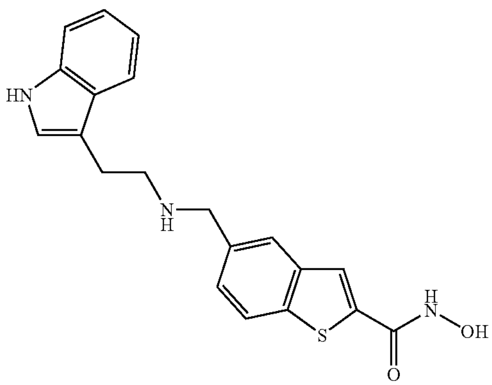 | C20H19N3O2S | 365.4 | 151.0 ± 28.2 (N = 2) |
| 146 | 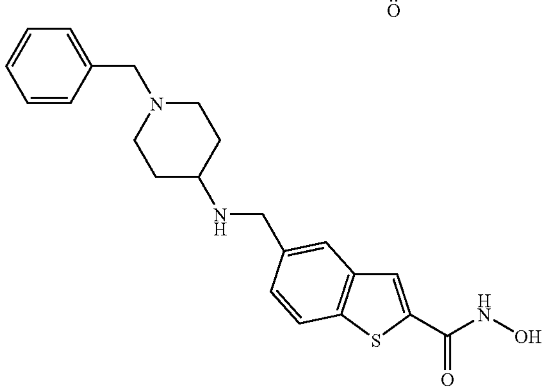 | C22H25N3O2S | 395.5 | 523.6 ± 102.0 (N = 3) |
| 147 | 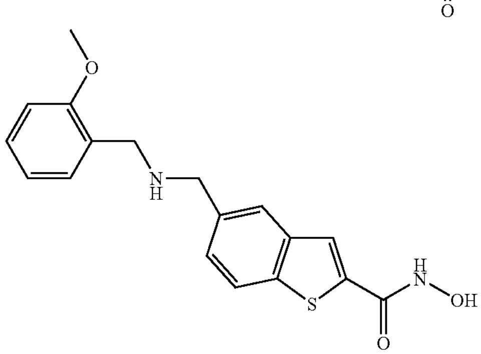 | C18H18N2O3S | 342.4 | 75.5 ± 7.7 (N = 2) |

TABLE 1-continued

| No. | Structure | Mol. Form. | MW | HDAC Inhibition |
|---|---|---|---|---|
| 148 | 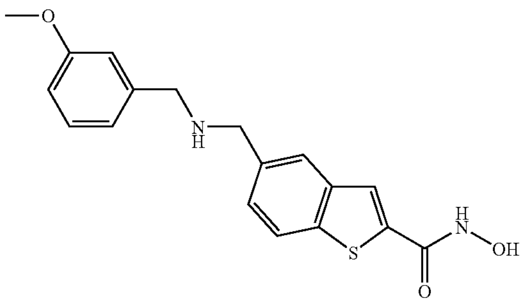 | C18H18N2O3S | 342.4 | 100.0 ± 12.7 (N = 2) |
| 149 | 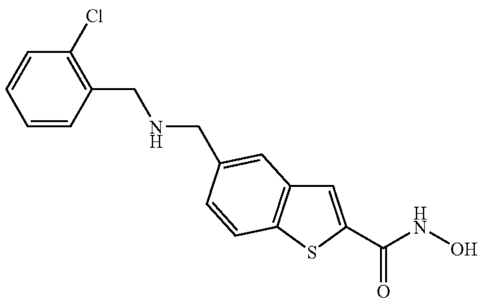 | C17H15ClN2O2S | 346.8 | 96.5 ± 34.4 (N = 4) |
| 150 | 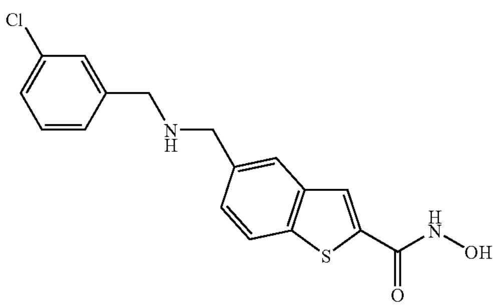 | C17H15ClN2O2S | 346.8 | 144.5 ± 0.7 (N = 2) |
| 151 | 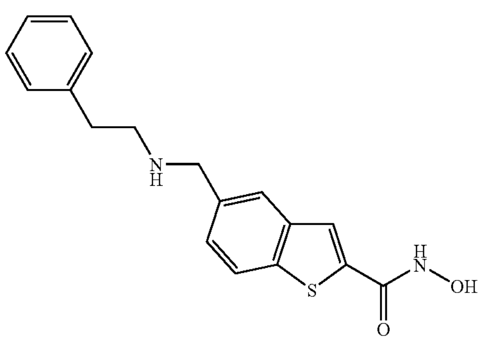 | C18H18N2O2S | 326.4 | 202.5 ± 14.8 (N = 2) |
| 152 | 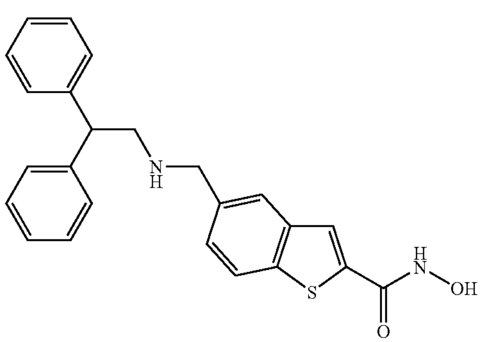 | C24H22N2O2S | 402.5 | 414.6 ± 91.6 (N = 3) |

TABLE 1-continued
| No. | Structure | Mol. Form. | MW | HDAC Inhibition |
|---|---|---|---|---|
| 153 | 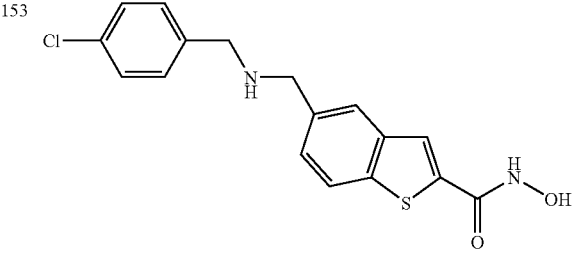 | C17H15ClN2O2S | 346.8 | 124.0 ± 24.0 (N = 2) |
| 154 | 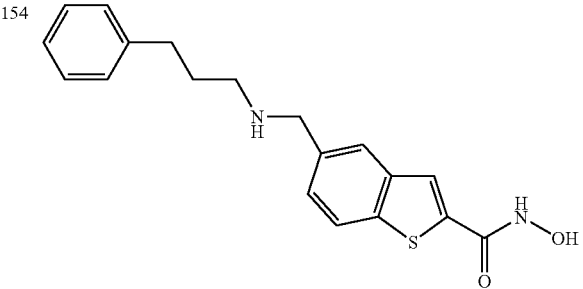 | C19H20N2O2S | 340.4 | 163.5 ± 37.4 (N = 2) |
| 155 | 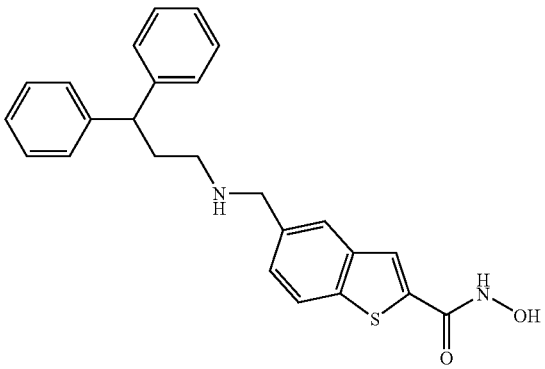 | C25H24N2O2S | 416.5 | 966.6 ± 215.1 (N = 3) |
| 156 | 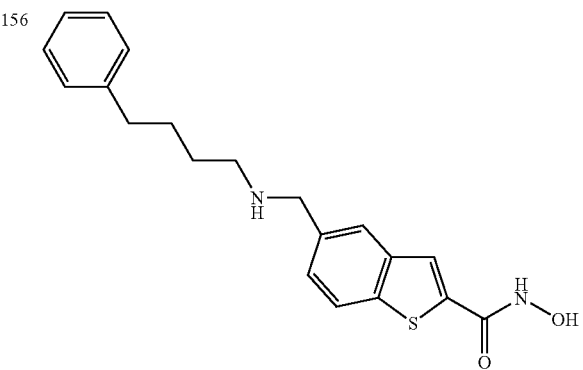 | C20H22N2O2S | 3564.5 | 275.5 ± 34.6 (N = 2) |

TABLE 1-continued

| No. | Structure | Mol. Form. | MW | HDAC Inhibition |
|---|---|---|---|---|
| 157 | 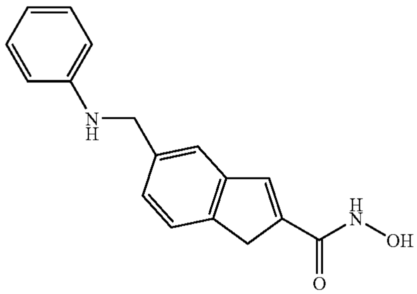 | C16H14N2O2S | 298.4 | 174.5 ± 38.8 (N = 2) |
| 158 | 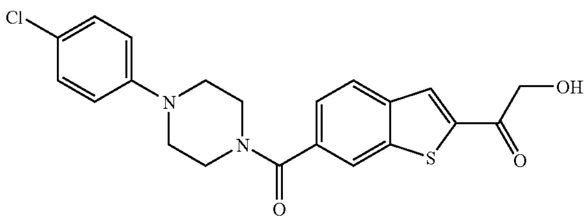 | C20H18ClN3O3S | 415.9 | 441.5 ± 98.2 (N = 2) |
| 159 | 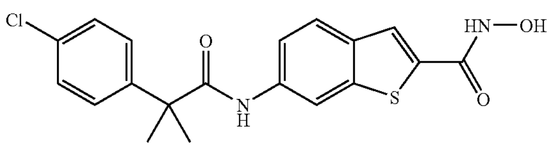 | C19H17ClN2O3S | 388.9 | 536.0 ± 168.2 (N = 2) |
| 160 | 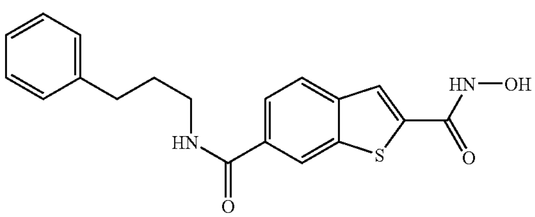 | C19H18N2O3S | 354.4 | 90.0 ± 11.3 (N = 2) |
| 161 | 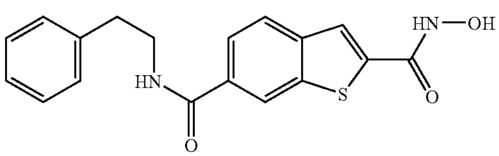 | C18H16N2O3S | 340.4 | 58.0 ± 0.0 (N = 2) |
| 162 | 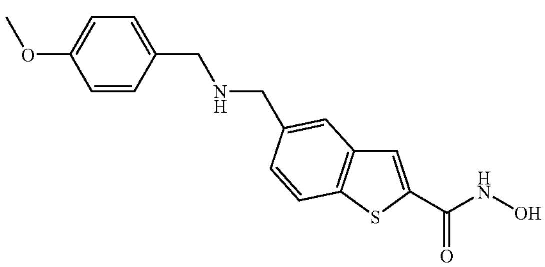 | C18H18N2O3S | 342.4 | 110.0 ± 14.1 (N = 2) |

TABLE 1-continued
| No. | Structure | Mol. Form. | MW | HDAC Inhibition |
|---|---|---|---|---|
| 163 | 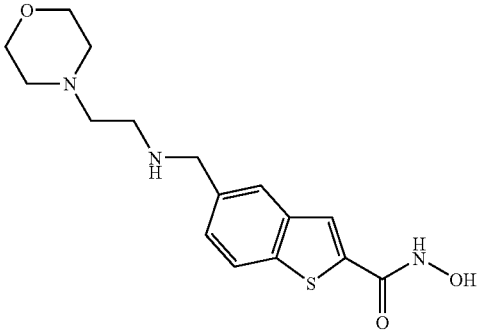 | C16H21N3O3S | 335.4 | 734.5 ± 34.6 (N = 2) |
| 164 | 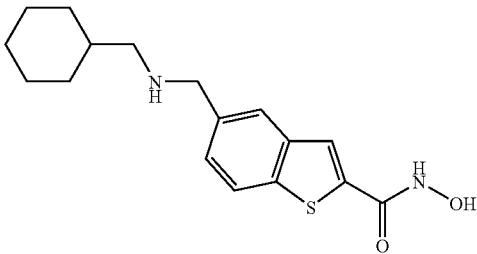 | C17H22N2O2S | 318.4 | 207.0 ± 38.1 (N = 2) |
| 165 | 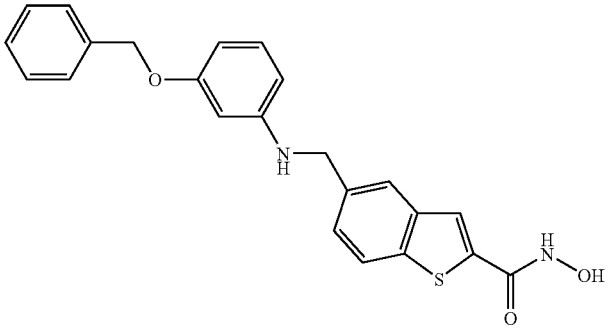 | C23H20N2O3S | 404.5 | 269.0 ± 63.6 (N = 2) |
| 166 | 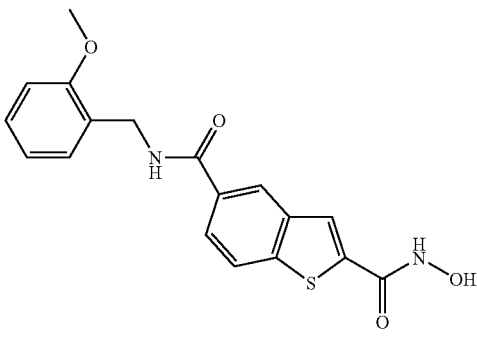 | C18H16N2O4S | 356.4 | 90.0 ± 5.6 (N = 2) |
| 167 | 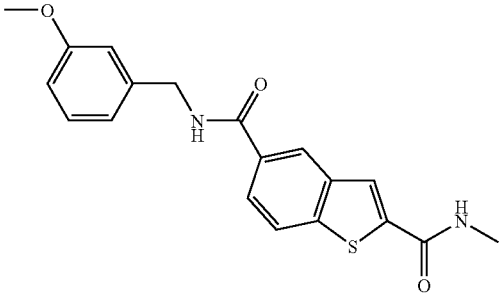 | C18H16N2O4S | 356.4 | 94.0 ± 5.6 (N = 2) |

TABLE 1-continued

| No. | Structure | Mol. Form. | MW | HDAC Inhibition |
|---|---|---|---|---|
| 168 | 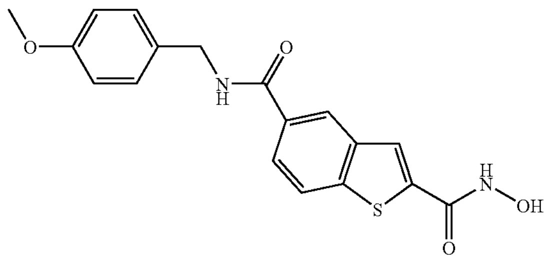 | C18H16N2O4S | 356.4 | 36.0 ± 1.4 (N = 2) |
| 169 | 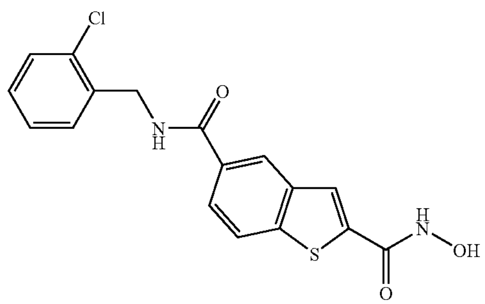 | C17H13ClN2O3S | 360.8 | 66.5 ± 2.1 (N = 2) |
| 170 | 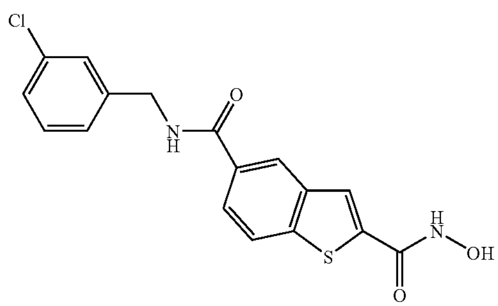 | C17H13ClN2O3S | 360.8 | 88.0 ± 0.0 (N = 2) |
| 171 | 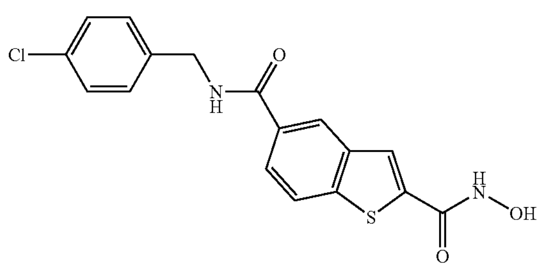 | C17H13ClN2O3S | 360.8 | 63.5 ± 4.9 (N = 2) |
| 172 | 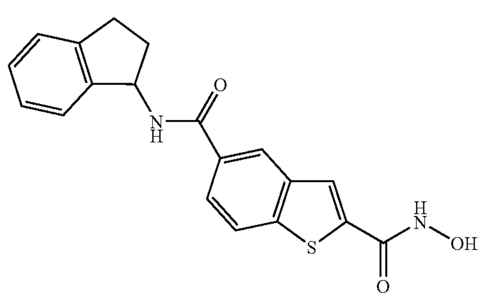 | C19H16N2O3S | 352.4 | 1363.4 ± 47.3 (N = 2) |

TABLE 1-continued

| No. | Structure | Mol. Form. | MW | HDAC Inhibition |
|---|---|---|---|---|
| 173 | 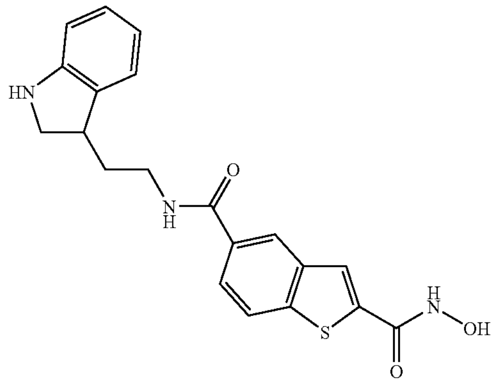 | C20H17N3O3S | 379.4 | 129.0 ± 18.3 (N = 2) |
| 174 | 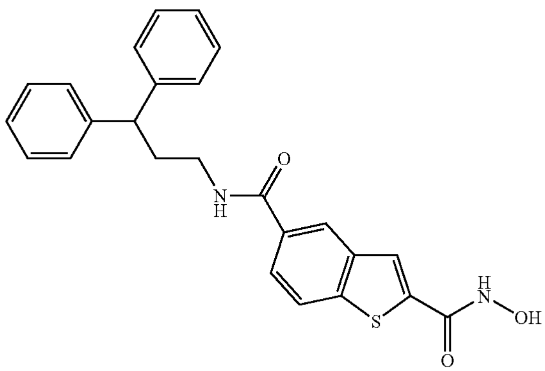 | C25H22N2O3S | 430.5 | 428.5 ± 102.5 (N = 2) |
| 175 | 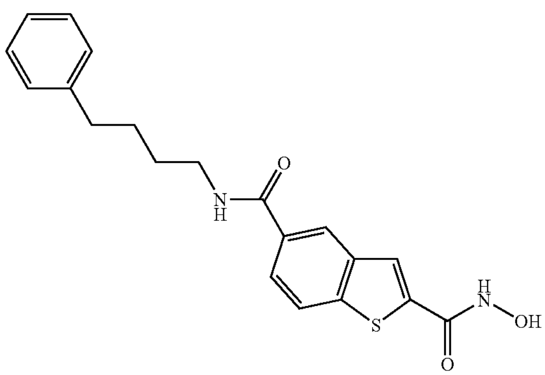 | C20H20N2O3S | 368.4 | 154.0 ± 8.4 (N = 2) |
| 176 | 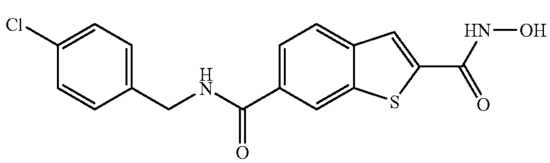 | C17H13ClN2O3S | 360.8 | 126.0 ± 31.1 (N = 2) |
| 177 | 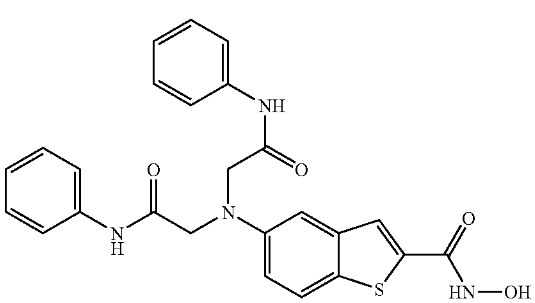 | C25H22N4O4S | 474.5 | 57.3 ± 18.5 (N = 3) |

TABLE 1-continued

| No. | Structure | Mol. Form. | MW | HDAC Inhibition |
|---|---|---|---|---|
| 178 | 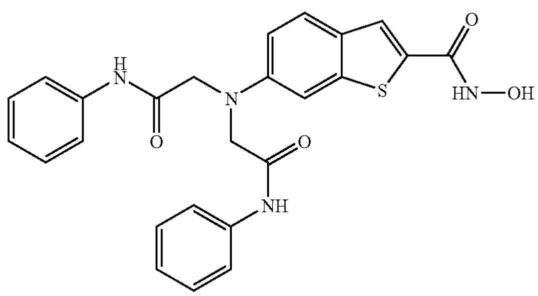 | C25H22N4O4S | 474.5 | 6.5 ± 0.7 (N = 2) |
| 179 | 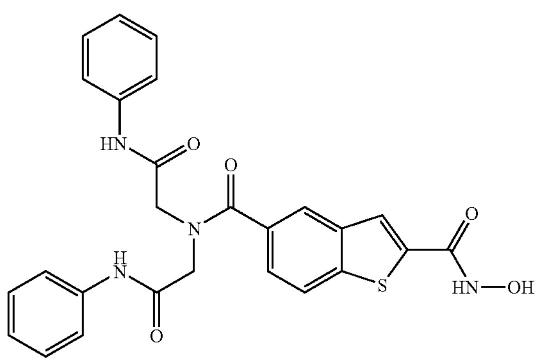 | C26H22N4O5S | 502.5 | 102.0 ± 26.2 (N = 3) |
| 180 | 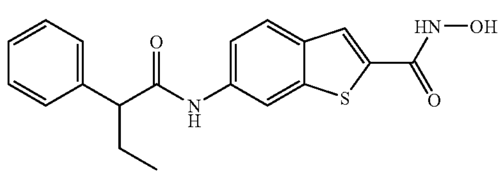 | C19H18N2O3S | 354.4 | 18.5 ± 2.1 (N = 2) |
| 181 | 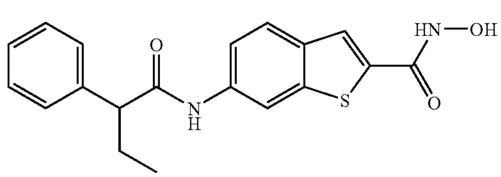 | C19H18N2O3S | 354.4 | 59.5 ± 3.5 (N = 2) |
| 182 | 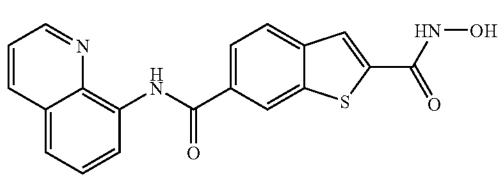 | C19H13N3O3S | 363.4 | 1069.5 ± 21.9 (N = 2) |
| 183 | 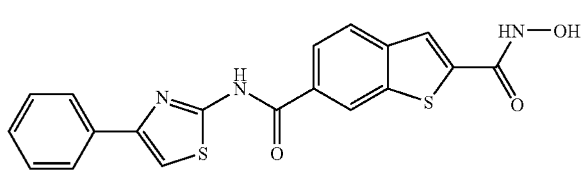 | C19H13N3O3S2 | 395.5 | 4135.5 ± 1891.5 (N = 2) |

TABLE 1-continued

| No. | Structure | Mol. Form. | MW | HDAC Inhibition |
|---|---|---|---|---|
| 184 | 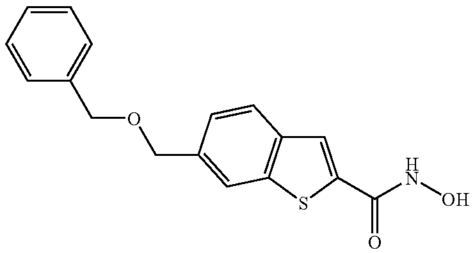 | C17H15NO3S | 313.4 | 199.0 ± 35.3 (N = 2) |
| 185 | 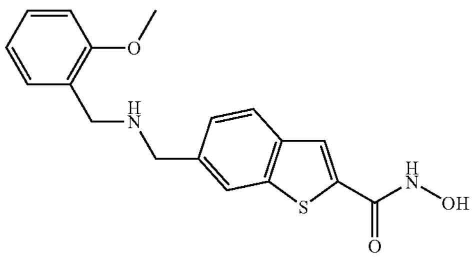 | C18H18N2O3S | 342.4 | 48.5 ± 6.3 (N = 2) |
| 186 | 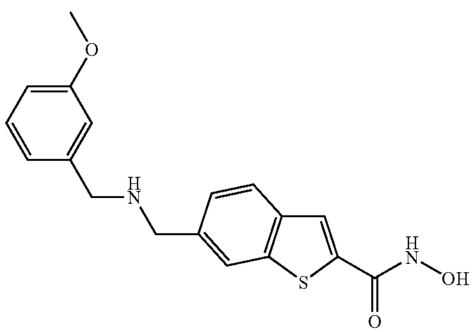 | C18H18N2O3S | 342.4 | 55.5 ± 9.1 (N = 2) |
| 187 | 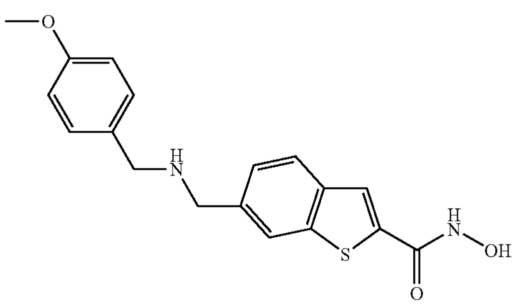 | C18H18N2O3S | 342.4 | 23.0 ± 1.4 (N = 2) |
| 188 | 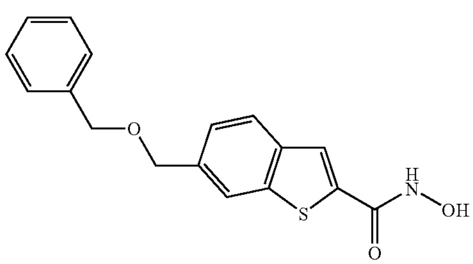 | C20H19N3O2S | 365.4 | 82.5 ± 16.2 (N = 2) |
| 189 | 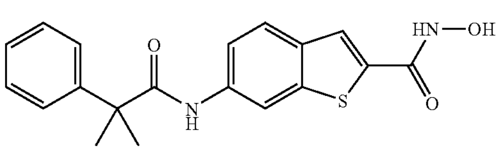 | C19H18N2O3S | 354.4 | 72.0 ± 14.1 (N = 2) |

TABLE 1-continued

| No. | Structure | Mol. Form. | MW | HDAC Inhibition |
|---|---|---|---|---|
| 190 | 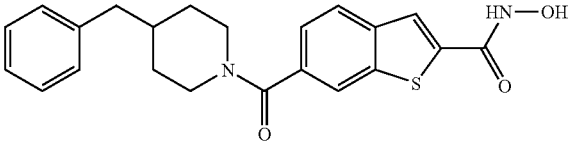 | C22H22N2O3S | 394.5 | 170.5 ± 38.8 (N = 2) |
| 191 | 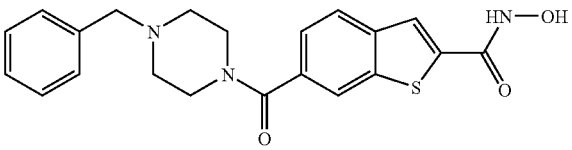 | C21H21N3O3S | 395.5 | 453.5 ± 113.8 (N = 2) |
| 192 | 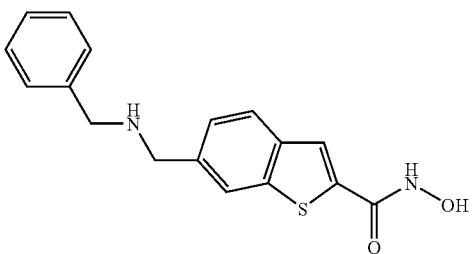 | C17H16N2O2S | 312.39 | 53 (N = 1) |
| 193 | 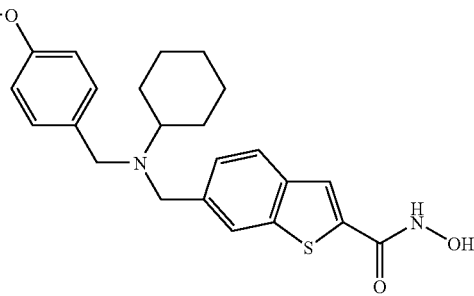 | C24H28N2O3S | 424.56 | 99 (N = 1) |
| 194 | 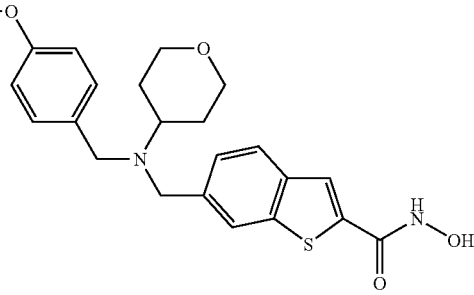 | C23H26N2O4S | 426.53 | 76 (N = 1) |

Table 2 below shows the chemical structures and HDAC enzymatic assay results for a selection of novel compounds containing a thiophene backbone designed and synthesized in accordance with the present invention.

TABLE 2

| No. | Structure | Mol. Form. | MW | HDAC Inhibition |
|---|---|---|---|---|
| 54 | 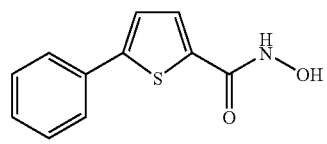 | C11H9NO2S | 219.2576 | 219 (N = 1) |

TABLE 2-continued
| No. | Structure | Mol. Form. | MW | HDAC Inhibition |
|---|---|---|---|---|
| 55 | 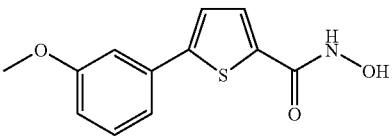 | C12H11NO3S | 249.2838 | 444.5 ± 54.4 (N = 2) |
| 56 | 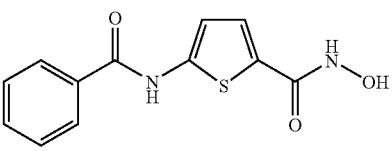 | C12H10N2O3S | 262.2826 | 713.5 ± 122.3 (N = 2) |
| 57 | 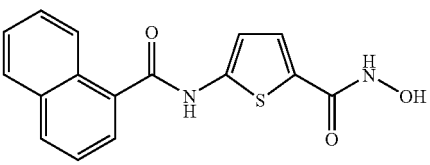 | C16H12N2O3S | 312.3424 | 363 ± 16.9 (N = 2) |
| 58 | 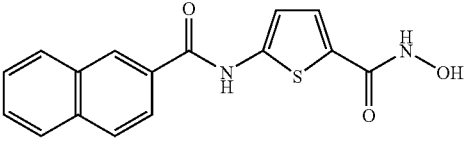 | C16H12N2O3S | 312.3424 | 730 ± 127.2 (N = 2) |
| 59 | 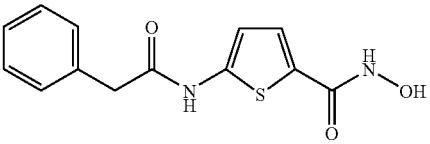 | C13H12N2O3S | 276.3094 | 63.5 ± 7.7 (N = 2) |
| 60 | 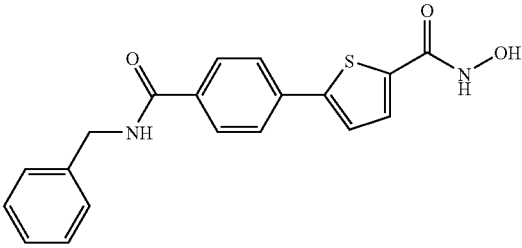 | C19H16N2O3S | 352.407 | 464 ± 65 (N = 2) |
| 61 | 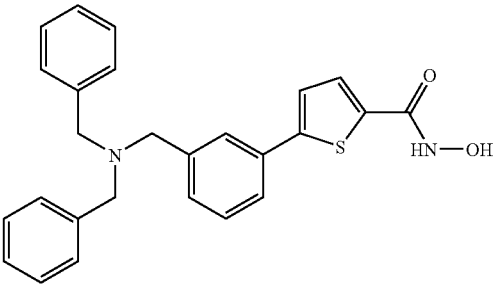 | C26H24N2O2S | 428.5478 | 1001 (N = 1) |

TABLE 2-continued

| No. | Structure | Mol. Form. | MW | HDAC Inhibition |
|---|---|---|---|---|
| 62 | 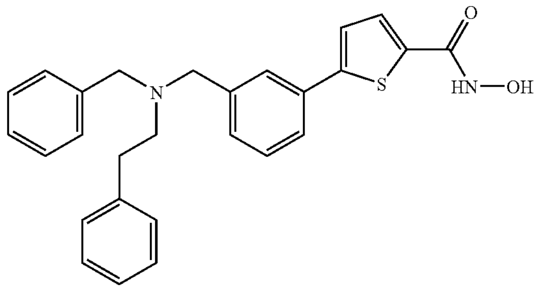 | C27H26N2O2S | 442.5746 | 933 ± 22.6 (N = 1) |
| 63 | 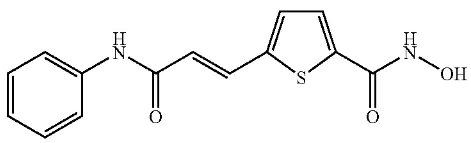 | C14H12N2O3S | 288.3204 | 397 (N = 1) |
| 64 | 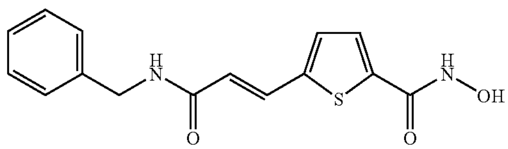 | C15H14N2O3S | 302.3472 | 206 (N = 1) |
| 65 | 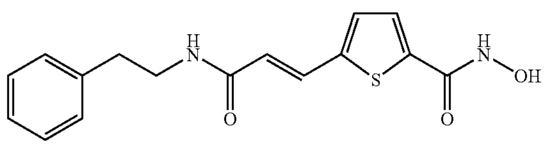 | C16H16N2O3S | 316.374 | 41 (N = 1) |
| 66 | 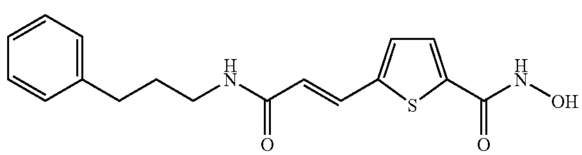 | C17H18N2O3S | 330.4008 | 70 (N = 1) |
| 67 | 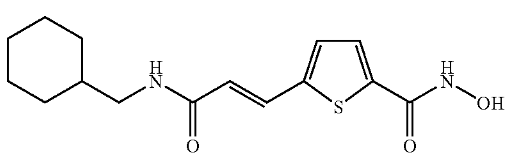 | C15H20N2O3S | 308.3946 | 120 (N = 1) |
| 68 | 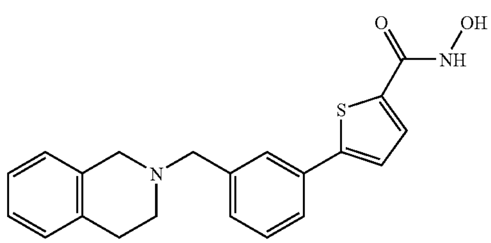 | C21H20N2O2S | 364.4612 | 417 (N = 1) |

TABLE 2-continued
| No. | Structure | Mol. Form. | MW | HDAC Inhibition |
|---|---|---|---|---|
| 69 | 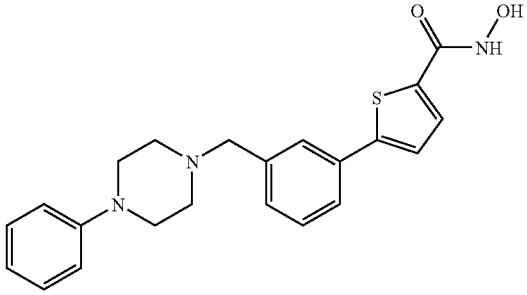 | C22H23N3O2S | 393.5026 | 174 (N = 1) |
| 70 | 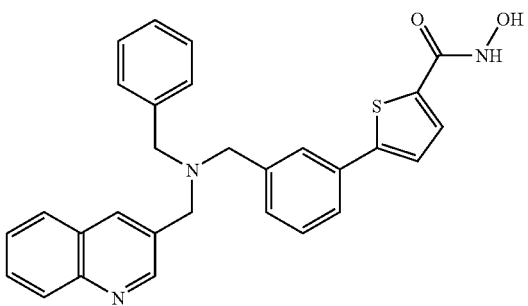 | C29H25N3O2S | 479.5954 | 399 (N = 1) |
| 71 | 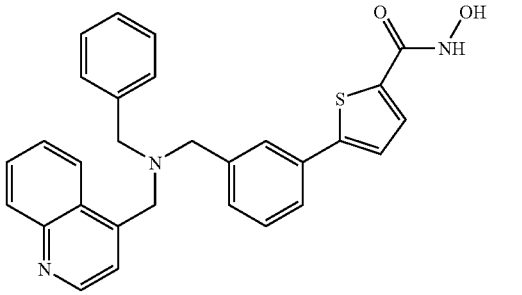 | C29H25N3O2S | 479.5954 | 461 (N = 1) |
| 72 | 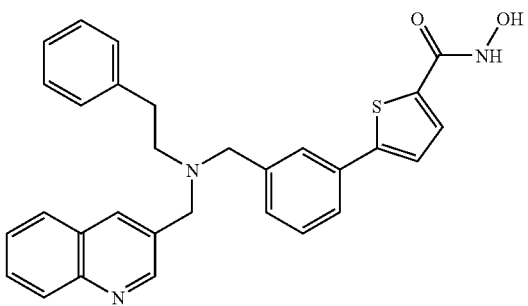 | C30H27N3O2S | 493.6222 | 570 (N = 1) |
| 73 | 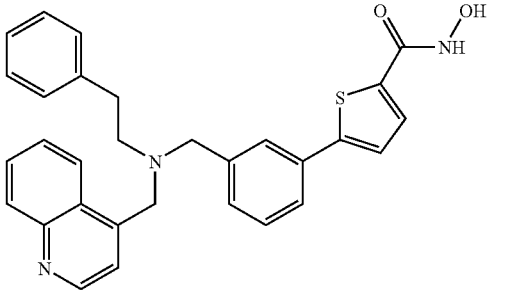 | C30H27N3O2S | 493.6222 | 705.5 ± 92.6 (N = 2) |

TABLE 2-continued

| No. | Structure | Mol. Form. | MW | HDAC Inhibition |
|---|---|---|---|---|
| 74 | 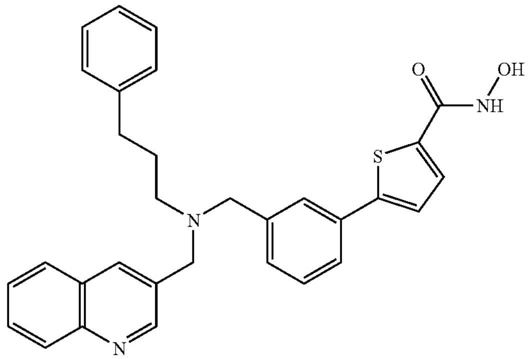 | C31H29N3O2S | 507.649 | 461 (N = 1) |
| 75 | 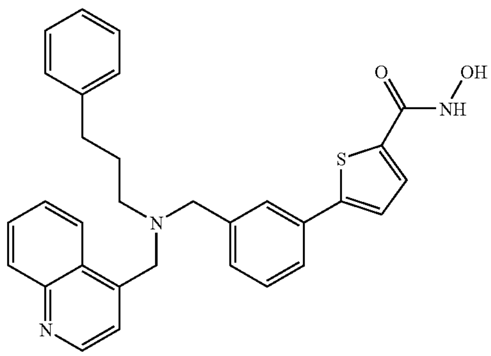 | C31H29N3O2S | 507.649 | 919.5 ± 569.2 (N = 2) |
| 76 | 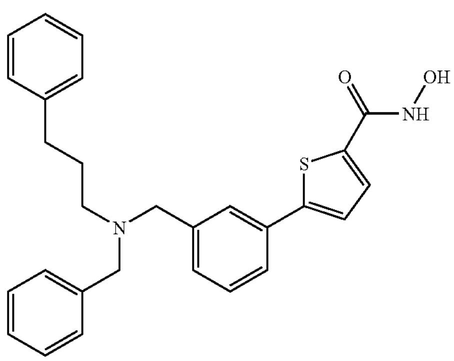 | C28H28N2O2S | 456.6014 | 1007 (N = 1) |
| 77 | 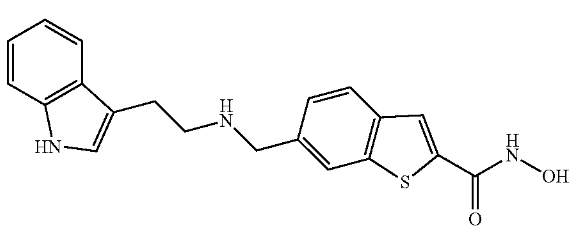 | C22H20N2O3S | 392.4716 | 222 (N = 1) |
| 78 | 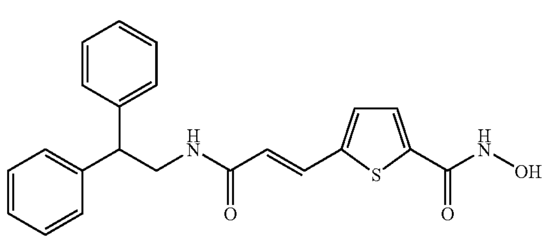 | C21H18N2O4S | 394.4442 | 792 (N = 1) |

TABLE 2-continued
| No. | Structure | Mol. Form. | MW | HDAC Inhibition |
|---|---|---|---|---|
| 79 | 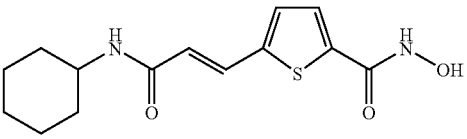 | C14H18N2O3S | 294.3678 | 666 (N = 1) |
| 80 | 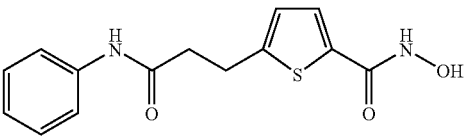 | C14H14N2O3S | 290.3362 | 481 (N = 1) |
| 81 | 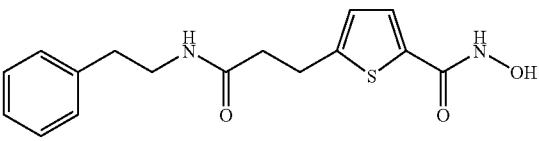 | C16H18N2O3S | 318.3898 | 690 (N = 1) |
| 82 | 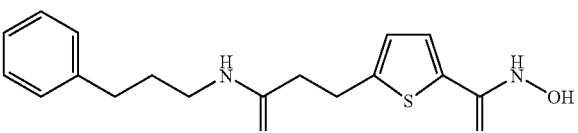 | C17H20N2O3S | 332.4166 | 526 (N = 1) |
| 83 | 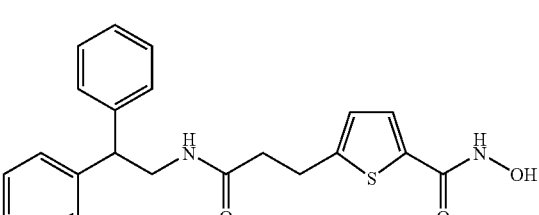 | C22H22N2O3S | 394.4874 | 581 (N = 1) |
| 195 | 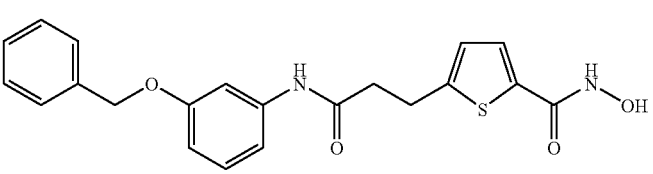 | C21H20N2O4S | 396.5 | 127.0 ± 11.3 (N = 2) |
| 196 | 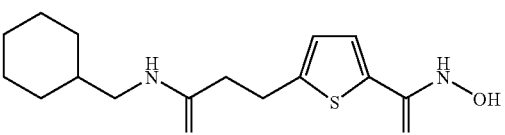 | C15H22N2O3S | 310.4 | 1450.5 ± 111.0 (N = 2) |
| 197 | 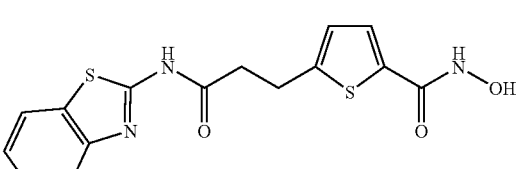 | C15H13N3O3S2 | 347.4 | 133.5 ± 7.7 (N = 2) |
| 198 | 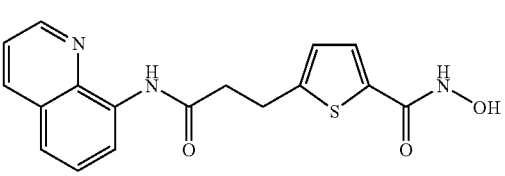 | C17H13N3O3S | 339.4 | 668.5 ± 19.0 (N = 2) |

TABLE 2-continued

| No. | Structure | Mol. Form. | MW | HDAC Inhibition |
|---|---|---|---|---|
| 199 | 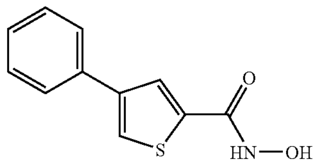 | C11H9NO2S | 219.3 | 9257.5 ± 1177.3 (N = 2) |

Example 3

HDAC Inhibition in Cell Lines

MTS Assay

The novel compounds of the present invention were tested for their ability to inhibit proliferation of the murine erythroleukemia cell line SC9.

The MTS assay, also referred to as the Cell Titer 96 Aqueous One Solution Cell Proliferation Assay, is a calorimetric method for determining the number of viable cells in proliferation, cytotoxicity or chemosensitivity assays. The MTS reagent contains a novel tetrazolium compound [3-(4,5-dimethylthiazol-2-yl)-5-(3-carboxymethoxyphenyl)-2-(4-sulfophenyl)-2H-tetrazolium, inner salt] and electron coupling reagent (phenazine ethosulfate;PES). Murine erythroleukemia cells (SC-9) were incubated with vehicle or increasing concentrations of compound for 48 hours. Cell proliferation was quantitated by adding a small amount of the MTS reagent directly to culture wells, incubating for 1-4 hours and then recording the absorbance at 490 nM with a 96-well plate reader. The quantity of formazan product, as measured by 490 nM absorbance, is directly proportional to the number of living cells in culture.

Results

The results of the SC9-cell based MTS assay from a select group of novel compounds show that the compounds are able to inhibit cellular proliferation at a concentration below 1000 nm. Several of the compounds are able to inhibit cellular proliferation at a concentration range of about 500-1000 nm. Several other compounds are able to inhibit cellular proliferation at a concentration range of about 100-500 nm. Several other compounds are able to inhibit cellular proliferation at a concentration of below 100 nm. Several other compounds are able to inhibit cellular proliferation at a concentration range of about 50-100 nm. Several other compounds are able to inhibit cellular proliferation at a concentration of below 50 nm. Several other compounds are able to inhibit cellular proliferation at a concentration range of about 50-100 nm. Several other compounds are able to inhibit cellular proliferation at a concentration of below 10 nm. Several other compounds are able to inhibit cellular proliferation at a concentration range of about 1-10 nm.

The results of the SC9-cell based MTS assay from a select group of novel compounds are summarized in Table 3 below:

TABLE 3

| Compound No. | Structure | MTS Assay |
|---|---|---|
| 6 | 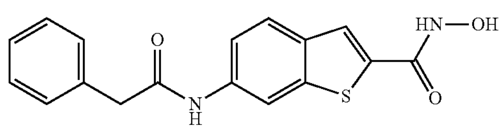 | 250 ± 57.2 (N = 2) |
| 13 | 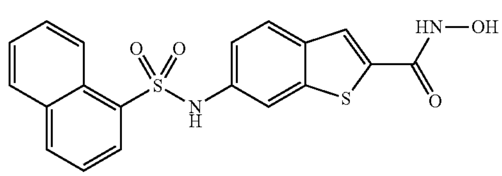 | 441 (N = 1) |
| 14 | 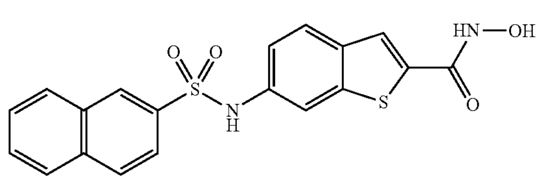 | 917 (N = 1) |

TABLE 3-continued

| Compound No. | Structure | MTS Assay |
|---|---|---|
| 25 | 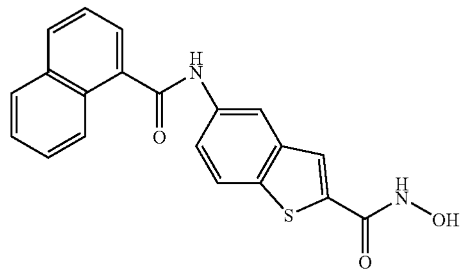 | 545 (N = 1) |
| 28 | 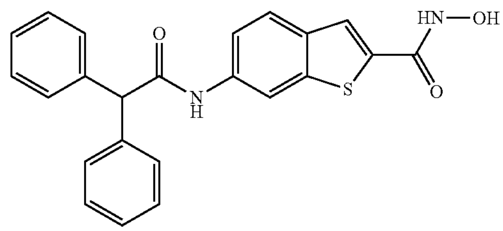 | 696 (N = 1) |
| 33 | 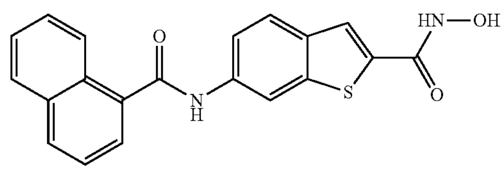 | 785 (N = 1) |
| 36 | 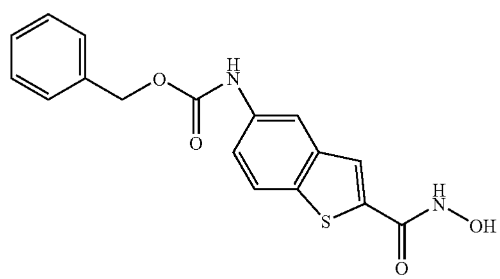 | 717 (N = 1) |
| 39 | 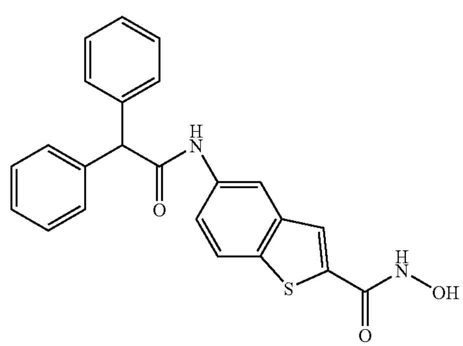 | 666 (N = 1) |
| 59 | 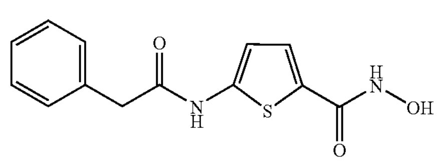 | 642 (N = 1) |

TABLE 3-continued
| Compound No. | Structure | MTS Assay |
|---|---|---|
| 86 | 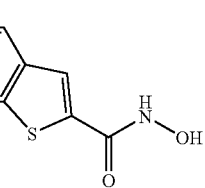 | 836 ± 28.9 (N = 2) |
| 88 | 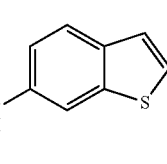 | 238.0 (N = 1) |
| 89 | 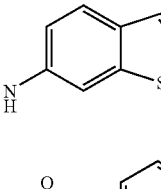 | 205.0 ± 37.5 (N = 3) |
| 90 | 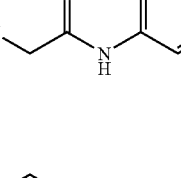 | 704 ± 96.1 (N = 2) |
| 91 | 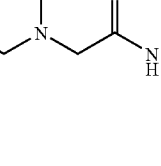 | 899 (N = 1) |
| 93 | 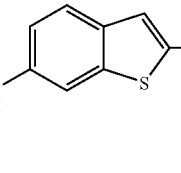 | 751 (N = 1) |
| 97 | 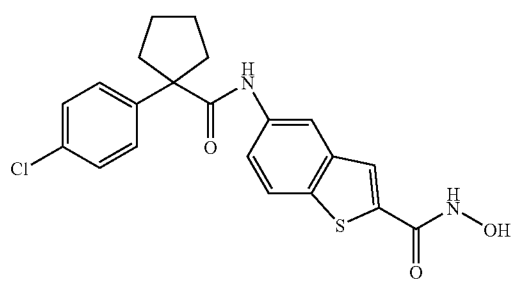 | 462.0 (N = 1) |

TABLE 3-continued

| Compound No. | Structure | MTS Assay |
|---|---|---|
| 98 | 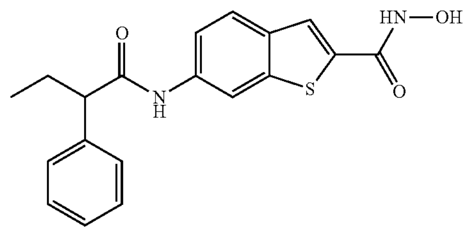 | 225 ± 26.7 (N = 5) |
| 99 | 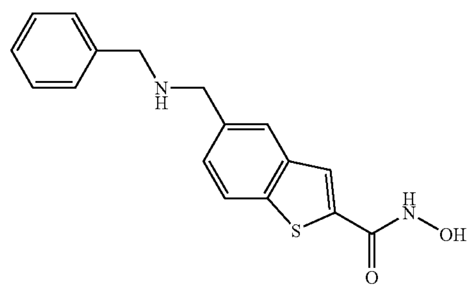 | 474 ± 65.7 (N = 2) |
| 100 | 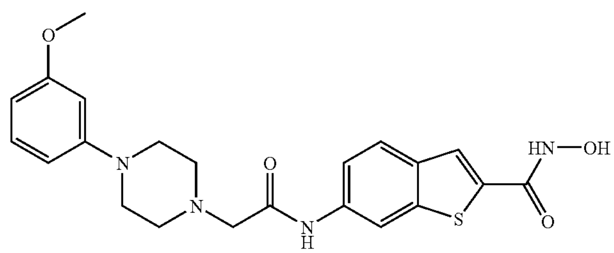 | 519.0 ± 65.7 (N = 2) |
| 101 | 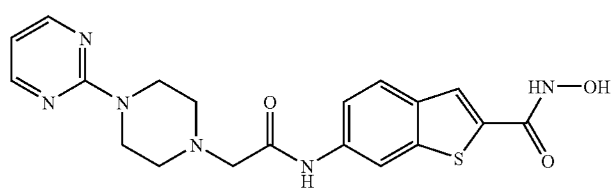 | 830 ± 393.2 (N = 1) |
| 106 | 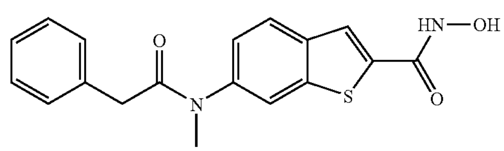 | 537 ± 124.5 (N = 3) |
| 107 | 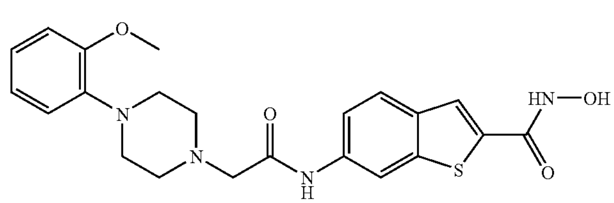 | 309 (N = 1) |
| 108 | 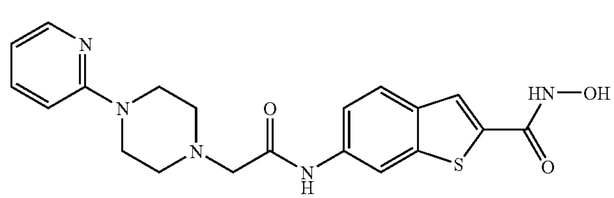 | 442 (N = 1) |

TABLE 3-continued
| Compound No. | Structure | MTS Assay |
|---|---|---|
| 110 | 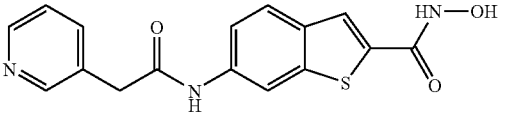 | 833 ± 65.0 (N = 2) |
| 115 | 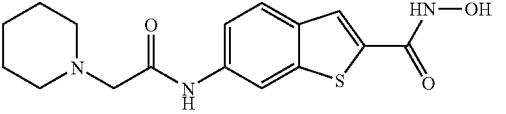 | 306 ± 78.5 (N = 3) |
| 119 | 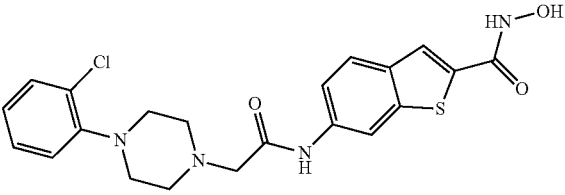 | 568 ± 227.0 (N = 3) |
| 123 | 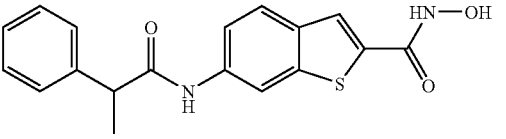 | 206 ± 79.2 (N = 3) |
| 126 | 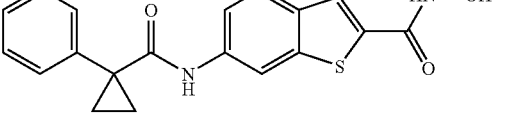 | 836 (N = 1) |
| 127 | 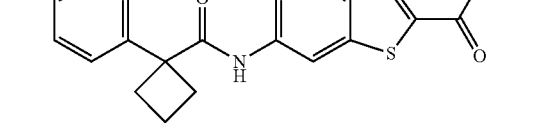 | 935 (N = 1) |
| 135 | 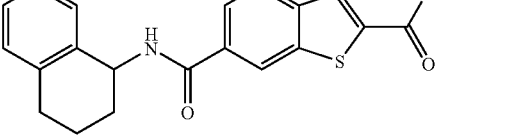 | 836 (N = 1) |
| 142 | 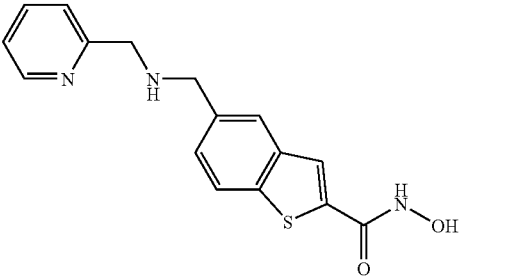 | 714 (N = 1) |

TABLE 3-continued
| Compound No. | Structure | MTS Assay |
|---|---|---|
| 145 | 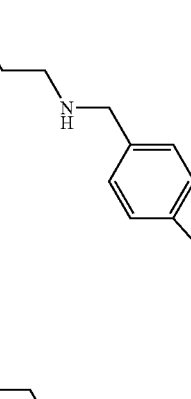 | 990 (N = 1) |
| 146 | 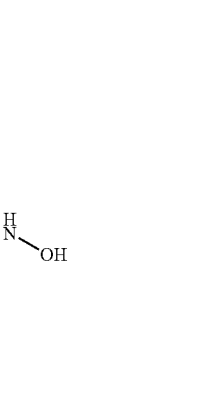 | 891 (N = 1) |
| 147 | 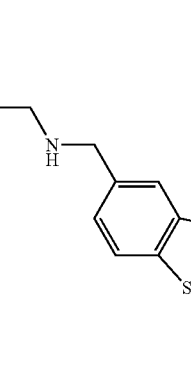 | 201 ± 59.3 (N = 2) |
| 148 | 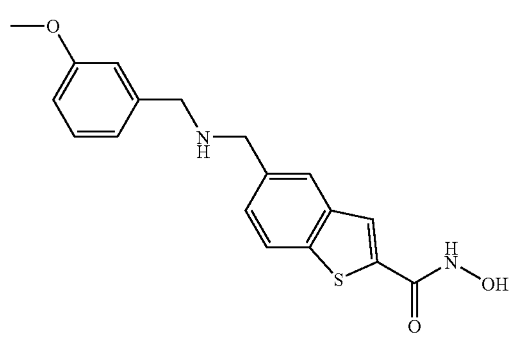 | 430 ± 132.2 (N = 2) |

TABLE 3-continued

| Compound No. | Structure | MTS Assay |
|---|---|---|
| 151 | phenethylaminomethyl-benzothiophene-2-carbohydroxamic acid | 947 (N = 1) |
| 153 | (4-chlorobenzyl)aminomethyl-benzothiophene-2-carbohydroxamic acid | 531 (N = 1) |
| 154 | (3-phenylpropyl)aminomethyl-benzothiophene-2-carbohydroxamic acid | 637 (N = 1) |
| 155 | (3,3-diphenylpropyl)aminomethyl-benzothiophene-2-carbohydroxamic acid | 390 (N = 1) |

TABLE 3-continued

| Compound No. | Structure | MTS Assay |
|---|---|---|
| 156 | 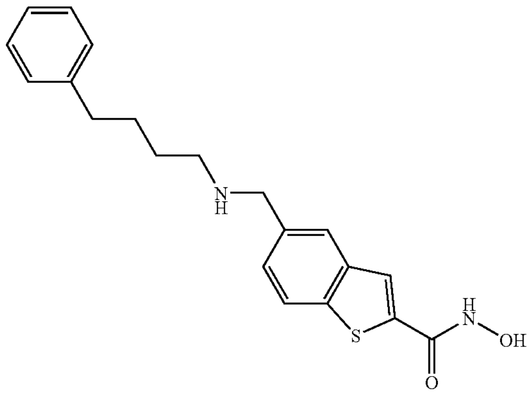 | 966 (N = 1) |
| 162 | 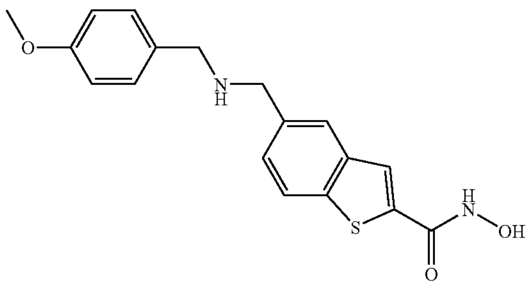 | 587 (N = 1) |
| 164 | 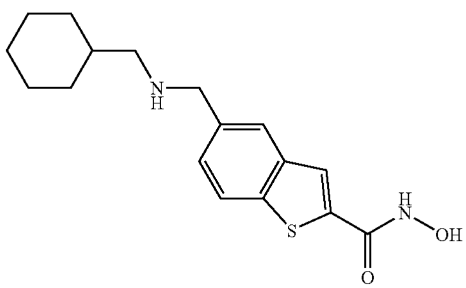 | 545 ± 24.0 (N = 2) |
| 177 | 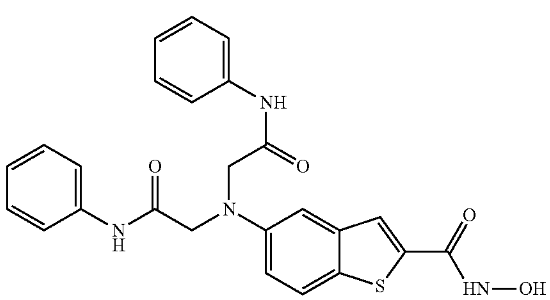 | 259 ± 48.7 (N = 2) |
| 178 | 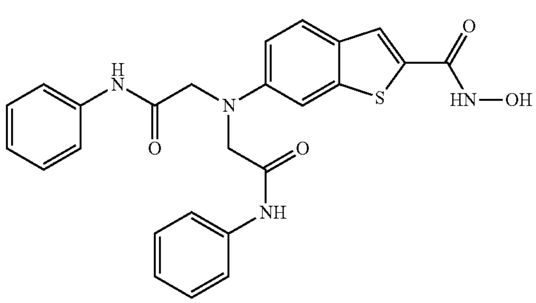 | 200 ± 19.7 (N = 2) |

TABLE 3-continued

| Compound No. | Structure | MTS Assay |
|---|---|---|
| 180 | 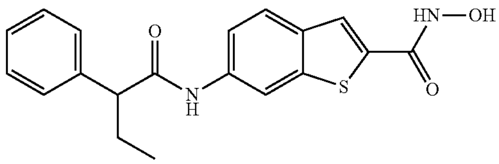 | 140.0 (N = 1) |
| 181 | 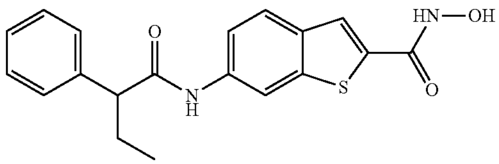 | 528.0 (N = 1) |
| 185 | 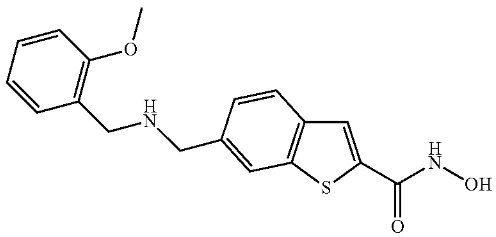 | 90.0 (N = 1) |
| 186 | 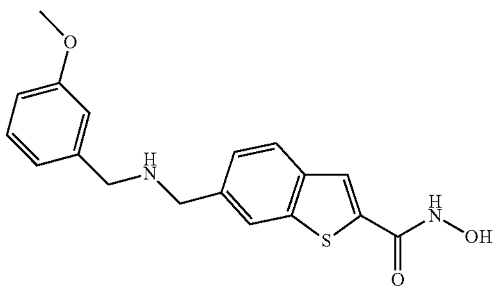 | 93.0 (N = 1) |
| 187 | 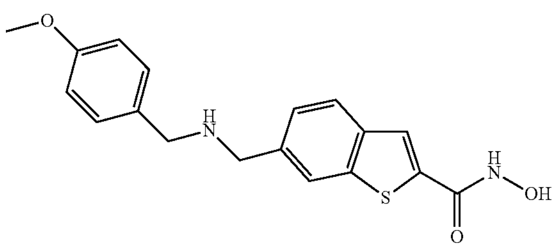 | 56.0 (N = 1) |
| 188 | 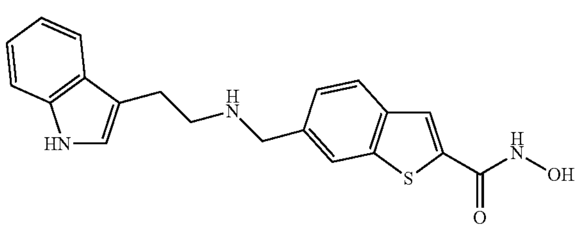 | 191.0 (N = 1) |
| 189 | 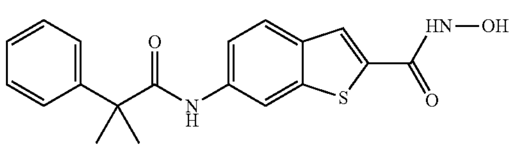 | 493.0 (N = 1) |

While this invention has been particularly shown and described with references to preferred embodiments thereof, it will be understood by those skilled in the art that various changes in form and details may be made therein without departing from the meaning of the invention described. Rather, the scope of the invention is defined by the claims that follow:

What is claimed is:

1. A compound represented by the following structural Formula:

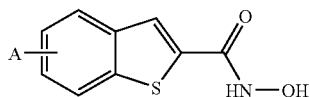

wherein A is a group selected from:

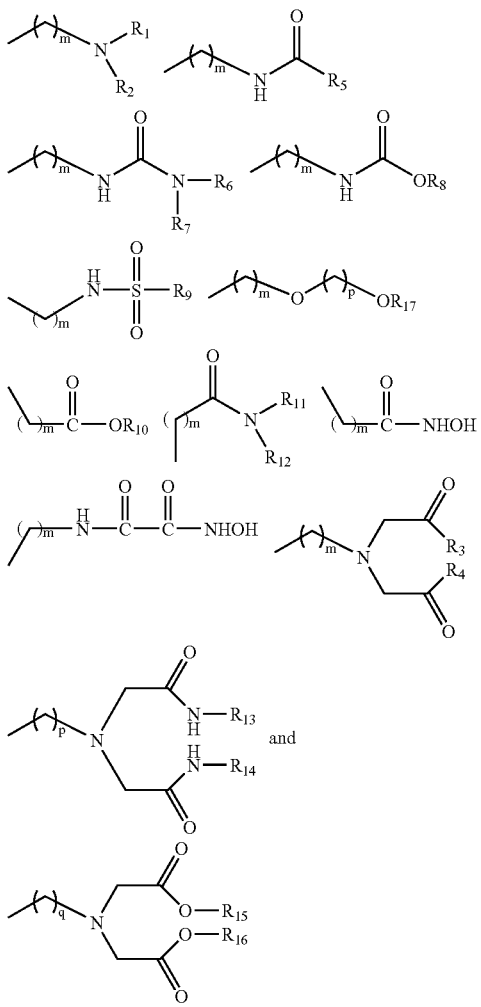

wherein $R_1$-$R_{17}$ are independently of each other a hydrogen or an unsubstituted or substituted alkyl, alkenyl, aryl, cycloalkyl, heterocyclyl, alkylaryl, cycloalkylaryl, alkylcycloalkyl, acyl, methanesulfonyl, or alkylheterocyclyl; or $R_1$ and $R_2$, $R_6$ and $R_7$, and $R_{11}$ and $R_{12}$, together with the nitrogen atom to which they are attached, form a nitrogen-containing heterocyclic ring;

m, p and q are independently of each other 0, 1 or 2;

or a stereoisomer, enantiomer, racemate, pharmaceutically acceptable salt, solvate, hydrate or polymorph thereof.

2. The compound of claim 1 of the Formula I:

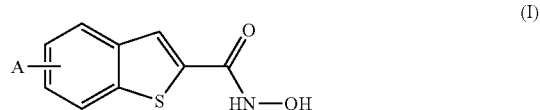

wherein A is a group selected from:

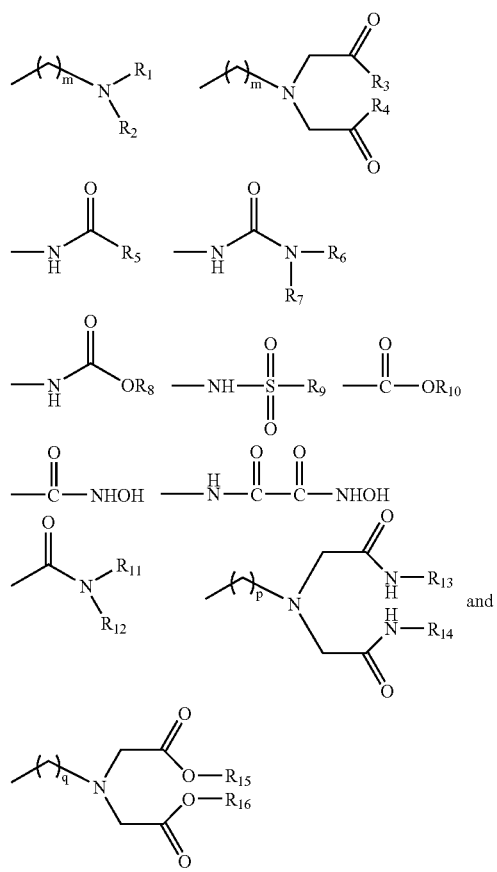

wherein $R_1$-$R_{16}$ are independently of each other a hydrogen or an unsubstituted or substituted alkyl, alkenyl, aryl, cycloalkyl, heterocyclyl, alkylaryl, alkylcycloalkyl or alkylheterocyclyl; or $R_1$ and $R_2$, $R_6$ and $R_7$, and $R_{11}$ and $R_{12}$, together with the nitrogen atom to which they are attached, form a nitrogen-containing heterocyclic ring;

m, p and q are independently of each other 0, 1 or 2;

or a stereoisomer, enantiomer, racemate, pharmaceutically acceptable salt, solvate, hydrate or polymorph thereof.

3. The compound of claim 1, wherein A is selected from:

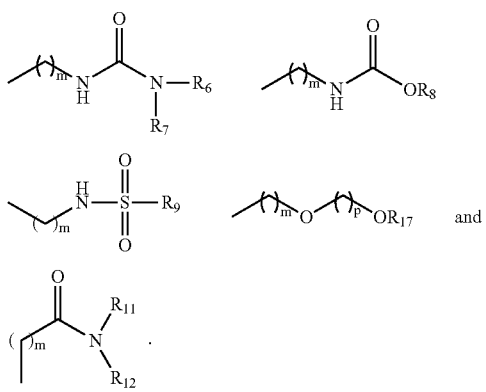

4. The compound of claim 1, wherein A is

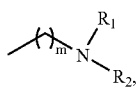

wherein m is zero or one.

5. The compound of claim 4, wherein at least one of $R_1$ and $R_2$ is phenyl, naphthyl, biphenyl, benzyl, —CH$_2$CH$_2$Ph, —CH$_2$CH$_2$CH$_2$Ph, —CH=CHPh, cyclohexyl, quinolinyl, isoquinolinyl, —CH$_2$-cyclohexyl, —CH$_2$-quinolinyl, —CH$_2$—isoquinolinyl, pyridyl, —CH(Ph)$_2$, methyl, ethyl, propyl, isopropyl, butyl, isobutyl sec-butyl or tert-butyl.

6. The compound of claim 1, wherein A is

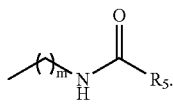

7. The compound of claim 6, wherein $R_5$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

8. The compound of claim 1, wherein A is

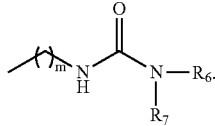

9. The compound of claim 8, wherein at least one of $R_6$ and $R_7$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

10. The compound of claim 1, wherein A is

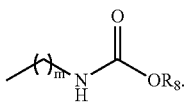

11. The compound of claim 10, wherein $R_8$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

12. The compound of claim 1, wherein A is

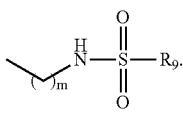

13. The compound of claim 12, wherein $R_9$ is phenyl, 1-naphthyl, 2-naphthyl, biphenyl, benzyl, —CH$_2$CH$_2$Ph, —CH=CHPh, cyclohexyl, quinolinyl, isoquinolinyl, thiophenyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

14. The compound of claim 1, wherein A is

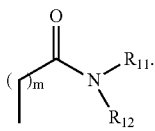

15. The compound of claim 14, wherein at least one of $R_{11}$ and $R_{12}$ is phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl sec-butyl or tert-butyl.

16. A compound selected from:
   6-Phenylacetylamino-benzo[b]thiophene-2-carboxylic acid hydroxyamide;
   6-Benzoylamino-benzo[b]thiophene-2-carboxylic acid hydroxyamide;
   6-[(Biphenyl-4-carbonyl)-amino]-benzo[b]thiophene-2-carboxylic acid hydroxyamide;
   6-(3-Phenyl-propionylamino)-benzo[b]thiophene-2-carboxylic acid hydroxyamide;
   6-[(Naphthalene-2-carbonyl)-amino]-benzo[b]thiophene-2-carboxylic acid hydroxyamide;
   6-Isobutyrylamino-benzo[b]thiophene-2-carboxylic acid hydroxyamide;
   Quinoline-2-carboxylic acid (2-hydroxycarbamoyl-benzo[b]thiophen-6-yl)-amide;
   N-(2-Hydroxycarbamoyl-benzo[b]thiophen-6-yl)-nicotinamide;
   6-Diphenylacetylamino-benzo[b]thiophene-2-carboxylic acid hydroxyamide;
   6-[(Naphthalene-1-carbonyl)-amino]-benzo[b]thiophene-2-carboxylic acid hydroxyamide;
   6-(3,4-Dimethoxy-benzoylamino)-benzo[b]thiophene-2-carboxylic acid hydroxyamide;

6-[2-(3,4-Dimethoxy-phenyl)-acetylamino]-benzo[b]
thiophene-2-carboxylic acid hydroxyamide;
6-[2-(4-Fluoro-phenyl)-acetylamino]-benzo[b]thiophene-
2-carboxylic acid hydroxyamide;
6-[2-(2,5-Dimethoxy-phenyl)-acetylamino]-benzo[b]
thiophene-2-carboxylic acid hydroxyamide;
6-[2-(3-Methoxy-phenyl)-acetylamino]-benzo[b]
thiophene-2-carboxylic acid hydroxyamide;
6-[2-(4-Chloro-phenyl)-acetylamino]-benzo[b]
thiophene-2-carboxylic acid hydroxyamide;
6-[2-(4-Methoxy-phenyl)-acetylamino]-benzo[b]
thiophene-2-carboxylic acid hydroxyamide;
6-(2-Phenyl-butyrylamino)-benzo[b]thiophene-2-carboxylic acid hydroxyamide;
6-(Methyl-phenylacetyl-amino)-benzo[b]thiophene-2-carboxylic acid hydroxyamide;
6-(2-Pyridin-2-yl-acetylamino)-benzo[b]thiophene-2-carboxylic acid hydroxyamide;
6-(2-Pyridin-3-yl-acetylamino)-benzo[b]thiophene-2-carboxylic acid hydroxyamide;
6-(2-Phenyl-propionylamino)-benzo[b]thiophene-2-carboxylic acid hydroxyamide;
6-{[1-(4-Chloro-phenyl)-cyclopropanecarbonyl]-amino}-benzo[b]thiophene-2-carboxylic acid hydroxyamide;
6-[(1-Phenyl-cyclopropanecarbonyl)-amino]-benzo[b]thiophene-2-carboxylic acid hydroxyamide;
6-{[1-(4-Chloro-phenyl)-cyclobutanecarbonyl]-amino}-benzo[b]thiophene-2-carboxylic acid hydroxyamide;
6-[2-(4-Chloro-phenyl)-2-methyl-propionylamino]-benzo[b]thiophene-2-carboxylic acid hydroxyamide;
6-(2S-Phenyl-butyrylamino)-benzo[b]thiophene-2-carboxylic acid hydroxyamide;
6-(2R-Phenyl-butyrylamino)-benzo[b]thiophene-2-carboxylic acid hydroxyamide;
6-(Benzoylamino-methyl)-benzo[b]thiophene-2-carboxylic acid hydroxyamide;
6-(Phenylacetylamino-methyl)-benzo[b]thiophene-2-carboxylic acid hydroxyamide;
6-{[(Naphthalene-1-carbonyl)-amino]-methyl}-benzo[b]thiophene-2-carboxylic acid hydroxyamide;
6-[(2-Methyl-benzoylamino)-methyl]-benzo[b]thiophene-2-carboxylic acid hydroxyamide;
6-[(4-Methyl-benzoylamino)-methyl]-benzo[b]thiophene-2-carboxylic acid hydroxyamide;
6-[(3-Methoxy-benzoylamino)-methyl]-benzo[b]thiophene-2-carboxylic acid hydroxyamide;
6-[(4-Methoxy-benzoylamino)-methyl]-benzo[b]thiophene-2-carboxylic acid hydroxyamide;
6-[(3,4-Dimethoxy-benzoylamino)-methyl]-benzo[b]thiophene-2-carboxylic acid hydroxyamide;
N-(2-Hydroxycarbamoyl-benzo[b]thiophen-6-ylmethyl)-nicotinamide;
6-(Isobutyrylamino-methyl)-benzo[b]thiophene-2-carboxylic acid hydroxyamide;
6-[(2-Methoxy-benzoylamino)-methyl]-benzo[b]thiophene-2-carboxylic acid hydroxyamide;
6-[(4-Chloro-benzoylamino)-methyl]-benzo[b]thiophene-2-carboxylic acid hydroxyamide;
6-Phenylmethanesulfonylamino-benzo[b]thiophene-2-carboxylic acid hydroxyamide;
6-Benzenesulfonylamino-benzo[b]thiophene-2-carboxylic acid hydroxyamide;
6-(Biphenyl-4-sulfonylamino)-benzo[b]thiophene-2-carboxylic acid hydroxyamide;
6-(Naphthalene-1-sulfonylamino)-benzo[b]thiophene-2-carboxylic acid hydroxyamide;
6-(Naphthalene-2-sulfonylamino)-benzo[b]thiophene-2-carboxylic acid hydroxyamide;
6-(Toluene-4-sulfonylamino)-benzo[b]thiophene-2-carboxylic acid hydroxyamide;
6-(Benzenesulfonylamino-methyl)-benzo[b]thiophene-2-carboxylic acid hydroxyamide;
6-(Phenylmethanesulfonylamino-methyl)-benzo[b]thiophene-2-carboxylic acid hydroxyamide;
6-[(Naphthalene-1-sulfonylamino)-methyl]-benzo[b]thiophene-2-carboxylic acid hydroxyamide;
6-[(Naphthalene-2-sulfonylamino)-methyl]-benzo[b]thiophene-2-carboxylic acid hydroxyamide;
6-[(Toluene-4-sulfonylamino)-methyl]-benzo[b]thiophene-2-carboxylic acid hydroxyamide;
6-[(2,4,6-Trimethyl-benzenesulfonylamino)-methyl]-benzo[b]thiophene-2-carboxylic acid hydroxyamide;
6-[(4-tert-Butyl-benzenesulfonylamino)-methyl]-benzo[b]thiophene-2-carboxylic acid hydroxyamide;
6-[(4-Fluoro-benzenesulfonylamino)-methyl]-benzo[b]thiophene-2-carboxylic acid hydroxyamide;
6-[(4-Chloro-benzenesulfonylamino)-methyl]-benzo[b]thiophene-2-carboxylic acid hydroxyamide;
6-[(3-Chloro-benzenesulfonylamino)-methyl]-benzo[b]thiophene-2-carboxylic acid hydroxyamide;
6-[(4-Bromo-benzenesulfonylamino)-methyl]-benzo[b]thiophene-2-carboxylic acid hydroxyamide;
6-[(3-Bromo-benzenesulfonylamino)-methyl]-benzo[b]thiophene-2-carboxylic acid hydroxyamide;
6-[(3-Methoxy-benzenesulfonylamino)-methyl]-benzo[b]thiophene-2-carboxylic acid hydroxyamide;
6-[(4-Nitro-benzenesulfonylamino)-methyl]-benzo[b]thiophene-2-carboxylic acid hydroxyamide;
6-[(4-Methoxy-benzenesulfonylamino)-methyl]-benzo[b]thiophene-2-carboxylic acid hydroxyamide;
6-[(Thiophene-2-sulfonylamino)-methyl]-benzo[b]thiophene-2-carboxylic acid hydroxyamide;
6-{[3-(4-Methoxy-phenoxy)-propane-1-sulfonylamino]-methyl}-benzo[b]thiophene-2-carboxylic acid hydroxyamide;
6-(3-Benzyl-ureido)-benzo[b]thiophene-2-carboxylic acid hydroxyamide;
(2-Hydroxycarbamoyl-benzo[b]thiophen-6-yl)-carbamic acid ethyl ester;
(2-Hydroxycarbamoyl-benzo[b]thiophen-6-yl)-carbamic acid benzyl ester;
6-(3-Phenethyl-ureido)-benzo[b]thiophene-2-carboxylic acid hydroxyamide;
6-(3-Benzyl-ureidomethyl)-benzo[b]thiophene-2-carboxylic acid hydroxyamide;
(2-Hydroxycarbamoyl-benzo[b]thiophen-6-ylmethyl)-carbamic acid benzyl ester;
6-[3-(4-Isopropyl-phenyl)-ureidomethyl]-benzo[b]thiophene-2-carboxylic acid hydroxyamide;
6-[3-(4-tert-Butyl-phenyl)-ureidomethyl]-benzo[b]thiophene-2-carboxylic acid hydroxyamide;
6-[3-(3,5-Bis-trifluoromethyl-phenyl)-ureidomethyl]-benzo[b]thiophene-2-carboxylic acid hydroxyamide;
6-[3 -(3-Phenoxy-phenyl)-ureidomethyl]-benzo[b]thiophene-2-carboxylic acid hydroxyamide;
5-Benzoylamino-benzo[b]thiophene-2-carboxylic acid hydroxyamide;
5-Phenylacetylamino-benzo[b]thiophene-2-carboxylic acid hydroxyamide;
5-(3-Phenyl-propionylamino)-benzo [b] thiophene-2-carboxylic acid hydroxyamide;
5-(3-Phenyl-acryloylamino)-benzo [b]thiophene-2-carboxylic acid hydroxyamide;

5-[(Naphthalene-1-carbonyl)-amino]-benzo[b]thiophene-2-carboxylic acid hydroxyamide;
5-[(Naphthalene-2-carbonyl)-amino]-benzo[b]thiophene-2-carboxylic acid hydroxyamide;
Quinoline-2-carboxylic acid (2-hydroxycarbamoyl-benzo[b]thiophen-5-yl)-amide;
N-(2-Hydroxycarbamoyl-benzo[b]thiophen-5-yl)-nicotinamide;
5-[(Biphenyl-4-carbonyl)-amino]-benzo[b]thiophene-2-carboxylic acid hydroxyamide;
5-Diphenylacetylamino-benzo[b]thiophene-2-carboxylic acid hydroxyamide;
5-Isobutyrylamino-benzo[b]thiophene-2-carboxylic acid hydroxyamide;
5-[2-(4-Fluoro-phenyl)-acetylamino]-benzo[b]thiophene-2-carboxylic acid hydroxyamide;
5-[2-(3-Methoxy-phenyl)-acetylamino]-benzo[b]thiophene-2-carboxylic acid hydroxyamide;
5-[2-(3,4-Dimethoxy-phenyl)-acetylamino]-benzo[b]thiophene-2-carboxylic acid hydroxyamide;
5-[2-(2,5-Dimethoxy-phenyl)-acetylamino]-benzo[b]thiophene-2-carboxylic acid hydroxyamide;
5-(2-Phenyl-butyrylamino)-benzo[b]thiophene-2-carboxylic acid hydroxyamide;
5-[2-(4-Chloro-phenyl)-acetylamino]-benzo[b]thiophene-2-carboxylic acid hydroxyamide;
5-[2-(4-Methoxy-phenyl)-acetylamino]-benzo[b]thiophene-2-carboxylic acid hydroxyamide;
5-{[1-(4-Chloro-phenyl)-cyclopentanecarbonyl]-amino}-benzo[b]thiophene-2-carboxylic acid hydroxyamide;
5-(Naphthalene-2-sulfonylamino)-benzo[b]thiophene-2-carboxylic acid hydroxyamide;
5-(Toluene-4-sulfonylamino)-benzo[b]thiophene-2-carboxylic acid hydroxyamide;
5-Benzenesulfonylamino-benzo[b]thiophene-2-carboxylic acid hydroxyamide;
5-Phenylmethanesulfonylamino-benzo[b]thiophene-2-carboxylic acid hydroxyamide;
5-(Naphthalene-1-sulfonylamino)-benzo[b]thiophene-2-carboxylic acid hydroxyamide;
5-(Biphenyl-4-sulfonylamino)-benzo[b]thiophene-2-carboxylic acid hydroxyamide;
(2-Hydroxycarbamoyl-benzo[b]thiophen-5-yl)-carbamic acid benzyl ester;
(2-Hydroxycarbamoyl-benzo[b]thiophen-5-yl)-carbamic acid ethyl ester;
5-(3-Benzyl-ureido)-benzo[b]thiophene-2-carboxylic acid hydroxyamide;
5-Dibenzylamino-benzo[b]thiophene-2-carboxylic acid hydroxyamide;
6-Dibenzylamino-benzo[b]thiophene-2-carboxylic acid methyl ester;
6-Dibenzylamino-benzo[b]thiophene-2-carboxylic acid hydroxyamide;
5-(Bis-phenylcarbamoylmethyl-amino)-benzo[b]thiophene-2-carboxylic acid hydroxyamide;
6-(Bis-phenylcarbamoylmethyl-amino)-benzo[b]thiophene-2-carboxylic acid hydroxyamide;
6-[2-(4-Phenyl-piperazin-1-yl)-acetylamino]-benzo[b]thiophene-2-carboxylic acid hydroxyamide;
6-(2-3,4-Dihydro-1H-isoquinolin-2-yl-acetylamino)-benzo[b]thiophene-2-carboxylic acid hydroxyamide;
6-[2-(4-Benzyl-piperidin-1-yl)-acetylamino]-benzo[b]thiophene-2-carboxylic acid hydroxyamide;
4-[(2-Hydroxycarbamoyl-benzo[b]thiophen-6-ylcarbamoyl)-methyl]-piperazine-1-carboxylic acid benzyl ester;
6-(2-Dibenzylamino-acetylamino)-benzo[b]thiophene-2-carboxylic acid hydroxyamide;
6-{2-[4(3-Methoxy-phenyl)-piperazin-1-yl]-acetylamino}-benzo[b]thiophene-2-carboxylic acid hydroxyamide;
6-[2-(4-Pyrimidin-2-yl-piperazin-1-yl)-acetylamino]-benzo[b]thiophene-2-carboxylic acid hydroxyamide;
6-{2-[4-(2-(2-Methoxy-phenyl)-piperazin-1-yl]-acetylamino}-benzo[b]thiophene-2-carboxylic acid hydroxyamide;
6-[2-(4-Pyridin-2-yl-piperazin-1-yl)-acetylamino]-benzo[b]thiophene-2-carboxylic acid hydroxyamide;
6-[2-(4-Acetyl-piperazin-1-yl)-acetylamino]-benzo[b]thiophene-2-carboxylic acid hydroxyamide;
6-(2-Piperidin-1-yl-acetylamino)-benzo[b]thiophene-2-carboxylic acid hydroxyamide;
6-(2-Morpholin-4-yl-acetylamino)-benzo[b]thiophene-2-carboxylic acid hydroxyamide;
6-[2-(Benzyl-phenethyl-amino)-acetylamino]-benzo[b]thiophene-2-carboxylic acid hydroxyamide;
{tert-Butoxycarbonylmethyl-[(2-hydroxycarbamoyl-benzo[b]thiophen-6-ylcarbamoyl)-methyl]-amino}-acetic acid tert-butyl ester;
6-{2-[4-(2-Chloro-phenyl)-piperazin-1-yl]-acetylamino}-benzo[b]thiophene-2-carboxylic acid hydroxyamide;
6-{2-[4-(3-Chloro-phenyl)-piperazin-1-yl]-acetylamino}-benzo[b]thiophene-2-carboxylic acid hydroxyamide;
4-[(2-Hydroxycarbamoyl-benzo[b]thiophen-6-ylcarbamoyl)-methyl]-[1,4]diazepane-1-carboxylic acid benzyl ester;
4-[(2-Hydroxycarbamoyl-benzo[b]thiophen-6-ylcarbamoyl)-methyl]-piperazine-1-carboxylic acid ethyl ester;
6-{2-[4(4-Methoxy-phenyl)-piperazin-1-yl]-acetylamino}-benzo[b]thiophene-2-carboxylic acid hydroxyamide;
Benzo[b]thiophene-2,6-dicarboxylic acid 2-hydroxyamide 6-{[2-(1H-indol-2-yl)-ethyl]-amide};
Benzo[b]thiophene-2,6-dicarboxylic acid 6-benzylamide 2-hydroxyamide;
Benzo[b]thiophene-2,6-dicarboxylic acid 2-hydroxyamide 6-[(pyridin-2-ylmethyl)-amide];
Benzo[b]thiophene-2,6-dicarboxylic acid 6-[(1-benzyl-piperidin-4-yl)-amide]2-hydroxyamide;
Benzo[b]thiophene-2,6-dicarboxylic acid 6-[(2,2-diphenyl-ethyl)-amide]2-hydroxyamide;
Benzo[b]thiophene-2,6-dicarboxylic acid 6-[(1,2-diphenyl-ethyl)-amide]2-hydroxyamide;
Benzo[b]thiophene-2,6-dicarboxylic acid 6-benzhydrylamide 2-hydroxyamide;
Benzo[b]thiophene-2,6-dicarboxylic acid 6-[(1H-benzoimidazol-2-ylmethyl)-amide]2-hydroxyamide;
Benzo[b]thiophene-2,6-dicarboxylic acid 2-hydroxyamide 6-[(2-pyridin-2-yl-ethyl)-amide];
Benzo[b]thiophene-2,6-dicarboxylic acid 2-hydroxyamide 6-[(1,2,3,4-tetrahydro-naphthalen-1-yl)-amide];
6-(Piperidine-1-carbonyl)-benzo[b]thiophene-2-carboxylic acid hydroxyamide;
Benzo[b]thiophene-2,6-dicarboxylic acid 2-hydroxyamide 6-phenylamide;
Benzo[b]thiophene-2,6-dicarboxylic acid 2-hydroxyamide 6-indan-1-ylamide;
6-(4-Phenyl-piperazine-1-carbonyl)-benzo[b]thiophene-2-carboxylic acid hydroxyamide;
6-[4-(4-Chloro-phenyl)-piperazine-1-carbonyl]-benzo[b]thiophene-2-carboxylic acid hydroxyamide;
Benzo[b]thiophene-2,6-dicarboxylic acid 2-hydroxyamide 6-[(3-phenyl-propyl)-amide];

Benzo[b]thiophene-2,6-dicarboxylic acid 2-hydroxyamide 6-(phenethyl-amide);
6-(4-Benzyl-piperidine-1-carbonyl)-benzo [b]thiophene-2-carboxylic acid hydroxamide;
6-(4-Benzyl-piperazine-1-carbonyl)-benzo [b]thiophene-2-carboxylic acid hydroxamide;
Benzo[b]thiophene-2,6-dicarboxylic acid 2-hydroxamide 6-quinolin-8-ylamide;
Benzo[b]thiophene-2,6-dicarboxylic acid 2-hydroxamide 6-[(4-phenyl-thiazol-2-yl)-amide];
Benzo[b]thiophene-2,5-dicarboxylic acid 2-hydroxamide 5-(2-methoxy-benzylamide);
Benzo[b]thiophene-2,5-dicarboxylic acid 2-hydroxamide 5-(3-methoxy-benzylamide);
Benzo[b]thiophene-2,5-dicarboxylic acid 2-hydroxamide 5-(4-methoxy-benzylamide);
Benzo [b]thiophene-2,5-dicarboxylic acid 5-(2-chloro-benzylamide) 2-hydroxamide;
Benzo [b]thiophene-2,5-dicarboxylic acid 5-(3-chloro-benzylamide) 2-hydroxamide;
Benzo [b]thiophene-2,5-dicarboxylic acid 5-(4-chloro-benzylamide) 2-hydroxamide;
Benzo [b]thiophene-2,5-dicarboxylic acid 2-hydroxamide 5-indan-1-ylamide;
Benzo [b]thiophene-2,5-dicarboxylic acid 2-hydroxamide 5-{[2-(1H-indol-3-yl)-ethyl]-amide};
Benzo [b]thiophene-2,5-dicarboxylic acid 5-[(3,3-diphenyl-propyl)-amide]2-hydroxamide;
Benzo [b]thiophene-2,5-dicarboxylic acid 2-hydroxamide 5-[(4-phenyl-butyl)-amide];
Benzo [b]thiophene-2,5-dicarboxylic acid 2-hydroxamide 5-phenylamide;
Benzo [b]thiophene-2,5-dicarboxylic acid 2-hydroxamide 5-(phenethyl-amide);
Benzo [b]thiophene-2,5-dicarboxylic acid 5-benzylamide 2-hydroxamide;
Benzo [b]thiophene-2,5-dicarboxylic acid 2-hydroxamide 5-[(3-phenyl-propyl)-amide];
Benzo [b]thiophene-2,5-dicarboxylic acid 5-(bis-phenyl-carbamoylmethyl-amide) 2-hydroxamide;
5-[(3-Methoxy-benzylamino)-methyl]-benzo [b]thiophene-2-carboxylic acid hydroxamide;
5-(Benzylamino-methyl)-benzo[b]thiophene-2-carboxylic acid hydroxamide;
5-Phenylaminomethyl-benzo[b]thiophene-2-carboxylic acid hydroxamide;
5-[(3-Benzyloxy-phenylamino)-methyl]-benzo[b] thiophene-2-carboxylic acid hydroxamide;
5-[(4-Methoxy-benzylamino)-methyl]-benzo [b]thiophene-2-carboxylic acid hydroxamide;
5-[(2-Chloro-benzylamino)-methyl]-benzo [b]thiophene-2-carboxylic acid hydroxamide;
5-[(4-Chloro-benzylamino)-methyl]-benzo [b]thiophene-2-carboxylic acid hydroxamide;
5-[(Benzhydryl-amino)-methyl]-benzo[b]thiophene-2-carboxylic acid hydroxamide;
5-(Phenethylamino-methyl)-benzo [b]thiophene-2-carboxylic acid hydroxamide;
5-[(2,2-Diphenyl-ethylamino)-methyl]-benzo [b]thiophene-2-carboxylic acid hydroxamide;
5-{[2-(3,4-Bis-benzyloxy-phenyl)-ethylamino]-methyl}-benzo[b]thiophene-2-carboxylic acid hydroxamide;
5-[(3-Phenyl-propylamino)-methyl]-benzo [b]thiophene-2-carboxylic acid hydroxamide;
5-[(3,3-Diphenyl-propylamino)-methyl]-benzo[b] thiophene-2-carboxylic acid hydroxamide;
5-[(4-Phenyl-butylamino)-methyl]-benzo[b]thiophene-2-carboxylic acid hydroxamide;
5-[(2-Morpholin-4-yl-ethylamino)-methyl]-benzo[b] thiophene-2-carboxylic acid hydroxamide;
5-[(Cyclohexylmethyl-amino)-methyl]-benzo [b]thiophene-2-carboxylic acid hydroxamide;
5-[(2-Methoxy-benzylamino)-methyl]-benzo [b]thiophene-2-carboxylic acid hydroxamide;
5-[(3-Chloro-benzylamino)-methyl]-benzo [b]thiophene-2-carboxylic acid hydroxamide;
5-{[(1H-Benzoimidazol-2-ylmethyl)-amino]-methyl}-benzo[b]thiophene-2-carboxylic acid hydroxamide;
5-{[(Pyridin-2-ylmethyl)-amino]-methyl}-benzo[b] thiophene-2-carboxylic acid hydroxamide;
5-{[2-(3,4-Dimethoxy-phenyl)-ethylamino]-methyl}-benzo[b]thiophene-2-carboxylic acid hydroxamide;
5-{[2-(1H-Indol-3-yl)-ethylamino]-methyl}-benzo[b] thiophene-2-carboxylic acid hydroxamide;
5-[(1-Benzyl-piperidin-4-ylamino)-methyl]-benzo[b] thiophene-2-carboxylic acid hydroxamide;
6-(Benzylamino-methyl)-benzo[b]thiophene-2-carboxylic acid hydroxamide;
6-[(2-Methoxy-benzylamino)-methyl]-benzo[b] thiophene-2-carboxylic acid hydroxamide;
6-[(3-Methoxy-benzylamino)-methyl]-benzo[b] thiophene-2-carboxylic acid hydroxamide;
6-Phenylaminomethyl-benzo[b]thiophene-2-carboxylic acid hydroxamide;
6-(Phenethylamino-methyl)-benzo[b]thiophene-2-carboxylic acid hydroxamide;
6-[(3-Phenyl-propylamino)-methyl]-benzo[b]thiophene-2-carboxylic acid hydroxamide;
6-[(2-Chloro-benzylamino)-methyl]-benzo[b]thiophene-2-carboxylic acid hydroxamide;
6-[(3-Chloro-benzylamino)-methyl]-benzo[b]thiophene-2-carboxylic acid hydroxamide;
6-[(4-Chloro-benzylamino)-methyl]-benzo[b]thiophene-2-carboxylic acid hydroxamide;
6-{[(Benzo[1,3]dioxol-5-ylmethyl)-amino]-methyl}-benzo[b]thiophene-2-carboxylic acid hydroxamide;
6-(Indan-1-ylaminomethyl)-benzo[b]thiophene-2-carboxylic acid hydroxamide;
6-[(9H-Fluoren-9-ylamino)-methyl]-benzo[b]thiophene-2-carboxylic acid hydroxamide;
6-[(1,2-Diphenyl-ethylamino)-methyl]-benzo[b] thiophene-2-carboxylic acid hydroxamide;
6-[(Cyclohexylmethyl-amino)-methyl]-benzo [b]thiophene-2-carboxylic acid hydroxamide;
6-[(1,2,3,4-Tetrahydro-naphthalen-1-ylamino)-methyl]-benzo [b]thiophene-2-carboxylic acid hydroxamide;
6-{[2-(2-Methyl-1H-indol-3-yl)-ethylamino]-methyl}-benzo[b]thiophene-2-carboxylic acid hydroxamide;
6-{[(Pyridin-2-ylmethyl)-amino]-methyl}-benzo[b] thiophene-2-carboxylic acid hydroxamide;
6-[(1-Benzyl-piperidin-4-ylamino)-methyl]-benzo [b]thiophene-2-carboxylic acid hydroxamide;
6-[(4-Methoxy-benzylamino)-methyl]-benzo [b]thiophene-2-carboxylic acid hydroxamide;
6-{[2-(1H-Indol-3-yl)-ethylamino]-methyl}-benzo[b] thiophene-2-carboxylic acid hydroxamide;
6-[(4-Methoxy-benzylamino)-methyl]-benzo[b] thiophene-2-carboxylic acid ethyl ester;
6-{[Cyclohexyl-(4-methoxy-benzyl)-amino]-methyl}-benzo[b]thiophene-2-carboxylic acid hydroxamide;
6-{[(4-Methoxy-benzyl)-(tetrahydro-pyran-4-yl)-amino]-methyl}-benzo [b]thiophene-2-carboxylic acid hydroxamide;

6-{[(2-Hydroxy-ethyl)-(4-methoxy-benzyl)-amino]-methyl}-benzo [b]thiophene-2-carboxylic acid hydroxyamide;

6-{[Isopropyl-(4-methoxy-benzyl)-amino]-methyl}-benzo[b]thiophene-2-carboxylic acid hydroxyamide;

6-{[(4-Methoxy-benzyl)-methyl-amino]-methyl}-benzo [b]thiophene-2-carboxylic acid hydroxyamide;

6-[(Acetyl-benzyl-amino)-methyl]-benzo[b]thiophene-2-carboxylic acid hydroxyamide;

6-[(Benzyl-methanesulfonyl-amino)-methyl]-benzo [b]thiophene-2-carboxylic acid hydroxyamide; and N-Hydroxy-N'-(2-hydroxycarbamoyl-benzo [b]thiophen-6-yl)-oxalamide; or a stereoisomer, enantiomer, racemate, pharmaceutically acceptable salt, solvate, hydrate or polymorph thereof.

17. A pharmaceutical composition comprising a pharmaceutically effective amount of the compound of any of claims 1-15 and 16, and a pharmaceutically acceptable carrier.

* * * * *